United States Patent
Sandau et al.

(10) Patent No.: US 9,603,379 B2
(45) Date of Patent: Mar. 28, 2017

(54) FELINE BITTER TASTE RECEPTORS AND METHODS

(71) Applicant: Applied Food Biotechnology, Inc., St. Charles, MO (US)

(72) Inventors: Michelle M. Sandau, Saint Charles, MO (US); Nancy E. Rawson, Chesterfield, MO (US)

(73) Assignee: APPLIED FOOD BIOTECHNOLOGY, INC, St. Charles, MO (US)

( * ) Notice: Subject to any disclaimer, the term of this patent is extended or adjusted under 35 U.S.C. 154(b) by 0 days.

(21) Appl. No.: 14/774,948

(22) PCT Filed: Mar. 6, 2014

(86) PCT No.: PCT/US2014/021110
§ 371 (c)(1),
(2) Date: Sep. 11, 2015

(87) PCT Pub. No.: WO2014/149829
PCT Pub. Date: Sep. 25, 2014

(65) Prior Publication Data
US 2016/0015062 A1    Jan. 21, 2016

Related U.S. Application Data

(60) Provisional application No. 61/945,500, filed on Feb. 27, 2014, provisional application No. 61/788,528, filed on Mar. 15, 2013.

(51) Int. Cl.
| | |
|---|---|
| C07K 14/705 | (2006.01) |
| C07K 16/28 | (2006.01) |
| G01N 33/50 | (2006.01) |
| A23L 1/22 | (2006.01) |
| A23K 40/30 | (2016.01) |
| A23K 20/147 | (2016.01) |
| A23K 50/40 | (2016.01) |
| A23L 27/00 | (2016.01) |
| A23L 33/10 | (2016.01) |

(52) U.S. Cl.
CPC ........ *A23L 1/22083* (2013.01); *A23K 20/147* (2016.05); *A23K 40/30* (2016.05); *A23K 50/40* (2016.05); *A23L 27/86* (2016.08); *A23L 33/10* (2016.08); *C07K 14/705* (2013.01); *G01N 33/5041* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,022,488 B2 | 4/2006 | Servant et al. | |
| 7,244,584 B2 * | 7/2007 | Zuker ............... | C07K 14/705 435/252.3 |
| 7,413,867 B2 | 8/2008 | Bufe et al. | |
| 7,527,944 B2 | 5/2009 | Li et al. | |
| 7,541,158 B2 | 6/2009 | Li et al. | |
| 8,071,719 B2 | 12/2011 | Zoller et al. | |
| 8,158,442 B2 | 4/2012 | Bufe et al. | |
| 8,187,822 B2 | 5/2012 | Brune et al. | |
| 8,273,542 B2 | 9/2012 | Li et al. | |
| 8,309,314 B2 | 11/2012 | Behrens et al. | |
| 8,309,701 B2 | 11/2012 | Drayna et al. | |
| 8,334,367 B2 | 12/2012 | Adler | |
| 2004/0214239 A1 | 10/2004 | Servant et al. | |
| 2011/0281753 A1 | 11/2011 | Moyer et al. | |
| 2011/0311991 A1 | 12/2011 | Slack et al. | |
| 2012/0015841 A1 | 1/2012 | Shekdar et al. | |
| 2013/0030059 A1 | 1/2013 | Li et al. | |
| 2014/0273001 A1 | 9/2014 | Sandau et al. | |

FOREIGN PATENT DOCUMENTS

| | | |
|---|---|---|
| WO | 0118050 A2 | 3/2001 |
| WO | 2006053771 A2 | 5/2006 |
| WO | 2011012298 A1 | 2/2011 |
| WO | 2011050955 A1 | 5/2011 |
| WO | 2012013480 A1 | 2/2012 |

OTHER PUBLICATIONS

Bachmanov AA et al. "Taste Receptor Genes"; NIH Public Access Author Manuscript; available in PMC Aug. 5, 2009 (Published in final edited form as: Annu Rev Nutr.; 2007; 27:389-414); 26 pgs.
Behrens M. et al. "Bitter taste receptor research comes of age: From characterization to modulation ofTAS2Rs". Semin Cell Dev Biol (2012), http://dx.doi.org/10.1016/j.semcdb.2012.08.006; Epub Aug. 27, 2012 (7 pages).
Conte et al.; "Evolutionary relationships of the Tas2r receptor gene families in mouse and human"; Physiol Genomics, 14; 2003; pp. 73-82.
Conte; "Functional expression of mammalian bitter taste receptors in Caenorhabditis elegans"; Biochimie 88; 2006; 801-806.
Dong D. et al. "Dynamic Evolution of Bitter Taste Receptor Genes in Vertebrates" BMC Evolutionary Biology 2009,9:12 doi:10.1186/1471-2148-9-12 (9 pages).
Go et al.; Lineage-Specific Expansion and Contractions of the Bitter Taste Receptor Gene Repertoire in Vertebrates; Mol. Biol. Evol. 23(5):964-972. 2006.
Go Y. et al. "Lineage-Specific Loss of Function of Bitter Taste Receptor Genes in Humans and NonhumanPrimates"; Genetics; May 2005; 170: 313-326.
Imai H. et al. "Functional Diversity of Bitter Taste Receptor TAS2R16 in Primates" Biol Lett. Aug. 23, 2012;8(4):652-6. doi: 10.1098/rsbl.2011.1251. Epub Mar. 7, 2012.
International Search Report; International Application No. PCT/US2014/021110; Filing Date: Mar. 6, 2014; Mailing Date: Jul. 11, 2014; 7 pgs.

(Continued)

*Primary Examiner* — John Ulm
(74) *Attorney, Agent, or Firm* — Cantor Colburn LLP

(57) ABSTRACT

A family of novel feline bitter taste receptors, referred to as feline TAS2R (fTAS2R), are disclosed herein. Isolated polynucleotides encoding the novel feline bitter taste receptors and chimeric polypeptides are also disclosed, as are expression vectors and host cells for expression of the novel feline bitter taste receptors. Methods of identifying compounds that bind to the novel feline bitter taste receptors and modulate their activity are disclosed.

16 Claims, 2 Drawing Sheets

(56) References Cited

OTHER PUBLICATIONS

Jiang et al.; "Major taste loss in carnivorous mammals"; PNAS, vol. 109 No. 13;2012; pp. 4956-4961.
Li H. et al. "Selection on the Human Bitter Taste Gene, TAS2R16, inEurasian Populations" Human Biology vol. 83, Issue 3, Article 3, 2011 (17 pages); Available at: http://digitalcommons.wayne.edu/humbiol/vol83/iss3/3.
Mueller et al.; "The receptors and coding logic for bitter taste"; Nature, 434; 2005; pp. 225-229.
Mullikin JC et al.; "Light whole genome sequence for SNP discovery across domestic cat breeds" BMC Genomics;2010; 11: 406; 8 pages.
NCBI Reference Sequence: XP_003988467.1; Nov. 6, 2012; Predicted, Low quality protein: taste receptor type 2 member 20-like [Felis catus]; 1 pg.
Non-Final Office Action for U.S. Appl. No. 14/198,795, filed Mar. 6, 2014; Notification Date Mar. 5, 2015; 13 pages.
Pontius Ju et al.; Initial sequence and comparative analysis of the cat genome: Genome Res.; 2007; 17:1675-1689.
Third-Party Pre-issuance submission under 37 CFR 1.290, Concise Description of Relevance, submitted in U.S. Appl. No. 14/198795 on Mar. 17, 2015 (8 pages).
Ueda et al.; "Functional Interaction between T2R Taste Receptors and G-Protein α Subunits Expressed in Taste Receptor Cells"; The Journal of Neuroscience, 23(19); 2003; 7376-7380.
Written Opinion dated Jul. 11, 2014; International Application No. PCT/US2014/021110; Filing Date: Mar. 6, 2014; 8 pgs.
XP002725495; NCBI Reference Sequence: XP_003981606.1; Nov. 6, 2012; Predicted: taste receptor type 2 member 1-like [Felis catus]; 1 pg.
XP002725979; NCBI Reference Sequence: XP_003982855.1; Nov. 6, 2012;Predicted: taste receptor type 2 member 7-like [Felis catus]; 1 pg.
XP002725980; NCBI Reference Sequence: XP_003983201.1; Nov. 6, 2012; Predicted: taset receptor type 2 member 3-like [Felis catus]; 1 pg.
XP002725981; NCBI Reference Sequence: XP_003983202.1; Nov. 6, 2012; Predicted: taste receptor type 2 member 4-like [Felis catus]; 1 pg.
XP002725982; NCBI Reference Sequence: XP_003988464.1; Nov. 6, 2012; Predicted: taste receptor type 2 member 7-like [Felis catus]; 1 pg.
XP002725983; NCBI Reference Sequence: XP_003988514.1; Nov. 6, 2012; Predicted: taste receptor type 2 member 9-like [Felis catus]; 1 pg.
XP002725984; NCBI Reference Sequence: XP_003988465.1; Nov. 6, 2012; Predicted: taste receptor type 2 member 10-like [Felis catus]; 1 pg.
XP002725985; NCBI Reference Sequence: XP_003988515.1; Nov. 6, 2012; Predicted: taste receptor type 2 member 7-like [Felis catus]; 1 pg.
XP002725986; NCBI Reference Sequence: XP_003983168.1; Nov. 6, 2012; Predicted: taste receptor type 2 member 38-like [Felis catus]; 1 pg.
XP002725987; NCBI Reference Sequence: XP_003988470.1; Nov. 6, 2012; Predicted: taste receptor type 2 member 42-like [Felis catus]; 1 pg.
XP002725988; NCBI Reference Sequence: XP_003988466.1; Nov. 6, 2012; Predicted: taste receptor type 2 member 46-like [Felis catus]; 1 pg.
XP002725989; NCBI Reference Sequence: XP_003988469.1; Nov. 6, 2012; Predicted: taste receptor type 2 member 42-like [Felis catus]; 1 pg.
XP002725990: retrived from EBI Database accession No. ENSFCAP00000024300; Jan. 2013; 1 pg.
Xu H et al. "Molecular Cloning and Evolutionary Analysis of Hog Badger Bitter Taste Receptor T2R2 Gene"; Hereditas (Beijing); 2009, 31(11): 1113-1120. DOI: 10.3724/SP.J.1005.2009.01113.

* cited by examiner

FIG. 1

|  | TM 3 110 120 130 140 TM 4 150 |  |
|---|---|---|
| human Tas2R16 | MFFNLLTFVWLNSLLTVFYCI KVSSFTHHI FLWLRWRI LRLFPWMLLGS | 134 |
| human Tas2R4  | FMFLDSSSVWFVTLLNI LYCVKI TNFQHSVFLLLKRNI SPKI PRLLLACV | 137 |
| feline Tas2R4 | WMFLESTSLWLVTLLNALYCVKI TDFQHSVFLLLKRKLSPKI PRLLLACV | 138 |
| human Tas2R9  | WTFANNSSLWFTSCLSI FYLLKI ANI SHPFFFWLKLKI NKVMLAI LLGSF | 138 |
| feline Tas2R9 | WTLSNHSSVWFTACLSI FYLLKI ANI SHPVFLWLKLNVTRVVLGLFLASF | 138 |
| human Tas2R10 | WVI GNQSSMWFATSLSI FYFLKI ANFSNYI FLWLKSRTNMV- LPFMI VFL | 136 |
| feline Tas2R10| WI I NQSNI WFATSLSTFYFLKI ANFSHHMFLWLKGRI NWW- LPLLMGSL | 137 |
| feline Tas2R12| WTGSNYFCI TCTTCLSVFYFFKI ANFSNPLFLWI KWRI HKVLLTI VLAAV | 138 |
| human Tas2R38 | WMI ANQANLWLAACLSLLYCSKLI RFSHTFLI CLASWWSRKI SQMLLGI I | 148 |
| feline Tas2R38| WMI TNQVGLWLTTCLSLLYCSKI ARFSHTLLHCVASWWSRKVPQMLLGAM | 148 |

|  | TM 4 160 170 180 190 200 |  |
|---|---|---|
| human Tas2R16 | MITCVTLPSAI GNYI QI QLLTMEHLPRNSTVTDKLENFHQYQFQAHT- - | 182 |
| human Tas2R4  | LI SAFTTCLYI TLSQASP- - - FPELVTTRNNTSFNI SEGI LSLVVSLV- - | 182 |
| feline Tas2R4 | LI SAFSTLLYVVLTQTSP- - - FPELLTGSNGTVCDI NKSI LSLVTSLV- - | 183 |
| human Tas2R9  | LI SLI I SVPKNDDMWYHL- - - FKVSHEENI TWKFKVSKI PG- - TFKQLTL | 183 |
| feline Tas2R9 | LTSI I I SVFLKEGSWGHV- - - - EVNHEENI TWEFRVSKAPS- - AFKLI I L | 182 |
| human Tas2R10 | LI SSLLNFAYI AKI LND- - - - YKT- KNDTV- WDLNMYKSEY- - FI KQI LL | 178 |
| feline Tas2R10| FI SWLFTFPQI VKI LSD- - - - SKVGNGNAT- WQLNMPKSEF- - LTKQI LV | 180 |
| feline Tas2R12| F- SFCLSLPFKDTVFTSL- - - I KNKVNAERNWTVSFTTRTYELFLSHMLL | 184 |
| human Tas2R38 | LCSCI CTVLCVWCFFSRPHFTVTTVLFMNNNTRLNWQI KDLNLFYSFLFC | 198 |
| feline Tas2R38| LFSCI CTAI CLGDFFSRSGFTFTTMLFVNN- TEFNLQI AKLSFYHSFI FC | 197 |

|  | TM 5 210 220 230 240 250 |  |
|---|---|---|
| human Tas2R16 | - VALVI PFI LFLASTI FLMASL- - - TKQI QHHSTGHCNPSMKARFTALRS | 228 |
| human Tas2R4  | - LSSSLQFI I NVTSASLLI HSLRRHI QKMQKNATGFWNPQTEAHVGAMKL | 231 |
| feline Tas2R4 | - LSSFLQFI MNVTSASLLI HSLRRHI QKMQKNATDFWNPQTEAHMGAMKL | 232 |
| human Tas2R9  | NLGVMVPFI LCLI SFFLLLFSLVRHTKQI RLHATGFRDPSTEAHMRAI KA | 233 |
| feline Tas2R9 | NLGALVPFALCLI SFVLLLFSLFRHAKQMQLYATGSRDCSTEAHMRAI KA | 232 |
| human Tas2R10 | NLGVI FFFTLSLI TCI FLI I SLWRHNRQMQSNVTGLRDSNTEAHVKAMKV | 228 |
| feline Tas2R10| NI GVLLLFTLFLI TCFLLI I SLWRHSRRMQLNVTGFQDPSTEAHMKAMKV | 230 |
| feline Tas2R12| NI MFI I PFAVSLASFVLLI CSLWSHTRQMKGRGG- - - DPTTKVHVRAMKA | 231 |
| human Tas2R38 | YLWSVPPFLLFLVSSGMLTVSLGRHMRTMKVYTRNSRDPSLEAHI KALKS | 248 |
| feline Tas2R38| TLASI PSLLFFLI SSGVLI VSLGRHMRTMRAKTKDSHDPSLEAHI KALRS | 247 |

|  | TM 6 260 270 280 TM 7 290 300 |  |
|---|---|---|
| human Tas2R16 | LAVLFVFTSYFLTI LI TI I GTLF- DKRCWMWVMEAFVYAFI LMHSTSLM | 277 |
| human Tas2R4  | MVYFLI LYI PYSVATLVQYLPFYAGMDMGTKSI CLI FATLYSPGHSVLI I | 281 |
| feline Tas2R4 | MI YFLI LYI PYSLATLLQYLPS- VRMDLGATSI CMI I STFYPPGHSVLI I | 281 |
| human Tas2R9  | VI I FLLLLI VYYPVFLVMTSSALI PQGKLVLMI GDI VTVI FPSSHSFI LI | 283 |
| feline Tas2R9 | VTI FLLFFI MYYAVFLVVTSSFLI PQGRVVLMFGGI VTVI FPSSHSFI LI | 282 |
| human Tas2R10 | LI SFI I LFI LYFI GMAI EI SCFTVRENKLLLMFGMTTTAI YPWGHSFI LI | 278 |
| feline Tas2R10| LI SFI I LFI LHFI GLAI EI ACFTMPEKKLLFI FGMTTTVLYPWGHSFI LI | 280 |
| feline Tas2R12| MI SFLLFFFMYYLSTI MMNLAYVI LDSLVAKI FANTLVFLYPSGHTFLLI | 281 |
| human Tas2R38 | LVSFFCFFVI SSCVAFI SVPLLI LWRDKI GVMVCVGI MAACPSGHAAI LI | 298 |
| feline Tas2R38| LVSFLCLYVVSFCAALVSVPLLMLWHNKI GVMI CVGI LAACPSI HAAI LI | 297 |

FIG. 2

```
                     10          20          30          40          50
feline Tas2R38   MLALTPVITVSYEVKSAFLFLSILEFTVGVLANAFIFLVNFWDVVRKQIL  50
human  Tas2R38   MLTLTRIRTVSYEVRSTFLFISVLEFAVGFLTNAFVFLVNFWDVVKRQAL  50

60          70          80          90         100
feline Tas2R38   SNCDLILLSLSLTRLFLHGLLFLDALQLTYFQRMKDPLSLSYQTIIMLWM 100
human  Tas2R38   SNSDCVLLCLSISRLFLHGLLFLSAIQLTHFQKLSEPLNHSYQAIIMLWM 100

110         120         130         140         150
feline Tas2R38   ITNQVGLWLTTCLSLLYCSKIARFSHTLLHCVASWVSRKVPQMLLGAMLF 150
human  Tas2R38   IANQANLWLAACLSLLYCSKLIRFSHTFLICLASWVSRKISQMLLGIILC 150

160         170         180         190         200
feline Tas2R38   SCICTAICLGDFFSRSGFTFTTMLFVNN-TEFNLQIAKLSFYHSFIFCTL 199
human  Tas2R38   SCICTVLCVWCFFSRPHFTVTTVLFMNNNTRLNWQIKDLNLFYSFLFCYL 200

210         220         230         240         250
feline Tas2R38   ASIPSLLFFLISSGVLIVSLGRHMRTMRAKTKDSHDPSLEAHIKALRSLV 249
human  Tas2R38   WSVPPFLLFLVSSGMLTVSLGRHMRTMKVYTRNSRDPSLEAHIKALKSLV 250

260         270         280         290         300
feline Tas2R38   SFLCLYVVSFCSALVSVPLLMLWHNKIGVMICVGILAACPSIHAALISG  299
human  Tas2R38   SFHCFFVISSCVAFISVPLLILWRDKIGVMCVGIMAACPSGHAALISG  300

310         320         330
feline Tas2R38   NAKLRRAVETILLWQNSLKIGADHKADARTPGLC.              335
human  Tas2R38   NAKLRRAVMTILLWAQSSLKVRADHKADSRTL---C             333
```

FELINE BITTER TASTE RECEPTORS AND METHODS

CROSS REFERENCE TO RELATED APPLICATIONS

This application is a National Stage application of International Application No. PCT/US14/021110, filed Mar. 6, 2014, which claims the benefit of U.S. Provisional Application No. 61/788,528, filed Mar. 15, 2013, and U.S. Provisional Application No. 61/945,500, filed Feb. 27, 2014, the disclosure of each of which is incorporated herein by reference.

BACKGROUND

The taste system provides sensory information about the chemical composition of the external world. Mammals are believed to have at least five basic taste modalities: sweet, bitter, sour, salty, and umami. Each taste modality is thought to be mediated by a distinct protein receptor or receptors that are expressed in taste receptor cells found on the surface of the tongue. The taste receptors that recognize bitter, sweet, and umami taste stimuli belong to the G-protein-coupled receptor (GPCR) superfamily. Subtle differences in a receptor may alter which ligands bind and what signal is generated once the receptor is stimulated.

Various members of the GPCR superfamily mediate many other physiological functions, such as endocrine function, exocrine function, heart rate, lipolysis, and carbohydrate metabolism. The biochemical analysis and molecular cloning of a number of such receptors has revealed many basic principles regarding the domain structure and function of these receptors.

The ability of mammals to taste the five primary modalities is thought to be largely similar, however due to diet and environmental differences, taste receptors have evolved to be somewhat different across mammalian species. For example, the gene encoding the Taste Receptor, Type 1 protein, member 2, TAS1R2, a component of the receptor for sweet compounds, has mutated to a nonfunctional pseudogene in felines and several other obligate carnivores, while aquatic mammals such as dolphin have lost most functional taste receptors.

The bitter taste modality is usually described as disagreeable. Many natural and synthetic toxins have been characterized as bitter tastants. As a result, it is hypothesized that bitter taste perception has evolved as a means to discourage the consumption of toxic compounds often found in plants. Estimates for the number of bitter tasting compounds are in the tens of thousands. Compounds that block bitter taste perception have also been identified, for example p-(dipropylsulfamoyl)benzoic acid (probenecid) which acts on a subset of Taste Receptor, Type 2 ("TAS2R") proteins, a family of monomeric G protein-coupled receptors, embedded in the surface of taste cells.

Research has shown that molecular diversity in the TAS2Rs of humans and other primates leads to functional differences in individuals' bitter taste perception (Imai et al., 2012, Biol Lett. 8(4): 652-656; Li et al., 2011, Human Biology 83: 363-377). The exposure to the specific flora of a geographic region is thought to be a major driving force of selection on TAS2Rs.

Humans encode about 26 functional TAS2Rs, allowing for the detection of an enormous number of compounds. About 550 compounds have been identified thus far as bitter tastants for humans. A subset of human TAS2Rs (hTAS2Rs) are currently believed to be promiscuous, i.e., activated by multiple ligands belonging to several chemical classes, while other hTAS2Rs bind ligands of only particular chemical classes. Additionally, several hTAS2Rs are orphan receptors, with no compounds identified as yet that stimulate them.

Signal transduction of bitter stimuli is accomplished via the α-subunit of gustducin. This G protein subunit activates a taste phosphodiesterase and decreases cyclic nucleotide levels. Further steps in the transduction pathway are still unknown. The βγ-subunit of gustducin also mediates taste by activating IP3 (inositol triphosphate) and DAG (diglyceride). These second messengers may open gated ion channels or may cause release of internal calcium. Though all TAS2Rs are located in gustducin-containing cells, knockout of gustducin does not completely abolish sensitivity to bitter compounds, suggesting a redundant mechanism for bitter tasting.

hTAS2R38 is the most extensively studied bitter taste receptor. Early in the twentieth century a dichotomy in the perception of phenylthiocarbamide (PTC), a bitter tasting compound, was observed in a sample of people. Most people could taste PTC, but about 25% could not. Researchers noticed the taster/non-taster phenotype had a degree of heritability. Later it was determined that the difference in phenotype between the two groups could be ascribed to a difference in genotype, more specifically single nucleotide polymorphisms (SNPs) at three positions within the hTAS2R38 DNA.

Other species display a TAS2R repertoire much different from that of humans. For example, the mouse has 34 full-length TAS2Rs encoded in its genome, while the chicken has only 3 (Go et al., Genetics. 2005 May; 170(1): 313-26). Although some compounds can be detected by multiple TAS2Rs, it is almost certain that differences in TAS2R repertoire across species result in differences in bitter taste perception.

Bitter taste perception is mediated by G protein-coupled receptors (GPCRs) of the taste receptor 2 family (TAS2R). The TAS2R genes encode a family of related seven transmembrane G-protein coupled receptors involved in taste transduction, which interact with a G-protein to mediate taste signal transduction. In particular, TAS2Rs interact in a ligand-specific manner with the G protein Gustducin.

To date, much work has been done to characterize human TAS2Rs (hTAS2Rs). The human genome encodes about 26 functional TAS2Rs that are glycoproteins. All hTAS2Rs share a conserved site for Asn-linked glycosylation within the center of the second extracellular loop. The hTAS2Rs also have the ability to form homo- and hetero-oligomers with other GPCR when expressed in vitro, however at present no evidence exists that TAS2R receptor oligomerization has functional implications.

Bitter taste receptor cells represent a distinct subpopulation of chemosensory cells characterized by the expression of TAS2R genes and completely segregated from those receptor cells devoted to the detection of other taste stimuli. Each bitter taste receptor cell expresses multiple bitter taste receptors, although the extent of co-expression is still a matter of debate.

In addition to their expression in the gustatory system, TAS2Rs are found in non-gustatory tissues. Among these extra-oral sites are the respiratory epithelia, gastrointestinal tissues, reproductive organs, and brain. Bitter taste receptors are implicated in differentiation or maturation of sperm in mice. The non-gustatory expression of TAS2Rs is known to be used to regulate digestion and respiration.

Activation of TAS2R receptors in an enteroendocrine cell line (STC-1 cells) results in release of the peptide hormone cholecystokinin (CCK), which can reduce gut motility. Consequently, intake of a potential toxin that activates the TAS2R pathway may decrease the rate at which food passes through the stomach and lower the drive for continued eating. The release of CCK also excites sensory nerve processes of the vagus nerve to carry the signal to the brain, suggesting that regulation of food intake involves both peripheral and central controls. Activation of the TAS2R signaling network may also or alternatively indirectly increase elimination of absorbed toxins from gut epithelium before the toxins can enter circulation since some data suggest that the CCK-secreting enteroendocrine cells are involved in a paracrine signaling system that reduces transfer of toxic substances from the gut into the circulation. Lower in the gut, activation of TAS2R receptors has a different effect. When some bitter-tasting ligands are applied to the colonic epithelium, they induce the secretion of anions, which leads to fluid secretion by the epithelium which may flush out any noxious irritant from the colon.

Solitary chemosensory cells (SCCs) are also present throughout the upper respiratory system and express the entire suite of taste-related signaling molecules, including TAS2R receptors, PLCβ2, gustducin, and the transduction channel TrpM5. The SCCs synapse onto polymodal pain fibers of the trigeminal nerve. Inhalation of a toxin that activates TAS2R receptors of the SCCs will be irritating and evoke trigeminally-mediated reflex changes in respiration. Additionally, the activated trigeminal nerve fibers release peptide modulators that result in local neurogenic inflammation of the respiratory epithelium, activating the immune system in response to the presence of the toxins.

The human bitter taste receptors, hTAS2R2, hTAS2R41, hTAS2R42, hTAS2R45, hTAS2R48, and hTAS2R60 are still considered orphan GPCRs since ligands have not yet been identified for these receptors.

Until recently, hTAS2R2 was annotated as a pseudogene due to a two base deletion at codon 160 found in sequences collected from 10 human populations (Karitiana, Surui, Waorani Indians from South America, Russians from Eastern Europe, Druze from the Middle East, Atayal, Chinese, Japanese from Eastern Asia, and Khmers and Melanesians from Southeast Asia) and from GenBank resources. hTAS2R2 has been found to be polymorphic with respect to that deletion, with the intact gene found in the Adygei (Eastern European), Mbuti (African Pygmies), and Biaka (African Pygmies) (Go Y et al., Genetics May 1, 2005, 170 (1): 313-326).

The feline genome has been sequenced with minimal coverage (Mullikin et al. BMC Genomics 2010 11: 406; Pontius et al., Genome Research 2007 17: 1675-1689). As a result, major gaps exist in the feline genome sequence and only slightly over 2000 feline genes have been annotated to date. As a comparison, the human genome has about 25,000 genes annotated. The sequences prior to a gap in the genomic assembly are of poor quality, so in addition to information that is missing, a large portion of the data present is of poor quality. Consequently, there is much to be discovered within feline genomics and in determining the molecular basis of feline taste perception. No feline TAS2R (fTAS2R) has been annotated in the feline genome or investigated biochemically to date. Additionally, with many feline breeds originating in a particular geographic region and therefore being exposed to unique flora, breed specific TAS2R differences may exist.

The identification and characterization of the feline TAS2R bitter receptors is useful to gain understanding of the taste profile of felines and its modulation.

SUMMARY

Disclosed herein are novel feline TAS2R receptors.

In an embodiment, an isolated feline TAS2R (fTAS2R) receptor polypeptide comprises an extracellular domain of a feline TAS2R receptor; a transmembrane region of a feline TAS2R receptor, or an intracellular domain of a feline TAS2R receptor, wherein the fTAS2R receptor comprises a sequence selected from SEQ ID NO:18, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:20, SEQ ID NO:22, SEQ ID NO:24, and SEQ ID NO:26, wherein the isolated fTAS2R receptor polypeptide does not consist of the amino acid sequence of SEQ ID NOs: 2, 4, 6, or 10.

In an embodiment, the isolated fTAS2R receptor polypeptide comprises an extracellular domain of a feline TAS2R receptor polypeptide comprising amino acids 1, 68-84; 146-179; or 249-257 of SEQ ID NO:2; amino acids 1-10, 73-88; 151-186; or 256-264 of SEQ ID NO:4; amino acids 1-8; 72-88; 150-186; or 256-265 of SEQ ID NO:6; amino acids 1-2; 69-87; 151-183; or 253-261 of SEQ ID NO:8; amino acids 1-8; 72-88; 150-187; or 257-265 of SEQ ID NO:10; amino acids 1-6; 72-88; 150-183; or 253-262 of SEQ ID NO:12; amino acids 1; 69-87; 150-181; or 251-260 of SEQ ID NO:14; amino acids 1-8; 69-88; 150-185; or 252-261 of SEQ ID NO:16; amino acids 1-17: 83-98; 161-198; or 268-277 of SEQ ID NO:18; amino acids 1; 69-88; 150-185; or 255-264 of SEQ ID NO:20; amino acids 1-2; 69-87; 149-181; or 251-260 of SEQ ID NO:22; amino acids 1-2; 69-87; 149-181; or 251-259 of SEQ ID NO:24; or amino acids 1-8; 72-88; 150-185; or 254-263 of SEQ ID NO:26; a transmembrane region of the feline TAS2R receptor polypeptide comprising amino acids 2-22, 47-67, 85-105, 125-145, 180-200, 228-248, or 258-278 of SEQ ID NO:2; amino acids 11-31, 52-72, 89-109, 130-150, 187-207, 235-255, or 265-285 of SEQ ID NO:4; amino acids 9-29, 51-71, 89-109, 129-149, 187-207, 235-255, or 266-286 of SEQ ID NO:6; amino acids 3-23, 48-68, 88-108, 130-150, 184-204, 232-252, or 262-282 of SEQ ID NO:8; amino acids 9-29, 51-71, 89-109, 129-149, 188-208, 236-256, or 266-286 of SEQ ID NO:10; amino acids 7-27, 51-71, 89-109, 129-149, 184-204, 232-252, or 263-283 of SEQ ID NO:12; amino acids 2-22, 2.48-68, 88-108, 129-149, 182-202, 230-250, or 261-281 of SEQ ID NO:14; amino acids 9-29, 48-68, 89-109, 129-149, 186-206, 231-251, or 262-282 of SEQ ID NO:16; amino acids 18-38, 62-82, 99-119, 140-160, 199-219, 247-267, or 278-298 of SEQ ID NO:18; amino acids 2-22, 48-68, 89-109, 129-149, 186-206, 234-254, or 265-285 of SEQ ID NO:20; amino acids 3-23, 48-68, 88-108, 128-148, 182-202, 230-250, or 261-281 of SEQ ID NO:22; amino acids 3-23, 48-68, 88-108, 128-148, 182-202, 230-250, or 260-280 of SEQ ID NO:24; or amino acids 9-29, 51-71, 89-109, 129-149, 186-206, 233-253, or 264-284 of SEQ ID NO:26, or an intracellular domain comprising: amino acids 23-46; 106-124; 201-227; or 279-298 of SEQ ID NO:2; amino acids 32-51; 110-129; 208-234; or 286-304 of SEQ ID NO:4; amino acids 30-50; 110-128; 208-234; or 287-316 of SEQ ID NO:6; amino acids 24-47; 109-129; 205-231; or 283-306 of SEQ ID NO:8; amino acids 30-50; 110-128; 209-235; or 287-311 of SEQ ID NO:10; amino acids 28-50; 110-128; 205-231; or 284-337 of SEQ ID NO:12; amino acids 23-48; 109-128; 203-229; or 282-300 of SEQ ID NO:14; amino acids 30-47; 110-128; 207-230; or 283-309 of SEQ ID NO:16; amino acids 39-61; 120-139; 220-246; or 299-334 of SEQ ID NO:18; amino acids 23-47; 110-128; 207-233; or 286-322 of SEQ ID NO:20; amino acids 24-47; 109-127; 203-229; or 282-299 of SEQ ID NO:22; amino acids 24-47; 109-127; 203-229; or 281-308 of SEQ ID NO:24; or amino acids 30-50; 110-128; 207-232; or 285-312 of SEQ ID NO:26.

A polynucleotide encoding the novel feline TAS2R receptor, fragment thereof, is also disclosed.

In an embodiment, the polynucleotide comprises a nucleotide sequence selected from: the nucleotide sequence of SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence encoding the amino acid sequence of SEQ ID NO: 8, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence that hybridizes to the complement of the polynucleotide having SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25 under high stringency conditions; and the complement of the foregoing nucleotide sequences.

Expression vectors and host cells comprising the polynucleotides, as well as oligonucleotides are also disclosed.

Antibodies and kits for detecting the fTAS2R receptor are also disclosed.

Also disclosed herein are methods for identifying compounds that interact with or modulate activity of a fTAS2R receptor polypeptide.

In an embodiment, the method comprises contacting a TAS2R receptor polypeptide herein with a test compound, and detecting interaction between the receptor polypeptide and the test compound.

In an embodiment, the method comprises contacting a TAS2R receptor polypeptide disclosed herein with a receptor ligand in the presence or absence of a test compound, and determining whether the test compound modulates binding of the ligand to the receptor or activation of the receptor by the ligand.

Additional methods are also disclosed.

In an embodiment, a method of preparing edible compositions comprises contacting an edible composition or a component thereof with a feline TAS2R receptor polypeptide for a time sufficient to reduce the amount of a bitter compound from the edible composition or component thereof.

In an embodiment, a method of preparing edible compositions for controlling palatability to an animal comprises adding a compound to an edible composition to decrease the palatability of the edible composition to an animal, wherein the compound is an agonist of or a positive modulator of a feline TAS2R receptor polypeptide.

In an embodiment, a method of formulating an edible composition with enhanced palatability comprises determining the presence of a compound which is an agonist, antagonist, or modulator of a feline TAS2R receptor polypeptide in an edible composition; and enhancing palatability of the edible composition by: if the compound is an agonist or a positive modulator, increasing the amount of an antagonist for the receptor in the edible composition or reducing the amount of the compound in the edible composition, or if the compound is an antagonist or a negative modulator, increasing the amount of the compound in the edible composition.

In an embodiment, a method of administering a bitter compound to an animal in need thereof comprises administering an edible composition to an animal, wherein the edible composition comprises a bitter compound and a compound that is an antagonist, or modulator of a feline TAS2R receptor polypeptide that alters acceptance of the edible composition by the animal compared to acceptance of the edible composition without the compound. The bitter compound can comprise a pharmaceutical, an oral care material, a nutritional supplement, or a repellant.

Also disclosed are flavor compositions for coating or incorporating into an edible composition to be administered to an animal and methods of manufacture thereof.

In an embodiment, the flavor composition comprises an agonist or an antagonist of a feline TAS2R receptor polypeptide, wherein the agonist is denatonium, aloin, or PTC and the antagonist is probenecid; optionally, a palatability enhancer; optionally, a compound to help adhere the flavor composition to the edible composition; and optionally, a compound for providing color or aroma; wherein the flavor composition is a liquid, solid, powder, paste, gel, spreadable formulation, granule, or sprayable formulation.

In an embodiment, the method of making the flavor composition comprises mixing an agonist or an antagonist of a feline TAS2R receptor polypeptide, wherein the agonist is denatonium, aloin, or PTC and the antagonist is probenecid; optionally, a palatability enhancer; optionally, a compound to help adhere the flavor composition to the edible composition; and optionally, a compound for providing color or aroma with an ingredient selected from the group consisting of meat products, meat by-products, fish products, fish by-products, dairy products, dairy by-products, sources of microbial proteins, vegetable proteins, carbohydrates and amino acids to obtain a flavor composition, wherein the flavor composition is a liquid, solid, powder, paste, gel, spreadable formulation, granule, or sprayable formulation.

These and other advantages, as well as additional inventive features, will be apparent from the following Drawings, Detailed Description, Examples, and Claims.

BRIEF DESCRIPTION OF THE DRAWINGS

FIG. 1 is a sequence alignment displaying the 3rd through the 7th transmembrane (TM) region (transmembrane regions in grey) of several human and feline bitter receptors: human TAS2R16 (SEQ ID NO:30), TAS2R4 (SEQ ID NO:27), TAS2R9 (SEQ ID NO:28), TAS2R10 (SEQ ID NO:29) AND TAS2R38 (SEQ ID NO:31); and feline bitter receptors, TAS2R4 (SEQ ID NO:8), 9 (SEQ ID NO:12), 10 (SEQ ID NO:14), 12 (SEQ ID NO:16), and 38 (SEQ ID NO:18).

FIG. 2 shows a sequence alignment for human TAS2R38 polypeptide (SEQ ID NO:31) and feline TAS2R38 polypeptide (SEQ ID NO:18) determined from sequencing of genomic DNA of five individual cats.

DETAILED DESCRIPTION

A family of novel feline bitter taste receptors, feline TAS2R (fTAS2R), are disclosed herein. These G-protein coupled receptors (GPCRs) are components of the feline taste transduction pathway, specifically, part of the bitter taste transduction pathway, and are involved in feline taste detection of bitter substances such as 6-n-propylthiouracil, sucrose octaacetate, raffinose undecaacetate, cycloheximide, denatonium, copper glycinate, and quinine. Polynucleotides encoding the novel feline bitter taste receptors are also disclosed, as are expression vectors and host cells for expression of the novel feline bitter taste receptors. Methods of expressing and isolating the nucleic acids and encoded polypeptides are also disclosed.

The nucleic acids provide probes for identification of cells in which the nucleic acids are expressed, e.g., taste cells. For example, probes for expression of TAS2R polypeptides can be used to identity taste cells present in foliate, circumvallate, and fungiform papillae. In particular, the TAS2R probes are useful to identify bitter sensing cells and can serve as tools for the generation of anatomical maps that elucidate the relationship between the bitter sensing cells and their projections into the central nervous system. Methods of identifying compounds that bind to the novel feline bitter taste receptors and modulate their activity are disclosed. In the methods, members of the fTAS2R family act as direct or indirect reporter molecules to identify modulators of taste receptor expressing cellular activity. Such compounds are useful for modulation of feline bitter taste receptor activity. Modulating the activity of feline bitter receptors receptor can be achieved by agonists, antagonists, inhibitors, and/or enhancers. These modulatory compounds can be used in the food and pharmaceutical industries to customize taste of foods or drugs, for example, to decrease the bitter taste of foods or drugs. Thus, the methods disclosed herein are useful for designing or formulating food, food palatants, treats, and medications in which aversive compounds are avoided or blocked, particularly for felines.

An "agonist", or "receptor agonist" as used herein, refers to a molecule that has an affinity for and stimulates functional activity of a cell receptor. The level of stimulation of the functional activity at the receptor can be, e.g., at least 5%, at least 10%, at least 30%, at least 50%, at least 80%, at least 100%, at least 200%, at least 300%, at least 500%, at least 1,000%, at least 10,000% over baseline.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that functions in a manner similar to a naturally occurring amino acid. Amino acids may be referred to herein by either their commonly known three-letter symbols or by the one-letter symbols recommended by the IUPAC-IUB Biochemical Nomenclature Commission.

A receptor "antagonist" as used herein refers to a type of receptor ligand that binds to the receptor at the same site as an agonist, but does not activate the functional response initiated by the active form of the receptor. Once bound, an antagonist will block agonist binding thereby inhibiting the functional response produced by agonist binding. Since agonists and antagonists "compete" for the same binding site on the receptor, the level of activity of the receptor will be determined by the relative affinity of each molecule for the site and their relative concentrations. The inhibition of the functional response elicited by an agonist by an antagonist applied prior, concomitantly or after the application of the agonist can be e.g., at least by 10%, at least 15%; at least 20%; at least 30%; at least 40%; at least 50%; at least 60%; at least 70%; at least 80%; at least 90%; at least 95%; at least 98%; at least 99%; at least 99.5%; or at least 100%. In certain embodiments, the antagonist and agonist are applied at the same molar concentration.

"Antibody" refers to a polypeptide that specifically binds and recognizes an antigen. The term "antibody" or "immunoglobulin," as used interchangeably herein, includes whole antibodies and any antigen binding fragment (antigen-binding portion) or single chain cognates thereof. Antibodies may be polyclonal or monoclonal. The term "monoclonal antibody" means an antibody obtained from a population of substantially homogeneous antibodies, i.e., the individual antibodies comprising the population are identical except for possible naturally occurring mutations that may be present in minor amounts. In some embodiments, the term "monoclonal antibody" refers to an antibody derived from a single cell clone.

An "antibody" comprises at least one heavy (H) chain and one light (L) chain. In naturally occurring IgGs, for example, these heavy and light chains are inter-connected by disulfide bonds and there are two paired heavy and light chains; these two are also inter-connected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR) or Joining (J) regions (JH or JL in heavy and light chains respectively). Each VH and VL is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

The term "antigen-binding portion" or "antigen-binding fragment" of an antibody, as used herein, refers to one or more fragments of an antibody that retain the ability to specifically bind to an antigen. It has been shown that certain fragments of a full-length antibody can perform the antigen-binding function of an antibody. Examples of binding fragments denoted as an antigen-binding portion or fragment of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment (Ward et al. (1989) Nature 341, 544-546), which consists of a VH domain; (vii) a dAb which consists of a VH or a VL domain; and (viii) an isolated complementarity determining region (CDR) or (ix) a combination of two or more isolated CDRs which may optionally be joined by a synthetic linker.

Furthermore, although the two domains of the Fv fragment, VL and VH, are coded for by separate genes, they can be joined, using recombinant methods, by a synthetic linker that enables them to be made as a single protein chain in which the VL and VH regions are paired to form monovalent molecules (such a single chain cognate of an immunoglobulin fragment is known as a single chain Fv (scFv). Such single chain antibodies are also encompassed within the term "antibody fragment." Antibody fragments are obtained using conventional techniques known to those with skill in the art, and the fragments are screened for utility in the same general manner as are intact antibodies. Antigen-binding fragments can be produced by recombinant DNA techniques, or by enzymatic or chemical cleavage of intact immunoglobulins.

An "anti-TAS2R" or a "TAS2R" antibody is an antibody or antibody fragment that specifically binds a polypeptide encoded by a TAS2R gene, cDNA, or a subsequence thereof.

The term "chimeric polypeptide" refers to a molecule, which does not occur in nature, in which all or a portion of an fTAS2R polypeptide sequence is part of the linear chimeric polypeptide sequence. The portion of an fTAS2R polypeptide sequence can be the amino acid sequence of one or more domains of the complete fTAS2R polypeptide. For example, the portion can be an extracellular domain of a fTAS2R polypeptide. The chimeric polypeptide can be made by any method known in the art. For example, the chimeric polypeptide can be made by a recombinant expression system or can be synthesized.

"Codon optimization" describes a method applied to nucleotide sequences encoding a polypeptide to modify the nucleotide sequence for enhanced expression of the polypeptide in the cells of a non-feline organism of interest, e.g. *Drosophila melanogaster* or *Saccharomyces cerevisae*, by replacing at least one, more than one, or all, codons of the native feline sequence with codons that are more frequently or most frequently used in the genes of the expression organism without changing the amino acids of the expressed polypeptide. In preferred embodiments, all codons of the nucleic acid encoding a polypeptide sequence, or fragment thereof, are codon-optimized. Many organisms display a bias for use of particular codons to code for insertion of a particular amino acid in a growing peptide chain. Differences in codon usage, sometimes referred to as codon bias or preference, between organisms is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Methods of codon-optimization are known in the art, for example the free, internet-accessible program JCat (Grote A, et al. JCat: a novel tool to adapt codon usage of a target gene to its potential expression host. Nucleic Acids Res. 2005 Jul. 1; 33(Web Server issue):W526-31.) or methodology disclosed in US20130017217 or WO2004058166, incorporated herein by reference.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. One of skill will further recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

"C terminal domain" refers to the region that spans the end of the last transmembrane domain and the C-terminus of the protein, and which is normally located within the cytoplasm.

"Cytoplasmic domains" or "intracellular domains" refers to the domains of TAS2R proteins that face the inside of the cell, e. g., the "C terminal domain" and the intracellular loops of the transmembrane domain, e. g., the intracellular loops between transmembrane regions 1 and 2, the intracellular loops between transmembrane regions 3 and 4, and the intracellular loops between transmembrane regions 5 and 6.

The term "extracellular domains" refers to the domains of TAS2R polypeptides that protrude from the cellular membrane and are exposed to the extracellular face of the cell. Such domains include the "N terminal domain" that is exposed to the extracellular face of the cell, as well as the extracellular loops of the transmembrane domain that are exposed to the extracellular face of the cell, i.e., the loops between transmembrane regions 2 and 3, and between transmembrane regions 4 and 5. The "N terminal domain" region starts at the N-terminus and extends to a region close to the start of the transmembrane domain. These extracellular domains are useful for in vitro ligand binding assays, both soluble and solid phase.

The term "feline" refers herein to any member of the Felidae family, including domestic cats and nondomestic cats. In some embodiments felines can include both wild or captive cats, including wild and exotic cats, such as cougars, cheetah, lynxes, ocelots, lions, tigers, jaguars, panthers, and leopards.

As used herein, "heterologous" means that the sequence or cell originates from a foreign species, or, if from the same species, is substantially modified from its native form in composition and/or genomic locus by deliberate human intervention, or that the sequence is designed de novo without reference to any natural sequence. For example, a promoter operably linked to a heterologous polynucleotide is from a species different from the species from which the polynucleotide was derived, or, if from the same or an analogous species, one or both are substantially modified from their original form and/or genomic locus, or the promoter is not the native promoter for the operably linked polynucleotide. "Heterologous sequences" are those that are not operatively linked or are not contiguous to each other in nature. A "heterologous polypeptide" as used herein refers to a polypeptide which is not naturally included in the polypeptide sequence of the fTAS2R receptor polypeptide. A "heterologous cell" for expression of a polypeptide or nucleic acid refers to a cell that does not normally express that polypeptide or nucleic acid.

"Homology" refers to the percent identity between polynucleotide or polypeptide molecules. Two DNA, or two polypeptide sequences are "substantially homologous" to each other when the sequences exhibit at least about 50%, specifically at least about 75%, more specifically at least about 80%-85%, at least about 90%, and most specifically at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively.

The term "immunoassay" is an assay that uses an antibody to specifically bind an antigen. The immunoassay is characterized by the use of specific binding properties of a particular antibody to isolate, target, and/or quantify the antigen.

As used herein "inhibition" or "blocking" of activity of a TAS2R receptor, or a ligand-binding fragment thereof, means that the functional response of a TAS2R receptor, or fragment, to an agonist is reduced or prevented when in the presence of the inhibitor, for example the TAS2R receptor interacts with an intracellular signaling pathway to produce a smaller functional response, e.g. the TAS2R receptor interacts with a G-protein to promote signal transduction that produces a smaller increase in intracellular Ca2+ than is elicited by the agonist in the absence of inhibition.

"Interaction" of a compound with a TAS2R receptor can mean binding of the compound to the receptor or modulation of a functional response of the receptor by the compound.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macro-molecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome. Purity and homogeneity are typically determined using analytical chemistry techniques, for example polyacrylamide gel electrophoresis or high performance liquid chromatography. A protein that is the predominant species present in a preparation is substantially purified. In particular, an isolated TAS2R nucleic acid is separated from open reading frames that flank the TAS2R gene and encode proteins other than a TAS2R. In some embodiments, the term "purified" means that the nucleic acid or protein is at least 85% pure, specifically at least 90% pure, more specifically at least 95% pure, or yet more specifically at least 99% pure.

A "ligand" as used herein refers to a molecule that binds to a macromolecule, such as a TAS2R receptor. The ligand can be a small molecule, or a biological moiety, such as a protein, a sugar, nucleic acid or lipid. The ligand can be a molecule that modulates TAS2R receptor activity. A molecule that modulates activity of a receptor can be an agonist, an antagonist, or a modulator as defined herein.

Ligands for various TAS2R receptors are known in the art. For example, ligands of a mammalian TAS2R1 can include adhumulone, adlupulone, amarogentin, arborescin, cascarillin, chloramphenicol, cis-isocohumulone, cis-isoloadhumulone, cohumulone, colupulone, dextromethorphan, diphenidol (diphenylthiourea, sulfocarbanilide, sym-diphenylthiourea, or thiocarbanilide), humulon (humulone), isoxanthohumol, lupulon, lupulone, parthenolide, picrotoxinin, sodium cyclamate, sodium thiocyanate, thiamine, trans-isoadhumulone, trans-isocohumulone, trans-isohumulone, xanthohumol, and yohimbine. The mammalian TAS2R1 can be from a human, a rodent, a canine, or a feline. In an embodiment, the mammalian TAS2R1 is a feline TAS2R1.

Ligands of a mammalian TAS2R3 can include chloroquine. The mammalian TAS2R3 can be from a human, a rodent, a canine, or a feline. In an embodiment, the mammalian TAS2R3 is a feline TAS2R3.

Ligands of a mammalian TAS2R4 can include amarogentin, arborescin, artemorin, azathioprine, brucine, campher, chlorpheniramine, colchicine, dapsone, denatonium benzoate, diphenidol, parthenolide, quassin, quinine, and yohimbine. The mammalian TAS2R4 can be from a human, a rodent, a canine, or a feline. In an embodiment, the mammalian TAS2R4 is a feline TAS2R4.

Ligands of a mammalian TAS2R7 can include caffeine, chlorpheniramine, cromolyn, diphenidol, papaverine, and quinine. The mammalian TAS2R7 can be from a human, a rodent, a canine, or a feline. In an embodiment, the mammalian TAS2R7 is a feline TAS2R7.

Ligands of a mammalian TAS2R9 can include ofloxacin, pirenzapin, and procainamid. The mammalian TAS2R9 can be from a human, a rodent, a canine, or a feline. In an embodiment, the mammalian TAS2R9 is a feline TAS2R9.

Ligands of a mammalian TAS2R10 can include (-)-alpha thujone, absinthin, arborescin, arglabin, artemorin, azathioprine, benzoin, caffeine, campher, cascarillin, chloramphenicol, chloroquine, chlorpheniramine, coumarin, cucurbitacin b, cucurbitacin e, cucurbitacins, cycloheximid, cycloheximide, dapsone, denatonium benzoate, dextromethorphan, diphenidol, erythromycin, famotidine, haloperidol, papaverine, parthenolide, picrotoxinin, quassin, quinine, strychnine, and yohimbine. The mammalian TAS2R10 can be from a human, a rodent, a canine, or a feline. In an embodiment, the mammalian TAS2R10 is a feline TAS2R10.

Ligands of a mammalian TAS2R38 can include 6-methyl-2-thiouracil, acetylthiourea, allyl isothiocyanate, caprolactam, chlorpheniramine, dimethylthioformamide, diphenidol, (diphenylthiourea, sulfocarbanilide, sym-diphenylthiourea, thiocarbanilide), ethylene thiourea, n,n-ethylene thiourea, ethylpyrazine, limonin, methimazole, n-ethylthiourea, n-methylthiourea, phenethyl isothiocyanate, phenylthiocarbamide (ptc), probenecid, propylthiouracil, sinigrin, sodium cyclamate, sodium_thiocyanate, and yohimbine. The mammalian TAS2R38 can be from a human, a rodent, a canine, or a feline. In an embodiment, the mammalian TAS2R38 is a feline TAS2R38.

Ligands of a mammalian TAS2R43 can include acesulfame K, aloin, amarogentin, arborescin, arglabin, aristolochic acid, caffeine, chloramphenicol, cromolyn, denatonium benzoate, diphenidol, falcarindiol, grossheimin (grossheimin), helicin, probenecid, quinine, and saccharin. The mammalian TAS2R43 can be from a human, a rodent, a canine, or a feline. In an embodiment, the mammalian TAS2R43 is a feline TAS2R43.

Ligands of a mammalian TAS2R44 can include acesulfame K, aloin, aristolochic acid, diphenidol, famotidine, parthenolide, quinine, and saccharin. The mammalian TAS2R44 can be from a human, a rodent, a canine, or a feline. In an embodiment, the mammalian TAS2R44 is a feline TAS2R44.

The term "ligand-binding fragment" of a TAS2R receptor, as used herein, refers to one or more fragments of the TAS2R receptor retaining the ability to specifically bind to a ligand of the TAS2R receptor.

A "modulator" is a molecule that modulates the functional response of a receptor by binding to a binding site that is distinct from the agonist binding site. A positive modulator or "enhancer" enhances the functional response of a receptor, while a negative modulator or "inhibitor" inhibits the functional response of a receptor. An "allosteric modulator" induces a conformational change in the receptor, which alters the affinity of the receptor for ligands, particularly at the agonist binding site. Positive allosteric modulators increase the affinity for ligands at the agonist binding site and/or enhance functional activity of a receptor, while negative allosteric modulators decrease the affinity for ligands at the agonist binding site and/or inhibit functional activity of a receptor. Modulators can include non-peptide molecules such as non-peptide mimetics, non-peptide allosteric effectors, and peptides.

The "modulating" or "altering" activity of a TAS2R receptor herein can refer to any change in TAS2R receptor activity occurring in response to binding of an agonist, antagonist, or modulator to the TAS2R receptor or a ligand binding fragment thereof, that is the alteration can be stimulating, antagonizing, or modulating the functional response of the receptor.

"Non-naturally occurring" in reference to a polynucleotide means that the polynucleotide sequence does not occur in nature in genomic DNA of an organism.

The term "nucleic acid", "polynucleotide", or "oligonucleotide" includes DNA molecules and RNA molecules. A polynucleotide may be single-stranded or double-stranded. Polynucleotides can contain known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs). A polynucleotide can be obtained by a suitable method known in the art, including isolation from natural sources, chemical synthesis, or enzymatic synthesis. Nucleotides may be referred to by their commonly accepted single-letter codes.

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

A "palatability enhancer" or "palatant" for animal edible composition, e.g., a food, is an additive that provides an aroma, taste, aftertaste, mouth feel, texture, and/or organoleptic sensation that is appealing to the target animal.

The terms "polypeptide," "peptide" and "protein" are used interchangeably herein to refer to a molecule formed from the linking, in a defined order, of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis, or enzymatic synthesis. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

Macromolecular structures of polypeptides can be described in terms of various levels of organization. "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units.

The term "primer" refers to an isolated single-stranded oligonucleotide of between about 10 to 50 nucleotides in length, preferably between about 15 to 50, more preferably 15 to 30 nucleotides in length and most preferably between about 18 and 28 nucleotides in length, that forms a duplex with a single stranded nucleic acid sequence of interest, and which is capable of acting as a point of initiation of nucleic acid synthesis to allow for polymerization of a complementary strand using a polymerase under appropriate conditions (i.e., in the presence of nucleotides and an inducing agent such as DNA polymerase and at a suitable temperature and pH). The primer must be sufficiently long to prime the synthesis of extension products in the presence of the inducing agent. The exact lengths of the primers will depend on many factors, including temperature, source of primer and the use of the method. Preferably, the primer is an oligodeoxyribonucleotide. In order to facilitate subsequent cloning of amplified sequences, primers may have restriction enzyme site sequences appended to their 5' ends. Such enzymes and sites are well known in the art. The primers themselves can be synthesized using techniques which are well known in the art. Generally, the primers can be made using oligonucleotide synthesizing machines which are commercially available. A "primer pair" is a pair of primer sequences chosen to amplify a particular DNA target sequence by PCR. One primer of the pair is complementary to the 3' end of the "sense" strand of the DNA target, e.g. a cDNA, and the other is complementary to the 3' end of the "anti-sense" strand of the DNA target.

As used herein, the term "probe" refers to an oligonucleotide which is capable of hybridizing to another nucleic acid of interest. A probe may be single-stranded or double-stranded. A probe herein is an oligonucleotide of between about 10 to 100 nucleotides in length, preferably between about 15 to 80, more preferably 20 to 50 nucleotides in length. Probes are useful in the detection, identification and isolation of particular nucleic acid sequences, for example via Southern hybridization or other methods known in the art. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "recombinant" can be used to describe a nucleic acid molecule and refers to a polynucleotide of genomic, RNA, DNA, cDNA, viral, semisynthetic, or synthetic origin which, by virtue of its origin or manipulation is not associated with all or a portion of the polynucleotide with which it is associated in nature. The term "recombinant" as used with respect to a protein or polypeptide can refer to a polypeptide produced by expression of a recombinant polynucleotide. In general, the gene of interest is cloned and then expressed in transformed organisms, by a method known in the art. The host organism expresses the foreign gene to produce the protein under expression conditions.

The term "solid support" refers to a material or group of materials having a rigid or semi-rigid surface or surfaces. Examples of materials include plastics (e.g., polycarbonate), complex carbohydrates (e.g., agarose and sepharose), acrylic resins (e.g., polyacrylamide and latex beads), nitrocellulose, glass, silicon wafers, and positively charged nylon. In some aspects, at least one surface of the solid support can be substantially flat, although in some aspects it may be desirable to physically separate regions for different molecules with, for example, wells, raised regions, pins, etched trenches, or the like. In certain aspects, the solid support(s) will take the form of beads, resins, gels, microspheres, or other geometric configurations.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a fTAS2R can be selected to obtain only those polyclonal antibodies that are specifically immunoreactive with the fTAS2R protein or an immunogenic portion thereof and not with other proteins, except for orthologs or polymorphic variants and alleles of the TAS2R protein. This selection may be achieved by subtracting out antibodies that cross-react with TAS2R molecules from other species or other TAS2R molecules. Antibodies can also be selected that recognize only fTAS2R GPCR family members but not other GPCRs. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

With respect to receptors, the terms "specific binding," "specifically binds," "selective binding," and "selectively binds" mean that a receptor, such as a TAS2R receptor, exhibits appreciable affinity for a particular ligand. "Appreciable" binding affinity includes binding with an affinity of at least $10^4$ $M^{-1}$, at least $10^5$ $M^{-1}$, specifically at least $10^6$ $M^{-1}$, more specifically at least $10^7$ $M^{-1}$, yet more specifically at least $10^8$ $M^{-1}$, or even yet more specifically at least $10^9$ $M^{-1}$. A binding affinity can also be indicated as a range of affinities, for example, $10^4$ $M^{-1}$ to $10^{10}$ $M^{-1}$, specifically $10^5$ $M^{-1}$ to $10^{10}$ $M^{-1}$, more specifically $10^6$ $M^{-1}$ to $10^{10}$ $M^{-1}$. Specific binding can be determined according to any art-recognized means for determining such binding. In some embodiments, specific binding is determined according to Scatchard analysis and/or competitive binding assays.

As used herein, "stimulation" or "activation" of a TAS2R receptor, or a ligand-binding fragment thereof, means that the TAS2R receptor, or fragment, is placed in a state in which it produces a functional response, for example the TAS2R receptor interacts with an intracellular signaling pathway to produce the functional response, e.g. the TAS2R receptor interacts with a G-protein to promote signal transduction that produces increased intracellular Ca2+.

"Substantially the same" biological activity refers to a polypeptide fragment, derivative, homolog, analog, or variant retaining at least about 50%, 55%, 60%, 65%, 70%, preferably at least about 75%, 80%, 85%, 90%, more preferably at least about 91%, 92%, 93%, 94%, 95%, and most preferably at least about 96%, 97%, 98%, 99% or greater biological activity of the parent polypeptide. The extent to which a polypeptide fragment, derivative, homolog, analog, or variant retains the biological activity of the parent polypeptide may be assessed by any means available in the art, including, but not limited to, the assays listed or described herein.

A "TAS2R binding partner" is a compound that directly or indirectly binds a TAS2R polypeptide disclosed herein.

A "TAS2R receptor polypeptide" (or TAS2R receptor or TAS2R) for use in assays described herein to measure ligand binding or receptor activity can comprise a TAS2R receptor; a domain of a TAS2R receptor, such as an extracellular domain, transmembrane region, transmembrane domain, cytoplasmic domain, a ligand-binding fragment, subunit association domain, active site, and the like; or a chimeric protein in which either a TAS2R receptor or a domain thereof is covalently linked to a heterologous protein.

Herein a "tastant" means a ligand that can bind to a specific TAS2R receptor or set of TAS2R receptors.

The term "taste perception" as used herein refers to a response (e.g., biochemical, behavioral) or sensitivity of a TAS2R receptor to a taste stimulus. Modification of taste perception includes an alteration of (enhancement of, reduction of, or change to) a biochemical response, an ingestive response, a taste preference, a metabolic response, or a general behavior of a mammal in response to a tastant. "Taste perception" does not require, though it can include, transmission of a neural signal resulting in the in vivo sensation of taste by a mammal.

The "transmembrane domain," which comprises the seven transmembrane regions, refers to the domain of TAS2R polypeptides that lies within the plasma membrane, and may also include the corresponding cytoplasmic (intracellular) and extracellular loops, also referred to as transmembrane domain "regions." Transmembrane regions can also bind ligand either in combination with the extracellular domain or alone, and are therefore also useful for in vitro ligand binding assays.

The term "transmembrane region" as used herein denotes a three-dimensional protein structure which is thermodynamically stable in a membrane, e.g., a single transmembrane alpha helix or a transmembrane beta barrel.

The term "vector" means a nucleic acid sequence to express a target gene in a host cell. Examples include a plasmid vector, a cosmid vector, a bacteriophage vector, and a viral vector. Examples of viral vectors include a bacteriophage vector, an adenovirus vector, a retrovirus vector, and an adeno-associated virus vector. For example, the vector may be an expression vector including a membrane targeting or secretion signaling sequence or a leader sequence, in addition to an expression control element such as promoter, operator, initiation codon, termination codon, polyadenylation signal, and enhancer. The vector may be manufactured in various ways known in the art depending on the purpose. An expression vector may include a selection marker for selecting a host cell containing the vector. Further, a replicable expression vector may include an origin of replication. The term "recombinant vector" or "expression vector" means a vector operably linked to a heterologous nucleotide sequence for the purpose of expression, production, and isolation of the heterologous nucleotide sequence. The heterologous nucleotide sequence can be a nucleotide sequence encoding all or part of a fTAS2R receptor or a chimeric polypeptide disclosed herein.

Human TAS2R (hTAS2R) gene and pseudogene nucleotide sequences were used as references to identify, via a bioinformatics approach, previously unknown feline TAS2R (fTAS2R) genes. Subsequently, isolated feline genomic DNA was used to clone the fTAS2R genes. The nucleotide sequence of the cloned fTAS2R genes of several felines was then determined by sequencing, e.g., Sanger sequencing, and used to establish a consensus nucleotide sequence for the gene, and to identify any variant sites in the sequence.

Polynucleotides encoding a fTAS2R receptor are disclosed. In an embodiment, the polynucleotides are isolated. The polynucleotide can comprise a nucleotide sequence selected from the nucleotide sequence of SEQ ID NO:1, SEQ ID NO: 3, SEQ ID NO: 5, SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence encoding the amino acid sequence of SEQ ID NO:2, SEQ ID NO: 4, SEQ ID NO: 6, SEQ ID NO: 8, SEQ ID NO:10, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence encoding a fTAS2R having an amino acid sequence having at least 70% homology to the amino acid sequence of SEQ ID NO:2, SEQ ID NO: 4, SEQ ID NO: 6, SEQ ID NO: 8, SEQ ID NO:10, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence encoding a fTAS2R and having at least 70% homology to the nucleotide sequence of SEQ ID NO:1, SEQ ID NO: 3, SEQ ID NO: 5, SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence that hybridizes to the complement of the polynucleotide having SEQ ID NO:1, SEQ ID NO: 3, SEQ ID NO: 5, SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25 under high stringency conditions; a nucleotide sequence comprising at least 15 contiguous nucleotides of the nucleotide sequence of any one of the foregoing nucleotide sequences; and the complement of any one of the foregoing nucleotide sequences. In an embodiment, the percent homology is at least 90%. In an embodiment, the percent homology is at least 95%, preferably at least 98%, more preferably at least 99%. In an embodiment, the polynucleotide comprises a nucleotide sequence selected from: the nucleotide sequence of SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence encoding the amino acid sequence of SEQ ID NO: 8, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence that hybridizes to the complement of the polynucleotide having SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25 under high stringency conditions; and the complement of the foregoing nucleotide sequences. In an embodiment, the polynucleotide comprises a nucleotide sequence selected from: the nucleotide sequence of SEQ ID NO: 17; a nucleotide sequence encoding the amino acid sequence of SEQ ID NO: 18; a nucleotide sequence that hybridizes to the complement of the polynucleotide having SEQ ID NO: 17 under high stringency conditions; and the complement of the foregoing nucleotide sequences. In an embodiment, the nucleotide sequence is codon-optimized for expression in a non-feline cell. In an embodiment, the non-feline cell is *Escherichia coli*, a *Saccharomyces cerevisae* cell, a *Drosophila melanogaster* cell, a *Caenorhabditis elegans* cell, or a mammalian cell. In an embodiment, the mammalian cell is a human or murine cell. Examples of codon-optimized sequences for expression of the novel fTAS2R receptor polypeptides in *Escherichia coli*, *Saccharomyces cerevisae* cell, *Drosophila melanogaster*, *Caenorhabditis elegans*, human, or murine cells are disclosed in SEQ ID NOs: 58-135.

Further disclosed are polynucleotides comprising a sequence having at least 60%, at least 70%, at least 80%, at least 90%, at least 95%, at least 97%, at least 98%, at least 99% homology with SEQ ID NOs:1, 3, 5, 7, 9, 11, 13, 15, 17, 19, 21, 23, 25, or the complement of SEQ ID NOs:1, 3, 5, 7, 9, 11, 13, 15, 17, 19, 21, 23, or 25.

Also disclosed are compositions comprising at least two polynucleotides disclosed herein. In an embodiment each polynucleotide encodes a portion of a different fTAS2R receptor. In an embodiment, the composition comprises at least 3, 4, or 5 of the polynucleotides disclosed herein.

In an embodiment, the composition comprises at least 6, 7, 8, 9, 10, 11, 12, or 13 of the polynucleotides disclosed herein. In an embodiment each polynucleotide of the composition encodes a different fTAS2R receptor, or fragment thereof. In an embodiment, the composition comprises a polynucleotide comprising SEQ ID NO: 17 and/or SEQ ID NO: 21. In an embodiment, the composition comprises a primer pair for amplifying a portion of a nucleic acid encoding a feline TAS2R polypeptide. In an embodiment, the primer pairs are selected from the primer pairs of Table 5. The primer pairs disclosed herein are useful for determination of the nucleotide sequence of a particular TAS2R polynucleotide, or fragment thereof, using PCR. The pairs of single-stranded DNA primers can be annealed to sequences within or surrounding the fTAS2R gene in order to prime amplifying DNA synthesis of the fTAS2R gene itself. Allele-specific primers can also be used. Such primers anneal only to particular fTAS2R mutant alleles, and thus will only amplify a product in the presence of the mutant allele as a template.

A single nucleotide polymorphism in the nucleic acid sequence encoding fTAS2R38 was identified at nucleotide 220 of the cDNA sequence (SEQ ID NO:17) from sequencing amplified feline genomic DNA from multiple subjects. The two alleles observed at the nucleotide 220 were G and A. The G220A nucleic acid variation corresponds to an amino acid variation D74N in the fTAS2R38 protein sequence (SEQ ID NO:18). In an embodiment, a disclosed polynucleotide comprises a nucleotide sequence of at least 15 contiguous nucleotides of SEQ ID NO:17 containing nucleotide 220, wherein an A is present at nucleotide 220; or the complement of the nucleotide sequence. In an embodiment, the polynucleotide comprises at least 20 contiguous nucleotides of SEQ ID NO:17 containing nucleotide 220, wherein an A is present at nucleotide 220; or the complement of the nucleotide sequence. In an embodiment, a disclosed fTAS2R38 polypeptide comprises SEQ ID NO:18 with N present at residue 74 of the sequence, or a fragment thereof comprising the N74 residue.

In another aspect, isolated fTAS2R receptor polypeptides are disclosed.

In an embodiment, the isolated fTAS2R polypeptide is encoded by a polynucleotide disclosed herein.

In an embodiment, the isolated fTAS2R polypeptide can comprise the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or an amino acid sequence having at least 70%, at least 80%, at least 90%, at least 95%, at least 97%, at least 98%, at least 99% homology with the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In an embodiment, the isolated fTAS2R polypeptide comprises the amino acid sequence of SEQ ID NO:8, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or an amino acid sequence having at least 70%, at least 80%, at least 90%, at least 95%, at least 97%, at least 98%, at least 99% homology with one of the foregoing amino acid sequences. In an embodiment, the isolated fTAS2R polypeptide comprises the amino acid sequence of SEQ ID NO:18 or SEQ ID NO:22.

Sensory GPCRs, such as the TAS2R bitter taste receptors, have a domain structure including an N-terminal domain; extracellular domains; a transmembrane domain comprising seven transmembrane regions, cytoplasmic, and extracellular loops; cytoplasmic domains; and a C-terminal domain. These domains can be structurally identified using methods known in the art, such as sequence analysis programs that identify hydrophobic and hydrophilic domains. Such domains are useful for making chimeric proteins and for in vitro assays disclosed herein, e.g., ligand binding assays.

The seven transmembrane regions and extracellular and cytoplasmic loops can be identified using standard methods known in the art. For example, transmembrane regions of the fTAS2R proteins can be identified using software, TOPCONS, available on the internet from the Stockholm Bioinformatics Center, Stockholm University (Andreas Bernsel, et al. (2009) Nucleic Acids Research 37(Webserver issue), W465-8). The seven transmembrane regions and extracellular and cytoplasmic loops of the fTAS2R identified by TOPCONS are shown in the following table:

TABLE 1

TOPCONS prediction of seven transmembrane regions, extracellular loops, and intracellular loops fTAS2R1 (SEQ ID NO: 2)
Transmembrane domains: 1: 2-22, 2: 47-67, 3: 85-105, 4: 125-145, 5: 180-200, 6: 228-248, 7: 258-278
Extracellular domain: 1, 68-84; 146-179; 249-257.
Intracellular domain: 23-46; 106-124; 201-227; 279-298 fTAS2R2 (SEQ ID NO: 4)
Transmembrane domains: 1: 11-31, 2: 52-72, 3: 89-109, 4: 130-150, 5: 187-207, 6: 235-255, 7: 265-285
Extracellular domain: 1-10, 73-88; 151-186; 256-264
Intracellular domain: 32-51; 110-129; 208-234; 286-304 fTAS2R3 (SEQ ID NO: 6)
Transmembrane domains: 1: 9-29, 2: 51-71, 3: 89-109, 4: 129-149, 5: 187-207, 6: 235-255, 7: 266-286
Extracellular domain: 1-8; 72-88; 150-186; 256-265
Intracellular domain: 30-50; 110-128; 208-234; 287-316 fTAS2R4 (SEQ ID NO: 8)
Transmembrane domains: 1: 3-23, 2: 48-68, 3: 88-108, 4: 130-150, 5: 184-204, 6: 232-252, 7: 262-282
Extracellular domain: 1-2; 69-87; 151-183; 253-261
Intracellular domain: 24-47; 109-129; 205-231; 283-306 fTAS2R7 (SEQ ID NO: 10)
Transmembrane domains: 1: 9-29, 2: 51-71, 3: 89-109, 4: 129-149, 5: 188-208, 6: 236-256, 7: 266-286
Extracellular domain: 1-8; 72-88; 150-187; 257-265
Intracellular domain: 30-50; 110-128; 209-235; 287-311 fTAS2R9 (SEQ ID NO: 12)
Transmembrane domains: 1: 7-27, 2: 51-71, 3: 89-109, 4: 129-149, 5: 184-204, 6: 232-252, 7: 263-283
Extracellular domain: 1-6; 72-88; 150-183; 253-262
Intracellular domain: 28-50; 110-128; 205-231; 284-337 fTAS2R10 (SEQ ID NO: 14)
Transmembrane domains: 1: 2-22, 2. 48-68, 3: 88-108, 4: 129-149, 5: 182-202, 6: 230-250, 7: 261-281

TABLE 1-continued

TOPCONS prediction of seven transmembrane regions, extracellular loops, and intracellular loops Extracellular domain: 1; 69-87; 150-181; 251-260
Intracellular domain: 23-48; 109-128; 203-229; 282-300 fTAS2R12 (SEQ ID NO: 16)
Transmembrane domains: 1: 9-29, 2: 48-68, 3: 89-109, 4: 129-149, 5: 186-206, 6: 231-251, 7: 262-282
Extracellular domain: 1-8; 69-88; 150-185; 252-261
Intracellular domain: 30-47; 110-128; 207-230; 283-309 fTAS2R38 (SEQ ID NO: 18)
Transmembrane domains: 1: 18-38, 2: 62-82, 3: 99-119, 4: 140-160, 5: 199-219, 6: 247-267, 7: 278-298
Extracellular domain: 1-17: 83-98; 161-198; 268-277
Intracellular domain: 39-61; 120-139; 220-246; 299-334 fTAS2R42 (SEQ ID NO: 20)
Transmembrane domains: 1: 2-22, 2: 48-68, 3: 89-109, 4: 129-149, 5: 186-206, 6: 234-254, 7: 265-285
Extracellular domain: 1; 69-88; 150-185; 255-264
Intracellular domain: 23-47; 110-128; 207-233; 286-322 fTAS2R43 (SEQ ID NO: 22)
Transmembrane domains: 1: 3-23, 2: 48-68, 3: 88-108, 4: 128-148, 5: 182-202, 6: 230-250, 7: 261-281
Extracellular domain: 1-2; 69-87; 149-181; 251-260
Intracellular domain: 24-47; 109-127; 203-229; 282-299 fTAS2R44 (SEQ ID NO: 24)
Transmembrane domains: 1: 3-23, 2: 48-68, 3: 88-108, 4: 128-148, 5: 182-202, 6: 230-250, 7: 260-280
Extracellular domain: 1-2; 69-87; 149-181; 251-259
Intracellular domain: 24-47; 109-127; 203-229; 281-308 fTAS2R67 (SEQ ID NO: 26)
Transmembrane domains: 1: 9-29, 2: 51-71, 3: 89-109, 4: 129-149, 5: 186-206, 6: 233-253, 7: 264-284
Extracellular domain: 1-8; 72-88; 150-185; 254-263
Intracellular domain: 30-50; 110-128; 207-232; 285-312

Alternative predictions of the transmembrane regions and extracellular and cytoplasmic loops of the fTAS2R proteins can be generated using different software also available on the internet from the Stockholm Bioinformatics Center, including SCAMPI (Andreas Bernsel, et al. (2008) Proc. Natl. Acad. Sci. USA. 105, 7177-7181); PRODIV (Hakan Viklund and Arne Elofsson (2004) Protein Science 13, 1908-1917), and OCTAPUS (Hakan Viklund and Arne Elofsson (2008) Bioinformatics. 24, 1662-1668.) Additional methods known in the art to predict the structural regions include hydropathy prediction methods of Goldman-Engleman-Steitz, or Kyte-Doolittle (J. Mol. Biol. 157: 105-132 (1982), or Hopp-Woods. Secondary structure prediction methods include Garnier-Robson, or Deléage & Roux or Chou-Fasman. As known in the art, the various available algorithms may predict slightly different boundaries for transmembrane regions based on the amino acid sequence.

In an embodiment, the isolated TAS2R receptor polypeptide can comprise at least one extracellular domain of a feline TAS2R receptor; at least one transmembrane domain of a feline TAS2R receptor; or at least one intracellular domain of a feline TAS2R receptor, wherein the feline TAS2R receptor comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or an amino acid sequence having at least 70%, at least 80%, at least 90%, at least 95% homology, specifically at least 97% homology, more specifically at least 99% homology with the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26, wherein the isolated fTAS2R receptor polypeptide does not consist of the amino acid sequence of SEQ ID NOs: 2, 4, 6, or 10.

In an embodiment, the extracellular domain of the fTAS2R polypeptide can comprise amino acids 1, 68-84; 146-179; or 249-257 of SEQ ID NO:2; amino acids 1-10, 73-88; 151-186; or 256-264 of SEQ ID NO:4; amino acids 1-8; 72-88; 150-186; or 256-265 of SEQ ID NO:6; amino acids 1-2; 69-87; 151-183; or 253-261 of SEQ ID NO:8; amino acids 1-8; 72-88; 150-187; or 257-265 of SEQ ID NO:10; amino acids 1-6; 72-88; 150-183; or 253-262 of SEQ ID NO:12; amino acids 1; 69-87; 150-181; or 251-260 of SEQ ID NO:14; amino acids 1-8; 69-88; 150-185; or 252-261 of SEQ ID NO:16; amino acids 1-17: 83-98; 161-198; or 268-277 of SEQ ID NO:18; amino acids 1; 69-88; 150-185; or 255-264 of SEQ ID NO:20; amino acids 1-2; 69-87; 149-181; or 251-260 of SEQ ID NO:22; amino acids 1-2; 69-87; 149-181; or 251-259 of SEQ ID NO:24; or amino acids 1-8; 72-88; 150-185; or 254-263 of SEQ ID NO:26.

In an embodiment, the transmembrane domain of the fTAS2R polypeptide can comprise amino acids 2-22, 47-67, 85-105, 125-145, 180-200, 228-248, or 258-278 of SEQ ID NO:2; amino acids 11-31, 52-72, 89-109, 130-150, 187-207, 235-255, or 265-285 of SEQ ID NO:4; amino acids 9-29, 51-71, 89-109, 129-149, 187-207, 235-255, or 266-286 of SEQ ID NO:6; amino acids 3-23, 48-68, 88-108, 130-150, 184-204, 232-252, or 262-282 of SEQ ID NO:8; amino acids 9-29, 51-71, 89-109, 129-149, 188-208, 236-256, or 266-286 of SEQ ID NO:10; amino acids 7-27, 51-71, 89-109, 129-149, 184-204, 232-252, or 263-283 of SEQ ID NO:12; amino acids 2-22, 2.48-68, 88-108, 129-149, 182-202, 230-250, or 261-281 of SEQ ID NO:14; amino acids 9-29, 48-68, 89-109, 129-149, 186-206, 231-251, or 262-282 of SEQ ID NO:16; amino acids 18-38, 62-82, 99-119, 140-160, 199-219, 247-267, or 278-298 of SEQ ID NO:18; amino acids 2-22, 48-68, 89-109, 129-149, 186-206, 234-254, or 265-285 of SEQ ID NO:20; amino acids 3-23, 48-68, 88-108, 128-148, 182-202, 230-250, or 261-281 of SEQ ID NO:22; amino acids 3-23, 48-68, 88-108, 128-148, 182-202, 230-250, or 260-280 of SEQ ID NO:24; or amino acids 9-29, 51-71, 89-109, 129-149, 186-206, 233-253, or 264-284 of SEQ ID NO:26.

In an embodiment, the intracellular domain of the fTAS2R polypeptide can comprise amino acids 23-46; 106-124; 201-227; or 279-298 of SEQ ID NO:2; amino acids 32-51; 110-129; 208-234; or 286-304 of SEQ ID NO:4; amino acids 30-50; 110-128; 208-234; or 287-316 of SEQ ID NO:6; amino acids 24-47; 109-129; 205-231; or 283-306 of SEQ ID NO:8; amino acids 30-50; 110-128; 209-235; or 287-311 of SEQ ID NO:10; amino acids 28-50; 110-128; 205-231; or 284-337 of SEQ ID NO:12; amino acids 23-48; 109-128; 203-229; or 282-300 of SEQ ID NO:14; amino acids 30-47; 110-128; 207-230; or 283-309 of SEQ ID NO:16; amino acids 39-61; 120-139; 220-246; or 299-334 of SEQ ID NO:18; amino acids 23-47; 110-128; 207-233; or 286-322 of SEQ ID NO:20; amino acids 24-47; 109-127; 203-229; or 282-299 of SEQ ID NO:22; amino acids 24-47; 109-127; 203-229; or 281-308 of SEQ ID NO:24; or amino acids 30-50; 110-128; 207-232; or 285-312 of SEQ ID NO:26.

In an embodiment, the fTAS2R receptor polypeptide comprises a transmembrane region 2, a transmembrane region 3, a transmembrane region 4, a transmembrane region 5, a transmembrane region 6, and a transmembrane region 7, wherein each transmembrane region comprises at least 20 consecutive amino acids of the corresponding transmembrane region sequence independently selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26; or a transmembrane region 3, a transmembrane region 6, and a transmembrane region 7, wherein each transmembrane region comprises at least 20 consecutive amino acids of the corresponding transmembrane region sequence independently selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26; an extracellular domain 3 comprising at least 15 consecutive amino acids selected from amino acids 146-179 of SEQ ID NO:2; amino acids 151-186 of SEQ ID NO:4; amino acids 150-186 of SEQ ID NO:6; amino acids 151-183 of SEQ ID NO:8; amino acids 150-187 of SEQ ID NO:10; amino acids 150-183 of SEQ ID NO:12; amino acids 150-181 of SEQ ID NO:14; amino acids 150-185 of SEQ ID NO:16; amino acids 161-198 of SEQ ID NO:18; amino acids 150-185 of SEQ ID NO:20; amino acids 149-181 of SEQ ID NO:22; amino acids 149-181 of SEQ ID NO:24; and amino acids 150-185 of SEQ ID NO:26; and an extracellular domain 4 comprising at least 8 consecutive amino acids selected from amino acids 249-257 of SEQ ID NO:2; amino acids 256-264 of SEQ ID NO:4; amino acids 256-265 of SEQ ID NO:6; amino acids 253-261 of SEQ ID NO:8; amino acids 257-265 of SEQ ID NO:10; amino acids 253-262 of SEQ ID NO:12; amino acids 251-260 of SEQ ID NO:14; amino acids 252-261 of SEQ ID NO:16; amino acids 268-277 of SEQ ID NO:18; amino acids 255-264 of SEQ ID NO:20; amino acids 251-260 of SEQ ID NO:22; amino acids 251-259 of SEQ ID NO:24; and amino acids 254-263 of SEQ ID NO:26.

Also disclosed are polynucleotides encoding the polypeptide comprising at least one extracellular domain of a feline TAS2R receptor; at least one transmembrane domain of a feline TAS2R receptor; or at least one intracellular domain of a feline TAS2R receptor.

In another aspect, chimeric polypeptides comprising an extracellular domain, an intracellular domain, or a transmembrane region of a feline TAS2R receptor polypeptide, and further comprising a heterologous polypeptide are disclosed. The intracellular domain, extracellular domain, or the transmembrane region of the feline TAS2R receptor polypeptide can be any of those disclosed herein.

The heterologous polypeptide can be any suitable polypeptide known in the art, or a portion of such polypeptide as may be useful herein. The heterologous polypeptide can be, for example, a sequence to determine cellular localization and expression, to permit proper folding of the chimeric polypeptide in an expression system, and/or to facilitate isolation of the chimeric polypeptide. The heterologous polypeptide can be linked to any portion of the chimeric polypeptide, for example to the amino terminal end or the carboxy terminal end of the fTAS2R sequence. For example, the heterologous polypeptide can be the first 45 amino acids of rat somatostatin, the FLAG® tag, a 6× histidine (his) tag, MYC, a fluorescent protein tag, V5, and/or glutathione S-transferase (GST). When the heterologous polypeptide is the first 45 amino acids of rat somatostatin, it is typically placed at the amino terminal end of the chimeric polypeptide to permit membrane targetting. When the heterologous polypeptide is a tag to permit easier isolation of the chimeric polypeptide, e.g., a 6× histidine tag, it can be placed at the amino terminus of the chimeric polypeptide. Determination of a suitable location for the heterologous polypeptide in the chimeric polypeptide relative to the amino end or the carboxy end of the fTAS2R sequence to obtain a particular functional aspect of the heterologous polypeptide on the chimeric polypeptide can be made by one of skill in the art.

Also disclosed are polynucleotides encoding the chimeric polypeptides.

Also disclosed is a composition comprising at least two fTAS2R polypeptides disclosed herein. In an embodiment, the composition comprises at least 3, 4, or 5 polypeptides disclosed herein. In an embodiment, the composition comprises at least 6, 7, 8, 9, 10, 11, 12, or 13 polypeptides disclosed herein. In an embodiment each polypeptide in the composition is a different fTAS2R receptor. In an embodiment, the composition comprises a polypeptide comprising SEQ ID NO:18 and a polypeptide comprising SEQ ID NO:22.

Unless otherwise indicated, a particular polypeptide sequence also implicitly encompasses conservatively modified variants thereof. A conservative amino acid substitution in a polypeptide sequence includes the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. One of skill in the art can readily determine regions of the molecule of interest that can tolerate change by reference to Hopp/Woods and Kyte-Doolittle plots.

Unless otherwise indicated, a particular nucleic acid sequence also implicitly encompasses conservatively modified variants thereof (e.g. degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

Percent identity (homology) can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN (Dayhoff, M. O. in Atlas of Protein Sequence and Structure M. O. Dayhoff ed., 5 Suppl. 3:353-358, National Biomedical Research Foundation, Washington, D.C.), which adapts the local homology algorithm of Smith and Waterman 1981 Advances in Appl Math 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, nucleotide homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. Molecular Cloning: A Laboratory Manual (2d ed., Cold Spring Harbor Laboratory Press, Cold Spring Harbor, N.Y. (1989) or Current Protocols in Molecular Biology, John Wiley & Sons, N.Y., 6.3.1-6.3.6, 1991. In an embodiment, high stringency conditions are 6×SSC (1×SSC=0.15 M sodium chloride, 0.015 M sodium citrate, pH 7) at 45° C., followed by a wash in 0.2×SSC, 0.1% SDS at 65° C. or an equivalent thereto. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are known in the art, and for purposes herein, include conditions equivalent to hybridization in 6× sodium chloride/sodium citrate (SSC) at 45° C., followed by a wash in 0.2×SSC, 0.1% SDS at 65° C.

Disclosed herein is an expression vector comprising a polynucleotide encoding a feline TAS2R polypeptide disclosed herein, or a fragment thereof. In an embodiment, the recombinant vector comprises a polynucleotide consisting of SEQ ID NO:1, 3, 5, 7, 9, 11, 13, 15, 17, 19, 21, 23, or 25; a polynucleotide consisting of the complement of SEQ ID NO:1, 3, 5, 7, 9, 11, 13, 15, 17, 19, 21, 23, or 25; or a polynucleotide consisting of a sequence having at least 90%, at least 95%, at least 97%, at least 98%, at least 99% homology with SEQ ID NO:1, 3, 5, 7, 9, 11, 13, 15, 17, 19, 21, 23, 25, or the complement of SEQ ID NO:1, 3, 5, 7, 9, 11, 13, 15, 17, 19, 21, 23, or 25. In an embodiment, the recombinant vector comprises a polynucleotide comprising a nucleotide sequence selected from: the nucleotide sequence of SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence encoding the amino acid sequence of SEQ ID NO: 8, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence that hybridizes to the complement of the polynucleotide having SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25 under high stringency conditions; and the complement of the foregoing nucleotide sequences. In an embodiment, the vector comprises a polynucleotide sequence of SEQ ID NO:17 or SEQ ID NO:21. Also disclosed is an expression vector comprising a polynucleotide encoding a chimeric polypeptide disclosed herein.

The recombinant vector may be constructed for use in prokaryotic or eukaryotic host cells. For example, when a prokaryotic cell is used as a host cell, the expression vector used generally includes a strong promoter capable of initiating transcription (for example, pLλ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example f1 origin of replication, SV40 origin of replication, pMB1 origin of replication, adeno origin of replication, AAV origin of replication, or BBV origin of replication, but is not limited thereto. A promoter in an expression vector for a eukaryotic host cell may be a promoter derived from the genomes of mammalian cells (for example, a metallothionein promoter or an EF-1alpha promoter) or a promoter derived from mammalian viruses (for example, an adenovirus late promoter, a Vaccinia virus 7.5K promoter, a Sindbis promoter, a SV40 promoter, a cytomegalovirus promoter, and a tk promoter of HSV). A transcription termination sequence in an expression vector for a eukaryotic host cell may be, in general, a polyadenylation sequence.

Further disclosed is a host cell comprising an expression vector or a polynucleotide disclosed herein. A suitable host cell can be transformed with at least one of the recombinant vectors or at least one polynucleotide disclosed herein, for example a polynucleotide consisting of SEQ ID NO:1, 3, 5, 7, 9, 11, 13, 15, 17, 19, 21, 23, or 25.

The host cell of the vector may be any cell that can be practically utilized by the expression vector. For example, the host cell may be a higher eukaryotic cell, such as a mammalian cell, or a lower eukaryotic cell, such as a yeast cell. Further, the host cell may be a prokaryotic cell, such as a bacterial cell. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*; or an intestinal bacterium, such as *Salmonella typhimurium, Serratia marcescens*, and various *Pseudomonas* species. A eukaryotic host cell may be a yeast (e.g., *Saccharomyces cerevisiae*), an insect cell, a plant cell, or an animal cell, for example, mouse Sp2/0, CHO (Chinese hamster ovary) K1, CHO DG44, PER.C6, W138, BHK, COS-7, 293, HepG2, Huh7, 3T3, RIN, HeLa, HEK-293, or a MDCK cell line. In some embodiments, fish cells are useful herein.

The polynucleotide or recombinant vector including the polynucleotide may be transferred into the host cell using a method known in the art. For example, when a prokaryotic cell is used as the host cell, the transfer may be performed using a CaCl$_2$ method or an electroporation method, and when a eukaryotic cell is used as the host cell, the transfer may be performed by microinjection, calcium phosphate precipitation, electroporation, liposome-mediated transfection, LIPOFECTAMINE® (Life Technologies Corporation) transfection, or gene bombardment, but is not limited thereto.

After the expression vector is introduced into the cells, the transfected cells can be cultured under conditions favoring expression of the fTAS2R. The fTAS2R can be recovered from the culture using standard techniques known in the art.

The expression vectors disclosed herein are particularly useful for assays to identify and characterize tastants. Means to introduce/express the nucleic acids and vectors, either individually or as libraries, are well known in the art. A variety of individual cell, organ, or whole animal parameters can be measured by a variety of means. The disclosed fTAS2R sequences can be expressed, for example, in animal taste tissues by delivery with a transmissible agent, e.g., adenovirus expression vector.

Nucleic acid assays for the presence of DNA and RNA for a TAS2R family member in a sample include numerous techniques known to those skilled in the art, such as Southern analysis, Northern analysis, dot blots, RNase protection, S1 analysis, amplification techniques such as polymerase chain reaction (PCR) and ligase chain reaction (LCR), and in situ hybridization. In addition, a TAS2R protein can be detected with the various immunoassay techniques known in the art. The test sample is typically compared to both a positive control (e.g., a sample expressing a recombinant TAS2R protein) and a negative control.

The nucleic acid and amino acid sequence information disclosed herein also makes possible identification of binding partner compounds with which a TAS2R polypeptide or polynucleotide will interact. Methods to identify binding partner compounds include solution assays, in vitro assays wherein TAS2R polypeptides are immobilized, and cell-based assays.

Specific binding molecules, including natural ligands and synthetic compounds, can be identified or developed using isolated or recombinant TAS2R products, TAS2R variants, or cells expressing such products. Binding partners are useful for purifying TAS2R products and detection or quantification of TAS2R products in fluid and tissue samples using known immunological procedures. Binding molecules are also useful in modulating (i.e., blocking, inhibiting or stimulating) biological activities of TAS2R, especially those activities involved in signal transduction. Binding molecules also are useful in methods for predicting the taste perception of an organism such as a mammal by detecting a TAS2R polypeptide in a biological sample of a feline.

Methods to identify compounds that bind and/or modulate fTAS2R receptors are disclosed.

In an embodiment, the method comprises contacting TAS2R receptor with a test compound suspected of binding TAS2R receptor; and detecting binding between the compound and the TAS2R receptor. Binding can be determined by any binding assay known to the skilled artisan, including gel-shift assays, Western blots, radiolabeled competition assay, phage-based expression cloning, co-fractionation by chromatography, co-precipitation, cross-linking, interaction trap/two-hybrid analysis, southwestern analysis, and ELISA. The methods may also use ligands that are attached to a label, such as a radiolabel (e. g., $^{125}I$, $^{35}S$, $^{32}P$, $^{33}P$, $^{3}H$), a fluorescence label, a chemiluminescent label, an enzymic label, and an immunogenic label. In one variation, a composition comprising a cell expressing TAS2R receptor on its surface is used in the method. In another variation, isolated TAS2R receptor or cell membranes comprising TAS2R receptor are employed. The binding may be measured directly, e. g., by using a labeled compound, or may be measured indirectly. Compounds identified as binding a TAS2R receptor may be further tested in other assays including TAS2R activity assays and/or in vivo models, in order to confirm or quantitate their activity.

Ligand binding to a TAS2R protein, a domain, or chimeric protein can be tested in solution, in a bilayer membrane, attached to a solid phase, in a lipid monolayer, or in vesicles. Ligand binding to a TAS2R receptor can be tested using, e.g., changes in spectroscopic characteristics (e.g., fluorescence, absorbance, refractive index), or in hydrodynamic (e.g., shape), chromatographic, or solubility properties.

The TAS2R polypeptide or polynucleotide employed in such a test may either be free in solution, attached to a solid support, borne on a cell surface, located intracellularly, or associated with a portion of a cell. One skilled in the art can, for example, measure the formation of complexes between a TAS2R receptor or polynucleotide and the compound being tested. Alternatively, one skilled in the art can examine the diminution in complex formation between a TAS2R receptor or polynucleotide and its substrate caused by the compound being tested. In some embodiments, the recognition sites of the TAS2R receptor or polynucleotide are coupled with a monitoring system, either electrical or optical. An appropriate chemical stimulus can bind to the receptor's ligand binding domain, changing the receptor conformation to a degree that the coupled electronics or optical changes can be observed on a read-out. In an embodiment, the solid support is formulated into a feline-specific electronic tongue or biosensor.

In an embodiment of a solution assay, the methods can comprise the steps of contacting a TAS2R receptor with one or more test compound and identifying the compounds that bind to the TAS2R receptor. Identification of the compounds that bind the TAS2R receptor can be achieved by isolating the TAS2R polypeptide/binding partner complex, and separating the binding partner compound from the TAS2R polypeptide. In one aspect, the TAS2R polypeptide/binding partner complex is isolated using an antibody immunospecific for either the TAS2R receptor or the test compound. In still other embodiments, either the TAS2R receptor or the test compound comprises a label or tag that facilitates its isolation, and methods to identify binding partner compounds include a step of isolating the TAS2R polypeptide/binding partner complex through interaction with the label or tag.

In one variation of an in vitro assay, the method comprises the steps of contacting an immobilized TAS2R receptor with a test compound and detecting binding of the test compound to the TAS2R receptor. In an alternative embodiment, the test compound is immobilized and binding of TAS2R receptor is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into a feline-specific electronic tongue or biosensor.

In another embodiment, cell-based assays are used to identify binding partner compounds of a TAS2R receptor. In one embodiment, the method comprises the steps of contacting a TAS2R receptor expressed on the surface of a cell with a test compound and detecting binding of the test compound to the TAS2R receptor. In some embodiments, the detection comprises detecting a physiological event in the cell caused by the binding of the molecule.

In another embodiment, high throughput screening (HTS) for compounds having suitable binding affinity to TAS2R receptor is employed. Briefly, large numbers of different test compounds are synthesized on a solid substrate. The test compounds are contacted with TAS2R receptor and washed.

Bound TAS2R receptor is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed TAS2R receptor can be used for HTS binding assays in conjunction with a ligand, such as an amino acid or carbohydrate. The identified ligand is labeled with a suitable radioisotope, including, $^{121}$I, $^{3}$H, $^{35}$S or $^{32}$P, by methods that are well known to those skilled in the art. Alternatively, the ligands may be labeled by well-known methods with a suitable fluorescent derivative (Baindur et al., Drug Dev. Res., 1994, 33, 373-398; Rogers, Drug Discovery Today, 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand. Alternative methods include a scintillation proximity assay (SPA) or a FlashPlate format in which such separation is unnecessary. Binding of fluorescent ligands can be detected in various ways, including fluorescence energy transfer (FRET), direct spectrophotofluorometric analysis of bound ligand, or fluorescence polarization.

In still other embodiments, either the TAS2R receptor or the test compound comprises a label or tag that facilitates its isolation, and methods to identify test compounds include a step of isolating the TAS2R polypeptide/test compound complex through interaction with the label or tag. An exemplary tag of this type is a poly-histidine sequence, generally around six histidine residues, that permits isolation of a compound so labeled using nickel chelation. Other labels and tags, such as the FLAG tag (Eastman Kodak, Rochester, N.Y.), are well known and routinely used in the art.

Detection of binding can be accomplished using a radioactive label on the compound that is not immobilized, using a fluorescent label on the non-immobilized compound, using an antibody immunospecific for the non-immobilized compound, using a label on the non-immobilized compound that excites a fluorescent support to which the immobilized compound is attached, as well as other techniques well known and routinely practiced in the art.

Other assays may be used to identify specific ligands of a TAS2R receptor, including assays that identify ligands of the target protein through measuring direct binding of test ligands to the target, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system, a genetic assay for detecting interactions between two proteins or polypeptides.

In any of the methods disclosed herein, to be considered a ligand of the TAS2R receptor polypeptide, the test compound must alter the measured interaction by an amount sufficient to achieve a statistically significant difference between the responses in the presence vs. the absence of the test compound. In an embodiment, to be considered a ligand, the test compound must alter the measured interaction by an amount sufficient to achieve a statistically significant difference between the responses in the presence vs. the absence of the test compound. Statistical significance can be determined by any appropriate statistical test known in the art, such as a t-test. For example, to be of statistical significance, the p-value is at least 0.05, at least 0.01, or at least 0.001.

Also disclosed are methods of identifying compounds that modulate (i.e., increase or decrease) activity of TAS2R receptor comprising contacting a TAS2R receptor with a compound, and determining whether the compound modifies activity of TAS2R receptor. In another embodiment, the method comprises contacting a TAS2R receptor with a known TAS2R receptor ligand in the presence or absence of a test compound. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist.

In an embodiment, TAS2R protein activity is measured by expressing a TAS2R gene in a heterologous cell with a promiscuous G-protein that links the receptor to a phospholipase C signal transduction pathway (see Offermanns & Simon, J. Biol. Chem. 270:15175-15180 (1995)). Optionally the cell line is a eukaryotic cell line which does not naturally express TAS2R genes (e.g., Life Technologies Cat# R700-07) and the promiscuous G-protein is G$\alpha$15 (Offermanns & Simon, supra).

In an embodiment, a TAS2R polypeptide is expressed in a eukaryotic cell as a chimeric receptor with a heterologous, chaperone sequence that facilitates its maturation, targeting through the secretory pathway or membrane localization. In a preferred embodiment, the heterologous sequence is a rhodopsin sequence, such as an N-terminal fragment of a rhodopsin. Such chimeric TAS2R receptors can be expressed in any eukaryotic cell, such as Life Technologies Cat# R700-07 cells. Preferably, the cells comprise a functional G protein, e.g., G$\alpha$15, that is capable of coupling the receptor to an intracellular signaling pathway or to a signaling protein such as phospholipase C$\beta$. Activation of such expressed receptors in such cells can be detected using any standard method, such as by detecting changes in intracellular calcium by detecting FURA-2 dependent fluorescence in the cell.

In another embodiment, transcription levels can be measured to assess the effects of a test compound on signal transduction. A host cell containing a TAS2R protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using Northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, luciferase, [beta]-galactosidase and alkaline phosphatase. Furthermore, the protein of interest can be used as an indirect reporter via attachment to a second reporter such as green fluorescent protein (see, e.g., Mistili & Spector, Nature Biotechnology 15:961-964 (1997)). The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

In an embodiment, a method for identifying an agonist of a feline TAS2R receptor comprises contacting a feline Tas2R receptor polypeptide disclosed herein with a test compound; and detecting an increase in biological activity of the receptor in the presence of the compound relative to biological activity of the polypeptide in the absence of the compound.

In an embodiment, a method for identifying an antagonist of a feline Tas2R receptor comprises contacting a feline Tas2R receptor polypeptide disclosed herein with a test compound; and detecting a decrease in biological activity of the receptor in the presence of the compound relative to biological activity of the polypeptide in the absence of the compound.

Receptor-G-protein interactions can also be examined. For example, binding of the G-protein to the receptor or its release from the receptor can be examined. For example, in the absence of GTP, an agonist will lead to the formation of a tight complex of a G protein (all three subunits) with the receptor. This complex can be detected in a variety of ways, as noted above. Such an assay can be modified to search for antagonists, e.g., by adding an agonist to the receptor and G protein in the absence of GTP, which form a tight complex, and then screen for antagonists by looking at dissociation of the receptor-G protein complex. In the presence of GTP, release of the alpha subunit of the G protein from the other two G protein subunits serves as a criterion of activation.

In some embodiments, TAS2R-Gustducin interactions are monitored as a function of TAS2R receptor activation. Ligand dependent coupling of TAS2R receptors with Gustducin can be used as a marker to identify modifiers of any member of the TAS2R family.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, Nature 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. The generation of IP3 can be measured using various commercially available kits. Some exemplary kits to detect the generation of IP3 use antibodies specific for IP3 which can detect IP3 in a cell lysate in a western blot or an ELISA; alternatively the antibodies are fluorescently labeled and detected using a plate reader.

Modulation of receptor activity (taste transduction) can be assayed by measuring changes in intracellular Ca2+ levels, which change in response to modulation of the TAS2R signal transduction pathway via administration of a molecule that associates with a TAS2R protein. Changes in Ca2+ levels are optionally measured using fluorescent Ca2+ indicator dyes and fluorometric imaging.

In an embodiment, assays for G-protein coupled receptors include cells that are loaded with ion or voltage sensitive dyes to report receptor activity. Assays for determining activity of such receptors can also use known agonists and antagonists for other G-protein coupled receptors as positive or negative controls to assess activity of tested compounds. In assays for identifying modulatory compounds (e.g., agonists, antagonists, modulators), changes in the level of ions in the cytoplasm or membrane voltage will be monitored using an ion sensitive or membrane voltage fluorescent indicator, respectively. Ion-sensitive indicators and voltage probes that may be employed are commercially available from a variety of sources. For G-protein coupled receptors, promiscuous G-proteins such as Gα15 and Gα16 can be used in the assay of choice. Such promiscuous G-proteins allow coupling of a wide range of receptors.

Activated GPCR proteins become substrates for kinases that phosphorylate the C-terminal tail of the receptor (and possibly other sites as well). Thus, agonists will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR proteins. For example, compounds that modulate the duration a taste receptor stays active would be useful as a means of prolonging a desired taste or cutting off an unpleasant one.

Changes in ion flux may be assessed by determining changes in polarization (i.e., electrical potential) of the cell or membrane expressing a TAS2R protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode. Whole cell currents are conveniently determined using standard methodology known in the art. Other known assays include: radiolabeled ion flux assays and fluorescence assays using voltage-sensitive dyes. Generally, the compounds to be tested are present in the range from 1 pM to 100 mM.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., Proc. Natl. Acad. Sci. U.S.A. 88:9868-9872 (1991) and Dhallan et al., Nature 347:184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, the changes in intracellular cAMP or cGMP can be measured using immunoassays. The method described in Offermanns & Simon, J. Biol. Chem. 270: 15175-15180 (1995) may be used to determine the level of cAMP. Also, the method described in Felley-Bosco et al., Am. J. Resp. Cell and Mol. Biol. 11:159-164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of counts per minute (cpm) in the presence of agonist to cpm in the presence of buffer control. Likewise, fold inhibition is determined by calculating the ratio of cpm in the presence of antagonist to cpm in the presence of buffer control (which may or may not contain an agonist).

The effects of the test compounds upon the function of the polypeptides can be measured by examining any of the parameters described above. Any suitable physiological change that affects GPCR activity can be used to assess the influence of a test compound on the polypeptides disclosed herein. When the functional consequences are determined using intact cells, animals or animal behavior, one can also measure a variety of effects such as neurotransmitter release, hormone release, transcriptional changes to both known and uncharacterized genetic markers (e.g., Northern blots), changes in cell metabolism such as cell growth or pH changes, and changes in intracellular second messengers such as $Ca^{2+}$, IP3, cGMP, or cAMP.

Samples or assays that are treated with a test compound that is a potential TAS2R agonist are compared to control samples without the test compound, to examine the extent of modulation. Activation of a TAS2R protein is achieved when the TAS2R activity value relative to the control is 110%, optionally 150%, 200-500%, or 1000-2000%.

Samples or assays that are treated with a known agonist and a test compound that is a potential TAS2R antagonist are compared to control samples treated with the known agonist without the test compound, to examine the extent of modulation. The control samples are assigned a relative value of 100%. Inhibition of a TAS2R protein is achieved when the TAS2R activity value relative to the control is about 90%, optionally 50%, optionally 25-0%.

Agents that modulate TAS2R receptor activity or expression also may be identified, for example, by incubating a putative modulator with a cell containing a TAS2R polypeptide or polynucleotide and determining the effect of the putative modulator on TAS2R receptor activity or expression. In an embodiment, to be considered a modulator, the putative modulator must alter the measured interaction by an amount sufficient to achieve a statistically significant difference between the responses in the presence vs. the absence of the putative modulator. Statistical significance can be determined by any appropriate statistical test known in the art, such as a t-test. For example, to be of statistical significance, the p-value is at least 0.05, at least 0.01, or at least 0.001. The selectivity of a compound that modulates the activity of TAS2R receptor can be evaluated by comparing its effects on TAS2R receptor to its effect on other TAS2R receptors. Selective modulators may include, for example, antibodies and other proteins, peptides, or organic molecules that specifically bind to a TAS2R polypeptide or a TAS2R receptor-encoding nucleic acid. Compounds identified as modulating TAS2R receptor activity may be further tested in other assays including in vivo models, in order to confirm or quantitate their activity.

TAS2R polynucleotides and polypeptides, and their homologs, are useful tools for identifying taste receptor expressing cells, for taste perception, and for examining taste transduction. TAS2R family member-specific reagents that specifically hybridize to TAS2R nucleic acids, such as TAS2R probes and primers, and TAS2R specific reagents that specifically bind to a TAS2R protein, e.g., TAS2R antibodies are used to examine taste cell expression and taste transduction regulation. For example, a TAS2R antibody can be used to identify and/or isolate feline taste cells expressing the particular TAS2R from a mixed feline cell population. For example, polynucleotide probes disclosed herein may be used in tissue distribution studies and diagnostic assays.

Also provided are kits for screening for modulators of TAS2R family members. Such kits can be prepared from readily available materials and reagents. For example, such kits can comprise any one or more of the following materials: TAS2R nucleic acids or proteins, reaction tubes, and instructions for testing TAS2R activity. Optionally, the kit contains a biologically active TAS2R receptor. A wide variety of kits and components can be prepared, depending upon the intended user of the kit and the particular needs of the user.

Antibodies to the fTAS2R receptors and the chimeric polypeptides are also disclosed.

For preparation of monoclonal or polyclonal anti-fTAS2R antibodies, any technique known in the art can be used. Techniques for the production of single chain antibodies (U.S. Pat. No. 4,946,778) can be adapted to produce antibodies to polypeptides disclosed herein. Also, transgenic mice, or other organisms such as other mammals, may be used to express humanized antibodies. Alternatively, phage display technology can be used to identify antibodies and heteromeric Fab fragments that specifically bind to selected antigens. In one embodiment isolated DNA sequences encoding a monoclonal antibody or a binding fragment thereof are obtained by screening a DNA library from human B cells according to the general protocol outlined by Huse et al., Science 246:1275-1281 (1989).

Monoclonal antibodies and polyclonal sera can be collected and titered against the protein immunogen in an immunoassay, for example, a solid phase immunoassay with the immunogen immobilized on a solid support. Typically, polyclonal antisera with a titer of $10^4$ or greater are selected and tested for their cross reactivity against non-TAS2R proteins, or even other TAS2R family members or other related proteins from other organisms, using a competitive binding immunoassay. Specific polyclonal antisera and monoclonal antibodies will usually bind with a $K_d$ of at least about 0.1 mM, more usually at least about 1 µM, specifically at least about 0.1 µM or better, and more specifically 0.01 µM or better.

Immunoassays can be used to detect, qualitatively or quantitatively, a fTAS2R, e.g., to identify taste receptor cells, especially bitter taste receptor cells, and variants of TAS2R family members.

The anti-fTAS2R antibodies can also be used to isolate feline taste cells from a mixed population of cells obtained from a feline. In an embodiment, isolation of the feline taste cells bound to the anti-fTAS2R antibody can be achieved by flow cytometry. Other methods known in the art can also be used.

As known in the art, taste behavior can be determined in a short term assay which directly measures taste preferences by counting licking responses of an animal, e.g., a mouse, using a multi-channel gustometer (e.g., the Davis MS160-Mouse gustometer, DiLog instruments, Tallahassee, Fla.). The mean rate that a mouse will lick a tastant relative to their sampling of an appropriate control (ratio defined as lick rate relative to control) indicates whether the stimulus is appetitive, neutral or aversive. In addition, the change in intake of a palatable stimulus can be evaluated in the presence of the test stimulus to assess enhancement or suppression of the palatable stimulus.

In a further embodiment, animals can be trained to discriminate qualitatively distinct stimuli using operant testing methods known in the art. These animals can then be used to determine qualitative similarity between two stimuli, regardless of palatability or preference.

To determine if the fTAS2R receptors are activating brain areas reported to be involved in appetitive or aversive taste responses, electrodes may be attached to these brain areas and animals tested in an awake or anesthetized state.

Alternatively, other noninvasive methods to monitor neural activity such as positron emission tomography (PET) or electroencephalography may be used to monitor neural activity associated with appetitive or aversive taste responses. Such methods may also be used to evaluate the impact of various factors such as age, experience or nutritional state on neural activity elicited by stimuli identified in cell-based experiments to modify receptor function.

Also provided are kits comprising at least one composition, polypeptide, or nucleic acid disclosed herein, optionally contained in a single package. The kits may optionally include, e.g., instructions for use of the kit components in detecting a fTAS2R receptor or a polynucleotide encoding a fTAS2R receptor, or compounds altering the activity of a TAS2R receptor.

In an embodiment, the kit comprises at least one anti-TAS2R antibody disclosed herein and reagents for detecting a complex between the antibody and the TAS2R antigen. For example, the kit can include a buffer that enables binding reaction between the antibody and the TAS2R antigen in a biological sample, or components for producing the buffer.

The activity of TAS2R polypeptides can be assessed using a variety of in vitro and in vivo assays to determine functional, chemical, and physical effects, e.g., measuring ligand binding (e.g., radioactive ligand binding), second messengers (e.g., cAMP, cGMP, IP3, DAG, or $Ca^{2+}$), ion flux, phosphorylation levels, transcription levels, neurotransmitter levels, and the like. Furthermore, such assays can be used to test for inhibitors and activators of TAS2R family members. Such modulators of taste transduction activity are useful for customizing taste perception, for example to modify the detection of bitter tastes.

The TAS2R protein of the assay will typically be selected from a polypeptide having a sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; a conservatively modified variant of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or a sequence that is at least 70%, at least 80%, at least 90%, at least 95%, at least 97%, at least 98%, at least 99% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In an embodiment, the polypeptide has a sequence of SEQ ID NO:18 or SEQ ID NO:22.

In some embodiments, the polypeptide of the assays will comprise a domain of a TAS2R protein, such as an extracellular domain, transmembrane region, transmembrane domain, cytoplasmic domain, ligand binding domain, subunit association domain, active site, and the like. Either the TAS2R protein or a domain thereof can be covalently linked to a heterologous protein to create a chimeric protein used in the assays described herein. In an embodiment, the polypeptide has a domain from SEQ ID NO:18 or SEQ ID NO:22.

Modulators of TAS2R receptor activity are tested using TAS2R polypeptides as described above, either recombinant or naturally occurring. The protein can be isolated, expressed in a cell, expressed in a membrane derived from a cell, expressed in tissue or in an animal, either recombinant or naturally occurring. For example, sections or dissociated cells from a TAS2R-expressing tissue, transformed cells, or membranes can be used. Assays may also be prepared using TAS2R polypeptides in artificial/synthetic membrane systems. Modulation is tested using any of the in vitro or in vivo assays described herein. Taste transduction can also be examined in vitro with soluble or solid state reactions, using a full-length TAS2R-GPCR or a chimeric molecule such as an extracellular domain or transmembrane region, or combination thereof, of a TAS2R receptor covalently linked to a heterologous signal transduction domain, or a heterologous extracellular domain and/or transmembrane region covalently linked to the transmembrane and/or cytoplasmic domain of a TAS2R receptor. Furthermore, ligand-binding domains of the protein of interest can be used in vitro in soluble or solid state reactions to assay for ligand binding. In numerous embodiments, a chimeric receptor will be made that comprises all or part of a TAS2R polypeptide as well an additional sequence that facilitates the localization of the TAS2R to the membrane, such as a rhodopsin, e.g., an N-terminal fragment of a rhodopsin protein.

The compounds tested as modulators or ligands of a TAS2R family member can be any compound, including small molecules, or more complex molecules such as biological molecules, for example a protein, sugar, nucleic acid or lipid. Alternatively, modulators can be genetically altered versions of a TAS2R gene. Essentially any chemical compound can be used as a potential modulator or ligand in the assays and methods disclosed herein. In certain useful embodiments the compounds can be dissolved in aqueous or organic solutions (for example, DMSO solutions). The assays are designed to screen libraries of chemicals, including large libraries by automating the assay steps and providing compounds from any convenient source to assays, which are typically run in parallel (e.g., in microtiter formats on microtiter plates in robotic assays).

Knowledge of the structure of two or more agonists for a single receptor allows the skilled person to rationally design further libraries of compounds to screen for interaction with the receptor. Computer modeling of such compounds is also facilitated. Screening the compound libraries enables the development of compositions to suppress or eliminate bitter tasting components of food in particular animal foods, nutrients and dietary supplements and pharmaceutical or homeopathic preparations containing such phytochemicals. Alternatively the screen allows for the identification of structurally related agonists to enhance a bitter response in the production of appetite suppressants, animal repellents, and the like.

Flavor compositions, edible compositions, and methods of manufacturing the edible compositions and flavor compositions are disclosed herein A flavor composition is a composition which can be added to an edible composition for an animal to improve acceptance of the edible composition for consumption by the animal. Examples of edible compositions include foods, treats, nutritional supplements, pharmaceuticals, oral care materials such as dental products, chewable products, drinkable products, and the like. The edible composition can be in the form of a tablet, capsule, caplet, edible film, wet food, liquid food, treat or kibble.

In one aspect, a flavor composition comprises a compound that is an agonist, antagonist, or modulator of a feline TAS2R receptor. In an embodiment; the flavor composition further comprises a palatability enhancer; optionally, an adhesive compound to help adhere the flavor composition to the edible composition; and optionally, a compound for providing color or aroma for a human, wherein the flavor composition is a solid, liquid, powder, paste, gel, sprayable formulation or spreadable formulation. In an embodiment, the flavor composition is a coating composition and further comprises the adhesive compound. Alteration or masking of perceived bitterness of an edible composition can be tested using any of the behavioral assays for palatability disclosed herein, such as a standard two bowl comparison.

"Basal food composition," as used herein, refers to an animal food combinable with the flavor composition. In one embodiment, the animal food is formulated for felines, and includes dry food, canned food, semi-dry food, edible treats, and the like, and combinations comprising one or more of the foregoing foods. Various sizes and shapes of the basal food composition may be employed as long as the food is acceptably consumable by a recipient (such as an animal, particularly a feline) in an amount so that the animal receives a normal daily ration providing the known essential nutrients. A basal food composition may be uncoated, or may be coated, for example, with a coating comprising lipids. If desired, feeding may be carried out by feeding the animal one or more times per day.

In an embodiment, the flavor composition is combined with an edible composition, for example a basal food composition (e.g. for a feline), in an amount effective to impart increased palatability of the edible composition to the animal. Effective amounts of such flavor compositions are readily determined by one of ordinary skill in the art without undue experimentation, particularly in view of the general guidance provided below.

In an embodiment, the flavor composition may be combined with a basal food composition in a manner such that the flavor composition is incorporated into the basal food composition. By incorporated it is meant that the flavor composition is intimately associated with the edible composition and does not become substantially dissociated, for example, during normal storage conditions. In one embodiment, the flavor composition is substantially uniformly dispersed throughout the edible composition. In other embodiments, the distribution of the flavor composition may intentionally not be uniform. In such embodiments the flavor composition may provide bits or pieces that are intermixed with the basal food. In various embodiments, the flavor composition may be deposited in the edible composition in an amount effective to provide about 0.5 wt % to about to about 3 wt %, specifically about 0.8 wt % to about 2.5 wt %, and more specifically about 1 wt % to about 2 wt % of the dry weight of the edible composition.

In another embodiment, the flavor composition is deposited on the surface of the edible composition, for example in the form of a coating. Coating the edible composition includes the topical deposition of the flavor composition onto the surface of the edible composition, such as by spraying, dusting, and the like. The coating comprising the flavor composition may comprise one or more fats to help adhere the flavor composition to the surface. It may further or alternatively comprise other components useful to facilitate adhesion of the flavor composition to the surface of the edible composition. It is possible, although not required, that the flavor composition be coated onto the edible composition uniformly or that uniform distribution of the flavor composition be achieved, for example, by repeatedly tumbling the coated food. One or more coats may be applied. The flavor composition may be deposited onto the surface of the edible composition in an amount effective to provide about 0.5 wt % to about to about 3 wt %, specifically about 0.8 wt % to about 2.5 wt %, and more specifically about 1 wt % to about 2 wt % of the dry weight of the basal animal food composition.

The flavor composition may be both dispersed in and coated onto the edible composition, such as a dry animal food composition. In one embodiment, the finished animal food product is packaged for sale and ultimately fed to the animal. In other embodiments, the flavor composition may be packaged for combination with a food prior to serving. In some embodiments, the animal is a feline.

In an embodiment, the flavor composition may further comprise an additional palatability enhancer such as a flavoring. Suitable flavorings include, for example, a vegetable flavoring, a meat flavoring, (e.g., liver flavoring), a cheese flavoring, yeast, sodium pyrophosphate, a fat, an acid phosphate, a phosphate salt, and/or other food or flavor ingredients utilized by the flavor industry in order to improve palatability. Suitable meat flavorings include, for example, meat-derived flavorings (e.g., beef, pork, bacon, lamb, ham, fish, chicken, turkey, and/or other poultry flavoring).

Palatability or acceptance of a food refers to the overall willingness of an animal, such as a feline, to eat a certain food. Developing preferred flavorants and palatability enhancers for animals such as pets is subjective. Flavorants which work for humans do not always work with felines. Similarly, a flavorant which is effective with one animal species may not work as well with a different animal species. The skilled artisan will appreciate that palatability testing is routinely used to determine preferences for animals with respect to food and flavorants. For purposes herein, such palatability testing will be effective and straight forward to implement for testing preferences for flavorants for any animal, including felines. Traditional methods of developing flavor compositions for increasing palatability employ a variety of candidate flavorants selected empirically, based on knowledge of how these ingredients are perceived by humans, and a "trial and error" approach is used to empirically test each candidate relative to a known target product or to identify more preferable palatants. The disclosed feline TAS2R receptor polypeptides permit intentional design of palatability enhancers based on the taste receptors for the target species and will substantively improve and shorten the process for palatant development.

In one embodiment, the flavor composition is a palatant for a feline food and the flavor composition exhibits improved palatability for the feline compared to the feline food without the flavor composition, as measured by improved consumption of the feline food comprising the palatant compared to the animal food in the absence of the palatant.

The flavor composition may be used as a liquid flavor in either unconcentrated or concentrated form. If the flavor composition is to be a dry flavor composition, the flavor composition may be dried in a suitable dryer such as, for example, a spray dryer, or an oven. The flavor composition may comprise a variety of other useful components, for example, maltodextran, gum, or a combination which may be useful for providing the composition with one or more preferred functionalities such as the ability to bind to a food or to retain a desired texture, viscosity, flowability, color, aroma or the like. Such components and their uses will be readily understood by the skilled food scientist.

Palatability testing can be performed by a standard two bowl comparison. In this test, each animal is presented with two bowls of food, each containing a measured amount of either a control ration or a test ration. The control and test rations contain the same basal compositions. The animal is allowed to select the food it prefers. The amount of food eaten from each bowl is measured. A direct comparison of the amount eaten from the two rations gives a reliable indication of relative palatability.

For example, a feline may be given two bowls with equal amounts of food, one containing the flavor composition to be tested and the other not containing the flavor composition. The amount of food in the two bowls is weighed prior to giving them to the feline. During the test, steps should be taken to ensure that the feline does not finish one bowl and continue to the other because it is still hungry. This can be accomplished, for example, by limiting the time of the feline with the two bowls, or by providing enough food in each bowl to fully satisfy the feline.

At the end of the test, the two bowls are weighed again to determine the amount of food eaten from each bowl. If more food is eaten from the bowl with the test flavor composition (bowl A), the ingestion ratio is recorded as a positive value to indicate that the flavor composition had a positive effect on the animal preference. If more food was eaten from the bowl with the control food (bowl B), the ratio is recorded as a negative value to indicate that the flavor composition did not perform as well as the control food.

For example, the flavor compositions are applied to a dry basal feline food composition and multiple felines, e.g., ten, are fed for a period of time (e.g. two days). The bowl position is changed daily to eliminate bias due to the animals showing a preference for right or left placement of the bowls. The preference of each animal for each bowl can be calculated as an intake ratio (IR) for that particular animal, for example the IR for animal 1=(grams consumed from bowl A)/(total grams consumed from bowl A+bowl B). The average preference is calculated as the average value of each day for the duration of the test period. Thus an IR value close to 0.5 indicates equal preference. IR values greater than 0.5 and typically above 0.55 indicate preference. The degree of preference estimation based on IR scores can be determined by number of animals used and statistical analysis of the data.

A method for making the flavor composition for coating or incorporating into an edible composition to be administered to an animal is disclosed.

In an embodiment, the method comprises mixing an agonist, an antagonist, or a modulator of a feline TAS2R receptor polypeptide; optionally, a palatability enhancer; optionally, a compound to help adhere the flavor composition to the edible composition; and optionally, a compound for providing color or aroma with an ingredient selected from the group consisting of meat products, meat by-products, fish products, fish by-products, dairy products, dairy by-products, sources of microbial proteins, vegetable proteins, carbohydrates and amino acids carrier to obtain a flavor composition, wherein the flavor composition is a liquid, solid, powder, paste, gel, spreadable formulation, granule, or sprayable formulation. In an embodiment, an agonist or an antagonist of the feline TAS2R receptor polypeptide is mixed into the composition. In an embodiment, the agonist is denatonium, aloin, or PTC and the antagonist is probenecid.

To make a liquid flavor composition, for example, commercially available liquid ingredients are combined in a mixer with an agonist, an antagonist, or a modulator of a feline TAS2R receptor polypeptide. Wet ingredients are ground or emulsified to a slurry and the liquid ingredients are combined therewith. A commercially available protease may be added to the slurry to hydrolyze proteins, and later inactivated with heat, acid or another method. Preservatives such as sorbic acid can also be added. Water is added to adjust the viscosity and the solids content of the slurry to facilitate spray application.

A dry formulation of the flavor composition can be prepared by combining commercially available dry ingredients, including amino acids, inorganic salts and organic materials with an agonist, an antagonist, or a modulator of a feline TAS2R receptor polypeptide in the desired proportions in a batch mixer and blending to homogeneity prior to drying.

According to another dry formulation embodiment, wet and dry ingredients are combined by mixing the wet ingredients with all or some of the dry ingredients in a mixer until a homogenous mixture is formed. The mixture is dried by evaporation or lyophilization, for example, to form a dry, powdery product that is then blended with any remaining dry ingredients in a tumbler until a homogeneous mixture is formed.

Methods of preparing an edible composition for an animal are disclosed.

In an embodiment, the method comprises contacting an edible composition or a component thereof with a fTAS2R receptor polypeptide disclosed herein for a time sufficient to reduce the amount of a bitter compound from the edible composition or component thereof. The time to reduce the amount of the bitter compound can be determined by one of skill in the art. The contacting can occur in a continuous, semi-continuous, or batch process. In an embodiment, the edible composition is for a feline In an embodiment, the method comprises adding a compound to an edible composition to decrease the palatability of the edible composition to an animal, wherein the compound is an agonist or a positive modulator of a feline bitter taste receptor. In an embodiment, the palatability is decreased to an extent that a feline consumes 10 to 30% less of the edible composition with the added compound than the edible composition without the added compound. In an embodiment, the decrease in palatability is measured as decrease in calories of edible composition consumed, weight of edible composition consumed, or volume of edible composition consumed.

A method of formulating an edible composition with enhanced palatability for an animal is disclosed.

In an embodiment, the method comprises determining the presence of a compound which is an agonist, antagonist, or modulator of a feline TAS2R receptor polypeptide in an edible composition; and enhancing palatability of the edible composition by if the compound is an agonist or a positive modulator, increasing the amount of an antagonist for the receptor in the edible composition or reducing the amount of the compound in the edible composition, or if the compound is an antagonist or a negative modulator, increasing the amount of the compound in the edible composition. The amount of the compound can be increased by applying a flavor composition comprising the compound to the edible composition such that the flavor composition is incorporated into or a leastleas partially coats the edible composition.

Also disclosed are methods of administering a bitter compound to an animal (e.g. a feline) in need thereof. The skilled artisan will appreciate that in some cases a human or other animal may be in need of a bitter compound (e.g. a pharmaceutical, a nutrient, or the like) and that it can be challenging to administer the compound to the animal.

In an embodiment, the method comprises administering a feline edible composition to a feline, wherein the edible composition comprises a feline bitter compound and a compound that alters perceived bitterness of the edible composition, masks the bitter compound in the edible composition, or acts as an agonist, antagonist, or modulator of a feline TAS2R receptor in the feline to alter bitter taste perception by the feline. In an embodiment, the bitter compound comprises a therapeutic, a nutritional supplement or an oral care product. A nutritional supplement refers to a supplement intended to provide nutrients that may otherwise not be consumed in sufficient quantities and includes vitamins, minerals, fiber, probiotics, fatty acids, and amino acids. A therapeutic or pharmaceutical refers to a compound, element, or mixture that when administered to a subject, alone or in combination with another compound, element, or mixture, confers, directly or indirectly, a physiological effect on the subject. An oral care product refers to a product used to promote healthy teeth, gums, freshen breath or prevent or treat oral disease.

Methods of manufacturing feline edible compositions are also disclosed.

In an embodiment, the method comprises contacting a feline food composition or a component thereof with a TAS2R receptor polypeptide herein for a time sufficient to remove a bitter compound from the food product or component. In an embodiment, the TAS2R receptor is bound to a solid support that can be separated from the food composition. In an embodiment, the contacting is a continuous operation. In an embodiment, the food composition is contacted with a plurality of TAS2R receptor polypeptides.

In an embodiment, the method comprises determining the presence of one or more bitter compounds in an edible composition; determining a bitterness profile of the edible composition based on the one or more bitter compounds determined to be present; and adding a compound to or removing a compound from the edible composition to enhance the palatability of the edible composition, wherein the compound alters the bitterness profile of the edible composition, masks one or more of the bitter compounds present in the edible composition, or acts as an agonist, antagonist or modulator of a feline bitter taste receptor. In an embodiment, adding the compound to the edible composition comprises applying a coating solution to the edible composition comprising the compound such that a coating at least partially surrounds the feline edible composition. In an embodiment, the edible composition is a basal food, a flavor composition, a treat, a therapeutic, or a nutritional supplement. The presence of a bitter compound in a edible composition can be determined by a method disclosed herein, or by any other method known in the art. A bitterness profile of an edible composition refers to an enumeration of bitter compounds determined to be present in the edible composition, and optionally further includes the amount of a given bitter compound in the edible composition. In an embodiment, the edible composition is for a feline.

Also disclosed are repellent compositions. In an embodiment, the repellent composition can comprise a feline TAS2R receptor agonist or positive modulator in a sufficient amount to elicit rejection, for example at least 0.05% to about 30% by weight, and optionally aromatics or perfumes such as rosemary oil, mint oil, cinnamon oil, limonene, or eugenol, and one or more inert ingredients such as a liquid diluents, carriers, thickeners, surface-active agents, preservatives, aromatics, deodorizers, antibacterial agents, antifungal agents, antimicrobial agents, biocide agents, and one or more of several types of adjuvant including, but not limited to, wetting agents, spreading agents, sticking agents, foam retardants, buffers and acidifiers. Suitable liquid diluents include water, petroleum distillates, or other liquid carriers with or without surface active agents. Examples of carriers include bentonite, fullers earth, additional clays, talc, chalk, quartz, attapulgite, montmorillonite or diatomaceous earth, vermiculite, highly dispersed silicic acid, alumina and silicates, calcite, marble, pumice, sepiolite and dolomite, inorganic and organic meals, sawdust, coconut shells, corn cobs and tobacco stalks. In an embodiment, the repellent composition can further comprise a propellant gas for dispensing as a spray, such as Figen 11/12 or propane/butane, e.g. in a ratio of 15:85. In an embodiment, the fTAS2R agonist is denatonium, aloin, or PTC.

Other embodiments of the present invention are described in the following non-limiting Examples.

EXAMPLES

Example 1

Determining Feline Bitter Taste Receptor (TAS2R) Gene and Polypeptide Sequences

In this example, feline TAS2R genes were identified, by querying the NCBI *Felis catus* whole genome shotgun contigs database with human bitter receptor gene sequences. Human gene sequences used are identified by NCBI Gene IDs in Table 2.

TABLE 2

NCBI Gene IDs for all functional and pseudogene hTAS2Rs used to identify feline bitter genes.

| Functional Genes | | Pseudogenes | |
|---|---|---|---|
| Human Bitter Receptor gene | Gene ID | Human Bitter Receptor gene | Gene ID |
| TAS2R1 (TAS2R1; TRB7) | 50834 | TAS2R2P (PS9; TAS2R2; TAS2R02; TAS2R2) | 338396 |
| TAS2R3 (TAS2R3) | 50831 | TAS2R12P (PS10; TAS2R12; TAS2R12; TAS2R26) | 266656 |
| TAS2R4 (TAS2R4) | 50832 | | |
| TAS2R5 (TAS2R5) | 54429 | | |
| TAS2R7 (TAS2R7; TRB4) | 50837 | TAS2R15P (PS8; TAS2R15) | 266657 |
| TAS2R8 (TAS2R8; TRB5) | 50836 | TAS2R18 (PS4; TAS2R18; TAS2R65; TAS2R65; TAS2R65P) | 338414 |
| TAS2R9 (TAS2R9; TRB6) | 50835 | | |
| TAS2R10 (TRB2; TAS2R10) | 50839 | | |
| TAS2R13 (TRB3; TAS2R13) | 50838 | TAS2R62P (PS1; TAS2R62; TAS2R62) | 338399 |
| TAS2R14 (TRB1; TAS2R14) | 50840 | | |
| TAS2R16 (TAS2R16) | 50833 | TAS2R63P (PS6; TAS2R63) | 338413 |
| TAS2R19 (TAS2R19; TAS2R23; TAS2R48; MSTP058; TAS2R23; TAS2R48) | 259294 | TAS2R64P (PS2; TAS2R64; TAS2R64P) | 338412 |
| | | TAS2R67P (PS5) | 448991 |
| TAS2R20 (TAS2R20; TAS2R49; TAS2R56; TAS2R49) | 259295 | TAS2R68P (PS7; TAS2R68P) | 100653053 |
| TAS2R30 (TAS2R30; TAS2R47; TAS2R47) | 259293 | | |
| TAS2R31 (TAS2R31; TAS2R44; TAS2R53; TAS2R44) | 259290 | | |
| TAS2R38 (PTC; TAS2R38; TAS2R61) | 5726 | | |
| TAS2R39 (TAS2R39; TAS2R57) | 259285 | | |
| TAS2R40 (GPR60; TAS2R40; TAS2R58) | 259286 | | |
| TAS2R41 (TAS2R41; TAS2R59) | 259287 | | |
| TAS2R42 (TAS2R24; TAS2R55; hTAS2R55; TAS2R55) | 353164 | | |
| TAS2R43 (TAS2R43; TAS2R52) | 259289 | | |
| TAS2R45 (GPR59; TAS2R45; ZG24P) | 259291 | | |
| TAS2R46 (TAS2R46; TAS2R54) | 259292 | | |
| TAS2R50 (TAS2R50; TAS2R51; TAS2R51) | 259296 | | |
| TAS2R60 (TAS2R56; TAS2R60) | 338398 | | |

Individual contigs among the hits were downloaded for manual identification of start (ATG) and stop (TAA, TGA, or TAG) codons and to determine if the gene is likely full length. When sequences from both feline genome assemblies were obtained, they were compared.

Predicted functional genes were identified based on a set of rules selected to include a protein which is approximately 300 amino acids in length, the start site and stop site are in similar locations as the human protein when the blasted sequences are aligned, then the sequence was compared to the sequence of the orthologous canine bitter gene to verify that similarity was reasonable. Table 3 identifies canine bitter gene sequences used.

TABLE 3

NCBI Gene IDs for all functional and pseudogene canine TAS2Rs used

| | Functional Genes | | | Pseudogenes | |
|---|---|---|---|---|---|
| | Canine Bitter Receptor gene | Gene ID | | Canine Bitter Receptor gene | Gene ID |
| 1 | TAS2R1 (CAFA-TAS2R1) | 100271742 | 1 | TAS2R8P | 100682910 |
| 2 | Cafa-TAS2R2 | 100271741 | 2 | TAS2R9P | 100686911 |
| 3 | TAS2R3 (CAFA-TAS2R3) | 100271736 | 3 | Cafa-TAS2R44P | GenBank: AB249699.1 |
| 4 | TAS2R4 | 100688996 | | | |
| 5 | TAS2R5 (CAFA-TAS2R5) | 100271743 | 4 | TAS2R46-like | 100682759 |
| 6 | TAS2R7 (CAFA-TAS2R7) | 100271739 | 5 | TAS2R60-like | 100856773 |
| 7 | TAS2R10 (CAFA-TAS2R10) | 100271734 | 6 | TAS2R104-like | 100682833 |
| 8 | Cafa-TAS2R12 | 100271738 | | | |
| 9 | TAS2R38 (CAFA-TAS2R38) | 100271737 | | | |
| 10 | TAS2R39 (CAFA-TAS2R39) | 100271735 | | | |
| 11 | TAS2R40 | 608842 | | | |

TABLE 3-continued

NCBI Gene IDs for all functional and pseudogene canine TAS2Rs used

| Functional Genes | | Pseudogenes | |
| --- | --- | --- | --- |
| Canine Bitter Receptor gene | Gene ID | Canine Bitter Receptor gene | Gene ID |
| 12 TAS2R41 | 482734 | | |
| 13 TAS2R42 (CAFA-TAS2R55) | 100271731 | | |
| 14 Cafa-TAS2R43 | 100271744 | | |
| 15 TAS2R62-like | 608741 | | |
| 16 Cafa-TAS2R67 | 100271740 | | |

Table 4 below summarizes the full length feline genes identified. The % protein similarity between the feline gene and closest human homologue is presented in the table.

TABLE 4

Full length Feline Bitter Receptor Genes Identified

| Predicted Feline Gene | Functional human homologue | Best % similarity to human sequence |
| --- | --- | --- |
| TAS2R1 | yes | 60.5% |
| TAS2R2 | NO | 74.8% |
| TAS2R3 | yes | 74.4% |
| TAS2R4 | yes | 71.9% |
| TAS2R7 | yes | 74.4% |
| TAS2R9 | yes | 68.3% |
| TAS2R10 | yes | 67.8% |
| TAS2R12 | NO | 51.0% |
| TAS2R38 | yes | 67.6% |
| TAS2R42 | NO | 56.1% |
| TAS2R43 | yes | 59.0% |
| TAS2R44 | yes | 59.9% |
| TAS2R67 | NO | 47.6% |

Cloning of each of the feline bitter genes to confirm the DNA sequence was performed after amplifying the desired gene by polymerase chain reaction (PCR) using the genomic DNA of a single cat. Potential primers to amplify each feline gene were designed using commercial software. Sets of primers were selected from among those designed based on predicted annealing temperature, fidelity, potential for dimerization and mispriming, and location of the desired sequence in order to amplify the feline gene sequence and determine the DNA sequence from isolated feline genomic DNA. Primer pairs used to amplify each gene are shown in Table 5.

TABLE 5

Primers for genomic amplification

| Gene Name | F/R | SEQ ID NO | Sequence | Length |
| --- | --- | --- | --- | --- |
| fTAS2R1 | F | 32 | TCATGGTGGAGGTGAAGGATTG | 22 |
| fTAS2R1 | R | 33 | AGGTATGGCAGGCATCGTCAGC | 22 |
| fTAS2R2 | F | 34 | CAGGAATTGGCAGAAGGTCAGAT | 23 |
| fTAS2R2 | R | 35 | GGAGAAGGAAATTGCCAGAAAGAG | 24 |
| fTAS2R3 | F | 36 | AAATTGGGCAGAGACAAGAGACAGG | 25 |
| fTAS2R3 | R | 37 | CGGCACCGGAACCACAAGAG | 20 |
| fTAS2R4 | F | 38 | GGGGACAATTGGAAAAGGAAACG | 23 |
| fTAS2R4 | R | 39 | CTCAAAGGCCCACGAAGTCAGAT | 23 |
| fTAS2R7 | F | 40 | AGGATCATGAAAGGGAACGGGTCT | 24 |
| fTAS2R7 | R | 41 | GACAAAGAGAAAGAGGCAAAATCG | 24 |
| fTAS2R9 | F | 42 | CCGACAAAGAGGGCAGAAAAAGAC | 24 |
| fTAS2R9 | R | 43 | GACCTCCTCCGGCTCAGAAGAAGT | 24 |
| fTAS2R10 | F | 44 | GATATACGTTGGGCGCTCCTACT | 23 |
| fTAS2R10 | R | 45 | AGTGAAACCCTTACAGTGAATAG | 23 |
| fTAS2R12 | F | 46 | CAAGCAGTGTGACAGCAGCAGGTA | 24 |
| fTAS2R12 | R | 47 | GGAGAGGAAGGAAAGAAACGCACA | 24 |
| fTAS2R38 | F | 48 | GAAGTCCTGGCTTGTAATGTA | 21 |
| fTAS2R38 | R | 49 | CAAAACAAACTTGGGGAACTT | 21 |
| fTAS2R42 | F | 50 | ACACTGGAATCGCAAAGAAACACG | 24 |
| fTAS2R42 | R | 51 | GATCCTCAAAGACTCCTCAATAAG | 24 |
| fTAS2R43 | F | 52 | GCACAACCAGCGACATCAGACATT | 24 |
| fTAS2R43 | R | 53 | CCCAGGCGCCCCAAAAGA | 18 |
| fTAS2R44 | F | 54 | GCACAACCAGCGACATCAGACATT | 24 |
| fTAS2R44 | R | 55 | CCGGTGAGGGTAGATTATTTCCA | 23 |
| fTAS2R67 | F | 56 | ACCCAGGCGCCCCAGTATCT | 20 |
| fTAS2R67 | R | 57 | GCTTCCGGCATTTTTATTCC | 20 |

The process of amplification and cloning of a representative gene, TAS2R38, is briefly described. The fTAS2R38 sequence was amplified via PCR using Easy A High Fidelity PCR Cloning Enzyme (Agilent, Santa Clara Calif.), custom primers, and feline genomic DNA as a template.

The resulting PCR product was ligated into the pGEM-T Easy Vector (Promega, Madison Wis.). DH5-α bacterial cells (Life Technologies; Carlsbad, Calif.) were transformed with the vector. Plasmid was purified from cultures of the transformed DH5-alpha cells using the Plasmid Miniprep Kit (Omega BioTec, Norcross, Ga.). Sequencing of the gene using the purified plasmid DNA was performed by the Core DNA Sequencing Facility at the University of Illinois, Champaign-Urbana. The sequencing data was analyzed with SeqMan Pro (DNAStar, Madison Wis.) to determine the quality of the data and to edit the data.

The gene sequence determined from the isolated feline genomic DNA sequencing was compared against the sequences obtained from the whole genome shotgun contigs and analyzed to identify specific nucleotide differences, predicted protein sequence, and protein structure. Sequences disclosed in the sequence listing for each of the feline bitter taste receptor gene cDNAs and polypeptides are identified by the SEQ ID NOs shown in Table 6.

TABLE 6

SEQ ID NOs of feline bitter taste receptor gene cDNA and polypeptide sequences

| SEQ ID NO. | Feline TAS2R Sequence |
|---|---|
| 1 | R1 cDNA |
| 2 | R1 polypeptide |
| 3 | R2 cDNA |
| 4 | R2 polypeptide |
| 5 | R3 cDNA |
| 6 | R3 polypeptide |
| 7 | R4 cDNA |
| 8 | R4 polypeptide |
| 9 | R7 cDNA |
| 10 | R7 polypeptide |
| 11 | R9 cDNA |
| 12 | R9 polypeptide |
| 13 | R10 cDNA |
| 14 | R10 polypeptide |
| 15 | R12 cDNA |
| 16 | R12 polypeptide |
| 17 | R38 cDNA |
| 18 | R38 polypeptide |
| 19 | R42 cDNA |
| 20 | R42 polypeptide |
| 21 | R43 cDNA |
| 22 | R43 polypeptide |
| 23 | R44 cDNA |
| 24 | R44 polypeptide |
| 25 | R67 cDNA |
| 26 | R67 polypeptide |

In general, the feline gene is named after its homologous human counterpart, as shown in Table 7. However for a feline gene similar to many human genes, such as fTAS2R43, the feline gene is named as its homologous canine counterpart.

TABLE 7

Corresponding genes in felines, canines and humans

| Predicted Feline Gene | Predicted Canine Gene | Human Gene |
|---|---|---|
| TAS2R1 | TAS2R1 | TAS1R1 |
| TAS2R2 | CAFA-T2R2 | TAS2R2P |
| TAS2R3 | TAS2R3 | TAS2R3 |
| TAS2R4 | TAS2R4 | TAS2R4 |
| TAS2R5P | TAS2R5 | TAS2R5 |
| TAS2R7 | TAS2R7 | TAS2R7 |
| TAS2R8P | TAS2R8P | TAS2R8 |
| TAS2R9 | TAS2R9P | TAS2R9 |
| TAS2R10 | TAS2R10 | TAS2R10 |
| TAS2R12 | TAS2R12 | TAS2R12P |
| TAS2R16P | N/A | TAS2R16 |
| TAS2R38 | TAS2R38 | TAS2R38 |
| TAS2R39P | TAS2R39 | TAS2R39 |
| TAS2R40P | TAS2R40 | TAS2R40 |
| TAS2R41P | TAS2R41 | TAS2R41 |
| TAS2R42 | TAS2R42 | hTAS2R42, 18P, 67P |
| TAS2R43 | TAS2R43 | hTAS2R13, 14, 19, 20, 30, 31, 43, 45, 46, 50, 15P, 63P, 64P, 68P |

TABLE 7-continued

Corresponding genes in felines, canines and humans

| Predicted Feline Gene | Predicted Canine Gene | Human Gene |
|---|---|---|
| TAS2R44 | CAFA-T2R44P | hTAS2R13, 14, 19, 20, 30, 31, 43, 45, 46, 50, 15P, 63P, 64P, 68P |
| TAS2R67 | CAFA-T2R67 | hTAS2R42, 18P, 67P |
| TAS2R60P | Tas2R60P-like | TAS2R60 |
| TAS2R62P | TAS2R62-like | TAS2R62P |

A sequence alignment of the 3rd through the 7th transmembrane (TM) regions of several human and feline bitter receptors is shown in FIG. 1. The sequence alignment illustrates the substantial degree of homology of this region in bitter taste receptors of the two species.

A sequence alignment of human TAS2R38 polypeptide (SEQ ID NO:31) and feline TAS2R38 polypeptide (SEQ ID NO:18) determined from sequencing genomic DNA of five individual cats is shown in FIG. 2. Amino acids in hTAS2R38 that differ from those in fTAS2R38 are boxed in FIG. 2. The positions of the human polymorphisms known to affect taste perception of 6-n-propylthiouracil (PROP), A49P, V262A, I293V (where AVI is a non-taster and PAV is a taster) are shaded grey in FIG. 2. The residues known to be important for phenylthiocarbamide (PTC) binding to the human TAS2R38 receptor are denoted in FIG. 2 by a thick black box (residues 99-100, 103, 255, and 259) These amino acids either directly bind PTC, contribute to the binding pocket, or are involved in receptor activation by associating with other amino acids.

TOPCONS was used to identify the seven transmembrane regions and the extracellular and cytoplasmic loops of each fTAS2R polypeptide. Results of this analysis are presented in Table 1.

Example 2

Expression Systems for Feline TAS2R

A. Generation of Expression Vectors for Feline TAS2R

This example describes generation of an expression vector for a representative feline bitter receptor, TAS2R38. An analogous process is conducted for each of the TAS2R receptors.

The full length gene of feline TAS2R38 was amplified by polymerase chain reaction (PCR) using gene-specific primers that span the entire coding region.

The TAS2R38 cDNA was subcloned into an expression cassette based on the plasmid/expression vector pcDNA3.1D-V5His (Life Technologies, Carlsbad, Calif., US), which contains within its multiple cloning sites the nucleotide sequence coding for the FLAG epitope to allow surface detection of the receptor, then the first 45 amino acids of the rat somatostatin receptor subtype 3 (RSS tag) to facilitate cell surface targeting of the transgene, and the nucleotide sequence coding for the herpes simplex virus (HSV) glycoprotein D epitope (HSV epitope) for facilitating immunocytochemical detection (HSV Tag) on the carboxy terminus.

The nucleic acid sequences encoding the FLAG tag, RSS tag, TAS2R38, and the HSV tag were fused, in that order, in frame to create a construct to allow translation into the receptor protein. The resulting receptor cDNA in the expression vector encodes the joined amino acid sequences of TAS2R38 preceded by the RSS tag and followed by the HSV tag.

The expression vector including the construct is called pcDNA3.11D-FLAGV5His-TAS2R38 and allows for expression of the TAS2R38 protein (SEQ ID NO:18).

Generation of an expression vector for each of the other fTAS2Rs disclosed herein was performed by analogous steps.

B. Generation of Cell Lines Transiently Expressing fTAS2R

Cell lines that transiently express a desired TAS2R disclosed herein were generated by transfecting the appropriate expression vector, e.g., pcDNA3.1D-FLAGV5His-TAS2R38, constructed as described above in Ex. 2A into cells of a eukaryotic cell line (Life Technologies, Cat# R700-07).

On day 0, 60,000 cells per well were plated on poly lysine coated, black 96 well plates with clear bottoms (Costar). The following day the cells were transfected with 150 ng TAS2R38 expression vector, e.g., pcDNA3.1D-FLAGV5His (Invitrogen) along with 45 ng of Gα16 chimera containing the last 44 amino acids of rat gustducin (Gα16gust44) with 0.5 ul Lipofectamine 2000 (Invitrogen) per well. Cells were then incubated 22-44 hours at 37° C. 5% $CO_2$.

The expression of fTAS2R38 was evaluated by testing for the presence of a functional response to a known hTAS2R38 ligand (e.g., PTC), determined via automated calcium imaging using a Fluo-4AM (Life Technologies Corporation) Calcium Assay. Fluo-4AM is a fluorescent indicator of intracellular calcium dynamics (change in concentration) and allows monitoring changes in the calcium concentration, particularly an increase in response to receptor activation occurring after agonist exposure.

Generation of cell lines transiently expressing the other fTAS2Rs disclosed herein was analogous.

Expression of the fTAS2Rs in the various cell lines generated was evaluated by flow cytometry. The extracellular FLAG tag was detected with a FLAG-specific antibody conjugated to fluorescein isothiocyanate (FITC). The percentage of cells expressing a given fTAS2R was determined by percent of cells positive for the FITC signal. The level of fTAS2R expression was determined by the geometric mean of the fluorescence intensity measured. The results for each of the expressed fTAS2R are shown in Table 8.

TABLE 8

Flow cytometry results for cell lines transiently expressing fTAS2Rs

| fTAS2R | % of cells expressing fTAS2R | Relative fTAS2R Expression level (Geometric Mean of fluorescence intensity) |
|---|---|---|
| Untransfected cells | 0 | 8,929 |
| TAS2R1 | 38 | 231,625 |
| TAS2R2 | 37 | 295,625 |
| TAS2R3 | 24 | 201,000 |
| TAS2R4 | 36 | 331,125 |
| TAS2R7 | 27 | 144,375 |
| TAS2R9 | 24 | 113,250 |
| TAS2R10 | 30 | 298,500 |
| TAS2R12 | 32 | 258,625 |
| TAS2R38 | 31 | 268,750 |
| TAS2R42 | 25 | 133,375 |
| TAS2R43 | 24 | 246,375 |
| TAS2R44 | 9 | 125,750 |
| TAS2R67 | 12 | 118,000 |

C. Screening of Transiently Transfected Cell Lines.

Testing for a functional response of fTAS2R38 to the known hTAS2R38 ligands, PTC and PROP, and of fTAS2R43 to the known hTAS2R43 ligands, aloin, denatonium and saccharine), was determined via automated calcium imaging using the Fluo-4AM (Life Technologies Corporation) Calcium Assay.

The fTAS2R38 was activated 81% over baseline by 100 µM PTC, but was not stimulated by 30 µM PROP. The fTAS2R43 was activated 45% over baseline by 300 µM aloin, and 17% over baseline by 1 mM denatonium, but was not stimulated by 6.7 mM saccharin. Furthermore, the responses to PTC, denatonium and aloin were inhibited by 1 mM probenecid.

Testing for a functional response of each of the other fTAS2Rs disclosed herein can be performed by analogous methods using known ligands to a corresponding homolog of each fTAS2R.

D. Generation of Cell Lines Stably Expressing fTAS2R

Cell lines stably expressing fTAS2R are also obtained.

For these experiments, the fTAS2R38 cDNA is subcloned into an expression cassette based on the plasmid/expression vector pcDNA3.1Zeo (Life Technologies, Carlsbad, Calif., US), which contains within its multiple cloning sites the nucleotide sequence coding for the first 45 amino acids of the rat somatostatin receptor subtype 3 (RSS tag) to facilitate cell surface targeting of the transgene, and the nucleotide sequence coding for the herpes simplex virus (HSV) glycoprotein D epitope (HSV epitope) for facilitating immunocytochemical detection (HSV Tag).

The nucleic acid sequences encoding the RSS tag, HSV tag, and fTAS2R38 are fused, in that order, in frame to create a construct to allow translation into the receptor protein. The resulting receptor cDNA in the expression vector encodes the joined amino acid sequences of fTAS2R38 preceded by the RSS tag and the HSV tag.

The expression vector including the construct is called pcDNA3.1Zeo-TAS2R38 and allows for expression of the fTAS2R38 protein (SEQ ID:18).

Generation of an expression vector for the other fTAS2Rs disclosed herein is analogous. The restriction enzymes used are adapted accordingly.

Cell lines that stably express a desired fTAS2R disclosed herein are generated by transfecting the appropriate expression vector, e.g., pcDNA3.1Zeo-TAS2R38, constructed as described above in Ex. 2A into a eukaryotic host cell line (Life Technologies Cat# R700-07) transformed with the Gα16 chimera containing the last 44 amino acids of rat gustducin (G[alpha]16-gustducin 44 cells) as described in WO2004/055048 (U.S. Pat. No. 7,919,236).

On day 0, the G[alpha]16-gustducin 44 cells are plated in a 6-well plate at a density of 900,000 cells per well and grown overnight in a selective growth media (DMEM with 10% (v/v) heat-inactivated fetal bovine serum, 2 mM L-glutamine, 100 units/ml penicillin, 100 µg/ml streptomycin).

On day 1, the medium is exchanged with 2 ml of antibiotic-free and serum-free growth medium. 10 µl Lipofectamine 2000 (Life Technologies Corporation) is dissolved in 250 µl DMEM and incubated for 5 minutes at room temperature. In parallel, 4 µg pcDNA3.1Zeo-TAS2R38 DNA is dissolved in 250 µl DMEM. These two resulting solutions are mixed and incubated for 20 minutes at room temperature before they are added to the cells into the cell culture medium. After 4 hours, the medium is replaced with antibiotic-free, serum-containing growth medium. The cells are incubated in humidified atmosphere (37 C., 5% CO2).

After 24 hours, the cells are re-plated in selective growth medium (DMEM with 10% (v/v) heat-inactivated fetal bovine serum, 2 mM L-glutamine, 100 units/ml penicillin, 100 μg/ml streptomycin, 200 μg/ml G418 and 200 μg/ml zeocin) and are further incubated in a humidified atmosphere (37 C, 5% CO2).

After 2 to 4 weeks of culture (replacing medium as necessary), zeocin-resistant colonies are selected and expanded.

The expression of fTAS2R38 is evaluated by testing for the presence of a functional response to a known hTAS2R38 ligand (e.g., PTC and PROP), determined via automated calcium imaging using the Fluo-4AM (Life Technologies Corporation) Calcium Assay. Fluo-4AM is a fluorescent indicator of intracellular calcium dynamics (change in concentration) and allows monitoring changes in the calcium concentration, particularly an increase in response to receptor activation occurring after agonist exposure. One clone is selected resulting in the G[alpha]16-gustducin 44/TAS2R38 cell line. The G[alpha]16-gustducin 44/TAS2R38 cell line was stimulated 90% over baseline in the presence of 100 μM PTC but was not stimulated with 30 μm PROP.

Generation of cell lines stably expressing the other fTAS2Rs disclosed herein is analogous Example 3

Cell-Based Screening for Ligands and Effectors of Feline TAS2Rs

Identification of agonists, antagonists and modulators of feline TAS2R38 receptor is performed by a cell-based screening assay in which the effect of a test compound on cells transfected with feline TAS2R38 and Gα16gust44 is compared against the effect of the test compound on untransfected cells.

Prior to the screening assay, the cells are loaded with the calcium sensitive dye Fluo-AM (Life Technologies) for one hour at 37° C. as described in Example 2B. The dye is washed out and the cells are assayed in Hank's Balanced Salt Solution (HBSS; Life Technologies) containing 20 mM HEPES in a Flexstation II (Molecular Devices). A 10 fold dilution series 0.01 mM-1 mM of test compounds is used to stimulate the cells. PTC, a known human TAS2R38 agonist, is among the test compounds The stimuli are injected and monitored for 100-180 seconds. Data is analyzed and graphed as a percentage over the baseline signal, which is the reading prior to stimulation. Stimulation of the fTAS2R38 expressing cell line by a particular test compound is considered to occur when the signal is greater than both the signal from the buffer alone in the receptor expressing cell line and the signal from the un-transfected cell line sample injected with the test compound.

Cell based screening for agonists, antagonists, and modulators for the other fTAS2Rs disclosed herein is analogous.

Example 4

Flavor and Repellant Compositions

Exemplary dry flavor compositions for an animal comprising an agonist, an antagonist, or a modulator of a feline TAS2R receptor disclosed herein are made in general accordance with the following formulation.

TABLE 9

Dry Flavor Composition

| Component | % by weight |
|---|---|
| identified agonist, antagonist or modulator of a feline TAS2R receptor | 0.01%-5% |
| grain-based meal or flour, such as corn, wheat, barley or rice; | 0%-50% |
| animal by-product meal, such as poultry or pork meal; | 0%-50% |
| brewers or distiller's yeasts; | 0%-50% |
| phosphate salts; | 0%-50% |
| fresh animal protein, such as poultry or pork protein; | 0%-50% |
| seafood-based protein; | 0%-50% |
| sugars or starches; | 0%-20% |
| dairy ingredients; | 0%-10% |
| animal fat; | 0%-5% |
| amino acid ingredients; | 0%-5% |
| phosphoric acid and/or sodium hydroxide; | 0%-5% |
| citric acid; | 0%-5% |
| specialized natural flavor spikes | 0%-5% |
| Final pH from 4.0-8.0 | |
| Final moisture from 1.0-5.0% | |

The identified agonist in the dry flavor composition is denatonium, aloin, or PTC or the identified antagonist is probenecid.

Exemplary liquid flavor compositions for an animal comprising an agonist, an antagonist, or a modulator of a feline TAS2R receptor are made in general accordance with the following formulation.

TABLE 10

Liquid Flavor Composition

| Component | % by weight |
|---|---|
| identified agonist, antagonist or modulator of a feline TAS2R receptor | 0.01%-5% |
| animal protein, such as poultry or pork protein; | 0%-40% |
| animal by-product meal, such as poultry or pork meal; | 0%-40% |
| seafood-based protein; | 0%-40% |
| grain-based meal or flour, such as corn, wheat, barley or rice; | 0%-30% |
| brewers or distiller's yeasts; | 0%-30% |
| phosphate salts; | 0%-10% |
| sugars or starches; | 0%-10% |
| dairy ingredients; | 0%-10% |
| phosphoric acid and/or sodium hydroxide; | 0%-10% |
| animal fat; | 0%-5% |
| amino acid ingredients | 0%-5% |
| citric acid | 0%-5% |
| specialized natural flavor spikes | 0%-5% |
| Final pH from 2.7-3.1 | |
| Final moisture from 60.0-80.0% | |

The identified agonist in the liquid flavor composition is denatonium, aloin, or PTC or the identified antagonist is probenecid.

An exemplary repellent composition in the form of an aerosol for spraying onto an object to deter companion cats from chewing or eating the object is made by formulating 50% active ingredient solution, the active ingredient being a feline TAS2R agonist or positive modulator, with 50% of a propellant gas such as Frigen 11/12 (a halogenated hydrocarbon) or propane/butane (e.g., in a 15:85 ratio) in an aerosol can. The active ingredient solution consists of from about 0.5% to about 30% by weight of a feline TAS2R agonist or positive modulator dissolved in a liquid diluent, e.g., water, optionally 0.5-1.5% of an aromatic or a perfume, and up to 29.5% isopropanol. The feline TAS2R agonist is denatonium, aloin, or PTC.

Embodiment 1

An isolated feline TAS2R (fTAS2R) receptor polypeptide comprising an extracellular domain of a feline TAS2R receptor; a transmembrane region of a feline TAS2R receptor, or an intracellular domain of a feline TAS2R receptor, wherein the fTAS2R receptor comprises a sequence selected from SEQ ID NO:18, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:20, SEQ ID NO:22, SEQ ID NO:24, and SEQ ID NO:26, wherein the isolated feline TAS2R (fTAS2R) receptor polypeptide does not consist of the amino acid sequence of SEQ ID NOs: 2, 4, 6, or 10.

Embodiment 2

The polypeptide of embodiment 1 wherein: the extracellular domain of the feline TAS2R receptor polypeptide comprises: amino acids 1, 68-84; 146-179; or 249-257 of SEQ ID NO:2; amino acids 1-10, 73-88; 151-186; or 256-264 of SEQ ID NO:4; amino acids 1-8; 72-88; 150-186; or 256-265 of SEQ ID NO:6; amino acids 1-2; 69-87; 151-183; or 253-261 of SEQ ID NO:8; amino acids 1-8; 72-88; 150-187; or 257-265 of SEQ ID NO:10; amino acids 1-6; 72-88; 150-183; or 253-262 of SEQ ID NO:12; amino acids 1; 69-87; 150-181; or 251-260 of SEQ ID NO:14; amino acids 1-8; 69-88; 150-185; or 252-261 of SEQ ID NO:16; amino acids 1-17; 83-98; 161-198; or 268-277 of SEQ ID NO:18; amino acids 1; 69-88; 150-185; or 255-264 of SEQ ID NO:20; amino acids 1-2; 69-87; 149-181; or 251-260 of SEQ ID NO:22; amino acids 1-2; 69-87; 149-181; or 251-259 of SEQ ID NO:24; or amino acids 1-8; 72-88; 150-185; or 254-263 of SEQ ID NO:26; the transmembrane region of the feline TAS2R receptor polypeptide comprises: amino acids 2-22, 47-67, 85-105, 125-145, 180-200, 228-248, or 258-278 of SEQ ID NO:2; amino acids 11-31, 52-72, 89-109, 130-150, 187-207, 235-255, or 265-285 of SEQ ID NO:4; amino acids 9-29, 51-71, 89-109, 129-149, 187-207, 235-255, or 266-286 of SEQ ID NO:6; amino acids 3-23, 48-68, 88-108, 130-150, 184-204, 232-252, or 262-282 of SEQ ID NO:8; amino acids 9-29, 51-71, 89-109, 129-149, 188-208, 236-256, or 266-286 of SEQ ID NO:10; amino acids 7-27, 51-71, 89-109, 129-149, 184-204, 232-252, or 263-283 of SEQ ID NO:12; amino acids 2-22, 48-68, 88-108, 129-149, 182-202, 230-250, or 261-281 of SEQ ID NO:14; amino acids 9-29, 48-68, 89-109, 129-149, 186-206, 231-251, or 262-282 of SEQ ID NO:16; amino acids 18-38, 62-82, 99-119, 140-160, 199-219, 247-267, or 278-298 of SEQ ID NO:18; amino acids 2-22, 48-68, 89-109, 129-149, 186-206, 234-254, or 265-285 of SEQ ID NO:20; amino acids 3-23, 48-68, 88-108, 128-148, 182-202, 230-250, or 261-281 of SEQ ID NO:22; amino acids 3-23, 48-68, 88-108, 128-148, 182-202, 230-250, or 260-280 of SEQ ID NO:24; or amino acids 9-29, 51-71, 89-109, 129-149, 186-206, 233-253, or 264-284 of SEQ ID NO:26; and the intracellular domain comprises: amino acids 23-46; 106-124; 201-227; or 279-298 of SEQ ID NO:2; amino acids 32-51; 110-129; 208-234; or 286-304 of SEQ ID NO:4; amino acids 30-50; 110-128; 208-234; or 287-316 of SEQ ID NO:6; amino acids 24-47; 109-129; 205-231; or 283-306 of SEQ ID NO:8; amino acids 30-50; 110-128; 209-235; or 287-311 of SEQ ID NO:10; amino acids 28-50; 110-128; 205-231; or 284-337 of SEQ ID NO:12; amino acids 23-48; 109-128; 203-229; or 282-300 of SEQ ID NO:14; amino acids 30-47; 110-128; 207-230; or 283-309 of SEQ ID NO:16; amino acids 39-61; 120-139; 220-246; or 299-334 of SEQ ID NO:18; amino acids 23-47; 110-128; 207-233; or 286-322 of SEQ ID NO:20; amino acids 24-47; 109-127; 203-229; or 282-299 of SEQ ID NO:22; amino acids 24-47; 109-127; 203-229; or 281-308 of SEQ ID NO:24; or amino acids 30-50; 110-128; 207-232; or 285-312 of SEQ ID NO:26.

Embodiment 3

The polypeptide of embodiment 1 or 2 comprising a transmembrane region 2, a transmembrane region 3, a transmembrane region 4, a transmembrane region 5, a transmembrane region 6, and a transmembrane region 7, wherein each transmembrane region comprises at least 20 consecutive amino acids of the corresponding transmembrane region sequence independently selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26; or a transmembrane region 3, a transmembrane region 6, and a transmembrane region 7, wherein each transmembrane region comprises at least 20 consecutive amino acids of the corresponding transmembrane region sequence independently selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26; an extracellular domain 3 comprising at least 15 consecutive amino acids selected from amino acids 146-179 of SEQ ID NO:2; amino acids 151-186 of SEQ ID NO:4; amino acids 150-186 of SEQ ID NO:6; amino acids 151-183 of SEQ ID NO:8; amino acids 150-187 of SEQ ID NO:10; amino acids 150-183 of SEQ ID NO:12; amino acids 150-181 of SEQ ID NO:14; amino acids 150-185 of SEQ ID NO:16; amino acids 161-198 of SEQ ID NO:18; amino acids 150-185 of SEQ ID NO:20; amino acids 149-181 of SEQ ID NO:22; amino acids 149-181 of SEQ ID NO:24; and amino acids 150-185 of SEQ ID NO:26; and an extracellular domain 4 comprising at least 8 consecutive amino acids selected from amino acids 249-257 of SEQ ID NO:2; amino acids 256-264 of SEQ ID NO:4; amino acids 256-265 of SEQ ID NO:6; amino acids 253-261 of SEQ ID NO:8; amino acids 257-265 of SEQ ID NO:10; amino acids 253-262 of SEQ ID NO:12; amino acids 251-260 of SEQ ID NO:14; amino acids 252-261 of SEQ ID NO:16; amino acids 268-277 of SEQ ID NO:18; amino acids 255-264 of SEQ ID NO:20; amino acids 251-260 of SEQ ID NO:22; amino acids 251-259 of SEQ ID NO:24; and amino acids 254-263 of SEQ ID NO:26.

Embodiment 4

The polypeptide of any one of embodiments 1-3, further comprising a heterologous polypeptide.

Embodiment 5

The polypeptide of embodiment 4, wherein the heterologous polypeptide is linked to the amino terminus or the carboxy terminus of the feline TAS2R receptor polypeptide.

Embodiment 6

The polypeptide of any one of embodiments 1-5 comprising the amino acid sequence of SEQ ID NO:8, SEQ ID

Embodiment 7

The polypeptide of any one of embodiments 1-6 consisting of the amino acid sequence of SEQ ID NO:8, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

Embodiment 8

The polypeptide of any one of embodiments 1-7 that is non-naturally occurring.

Embodiment 9

The polypeptide of any one of embodiments 1-8 having fTAS2R receptor activity or binding a ligand of an fTAS2R receptor.

Embodiment 10

The polypeptide of any one of embodiments 1-9, wherein the sequence is SEQ ID NO:18.

Embodiment 11

The polypeptide of any one of embodiments 1-10, wherein the fTAS2R is fTAS2R38 and amino acid 74 of SEQ ID NO:18 is N.

Embodiment 12

The polypeptide of any one of embodiments 1-11, wherein the extracellular domain comprises a sequence of at least 15 consecutive amino acids of extracellular domain 2 or 3 or of at least 8 consecutive amino acids of extracellular domain 4 of a fTAS2R receptor sequence; the transmembrane region comprises a sequence of at least 20 consecutive amino acids of a fTAS2R receptor sequence transmembrane region, and the intracellular domain comprise a sequence of at least 17 consecutive amino acids of a fTAS2R receptor sequence intracellular domain.

Embodiment 13

A composition comprising at least two polypeptides of any one of embodiments 1-12

Embodiment 14

An isolated polynucleotide encoding the polypeptide of any one of embodiments 1-12.

Embodiment 15

An isolated polynucleotide encoding a feline TAS2R (fTAS2R) receptor polypeptide, or fragment thereof comprising a nucleotide sequence selected from: the nucleotide sequence of SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; a nucleotide sequence encoding the amino acid sequence of SEQ ID NO: 8, SEQ ID NO: 12, SEQ ID NO:14, SEQ ID NO:16, SEQ ID NO: 18, SEQ ID NO: 20, SEQ ID NO: 22, SEQ ID NO: 24, or SEQ ID NO: 26; a nucleotide sequence that hybridizes to the complement of the polynucleotide having SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25 under high stringency conditions; and the complement of the foregoing nucleotide sequences.

Embodiment 16

A polynucleotide comprising at least 15 contiguous nucleotides of SEQ ID NO:17, wherein the contiguous nucleotides contain nucleotide 220 and an A is present at nucleotide 220; or the complement of the nucleotide sequence.

Embodiment 17

The polynucleotide of embodiment 16, comprising at least 20 contiguous nucleotides.

Embodiment 18

The polynucleotide of embodiment 16 or 17, comprising at least 25 contiguous nucleotides.

Embodiment 19

The polynucleotide of any one of embodiments 14-18, wherein the nucleotide sequence is codon-optimized for expression in a non-feline cell.

Embodiment 20

The polynucleotide of embodiment 19, wherein the non-feline cell is *Escherichia coli* E., a *Saccharomyces cerevisae* cell yeast, a *Drosophila melanogaster* cell, a *Caenorhabditis elegans* cell, or a mammalian cell.

Embodiment 21

The polynucleotide of embodiment 20, wherein the mammalian cell is a murine or human cell.

Embodiment 22

The polynucleotide of any one of embodiments 14-21 that is non-naturally occurring.

Embodiment 23

A composition comprising at least two polynucleotides of any one of embodiments 14-22.

Embodiment 24

A primer pair for amplifying at least a portion of a nucleic acid encoding a feline TAS2R polypeptide.

Embodiment 25

The composition of embodiment 24 comprising a primer pair selected from the primer pairs of Table 5.

Embodiment 26

A feline TAS2R receptor polypeptide encoded by the polynucleotide of any one of embodiments 14-22.

Embodiment 27

An expression vector comprising the polynucleotide of any one of embodiments 14-22.

Embodiment 28

A host cell comprising the expression vector of embodiment 27.

Embodiment 29

The host cell of embodiment 28 wherein the cell is a mammalian cell, a fish cell, a yeast cell, a bacterial cell, or an insect cell.

Embodiment 30

The host cell of embodiments 28 or 29 wherein the cell is a human, murine, or feline cell.

Embodiment 31

The host cell of embodiment 28 or 29 wherein the cell is a bacterial, insect, or yeast cell.

Embodiment 32

A cell culture comprising at least one cell of any one of embodiments 28-31.

Embodiment 33

An oligonucleotide comprising a nucleotide sequence of at least 15 and up to 100 contiguous nucleotides of SEQ ID NO: 7, SEQ ID NO:9, SEQ ID NO: 11, SEQ ID NO:13, SEQ ID NO:15, SEQ ID NO: 17, SEQ ID NO: 19, SEQ ID NO: 21, SEQ ID NO: 23, or SEQ ID NO: 25; or the complement of the nucleotide sequence.

Embodiment 34

The oligonucleotide of embodiment 33, comprising at least 18 and up to 50 contiguous nucleotides.

Embodiment 35

The oligonucleotide of embodiment 33 or 34, comprising at least 18 and up to 30 contiguous nucleotides.

Embodiment 36

An isolated antibody or a fragment thereof, that specifically binds an fTAS2R receptor epitope of the polypeptide of any one of embodiments 1-12 and 26.

Embodiment 37

A method for identifying a compound that interacts with a feline TAS2R receptor polypeptide comprising: contacting a polypeptide of any one of embodiments 1-12 and 26 with a test compound, and detecting interaction between the polypeptide and the test compound.

Embodiment 38

The method of embodiment 37, wherein detecting interaction between the polypeptide and the test compound comprises measuring an electrical property, measuring a change in an ion concentration, measuring a change in protein conformation, measuring binding of the test compound to the polypeptide, measuring a change in phosphorylation level, measuring a change in transcription level, measuring a change in second messenger level, measuring a change in neurotransmitter level, measuring a change in a spectroscopic characteristic, measuring a change in a hydrodynamic (e.g., shape) property, measuring a change in a chromatographic property, or measuring a change in solubility.

Embodiment 39

The method of embodiment 37 or 38, further comprising identifying the test compound as a compound that interacts with the receptor.

Embodiment 40

A method for identifying a compound which modulates a feline TAS2R receptor polypeptide which comprises: contacting the polypeptide of any one of embodiments 1 to 12 and 24 with a TAS2R receptor ligand in both the presence and absence of a test compound in separate assays, and determining whether the test compound modulates binding of the ligand to the receptor polypeptide or activation of the receptor polypeptide by the ligand.

Embodiment 41

The method of embodiment 40, wherein determining whether the test compound modulates binding of the ligand to the receptor or activation of the receptor by the ligand comprises measuring an electrical property, measuring an ion concentration, measuring a change in protein conformation, measuring a binding of the test compound to the polypeptide, measuring a change in phosphorylation level, measuring a change in transcription level, measuring a change in second messenger level, or measuring a change in neurotransmitter level.

Embodiment 42

The method of embodiment 40 or 41 further comprising identifying the test compound as a modulator.

Embodiment 43

The method of any one of embodiments 37 to 42, wherein the polypeptide is bound to a solid support, expressed in a host cell, in a bilayer membrane, in a lipid monolayer, or in a vesicle.

Embodiment 44

A method of preparing an edible composition comprising contacting an edible composition or a component thereof with a polypeptide of any one of embodiments 1 to 12 and 26 for a time sufficient to reduce the amount of a bitter compound from the edible composition or component thereof.

Embodiment 45

The method of embodiment 44 wherein the polypeptide is bound to a solid support that can be separated from the edible composition.

Embodiment 46

The method of embodiment 44 or 45 wherein the contacting is a continuous operation, a semi-continuous operation, or a batch operation.

Embodiment 47

The method of any one of embodiments 44-46 wherein the edible composition is a feline food composition, and the composition or a component thereof is contacted with a plurality of different polypeptides.

Embodiment 48

A method of formulating an edible composition with enhanced palatability comprising determining the presence of a compound which is an agonist, antagonist, or modulator of a feline TAS2R receptor polypeptide of any one of embodiments 1 to 12 and 26 in an edible composition; and enhancing palatability of the edible composition by if the compound is an agonist or a positive modulator, increasing the amount of an antagonist for the receptor in the edible composition or reducing the amount of the compound in the edible composition, or if the compound is an antagonist or a negative modulator, increasing the amount of the compound in the edible composition.

Embodiment 49

The method of embodiment 48 wherein increasing the amount of the compound comprises applying a flavor composition comprising the compound to the edible composition such that the flavor composition is incorporated into or at least partially coats the edible composition.

Embodiment 50

The method of embodiment 48 or 49, wherein the edible composition comprises a food, a flavor composition, a treat, a pharmaceutical, an oral care material, a nutritional supplement, a chewable product, or a drinkable product.

Embodiment 51

A method of administering a bitter compound to an animal in need thereof comprising administering an edible composition to an animal, wherein the edible composition comprises a bitter compound and a compound that is an agonist, antagonist, or modulator of a feline TAS2R receptor polypeptide of any one of embodiments 1 to 12 and 26 that alters acceptance of the edible composition by the animal compared to acceptance of the edible composition without the compound.

Embodiment 52

The method of embodiment 51 wherein the bitter compound comprises a pharmaceutical, oral care material, a repellant, or a nutritional supplement.

Embodiment 53

A method of preparing an edible composition for controlling palatability of the edible composition to an animal comprising adding a compound to an edible composition to decrease the palatability of the edible composition to an animal, wherein the compound is an agonist of or a positive modulator of a feline TAS2R receptor polypeptide of any one of embodiments 1 to 12 and 26.

Embodiment 54

The method of embodiment 53 wherein the palatability is decreased to an extent that an animal to whom the edible composition is administered consumes 10 to 30% less of the edible composition with the compound than of the edible composition without the added compound.

Embodiment 55

The method of embodiment 53 or 54 wherein the decrease is measured in calories of edible composition consumed, weight of edible composition consumed, or volume of edible composition consumed.

Embodiment 56

A method for making a flavor composition for coating or incorporating into an edible composition to be administered to an animal comprising: mixing an agonist or an antagonist of a feline TAS2R receptor polypeptide of any one of embodiments 1 to 12 and 26, wherein the agonist is denatonium, aloin, or PTC and the antagonist is probenecid with a carrier to obtain a flavor composition; optionally, mixing into the flavor composition a palatability enhancer, a compound to help adhere the flavor composition to the edible composition, or a compound for providing color or aroma; wherein the flavor composition is a liquid, solid, powder, paste, gel, spreadable formulation, granule, or sprayable formulation.

Embodiment 57

A flavor composition for coating or incorporating into an edible composition to be administered to an animal comprising: an agonist or an antagonist of a feline TAS2R receptor polypeptide of any one of embodiments 1 to 12 and 26, wherein the agonist is denatonium, aloin, or PTC and the antagonist is probenecid; optionally, a palatability enhancer; optionally, a compound to help adhere the flavor composition to the edible composition; and optionally, a compound for providing color or aroma; wherein the flavor composition is a liquid, solid, powder, paste, gel, spreadable formulation, granule, or sprayable formulation.

Embodiment 58

The flavor composition of embodiment 57 or the method of any one of embodiments 53-56, wherein the edible composition is a food, treat, nutritional supplement, pharmaceutical, oral care material, chewable product, repellant, or drinkable product.

Embodiment 59

The flavor composition of embodiment 57 or 58 or the method of any one of embodiments 53-56 wherein the edible composition is a dry food, a soft food, a semisoft food, a liquid, a tablet, capsule, caplet, granule, paste, colloidal mixture, dispersion, or gel.

Embodiment 60

The method of any one of embodiments 48 to 56 or the flavor composition of any one of embodiments 57 to 58, wherein the edible composition is for administration to a feline.

Embodiment 61

The polypeptide of any one of embodiments 1-12 and 26, wherein the fTAS2R receptor comprises a domain of fTAS2R38.

Embodiment 62

The polypeptide of any one of embodiments 1-12 and 26, wherein the fTAS2R receptor comprises a domain of fTAS2R42.

Embodiment 63

The polypeptide of any one of embodiments 1-12 and 26, wherein the fTAS2R receptor comprises a domain of fTAS2R43.

Embodiment 64

The polypeptide of any one of embodiments 1-12 and 26, wherein the fTAS2R receptor comprises a domain of fTAS2R44.

Embodiment 65

The polypeptide of any one of embodiments 1-12 and 26, wherein the fTAS2R receptor comprises a domain of fTAS2R67.

Embodiment 66

The polypeptide of any one of embodiments 1-12 and 26, wherein the fTAS2R receptor comprises a domain of fTAS2R12.

Embodiment 67

The polypeptide of any one of embodiments 1-12 and 26, wherein the fTAS2R receptor comprises a domain of fTAS2R10.

Embodiment 68

The polypeptide of any one of embodiments 1-12 and 26, wherein the fTAS2R receptor comprises a domain of fTAS2R9.

Embodiment 69

The polypeptide of any one of embodiments 1-12 and 26, wherein the fTAS2R receptor comprises a domain of fTAS2R7.

Embodiment 70

The polypeptide of any one of embodiments 1-12 and 26, wherein the fTAS2R receptor comprises a domain of fTAS2R4.

Embodiment 71

The polypeptide of any one of embodiments 1-12 and 26, wherein the fTAS2R receptor comprises a domain of fTAS2R3.

Embodiment 72

The polypeptide of any one of embodiments 1-12 and 26, wherein the fTAS2R receptor comprises a domain of fTAS2R2.

Embodiment 73

The polypeptide of any one of embodiments 1-12 and 26, wherein the fTAS2R receptor comprises a domain of fTAS2R1.

As used herein, the terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The modifier "about" used in connection with a quantity is inclusive of the stated value and has the meaning dictated by the context (e.g., includes the degree of error associated with measurement of the particular quantity).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Unless defined otherwise, technical and scientific terms used herein have the same meaning as is commonly understood by one of skill in the art to which this invention belongs.

All references are incorporated by reference herein.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated feline TAS2R (fTAS2R) receptor polypeptide comprising
the sequence SEQ ID NO:22,
wherein the polypeptide is covalently bound to a label, a solid support, a lipid monolayer, or a heterologous polypeptide.

2. The polypeptide of claim 1, wherein the polypeptide is covalently bound to a heterologous polypeptide.

3. The polypeptide of claim 2, wherein the heterologous polypeptide is covalently bound to the amino terminus or the carboxy terminus of the feline TAS2R receptor polypeptide.

4. A method for identifying a compound that interacts with a feline TAS2R receptor polypeptide comprising:
contacting the polypeptide of claim 1 with a test compound, and
detecting interaction between the polypeptide and the test compound.

5. A method for identifying a compound which modulates a feline TAS2R receptor polypeptide which comprises:
contacting the polypeptide of claim 1 with a TAS2R receptor ligand in both the presence and absence of a test compound in separate assays, and
determining whether the test compound modulates binding of the ligand to the receptor polypeptide or activation of the receptor polypeptide by the ligand.

6. The method of claim 4, wherein the polypeptide is bound to a solid support, expressed in a host cell, in a bilayer membrane, in a lipid monolayer, or in a vesicle.

7. A method of preparing an edible composition comprising
contacting an edible composition or a component thereof with the polypeptide of claim 1 for a time sufficient to reduce the amount of a bitter compound in the edible composition or component thereof.

8. The method of claim 7 wherein the polypeptide is bound to a solid support that can be separated from the edible composition.

9. The method of claim 7 wherein the edible composition is a feline food composition.

10. The method of claim 4, wherein detecting interaction between the polypeptide and the test compound comprises measuring an electrical property, measuring a change in an ion concentration, measuring a change in protein conformation, measuring binding of the test compound to the polypeptide, measuring a change in phosphorylation level, measuring a change in transcription level, measuring a change in second messenger level, measuring a change in neurotransmitter level, measuring a change in a spectroscopic characteristic, measuring a change in a hydrodynamic property, measuring a change in a chromatographic property, or measuring a change in solubility.

11. The method of claim 5, wherein determining whether the test compound modulates binding of the ligand to the receptor or activation of the receptor by the ligand comprises measuring an electrical property, measuring an ion concentration, measuring a change in protein conformation, measuring a binding of the test compound to the polypeptide, measuring a change in phosphorylation level, measuring a change in transcription level, measuring a change in second messenger level, or measuring a change in neurotransmitter level.

12. The method of claim 5, wherein the polypeptide is bound to a solid support, expressed in a host cell, in a bilayer membrane, in a lipid monolayer, or in a vesicle.

13. The method of claim 7, further comprising
contacting the edible composition or the component thereof with a polypeptide comprising a sequence selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:24, and SEQ ID NO:26.

14. The polypeptide of claim 1, wherein the polypeptide is covalently bound to a label.

15. The polypeptide of claim 1, wherein the polypeptide is covalently bound to a solid support.

16. The polypeptide of claim 1, wherein the polypeptide is covalently bound to a lipid monolayer.

* * * * *

SEQUENCE LISTING

<160> NUMBER OF SEQ ID NOS: 135

<210> SEQ ID NO 1
<211> LENGTH: 897
<212> TYPE: DNA
<213> ORGANISM: Felis catus

<400> SEQUENCE: 1

```
atgctagact tttacctcat tatccatttt cttcttccag tgatacaatg tctcatcgga    60
gttttagcaa atggcatcat tgtgatcgtg aatggcactg agttgatcaa gcagagaaag   120
atggttccgt tggatctcct tctttcctgc ctggcgattt ccaggatttg tctgcagtca   180
tttatcttct acattaatct ggttattctc tccttgatcg acttcctttcc acttgttaag  240 aattttgcgg ttttcatgtt tgtaaatgaa acgggacttt ggctggccac atggctcggc   300
gttttctact cgccaagat ctcccccatc gctcacccac tcttcttctg gttgaagagg    360
aggatatcca agttggtgcc atggctgatc atcgggtctc tgcttttgc ctccatccct    420 ttggttttct acagcaagca tacgtgggtt cttctcccaag aagtcttgtt gagacttttc   480
tccccaaatg caacaactca aatcaaagaa acatctgctt tacagattgt ctttcttgct   540
aggttttcac cgccgttcat tatcttcctc acttctactc tgctcctggt gttttctctg   600
gggagacata cgtggcagat gagaaacaca gcgacgggca ccagggacgg tagcacaggt   660
gtccatgtga gtgcgcttct gtccattctg tccttcttgg tcctctatct ctcccactac   720
atgacagctg ctttgctctc ttctcacatt tttgagctca gaagcttcat gtttctgttc   780
tgtatcttgg tgttcgggtc ctacccttcg ggacactcta ttatcttaat tcgggaaat    840 cgtaaactga acaaaatgc aaagaagttc ctcctccatg ggcagtgctg ccagtga       897
```

<210> SEQ ID NO 2
<211> LENGTH: 298
<212> TYPE: PRT
<213> ORGANISM: Felis catus

<400> SEQUENCE: 2

```
Met Leu Asp Phe Tyr Leu Ile Ile His Phe Leu Leu Pro Val Ile Gln
  1               5                  10                  15

Cys Leu Ile Gly Val Leu Ala Asn Gly Ile Ile Val Ile Val Asn Gly
             20                  25                  30

Thr Glu Leu Ile Lys Gln Arg Lys Met Val Pro Leu Asp Leu Leu Leu
         35                  40                  45

Ser Cys Leu Ala Ile Ser Arg Ile Cys Leu Gln Ser Phe Ile Phe Tyr
     50                  55                  60

Ile Asn Leu Val Ile Leu Ser Leu Ile Asp Phe Leu Pro Leu Val Lys
 65                  70                  75                  80

Asn Phe Ala Val Phe Met Phe Val Asn Glu Thr Gly Leu Trp Leu Ala
                 85                  90                  95

Thr Trp Leu Gly Val Phe Tyr Cys Ala Lys Ile Ser Pro Ile Ala His
            100                 105                 110

Pro Leu Phe Phe Trp Leu Lys Arg Arg Ile Ser Lys Leu Val Pro Trp
        115                 120                 125

Leu Ile Ile Gly Ser Leu Leu Phe Ala Ser Ile Pro Leu Val Phe Tyr
    130                 135                 140

Ser Lys His Thr Trp Val Leu Ser Gln Glu Val Leu Leu Arg Leu Phe
145                 150                 155                 160

Ser Pro Asn Ala Thr Thr Gln Ile Lys Glu Thr Ser Ala Leu Gln Ile
```

```
                165                 170                 175
Val Phe Leu Ala Arg Phe Ser Pro Pro Phe Ile Ile Phe Leu Thr Ser
            180                 185                 190

Thr Leu Leu Leu Val Phe Ser Leu Gly Arg His Thr Trp Gln Met Arg
        195                 200                 205

Asn Thr Ala Thr Gly Thr Arg Asp Gly Ser Thr Gly Val His Val Ser
    210                 215                 220

Ala Leu Leu Ser Ile Leu Ser Phe Leu Val Leu Tyr Leu Ser His Tyr
225                 230                 235                 240

Met Thr Ala Ala Leu Leu Ser Ser His Ile Phe Glu Leu Arg Ser Phe
            245                 250                 255

Met Phe Leu Phe Cys Ile Leu Val Phe Gly Ser Tyr Pro Ser Gly His
        260                 265                 270

Ser Ile Ile Leu Ile Ser Gly Asn Arg Lys Leu Lys Gln Asn Ala Lys
    275                 280                 285

Lys Phe Leu Leu His Gly Gln Cys Cys Gln
    290                 295
```

<210> SEQ ID NO 3
<211> LENGTH: 915
<212> TYPE: DNA
<213> ORGANISM: Felis catus

<400> SEQUENCE: 3

```
atggcctcct ctttgtcagc gattcctcac cttatcatca tgtcagcaga atttatcaca      60
gggattacag taaatggatt tcttgtaatc atcaacggta agaattgat caaaagcaga     120
aagctaacac caatgcaact cctttgcata tgtatagga tatcgagatt tggtttgttg     180
atggtgttaa tggtacaaag ttttttctct gtgttctttc cactctttta tagggtaaaa     240
atttatggtg catcaatgtt gttcttttgg atgttttta gctctgtcag tctttggttt     300
gccacctgcc tttctgtgtt ttactgcctc aagatatcag gcttcactca atcctatttt     360
ctttggctga aattcaggat ctcaaagtta atgccttggc tgcttctggg aagcctgctg     420
gcctccatga gcattgccgc tgtgtctttg gatgtaggtt accctaaaaa catgaacaat     480
aatgatttcc tcaagaatgc cacgctgaag aagactgaac tcaagatagg gccaattaat     540
ggagtgcttc ttgtcaactt ggcattgcta tttccactag ccatatttgt gatgtgtact     600
tttatgttat tcatttctct ctataggcac actcatcgga tgcaaaacag atctcatggt     660
gttagaaatg ccagcacaga agcccatata aatgcattaa aaacagtgat aacattcttt     720
tgcttcttta tttcttattt tgctgccttc atggccaata tgacattcag tattccttac     780
ggaagtcagt gcttctttgt ggtaaaggac ataatggcag catttccctc tggacattca     840
gttataatca tattgaataa ttctaaattc aacaaccat tcaggagact tctctgcctc     900
aaaaagaatc aatga                                                      915
```

<210> SEQ ID NO 4
<211> LENGTH: 304
<212> TYPE: PRT
<213> ORGANISM: Felis catus

<400> SEQUENCE: 4

```
Met Ala Ser Ser Leu Ser Ala Ile Pro His Leu Ile Ile Met Ser Ala
1               5                   10                  15

Glu Phe Ile Thr Gly Ile Thr Val Asn Gly Phe Leu Val Ile Ile Asn
            20                  25                  30
```

```
Gly Lys Glu Leu Ile Lys Ser Arg Lys Leu Thr Pro Met Gln Leu Leu
         35                  40                  45

Cys Ile Cys Ile Gly Ile Ser Arg Phe Gly Leu Leu Met Val Leu Met
 50                  55                  60

Val Gln Ser Phe Phe Ser Val Phe Phe Pro Leu Phe Tyr Arg Val Lys
 65                  70                  75                  80

Ile Tyr Gly Ala Ser Met Leu Phe Phe Trp Met Phe Ser Ser Val
                 85                  90                  95

Ser Leu Trp Phe Ala Thr Cys Leu Ser Val Phe Tyr Cys Leu Lys Ile
            100                 105                 110

Ser Gly Phe Thr Gln Ser Tyr Phe Leu Trp Leu Lys Phe Arg Ile Ser
            115                 120                 125

Lys Leu Met Pro Trp Leu Leu Leu Gly Ser Leu Ala Ser Met Ser
130                 135                 140

Ile Ala Ala Val Ser Leu Asp Val Gly Tyr Pro Lys Asn Met Asn Asn
145                 150                 155                 160

Asn Asp Phe Leu Lys Asn Ala Thr Leu Lys Lys Thr Glu Leu Lys Ile
                165                 170                 175

Gly Pro Ile Asn Gly Val Leu Leu Val Asn Leu Ala Leu Leu Phe Pro
            180                 185                 190

Leu Ala Ile Phe Val Met Cys Thr Phe Met Leu Phe Ile Ser Leu Tyr
            195                 200                 205

Arg His Thr His Arg Met Gln Asn Arg Ser His Gly Val Arg Asn Ala
210                 215                 220

Ser Thr Glu Ala His Ile Asn Ala Leu Lys Thr Val Ile Thr Phe Phe
225                 230                 235                 240

Cys Phe Phe Ile Ser Tyr Phe Ala Ala Phe Met Ala Asn Met Thr Phe
                245                 250                 255

Ser Ile Pro Tyr Gly Ser Gln Cys Phe Phe Val Val Lys Asp Ile Met
            260                 265                 270

Ala Ala Phe Pro Ser Gly His Ser Val Ile Ile Ile Leu Asn Asn Ser
            275                 280                 285

Lys Phe Gln Gln Pro Phe Arg Arg Leu Leu Cys Leu Lys Asn Gln
            290                 295                 300

<210> SEQ ID NO 5
<211> LENGTH: 951
<212> TYPE: DNA
<213> ORGANISM: Felis catus

<400> SEQUENCE: 5
atgtcagggc tccacaagtg ggtgtttctg gttctgtctg ccactcagtt cattctgggg      60
atgctgggga atggtttcat agtgttggtc agtggcagca gttggtttaa gaataagaca     120
atctctttgt ctgacttcat catcgctaac ctggctctct ccaggatcgt tctgctgtgg     180
attctcttgg ttgatggtgt tttaattgtg ttctcttcca aagtgcatga tgaagggata     240
ataatgcaaa ttattgatat tttctggaca tttacaaacc acctgagcat tggcttgcc     300 acctgtctca gtgcctctca ctgcctgaaa attgccagtt ctctcaccc tacattcctc     360 tggctcaagt ggagagtttc caggatggtc gtacagatga tcttgggtgc gctggtctta     420
tcgtgtgcca gtgccctgtc tctgatccat gaatttaaga tgtattctat tctcggtggg     480
atcgatggca cagggaatgt gactgagcac tttagaaaga aaagaaatga atataaattg     540
atccatgttc ttgggactct gtggaacctg cctcctctga ttgtgtctct ggcctcctac     600
```

```
tttctgctca tcgtctctct ggggaggcac acgcagcgga tggagcaaag cggcaccagc    660
tccggagatc caagcgctga ggcccacaag agggccatca aaatcatcct ctccttcctc    720
cttctcttcc tgctttactt tcttgccttt taattacat catccagtta tttcatacca     780
ggaactgaga tggtgaagat aattggagaa ctcattacca tgttttatcc tgctagccac    840
tcattcattc tcattctggg aaacagcaag ctgaagcata tgtttgtggg gatgctgcgg    900
tgtgagtctg gtcatctgaa gcctggatcc aaaggacctg tttccctgta g             951
```

<210> SEQ ID NO 6
<211> LENGTH: 316
<212> TYPE: PRT
<213> ORGANISM: Felis catus

<400> SEQUENCE: 6

```
Met Ser Gly Leu His Lys Trp Val Phe Leu Val Leu Ser Ala Thr Gln
1               5                   10                  15

Phe Ile Leu Gly Met Leu Gly Asn Gly Phe Ile Val Leu Val Ser Gly
            20                  25                  30

Ser Ser Trp Phe Lys Asn Lys Thr Ile Ser Leu Ser Asp Phe Ile Ile
        35                  40                  45

Ala Asn Leu Ala Leu Ser Arg Ile Val Leu Leu Trp Ile Leu Leu Val
    50                  55                  60

Asp Gly Val Leu Ile Val Phe Ser Ser Lys Val His Asp Glu Gly Ile
65                  70                  75                  80

Ile Met Gln Ile Ile Asp Ile Phe Trp Thr Phe Thr Asn His Leu Ser
                85                  90                  95

Ile Trp Leu Ala Thr Cys Leu Ser Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Met Val Val Gln Met Ile Leu Gly Ala Leu Val Leu Ser Cys Ala Ser
    130                 135                 140

Ala Leu Ser Leu Ile His Glu Phe Lys Met Tyr Ser Ile Leu Gly Gly
145                 150                 155                 160

Ile Asp Gly Thr Gly Asn Val Thr Glu His Phe Arg Lys Lys Arg Asn
                165                 170                 175

Glu Tyr Lys Leu Ile His Val Leu Gly Thr Leu Trp Asn Leu Pro Pro
            180                 185                 190

Leu Ile Val Ser Leu Ala Ser Tyr Phe Leu Leu Ile Val Ser Leu Gly
        195                 200                 205

Arg His Thr Gln Arg Met Glu Gln Ser Gly Thr Ser Ser Gly Asp Pro
    210                 215                 220

Ser Ala Glu Ala His Lys Arg Ala Ile Lys Ile Ile Leu Ser Phe Leu
225                 230                 235                 240

Leu Leu Phe Leu Leu Tyr Phe Leu Ala Phe Leu Ile Thr Ser Ser Ser
                245                 250                 255

Tyr Phe Ile Pro Gly Thr Glu Met Val Lys Ile Ile Gly Glu Leu Ile
            260                 265                 270

Thr Met Phe Tyr Pro Ala Ser His Ser Phe Ile Leu Ile Leu Gly Asn
        275                 280                 285

Ser Lys Leu Lys His Met Phe Val Gly Met Leu Arg Cys Glu Ser Gly
    290                 295                 300

His Leu Lys Pro Gly Ser Lys Gly Pro Val Ser Leu
305                 310                 315
```

<210> SEQ ID NO 7
<211> LENGTH: 921
<212> TYPE: DNA
<213> ORGANISM: Felis catus

<400> SEQUENCE: 7

```
atgcatcaga tactcttctt atctgctctt actgtctcag caattttgaa ttttgtagga      60
ctcgttgtaa atctgtttat cgtagtggtc aactacagga cttgggtcca agccacaga     120
atctcctctt ctaataggat cctgttcagc ttgggcgtca ccagatttat tatgctagga    180
ctgtttctcc tgaacattat ctacctgttc acctctccac atgtcgaaag gtcagtccac    240
ctatccactt ttttcctgtt gtgttggatg ttttggagt ctactagtct ctggcttgta     300
accttgctca atgccttgta ctgcgtgaag attactgact ccaacactc agtattcctc     360
ctgctgaaac gaaagctgtc cccaaagatc cccaggctgc tgctggcctg cgtgctgatc    420
tctgccttct ccactctcct gtatgttgtg ctcacacaaa catcacccctt tcctgagctt   480
ctgactggga gcaatggtac agtatgtgac atcaataaga gcatcttgtc tttggtgacc   540
tccttggtcc tgagctcctt tctccagttc atcatgaatg tgacttccgc ttccttgtta   600
atacattcct gaggagaca tatacagaag atgcagaaaa acgccactga tttttggaat    660
ccccagactg aagctcatat gggtgctatg aagctaatga tctatttcct catcctctac   720
attccatatt cacttgctac cctgctacag tatctcccctt ccgtacggat ggatttggga  780
gccacatcca tctgtatgat tatttccacc ttttatcctc aggacattc tgttctcatt    840
attctcacac atcctaaact gaaaacaaaa gcaagaagaa ttctttgttt caacatatgg  900
tggaatttca gtagtaaata g                                              921
```

<210> SEQ ID NO 8
<211> LENGTH: 306
<212> TYPE: PRT
<213> ORGANISM: Felis catus

<400> SEQUENCE: 8

```
Met His Gln Ile Leu Phe Leu Ser Ala Leu Thr Val Ser Ala Ile Leu
1               5                   10                  15

Asn Phe Val Gly Leu Val Val Asn Leu Phe Ile Val Val Asn Tyr
            20                  25                  30

Arg Thr Trp Val Gln Ser His Arg Ile Ser Ser Asn Arg Ile Leu
        35                  40                  45

Phe Ser Leu Gly Val Thr Arg Phe Ile Met Leu Gly Leu Phe Leu Leu
    50                  55                  60

Asn Ile Ile Tyr Leu Phe Thr Ser Pro His Val Glu Arg Ser Val His
65                  70                  75                  80

Leu Ser Thr Phe Phe Leu Leu Cys Trp Met Phe Leu Glu Ser Thr Ser
                85                  90                  95

Leu Trp Leu Val Thr Leu Leu Asn Ala Leu Tyr Cys Val Lys Ile Thr
            100                 105                 110

Asp Phe Gln His Ser Val Phe Leu Leu Lys Arg Lys Leu Ser Pro
        115                 120                 125

Lys Ile Pro Arg Leu Leu Leu Ala Cys Val Leu Ile Ser Ala Phe Ser
    130                 135                 140

Thr Leu Leu Tyr Val Val Leu Thr Gln Thr Ser Pro Phe Pro Glu Leu
145                 150                 155                 160
```

Leu Thr Gly Ser Asn Gly Thr Val Cys Asp Ile Asn Lys Ser Ile Leu
            165                 170                 175

Ser Leu Val Thr Ser Leu Val Leu Ser Ser Phe Leu Gln Phe Ile Met
        180                 185                 190

Asn Val Thr Ser Ala Ser Leu Leu Ile His Ser Leu Arg Arg His Ile
            195                 200                 205

Gln Lys Met Gln Lys Asn Ala Thr Asp Phe Trp Asn Pro Gln Thr Glu
        210                 215                 220

Ala His Met Gly Ala Met Lys Leu Met Ile Tyr Phe Leu Ile Leu Tyr
225                 230                 235                 240

Ile Pro Tyr Ser Leu Ala Thr Leu Leu Gln Tyr Leu Pro Ser Val Arg
            245                 250                 255

Met Asp Leu Gly Ala Thr Ser Ile Cys Met Ile Ile Ser Thr Phe Tyr
        260                 265                 270

Pro Pro Gly His Ser Val Leu Ile Leu Thr His Pro Lys Leu Lys
            275                 280                 285

Thr Lys Ala Lys Lys Ile Leu Cys Phe Asn Ile Trp Trp Asn Phe Ser
        290                 295                 300

Ser Lys
305

<210> SEQ ID NO 9
<211> LENGTH: 936
<212> TYPE: DNA
<213> ORGANISM: Felis catus

<400> SEQUENCE: 9

```
atgctggata aagtggagag caccttgatg ctcatagcag ctggagaatt tgcaatgggg      60
attttaggga atgcattcat tggattggta aactgcatga actggatcaa gaataggaag     120
attgcctcca ttgacttaat cctcacaagt ctggccatat ccagaatttg tctattatgt     180
atcatactat tagactattt tatactgggg ctgtatccag atgtctatac taccggtaaa     240
aaaatgagaa tcattgactt cttctggacg ctcaccaacc acctaaatgt ctggtttgcc     300
acctgcctca gcgtcttcta tttcctcaag atcgcgaatt tcttccatcc ccttttcctc     360
tggatgaagt ggaaaattga cagtgcgatt cctaggatcc tgctgggatg cttggccttc     420
tctgtgttca ttagccttgt tgtctctgag aatctgaacg atgatttcag gtcttgtgtt     480
aaggtaaaga agaaaacaaa cataactgtg aaatgcagag taaataaagc ccaatatgct     540
tctgtcaaga tttgcctcaa cctgttgacg ctattcccct tttccgtgtc cgtgatctca     600
tttctcctct tgctcctctc cctgtggaga cataccaggc agatgaagat cagtgccacg     660
gggtgcaggg accccagcat agaagcccat gtgggagcca tgaaagctgt catctccttc     720
ctcctccttt tcattgctta ctatttggct tttctcgtag ccacctccag ctactttatg     780
ccagagactg aactagctgt gatgattggt gagttgatag ctctcatcta tccaagccat     840
tcattgattc taattctggg gaacaataaa ttacggcagg cgtctctaag ggtgctgtgg     900
aaagtaaagt gtatcctaaa agaagaaat cactaa                                936
```

<210> SEQ ID NO 10
<211> LENGTH: 311
<212> TYPE: PRT
<213> ORGANISM: Felis catus

<400> SEQUENCE: 10

```
Met Leu Asp Lys Val Glu Ser Thr Leu Met Leu Ile Ala Ala Gly Glu
1               5                   10                  15

Phe Ala Met Gly Ile Leu Gly Asn Ala Phe Ile Gly Leu Val Asn Cys
            20                  25                  30

Met Asn Trp Ile Lys Asn Arg Lys Ile Ala Ser Ile Asp Leu Ile Leu
            35                  40                  45

Thr Ser Leu Ala Ile Ser Arg Ile Cys Leu Leu Cys Ile Ile Leu Leu
        50                  55                  60

Asp Tyr Phe Ile Leu Gly Leu Tyr Pro Asp Val Tyr Thr Thr Gly Lys
65                  70                  75                  80

Lys Met Arg Ile Ile Asp Phe Phe Trp Thr Leu Thr Asn His Leu Asn
                85                  90                  95

Val Trp Phe Ala Thr Cys Leu Ser Val Phe Tyr Phe Leu Lys Ile Ala
            100                 105                 110

Asn Phe Phe His Pro Leu Phe Leu Trp Met Lys Trp Lys Ile Asp Ser
            115                 120                 125

Ala Ile Pro Arg Ile Leu Leu Gly Cys Leu Ala Phe Ser Val Phe Ile
        130                 135                 140

Ser Leu Val Val Ser Glu Asn Leu Asn Asp Asp Phe Arg Ser Cys Val
145                 150                 155                 160

Lys Val Lys Lys Lys Thr Asn Ile Thr Val Lys Cys Arg Val Asn Lys
                165                 170                 175

Ala Gln Tyr Ala Ser Val Lys Ile Cys Leu Asn Leu Leu Thr Leu Phe
            180                 185                 190

Pro Phe Ser Val Ser Val Ile Ser Phe Leu Leu Leu Leu Ser Leu
            195                 200                 205

Trp Arg His Thr Arg Gln Met Lys Ile Ser Ala Thr Gly Cys Arg Asp
        210                 215                 220

Pro Ser Ile Glu Ala His Val Gly Ala Met Lys Ala Val Ile Ser Phe
225                 230                 235                 240

Leu Leu Leu Phe Ile Ala Tyr Tyr Leu Ala Phe Leu Val Ala Thr Ser
            245                 250                 255

Ser Tyr Phe Met Pro Glu Thr Glu Leu Ala Val Met Ile Gly Glu Leu
            260                 265                 270

Ile Ala Leu Ile Tyr Pro Ser His Ser Leu Ile Leu Ile Leu Gly Asn
        275                 280                 285

Asn Lys Leu Arg Gln Ala Ser Leu Arg Val Leu Trp Lys Val Lys Cys
290                 295                 300

Ile Leu Lys Arg Arg Asn His
305                 310

<210> SEQ ID NO 11
<211> LENGTH: 1014
<212> TYPE: DNA
<213> ORGANISM: Felis catus

<400> SEQUENCE: 11
atgccaagtg cagtggaggt aatatatatg gtcttgattg ctggtgaatt gactatagga      60
atctggggaa atgatttat tgtactggtt aactgcactg gttggctcca aaggcgagat      120
agctccgtga ttgacatcat cctggtgagt ttggccatct ccagaatctg tgtgttgtgt      180
gtggtatctg cagaaggctt tgttctgctg ctctctccac atgcgtatgc tcaaaatgag      240
acaataaaca ccttggatgc tttctggaca ctgagcaacc attcaagtgt ctggttcact      300
gcttgcctca gcattttcta cttactgaag atagccaaca tatcccaccc ggtgttcctc      360
```

```
tggctgaagc taaacgttac cagagtcgtc ctggggcttt ttctggcgtc cttcctcacc    420
tccataatta ttagtgtctt tttgaaagag ggatcctggg gtcacgtcga agtcaatcac    480
gaggaaaaca taacttggga attcagagtg agtaaagccc caagcgcttt caaactgatt    540
atcctgaacc tggggggctct agttcccttt gctctgtgcc taatctcctt tgtcttgtta    600
cttttctccc tctttagaca cgctaagcag atgcaacttt acgccaccgg gtccagggac    660
tgtagcacag aggcacacat gagggccata aaggcagtga ccatctttct gcttttcttc    720
atcatgtact atgcagtctt tcttgtagtc acttctagct tcctgattcc tcaaggacgg    780
ttagtgctga tgtttggtgg catagtcact gtcattttcc catcaagcca ttcgttcatc    840
ctgatcatgg gcaacagcaa gctgagggag gcctttctga aggtgctaag gtgtgtgaag    900
ggcttccaca aaagaaggaa acctcttgtt ccgcagagaa tcctgaatac ggggagaaag    960
aaatcaacaa aagactgtct cccttctccc cgggggttac attcatttgc ttaa         1014
```

<210> SEQ ID NO 12
<211> LENGTH: 337
<212> TYPE: PRT
<213> ORGANISM: Felis catus

<400> SEQUENCE: 12

```
Met Pro Ser Ala Val Glu Val Ile Tyr Met Val Leu Ile Ala Gly Glu
 1               5                  10                  15

Leu Thr Ile Gly Ile Trp Gly Asn Gly Phe Ile Val Leu Val Asn Cys
            20                  25                  30

Thr Gly Trp Leu Gln Arg Arg Asp Ser Val Ile Asp Ile Ile Leu
        35                  40                  45

Val Ser Leu Ala Ile Ser Arg Ile Cys Val Leu Cys Val Val Ser Ala
    50                  55                  60

Glu Gly Phe Val Leu Leu Leu Ser Pro His Ala Tyr Ala Gln Asn Glu
65                  70                  75                  80

Thr Ile Asn Thr Leu Asp Ala Phe Trp Thr Leu Ser Asn His Ser Ser
                85                  90                  95

Val Trp Phe Thr Ala Cys Leu Ser Ile Phe Tyr Leu Leu Lys Ile Ala
            100                 105                 110

Asn Ile Ser His Pro Val Phe Leu Trp Leu Lys Leu Asn Val Thr Arg
        115                 120                 125

Val Val Leu Gly Leu Phe Leu Ala Ser Phe Leu Thr Ser Ile Ile Ile
    130                 135                 140

Ser Val Phe Leu Lys Glu Gly Ser Trp Gly His Val Glu Val Asn His
145                 150                 155                 160

Glu Glu Asn Ile Thr Trp Glu Phe Arg Val Ser Lys Ala Pro Ser Ala
                165                 170                 175

Phe Lys Leu Ile Ile Leu Asn Leu Gly Ala Leu Val Pro Phe Ala Leu
            180                 185                 190

Cys Leu Ile Ser Phe Val Leu Leu Phe Ser Leu Phe Arg His Ala
        195                 200                 205

Lys Gln Met Gln Leu Tyr Ala Thr Gly Ser Arg Asp Cys Ser Thr Glu
    210                 215                 220

Ala His Met Arg Ala Ile Lys Ala Val Thr Ile Phe Leu Leu Phe Phe
225                 230                 235                 240

Ile Met Tyr Tyr Ala Val Phe Leu Val Val Thr Ser Ser Phe Leu Ile
                245                 250                 255
```

Pro Gln Gly Arg Val Val Leu Met Phe Gly Ile Val Thr Val Ile
                260                 265                 270

Phe Pro Ser Ser His Ser Phe Ile Leu Ile Met Gly Asn Ser Lys Leu
        275                 280                 285

Arg Glu Ala Phe Leu Lys Val Leu Arg Cys Val Lys Gly Phe His Lys
        290                 295                 300

Arg Arg Lys Pro Leu Val Pro Gln Arg Ile Leu Asn Thr Gly Arg Lys
305                 310                 315                 320

Lys Ser Thr Lys Asp Cys Leu Pro Ser Pro Arg Gly Leu His Ser Phe
                325                 330                 335

Ala

<210> SEQ ID NO 13
<211> LENGTH: 903
<212> TYPE: DNA
<213> ORGANISM: Felis catus

<400> SEQUENCE: 13

| | | | | | |
|---|---|---|---|---|---|
| atgttaagca | tagtggaagg | ccttctcatt | tttatagcag | ttagtgaatc | agtactgggg | 60 |
| gttttaggga | tggatttat | tggacttgta | aactgtatgg | actgtgtgaa | gaacaaaaag | 120 |
| ttttctatga | ttggcttcat | cttcaccggc | ttagctactt | ccagaatttg | tctgatattg | 180 |
| atagtaatgg | cagatggatt | tataaagata | ttctctccag | atatgtactc | ttctggtcac | 240 |
| ctaattgatt | atattagtta | cttatggata | attatcaatc | aatcaaacat | ctggtttgcc | 300 |
| accagcctca | gcaccttcta | cttcctgaag | atagcaaatt | tttcccacca | catgtttctc | 360 |
| tggttgaagg | gtagaatcaa | ttgggttctt | ccccttctga | tgggatcctt | gtttatttca | 420 |
| tggctcttta | cgttccctca | aattgtgaag | attcttagcg | acagtaaagt | ggggaatgga | 480 |
| aacgcaacct | ggcagctcaa | catgccgaag | agtgagttct | taactaagca | gattttggtc | 540 |
| aacataggag | tccttctcct | cttcacgcta | ttcctgatta | catgtttcct | gttaatcatt | 600 |
| tccctttgga | gacacagcag | gcggatgcaa | ttgaatgtca | ctggattcca | agaccccagt | 660 |
| acagaagcgc | atatgaaagc | catgaaagtt | ttgatatctt | tcatcatcct | ctttatcttg | 720 |
| cattttatag | gcctggccat | agaaatagca | tgcttcacaa | tgccagaaaa | aaaattgctg | 780 |
| tttatttttg | gtatgacgac | cacagtcttg | taccctgggg | gtcactcatt | tatcctcatt | 840 |
| ctcggaaaca | gcaagctaaa | gcaagcctct | ctgagagcac | tgcagcaggt | caagtgctgt | 900 |
| taa | | | | | | 903 |

<210> SEQ ID NO 14
<211> LENGTH: 300
<212> TYPE: PRT
<213> ORGANISM: Felis catus

<400> SEQUENCE: 14

Met Leu Ser Ile Val Glu Gly Leu Leu Ile Phe Ile Ala Val Ser Glu
1               5                   10                  15

Ser Val Leu Gly Val Leu Gly Asn Gly Phe Ile Gly Leu Val Asn Cys
                20                  25                  30

Met Asp Cys Val Lys Asn Lys Lys Phe Ser Met Ile Gly Phe Ile Phe
            35                  40                  45

Thr Gly Leu Ala Thr Ser Arg Ile Cys Leu Ile Leu Ile Val Met Ala
        50                  55                  60

Asp Gly Phe Ile Lys Ile Phe Ser Pro Asp Met Tyr Ser Ser Gly His
65                  70                  75                  80

Leu Ile Asp Tyr Ile Ser Tyr Leu Trp Ile Ile Asn Gln Ser Asn
                85                  90                  95

Ile Trp Phe Ala Thr Ser Leu Ser Thr Phe Tyr Phe Leu Lys Ile Ala
            100                 105                 110

Asn Phe Ser His His Met Phe Leu Trp Leu Lys Gly Arg Ile Asn Trp
        115                 120                 125

Val Leu Pro Leu Leu Met Gly Ser Leu Phe Ile Ser Trp Leu Phe Thr
130                 135                 140

Phe Pro Gln Ile Val Lys Ile Leu Ser Asp Ser Lys Val Gly Asn Gly
145                 150                 155                 160

Asn Ala Thr Trp Gln Leu Asn Met Pro Lys Ser Glu Phe Leu Thr Lys
                165                 170                 175

Gln Ile Leu Val Asn Ile Gly Val Leu Leu Leu Phe Thr Leu Phe Leu
            180                 185                 190

Ile Thr Cys Phe Leu Leu Ile Ile Ser Leu Trp Arg His Ser Arg Arg
        195                 200                 205

Met Gln Leu Asn Val Thr Gly Phe Gln Asp Pro Ser Thr Glu Ala His
210                 215                 220

Met Lys Ala Met Lys Val Leu Ile Ser Phe Ile Ile Leu Phe Ile Leu
225                 230                 235                 240

His Phe Ile Gly Leu Ala Ile Glu Ile Ala Cys Phe Thr Met Pro Glu
                245                 250                 255

Lys Lys Leu Leu Phe Ile Phe Gly Met Thr Thr Val Leu Tyr Pro
            260                 265                 270

Trp Gly His Ser Phe Ile Leu Ile Leu Gly Asn Ser Lys Leu Lys Gln
        275                 280                 285

Ala Ser Leu Arg Ala Leu Gln Gln Val Lys Cys Cys
290                 295                 300

<210> SEQ ID NO 15
<211> LENGTH: 930
<212> TYPE: DNA
<213> ORGANISM: Felis catus

<400> SEQUENCE: 15
atggcaagcg tattgaagaa tgtatttatg atactgtttg ctggagaatt cataatgggg    60
attttgggaa tggattcat tatattggtt aactgtattg actggatcag gaactggaaa    120
ttcttcgtaa ttgactttat tattacctgc ctagctattt ccagaatagt tctgttgtgc    180
ataataattt taggcatagg tttagatgta ccttgtgaag aaatatggaa caagaataat    240
caactaataa ggtttgaaat cctctggaca ggatccaatt atttctgcat aacctgtacc    300
acctgcctca gtgtcttcta tttcttcaag atagccaact tttccaaccc tcttttcctc    360
tggataaaat ggagaattca caaagtgctt ctcacgattg tactggccgc agtcttctct    420
ttctgcttgt ctcttccctt taaggataca gtgttcacga gtctgatcaa aaacaaggta    480
aacgcggaaa gaaattggac agtgagtttc acaacgagaa catatgagtt attttttgtct    540 catatgctcc tgaacataat gttcatcatc cccttttgcag tgtctctggc ttcctttgtc    600
cttttgatct gttccttatg gagccacacc aggcagatga agggcagagg tggggatcct    660
accacaaaag ttcacgtgag agccatgaag ctatgatttt cattcctact cttcttcttt    720
atgtactatt tgagcactat tatgatgaat tggcctacg tcatcctaga tagtttggtg    780
gcaaagattt ttgctaatac actagtattt ttatatccat ctggccatac atttcttctg    840

```
attttatgga ccagcaaatt gaaacaggct tctctctgtg tcctgaagaa gctgaagtgc    900
ctgcatctaa ggaaacccac acgcccataa                                    930
```

<210> SEQ ID NO 16
<211> LENGTH: 309
<212> TYPE: PRT
<213> ORGANISM: Felis catus

<400> SEQUENCE: 16

```
Met Ala Ser Val Leu Lys Asn Val Phe Met Ile Leu Phe Ala Gly Glu
1               5                   10                  15

Phe Ile Met Gly Ile Leu Gly Asn Gly Phe Ile Ile Leu Val Asn Cys
            20                  25                  30

Ile Asp Trp Ile Arg Asn Trp Lys Phe Phe Val Ile Asp Phe Ile Ile
        35                  40                  45

Thr Cys Leu Ala Ile Ser Arg Ile Val Leu Leu Cys Ile Ile Ile Leu
    50                  55                  60

Gly Ile Gly Leu Asp Val Pro Cys Glu Glu Ile Trp Asn Lys Asn Asn
65                  70                  75                  80

Gln Leu Ile Arg Phe Glu Ile Leu Trp Thr Gly Ser Asn Tyr Phe Cys
                85                  90                  95

Ile Thr Cys Thr Thr Cys Leu Ser Val Phe Tyr Phe Lys Ile Ala
            100                 105                 110

Asn Phe Ser Asn Pro Leu Phe Leu Trp Ile Lys Trp Arg Ile His Lys
        115                 120                 125

Val Leu Leu Thr Ile Val Leu Ala Ala Val Phe Ser Phe Cys Leu Ser
130                 135                 140

Leu Pro Phe Lys Asp Thr Val Phe Thr Ser Leu Ile Lys Asn Lys Val
145                 150                 155                 160

Asn Ala Glu Arg Asn Trp Thr Val Ser Phe Thr Arg Thr Tyr Glu
                165                 170                 175

Leu Phe Leu Ser His Met Leu Leu Asn Ile Met Phe Ile Ile Pro Phe
            180                 185                 190

Ala Val Ser Leu Ala Ser Phe Val Leu Leu Ile Cys Ser Leu Trp Ser
        195                 200                 205

His Thr Arg Gln Met Lys Gly Arg Gly Gly Asp Pro Thr Thr Lys Val
    210                 215                 220

His Val Arg Ala Met Lys Ala Met Ile Ser Phe Leu Leu Phe Phe Phe
225                 230                 235                 240

Met Tyr Tyr Leu Ser Thr Ile Met Met Asn Leu Ala Tyr Val Ile Leu
                245                 250                 255

Asp Ser Leu Val Ala Lys Ile Phe Ala Asn Thr Leu Val Phe Leu Tyr
            260                 265                 270

Pro Ser Gly His Thr Phe Leu Leu Ile Leu Trp Thr Ser Lys Leu Lys
        275                 280                 285

Gln Ala Ser Leu Cys Val Leu Lys Leu Lys Cys Leu His Leu Arg
    290                 295                 300

Lys Pro Thr Arg Pro
305
```

<210> SEQ ID NO 17
<211> LENGTH: 1005
<212> TYPE: DNA
<213> ORGANISM: Felis catus

<400> SEQUENCE: 17

```
atgttggctc tgactcctgt cataactgtg tcctatgaag tcaagagtgc atttctattc      60
ctttcaatcc tggaatttac agtggggggtc ctggccaatg ccttcatttt cctggtgaat    120
ttttgggacg tggtgaggaa gcagccactg agcaactgtg atcttattct tctgagtctc    180
agcctcaccc ggcttttcct gcacgggctg ctgtttctgr atgccctcca gcttacatac    240
ttccagagga tgaaagatcc gctgagcctc agctaccaga ccatcatcat gctctggatg    300
atcacaaacc aagttgggct gtggctcacc acctgcctca gtcttctcta ctgctccaag    360
attgcccgtt tctctcacac cctcctgcac tgtgtggcaa gctgggtctc ccggaaggtc    420
ccccagatgc tcctgggtgc aatgcttttc tcttgtatct gcaccgccat ctgtttgggg    480
gactttttta gtagatctgg cttcacattc acaactatgc tattcgtgaa taatacagaa    540
ttcaatttgc aaattgcaaa actcagtttc tatcactcct tcatcttctg cacactggcg    600
tccatcccgt cgttgttatt ttttctgatt tcttctgggg tgctgattgt ctccctgggg    660
aggcacatga ggacaatgag ggccaaaacc aaagactccc acgacccag cctggaagcc    720
catatcaaag ccctccgatc tcttgtctcc tttctctgcc tctatgtggt gtcattctgt    780
gctgccctcg tttcagtgcc tttactgatg ctgtggcaca acaagatcgg ggtaatgatc    840
tgtgtgggga tcctagcagc ttgtccctcg atacatgcag caatcctgat ctcaggcaat    900
gccaagctga ggagagctgt ggagaccatt ctactctggg ttcagaacag cctaaagata    960
ggggcagacc acaaggcaga tgccaggact ccaggcctat gttga              1005
```

<210> SEQ ID NO 18
<211> LENGTH: 334
<212> TYPE: PRT
<213> ORGANISM: Felis catus
<220> FEATURE:
<221> NAME/KEY: VARIANT
<222> LOCATION: (74)..(74)
<223> OTHER INFORMATION: X=D or N

<400> SEQUENCE: 18

```
Met Leu Ala Leu Thr Pro Val Ile Thr Val Ser Tyr Glu Val Lys Ser
1               5                   10                  15

Ala Phe Leu Phe Leu Ser Ile Leu Glu Phe Thr Val Gly Val Leu Ala
            20                  25                  30

Asn Ala Phe Ile Phe Leu Val Asn Phe Trp Asp Val Val Arg Lys Gln
        35                  40                  45

Pro Leu Ser Asn Cys Asp Leu Ile Leu Leu Ser Leu Ser Leu Thr Arg
    50                  55                  60

Leu Phe Leu His Gly Leu Leu Phe Leu Xaa Ala Leu Gln Leu Thr Tyr
65                  70                  75                  80

Phe Gln Arg Met Lys Asp Pro Leu Ser Leu Ser Tyr Gln Thr Ile Ile
                85                  90                  95

Met Leu Trp Met Ile Thr Asn Gln Val Gly Leu Trp Leu Thr Thr Cys
            100                 105                 110

Leu Ser Leu Leu Tyr Cys Ser Lys Ile Ala Arg Phe Ser His Thr Leu
        115                 120                 125

Leu His Cys Val Ala Ser Trp Val Ser Arg Lys Val Pro Gln Met Leu
    130                 135                 140

Leu Gly Ala Met Leu Phe Ser Cys Ile Cys Thr Ala Ile Cys Leu Gly
145                 150                 155                 160

Asp Phe Phe Ser Arg Ser Gly Phe Thr Phe Thr Thr Met Leu Phe Val
                165                 170                 175
```

```
Asn Asn Thr Glu Phe Asn Leu Gln Ile Ala Lys Leu Ser Phe Tyr His
                180                 185                 190
Ser Phe Ile Phe Cys Thr Leu Ala Ser Ile Pro Ser Leu Leu Phe Phe
            195                 200                 205
Leu Ile Ser Ser Gly Val Leu Ile Val Ser Leu Gly Arg His Met Arg
210                 215                 220
Thr Met Arg Ala Lys Thr Lys Asp Ser His Asp Pro Ser Leu Glu Ala
225                 230                 235                 240
His Ile Lys Ala Leu Arg Ser Leu Val Ser Phe Leu Cys Leu Tyr Val
                245                 250                 255
Val Ser Phe Cys Ala Ala Leu Val Ser Val Pro Leu Leu Met Leu Trp
            260                 265                 270
His Asn Lys Ile Gly Val Met Ile Cys Val Gly Ile Leu Ala Ala Cys
        275                 280                 285
Pro Ser Ile His Ala Ala Ile Leu Ile Ser Gly Asn Ala Lys Leu Arg
    290                 295                 300
Arg Ala Val Glu Thr Ile Leu Leu Trp Val Gln Asn Ser Leu Lys Ile
305                 310                 315                 320
Gly Ala Asp His Lys Ala Asp Ala Arg Thr Pro Gly Leu Cys
                325                 330

<210> SEQ ID NO 19
<211> LENGTH: 969
<212> TYPE: DNA
<213> ORGANISM: Felis catus

<400> SEQUENCE: 19
atgttagccg gactggataa aatctttctt acgctgtcaa cggcagaatt cgtaattgga      60
atgtcgggga atgtgttcgt tggactggtg aactgctctg aatggatcaa gaaccaaaaa     120 atctctttg ttgacttcat cctcacctgc ttggctctct cccgaatcac tcagctgctg      180
gtgtcactgt ggcaatcatt cgtaatgaca ctatctccgc ctttctattc cacttggaaa     240
tcagcaaaac ttattacttt gctttggaga ataacgaatc actggactac ctggtttacc     300
acctgcctga gcattttcta cctccttaaa atagctcact tctcccactc tttcttcctc     360
tggctgaagt ggagaacgaa cagagtggtt cttgccattc ttgtcctttc tttgcccttt     420
ctgctgtttg acttcctggt gctagaatca ttgaatgatt tcttcttaaa cgtctatgtg     480
atggatgaaa gtaatctgac attacataca aatgactgta aaagccttta tattaaaacc     540
ctgattcttc ttagtttttc ctataccatt cctattgttc tgtccctgac ctcactggtc     600
ctattgtttc tgtccttggt aagacacatc agaaatttgc agctcaacgt catgggctcc     660
ggggacgcca gcacacaggc cataagggg gccattaaaa tggttatgtc tttcctcctc      720
ctcttcacgg ttcatttttt ttccatccaa ttgacaaact ggatgctttt gatattttgg     780
aacaacaagt tcacaaagtt tatcatgttg gccatatatg tcttcccctc aggccactcg     840
ttaattttga ttctgggaaa cagcaaactg agacagacag ccttgaaggt actgcggcat     900
cttaaaagca ccttgaaaag agaaaaaaca gtttcgtctt tacagataga cgttccaggg     960
tctttctaa                                                            969

<210> SEQ ID NO 20
<211> LENGTH: 322
<212> TYPE: PRT
<213> ORGANISM: Felis catus
```

<400> SEQUENCE: 20

| | | | | | | | | | | | | | | |
|---|---|---|---|---|---|---|---|---|---|---|---|---|---|---|
|Met|Leu|Ala|Gly|Leu|Asp|Lys|Ile|Phe|Leu|Thr|Leu|Ser|Thr|Ala|Glu|
|1| | |5| | | |10| | | | |15| | |
|Phe|Val|Ile|Gly|Met|Ser|Gly|Asn|Val|Phe|Gly|Leu|Val|Asn|Cys| |
| | | |20| | | |25| | | |30| | | | |
|Ser|Glu|Trp|Ile|Lys|Asn|Gln|Lys|Ile|Ser|Phe|Val|Asp|Phe|Ile|Leu|
| | |35| | | |40| | | |45| | | | | |
|Thr|Cys|Leu|Ala|Leu|Ser|Arg|Ile|Thr|Gln|Leu|Leu|Val|Ser|Leu|Trp|
| |50| | | |55| | | |60| | | | | | |
|Gln|Ser|Phe|Val|Met|Thr|Leu|Ser|Pro|Pro|Phe|Tyr|Ser|Thr|Trp|Lys|
|65| | | |70| | | |75| | | | |80| | |
|Ser|Ala|Lys|Leu|Ile|Thr|Leu|Leu|Trp|Arg|Ile|Thr|Asn|His|Trp|Thr|
| | | |85| | | |90| | | |95| | | | |
|Thr|Trp|Phe|Thr|Thr|Cys|Leu|Ser|Ile|Phe|Tyr|Leu|Leu|Lys|Ile|Ala|
| | | |100| | | |105| | | |110| | | | |
|His|Phe|Ser|His|Ser|Phe|Phe|Leu|Trp|Leu|Lys|Trp|Arg|Thr|Asn|Arg|
| | |115| | | |120| | | |125| | | | | |
|Val|Val|Leu|Ala|Ile|Leu|Val|Leu|Ser|Leu|Pro|Phe|Leu|Leu|Phe|Asp|
| |130| | | |135| | | |140| | | | | | |
|Phe|Leu|Val|Leu|Glu|Ser|Leu|Asn|Asp|Phe|Phe|Leu|Asn|Val|Tyr|Val|
|145| | | |150| | | |155| | | | |160| | |
|Met|Asp|Glu|Ser|Asn|Leu|Thr|Leu|His|Thr|Asn|Asp|Cys|Lys|Ser|Leu|
| | | |165| | | |170| | | |175| | | | |
|Tyr|Ile|Lys|Thr|Leu|Ile|Leu|Leu|Ser|Phe|Ser|Tyr|Thr|Ile|Pro|Ile|
| | |180| | | |185| | | |190| | | | | |
|Val|Leu|Ser|Leu|Thr|Ser|Leu|Val|Leu|Leu|Phe|Leu|Ser|Leu|Val|Arg|
| |195| | | |200| | | |205| | | | | | |
|His|Ile|Arg|Asn|Leu|Gln|Leu|Asn|Val|Met|Gly|Ser|Gly|Asp|Ala|Ser|
|210| | | |215| | | |220| | | | | | | |
|Thr|Gln|Ala|His|Lys|Gly|Ala|Ile|Lys|Met|Val|Met|Ser|Phe|Leu|Leu|
|225| | | |230| | | |235| | | | |240| | |
|Leu|Phe|Thr|Val|His|Phe|Phe|Ser|Ile|Gln|Leu|Thr|Asn|Trp|Met|Leu|
| | | |245| | | |250| | | |255| | | | |
|Leu|Ile|Phe|Trp|Asn|Asn|Lys|Phe|Thr|Lys|Phe|Ile|Met|Leu|Ala|Ile|
| | |260| | | |265| | | |270| | | | | |
|Tyr|Val|Phe|Pro|Ser|Gly|His|Ser|Leu|Ile|Leu|Ile|Leu|Gly|Asn|Ser|
| |275| | | |280| | | |285| | | | | | |
|Lys|Leu|Arg|Gln|Thr|Ala|Leu|Lys|Val|Leu|Arg|His|Leu|Lys|Ser|Thr|
|290| | | |295| | | |300| | | | | | | |
|Leu|Lys|Arg|Glu|Lys|Thr|Val|Ser|Ser|Leu|Gln|Ile|Asp|Val|Pro|Gly|
|305| | | |310| | | |315| | | | |320| | |
|Ser|Phe| | | | | | | | | | | | | | |

<210> SEQ ID NO 21
<211> LENGTH: 900
<212> TYPE: DNA
<213> ORGANISM: Felis catus

<400> SEQUENCE: 21

```
atggtaaccg cgctaccgag cattttttcc atcgtggtaa taatagaatt tctcctagga    60
aattttgcca atggcttcat agcactggtg aacttcattg actggaccaa gagacaaaag   120
atctcctcag ttgatcacat tctcactgct ctggctgtct ccagaattgg tttgctctgg   180
gtaatattaa taaattggta tgcaactttg ttcagtccag atttctatag cttagaagta   240
```

-continued

```
agaattattt ttcaaactgc ctggacagta agcaatcatt ttagcatctg gctggctact    300
agcctcagca tattttattt gttcaaaata gccaacttct ccagccttat ttttcttcgc    360
ctcaagtgga gagttaaaag catagttctt gtgattctgt tggggtcctt gttctttttg    420
gtttgtcatg ttgtggcggt gagcgtatgt gagaaagtgc agactgacgt atatgaagga    480
aacggcacta ggaagaccaa attgagggac attttacagc tttcaaatat gactatattc    540
acactagcaa acttcatacc ctttggtatg tccctgacgt cttttgtgct gttgatcttt    600
tccctctgga aacatctcaa gaggatgcag ctctgtgata agggatctca agatcccagc    660
accaaggtcc acataagagc catgcagacc gtggtctcct ttctcttgtt ctttgccggt    720
tacttcttta ctctgacgat cacaatttgg agttctaatt ggccgcagaa cgagttcggc    780
ttcctccttt gccaggttat tggaatccta tatccttcaa tccactcgtt gatgctgatt    840
cggggaaaca agaagctaag acaggccttt ctgtcatttc tgtggcagct gaagtgctga    900
```

<210> SEQ ID NO 22
<211> LENGTH: 299
<212> TYPE: PRT
<213> ORGANISM: Felis catus

<400> SEQUENCE: 22

```
Met Val Thr Ala Leu Pro Ser Ile Phe Ser Ile Val Val Ile Ile Glu
1               5                   10                  15

Phe Leu Leu Gly Asn Phe Ala Asn Gly Phe Ile Ala Leu Val Asn Phe
            20                  25                  30

Ile Asp Trp Thr Lys Arg Gln Lys Ile Ser Ser Val Asp His Ile Leu
        35                  40                  45

Thr Ala Leu Ala Val Ser Arg Ile Gly Leu Leu Trp Val Ile Leu Ile
    50                  55                  60

Asn Trp Tyr Ala Thr Leu Phe Ser Pro Asp Phe Tyr Ser Leu Glu Val
65                  70                  75                  80

Arg Ile Ile Phe Gln Thr Ala Trp Thr Val Ser Asn His Phe Ser Ile
                85                  90                  95

Trp Leu Ala Thr Ser Leu Ser Ile Phe Tyr Leu Phe Lys Ile Ala Asn
            100                 105                 110

Phe Ser Ser Leu Ile Phe Leu Arg Leu Lys Trp Arg Val Lys Ser Ile
        115                 120                 125

Val Leu Val Ile Leu Leu Gly Ser Leu Phe Phe Leu Val Cys His Val
    130                 135                 140

Val Ala Val Ser Val Cys Glu Lys Val Gln Thr Asp Val Tyr Glu Gly
145                 150                 155                 160

Asn Gly Thr Arg Lys Thr Lys Leu Arg Asp Ile Leu Gln Leu Ser Asn
                165                 170                 175

Met Thr Ile Phe Thr Leu Ala Asn Phe Ile Pro Phe Gly Met Ser Leu
            180                 185                 190

Thr Ser Phe Val Leu Leu Ile Phe Ser Leu Trp Lys His Leu Lys Arg
        195                 200                 205

Met Gln Leu Cys Asp Lys Gly Ser Gln Asp Pro Ser Thr Lys Val His
    210                 215                 220

Ile Arg Ala Met Gln Thr Val Val Ser Phe Leu Leu Phe Phe Ala Gly
225                 230                 235                 240

Tyr Phe Phe Thr Leu Thr Ile Thr Ile Trp Ser Ser Asn Trp Pro Gln
                245                 250                 255
```

```
Asn Glu Phe Gly Phe Leu Leu Cys Gln Val Ile Gly Ile Leu Tyr Pro
            260                 265                 270

Ser Ile His Ser Leu Met Leu Ile Arg Gly Asn Lys Lys Leu Arg Gln
        275                 280                 285

Ala Phe Leu Ser Phe Leu Trp Gln Leu Lys Cys
    290                 295

<210> SEQ ID NO 23
<211> LENGTH: 927
<212> TYPE: DNA
<213> ORGANISM: Felis catus

<400> SEQUENCE: 23
atggtaagcg cgctaccaag cattttttcc attgcggtaa taatagaatt tctcctagga      60
aattttgcca atggcttcat agcactggtg aacttcattg actggaccaa gagacaaaag    120
atctcctcag ttgatcacat tctcgctgct ctggctgtct ccagaattgg tttgctctgg    180
gtaatgataa taaattggta tgcaacttgg ttcagtccag atttcaagag cttagaagta    240
agaattattt ttcaaactgc ctggacagta agcaatcatt ttagcatctg gctggctact    300
agcctcagca tattttattt gttcaaaata gccaacttct ccagcctatt tttccttcgc    360
ctcaagtgga gagttaaaag cgtcgtgctt gtgatgctgc tggggtcttt gttcttattg    420 tttttctcatg tggcggcagt gagcatatat gagaaagtgc agactaaggc atatgaaggg    480
aatgtcactt ggaggaccaa atggacgggc atggcacacc tctcaaatat gactgtattc    540
acactagcaa acttcatacc ctttgctacg tccctgacgt cttttgtgct gttgatcttt    600
tccctctgga gacatctcaa gcggatgcag ctctgtggca agggatccca agatcccagc    660
accaaggtcc acataagagc catgcagacg gtggtctcct ttctcttgtt ctttgccggt    720
tacgttctga atcaattgt tacagtttgg agttttaacg gctgcagaa ggaactgttc    780 atgttttgcc aggtacttgc cttcgtgtat ccttcgatcc actcgctgat gttgatttgg    840
ggaaacaaga agctaaaaca ggcctttctg tctgttttat accaggagaa gtactggctg    900
aaagaacaga aacactcaac tccatag                                         927

<210> SEQ ID NO 24
<211> LENGTH: 308
<212> TYPE: PRT
<213> ORGANISM: Felis catus

<400> SEQUENCE: 24

Met Val Ser Ala Leu Pro Ser Ile Phe Ser Ile Ala Val Ile Ile Glu
1               5                   10                  15

Phe Leu Leu Gly Asn Phe Ala Asn Gly Phe Ile Ala Leu Val Asn Phe
            20                  25                  30

Ile Asp Trp Thr Lys Arg Gln Lys Ile Ser Ser Val Asp His Ile Leu
        35                  40                  45

Ala Ala Leu Ala Val Ser Arg Ile Gly Leu Leu Trp Val Met Ile Ile
    50                  55                  60

Asn Trp Tyr Ala Thr Trp Phe Ser Pro Asp Phe Lys Ser Leu Glu Val
65                  70                  75                  80

Arg Ile Ile Phe Gln Thr Ala Trp Thr Val Ser Asn His Phe Ser Ile
                85                  90                  95

Trp Leu Ala Thr Ser Leu Ser Ile Phe Tyr Leu Phe Lys Ile Ala Asn
            100                 105                 110

Phe Ser Ser Leu Ile Phe Leu Arg Leu Lys Trp Arg Val Lys Ser Val
```

|   |   |   | 115 |   |   |   | 120 |   |   |   | 125 |   |
|---|---|---|---|---|---|---|---|---|---|---|---|---|
| Val | Leu | Val | Met | Leu | Leu | Gly | Ser | Leu | Phe | Leu | Phe | Ser | His | Val |

```
                    115                 120                 125
        Val Leu Val Met Leu Leu Gly Ser Leu Phe Leu Phe Ser His Val
        130                 135                 140
        Ala Ala Val Ser Ile Tyr Glu Lys Val Gln Thr Lys Ala Tyr Glu Gly
        145                 150                 155                 160
        Asn Val Thr Trp Arg Thr Lys Trp Thr Gly Met Ala His Leu Ser Asn
                            165                 170                 175
        Met Thr Val Phe Thr Leu Ala Asn Phe Ile Pro Phe Ala Thr Ser Leu
                    180                 185                 190
        Thr Ser Phe Val Leu Leu Ile Phe Ser Leu Trp Arg His Leu Lys Arg
                    195                 200                 205
        Met Gln Leu Cys Gly Lys Gly Ser Gln Asp Pro Ser Thr Lys Val His
        210                 215                 220
        Ile Arg Ala Met Gln Thr Val Val Ser Phe Leu Leu Phe Phe Ala Gly
        225                 230                 235                 240
        Tyr Val Leu Asn Leu Ile Val Thr Val Trp Ser Phe Asn Gly Leu Gln
                            245                 250                 255
        Lys Glu Leu Phe Met Phe Cys Gln Val Leu Ala Phe Val Tyr Pro Ser
                        260                 265                 270
        Ile His Ser Leu Met Leu Ile Trp Gly Asn Lys Lys Leu Lys Gln Ala
                275                 280                 285
        Phe Leu Ser Val Leu Tyr Gln Glu Lys Tyr Trp Leu Lys Glu Gln Lys
                290                 295                 300
        His Ser Thr Pro
        305
```

<210> SEQ ID NO 25
<211> LENGTH: 939
<212> TYPE: DNA
<213> ORGANISM: Felis catus

<400> SEQUENCE: 25

```
atgccatctg gaatcgaaaa tactttctg acagccgcgg taggaacatt catgattgga      60
atgttgggga atggtttcat cgcactcgtc aactgcattg actgggtgaa gcatcgaaag    120
ctctcgccag ctgactgcat cctcaccagc ctggctgtct ccagaatcat tcttctttgg    180
atgatactat tcgatttgct tgtaatggtg ttttggccac atctatataa cattgagaaa    240
ctagctaccg ctgttaatat ctgttggaca ctgaccaatc acctagctac ctggtttgcc    300
acctgcctga gtgttttcta tttctttagg atagccaatt tctcccaccg ctatttcacc    360
tggctgaggc ggagaattag cagggtgctc cctgtgcttc ctctggggtc tttattctta    420
ctggttttca actacaaatt attagttgga ttttctgatc tctgggctac catctaccac    480
aactatgaaa gaaactcaac tcggcccta gatgtaagta aaactgggta tcttaacagc    540
ttggttattc tcagtttcat ctacttaatc cccttcctc gtccctgac ctcactgctc     600
cttttatttc tctccttgat gagacatacc aggaacgtgc aactgaactc tagctcgagg    660
gacttcagca cggaggccca taaagggcc atgaaatgg tgatatcttt cctcctcctc    720
tccacggttc attttttttc catccagtta acaggttgga ttttcctttt actgaagaaa    780
catcatgcca acttgacggt gacgttgaca tcggctcttt ttccttcagg ccactcattt    840
atcctcattt ttggaaacag caagctgaga caaactgctt taggactact gtggcatctc    900
aattgccacc tgaaaatggt gaacccttta gcttcatag                            939
```

```
<210> SEQ ID NO 26
<211> LENGTH: 312
<212> TYPE: PRT
<213> ORGANISM: Felis catus

<400> SEQUENCE: 26
```

Met Pro Ser Gly Ile Glu Asn Thr Phe Leu Thr Ala Ala Val Gly Thr
1               5                   10                  15

Phe Met Ile Gly Met Leu Gly Asn Gly Phe Ile Ala Leu Val Asn Cys
            20                  25                  30

Ile Asp Trp Val Lys His Arg Lys Leu Ser Pro Ala Asp Cys Ile Leu
        35                  40                  45

Thr Ser Leu Ala Val Ser Arg Ile Ile Leu Leu Trp Met Ile Leu Phe
    50                  55                  60

Asp Leu Leu Val Met Val Phe Trp Pro His Leu Tyr Asn Ile Glu Lys
65                  70                  75                  80

Leu Ala Thr Ala Val Asn Ile Cys Trp Thr Leu Thr Asn His Leu Ala
                85                  90                  95

Thr Trp Phe Ala Thr Cys Leu Ser Val Phe Tyr Phe Arg Ile Ala
            100                 105                 110

Asn Phe Ser His Arg Tyr Phe Thr Trp Leu Arg Arg Ile Ser Arg
            115                 120                 125

Val Leu Pro Val Leu Pro Leu Gly Ser Leu Phe Leu Leu Val Phe Asn
    130                 135                 140

Tyr Lys Leu Leu Val Gly Phe Ser Asp Leu Trp Ala Thr Ile Tyr His
145                 150                 155                 160

Asn Tyr Glu Arg Asn Ser Thr Arg Pro Leu Asp Val Ser Lys Thr Gly
                165                 170                 175

Tyr Leu Asn Ser Leu Val Ile Leu Ser Phe Ile Tyr Leu Ile Pro Phe
            180                 185                 190

Leu Leu Ser Leu Thr Ser Leu Leu Leu Phe Leu Ser Leu Met Arg
            195                 200                 205

His Thr Arg Asn Val Gln Leu Asn Ser Ser Arg Asp Phe Ser Thr
            210                 215                 220

Glu Ala His Lys Arg Ala Met Lys Met Val Ile Ser Phe Leu Leu Leu
225                 230                 235                 240

Ser Thr Val His Phe Phe Ser Ile Gln Leu Thr Gly Trp Ile Phe Leu
                245                 250                 255

Leu Leu Lys Lys His His Ala Asn Leu Thr Val Thr Leu Thr Ser Ala
            260                 265                 270

Leu Phe Pro Ser Gly His Ser Phe Ile Leu Ile Phe Gly Asn Ser Lys
        275                 280                 285

Leu Arg Gln Thr Ala Leu Gly Leu Leu Trp His Leu Asn Cys His Leu
    290                 295                 300

Lys Met Val Lys Pro Leu Ala Ser
305                 310

```
<210> SEQ ID NO 27
<211> LENGTH: 299
<212> TYPE: PRT
<213> ORGANISM: Homo sapiens

<400> SEQUENCE: 27
```

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys

```
            20                  25                  30
Lys Thr Trp Val Lys Ser His Arg Ile Ser Ser Ser Asp Arg Ile Leu
             35                  40                  45

Phe Ser Leu Gly Ile Thr Arg Phe Leu Met Leu Gly Leu Phe Leu Val
         50                  55                  60

Asn Thr Ile Tyr Phe Val Ser Ser Asn Thr Glu Arg Ser Val Tyr Leu
 65                  70                  75                  80

Ser Ala Phe Phe Val Leu Cys Phe Met Phe Leu Asp Ser Ser Ser Val
                 85                  90                  95

Trp Phe Val Thr Leu Leu Asn Ile Leu Tyr Cys Val Lys Ile Thr Asn
             100                 105                 110

Phe Gln His Ser Val Phe Leu Leu Lys Arg Asn Ile Ser Pro Lys
         115                 120                 125

Ile Pro Arg Leu Leu Leu Ala Cys Val Leu Ile Ser Ala Phe Thr Thr
         130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
             165                 170                 175

Leu Val Val Ser Leu Val Leu Ser Ser Leu Gln Phe Ile Ile Asn
             180                 185                 190

Val Thr Ser Ala Ser Leu Leu Ile His Ser Leu Arg Arg His Ile Gln
             195                 200                 205

Lys Met Gln Lys Asn Ala Thr Gly Phe Trp Asn Pro Gln Thr Glu Ala
         210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                 245                 250                 255

Met Asp Met Gly Thr Lys Ser Ile Cys Leu Ile Phe Ala Thr Leu Tyr
             260                 265                 270

Ser Pro Gly His Ser Val Leu Ile Ile Thr His Pro Lys Leu Lys
         275                 280                 285

Thr Thr Ala Lys Lys Ile Leu Cys Phe Lys Lys
         290                 295

<210> SEQ ID NO 28
<211> LENGTH: 312
<212> TYPE: PRT
<213> ORGANISM: Homo sapiens

<400> SEQUENCE: 28

Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
             20                  25                  30

Ile Asp Trp Leu Lys Arg Arg Asp Ile Ser Leu Ile Asp Ile Ile Leu
             35                  40                  45

Ile Ser Leu Ala Ile Ser Arg Ile Cys Leu Leu Cys Val Ile Ser Leu
         50                  55                  60

Asp Gly Phe Phe Met Leu Leu Phe Pro Gly Thr Tyr Gly Asn Ser Val
 65                  70                  75                  80

Leu Val Ser Ile Val Asn Val Val Trp Thr Phe Ala Asn Asn Ser Ser
                 85                  90                  95
```

```
Leu Trp Phe Thr Ser Cys Leu Ser Ile Phe Tyr Leu Leu Lys Ile Ala
            100                 105                 110

Asn Ile Ser His Pro Phe Phe Trp Leu Lys Leu Lys Ile Asn Lys
        115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
210                 215                 220

Glu Ala His Met Arg Ala Ile Lys Ala Val Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Leu Ile Met Gly Asn Ser Lys
        275                 280                 285

Leu Arg Glu Ala Phe Leu Lys Met Leu Arg Phe Val Lys Cys Phe Leu
290                 295                 300

Arg Arg Arg Lys Pro Phe Val Pro
305                 310

<210> SEQ ID NO 29
<211> LENGTH: 307
<212> TYPE: PRT
<213> ORGANISM: Homo sapiens

<400> SEQUENCE: 29

Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
                20                  25                  30

Ile Asp Cys Ala Lys Asn Lys Leu Ser Thr Ile Gly Phe Ile Leu Thr
            35                  40                  45

Gly Leu Ala Ile Ser Arg Ile Phe Leu Ile Trp Ile Ile Thr Asp
50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Thr Lys Asn Asp Thr
145                 150                 155                 160
```

```
Val Trp Asp Leu Asn Met Tyr Lys Ser Glu Tyr Phe Ile Lys Gln Ile
            165                 170                 175

Leu Leu Asn Leu Gly Val Ile Phe Phe Thr Leu Ser Leu Ile Thr
        180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
    210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
    290                 295                 300

Arg Val Thr
305

<210> SEQ ID NO 30
<211> LENGTH: 291
<212> TYPE: PRT
<213> ORGANISM: Homo sapiens

<400> SEQUENCE: 30

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
```

```
            210                 215                 220
Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
                260                 265                 270

Ser Thr Ser Leu Met Leu Ser Ser Pro Thr Leu Lys Arg Ile Leu Lys
                275                 280                 285

Gly Lys Cys
        290

<210> SEQ ID NO 31
<211> LENGTH: 333
<212> TYPE: PRT
<213> ORGANISM: Homo sapiens

<400> SEQUENCE: 31

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
                20                  25                  30

Asn Ala Phe Val Phe Leu Val Asn Phe Trp Asp Val Val Lys Arg Gln
                35                  40                  45

Ala Leu Ser Asn Ser Asp Cys Val Leu Leu Cys Leu Ser Ile Ser Arg
            50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
                100                 105                 110

Leu Ser Leu Leu Tyr Cys Ser Lys Leu Ile Arg Phe Ser His Thr Phe
                115                 120                 125

Leu Ile Cys Leu Ala Ser Trp Val Ser Arg Lys Ile Ser Gln Met Leu
            130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                165                 170                 175

Asn Asn Asn Thr Arg Leu Asn Trp Gln Ile Lys Asp Leu Asn Leu Phe
                180                 185                 190

Tyr Ser Phe Leu Phe Cys Tyr Leu Trp Ser Val Pro Pro Phe Leu Leu
                195                 200                 205

Phe Leu Val Ser Ser Gly Met Leu Thr Val Ser Leu Gly Arg His Met
            210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
                260                 265                 270

Trp Arg Asp Lys Ile Gly Val Met Val Cys Val Gly Ile Met Ala Ala
                275                 280                 285
```

```
Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330
```

<210> SEQ ID NO 32
<211> LENGTH: 22
<212> TYPE: DNA
<213> ORGANISM: Felis catus

<400> SEQUENCE: 32
tcatggtgga ggtgaaggat tg                                        22

<210> SEQ ID NO 33
<211> LENGTH: 22
<212> TYPE: DNA
<213> ORGANISM: Felis catus

<400> SEQUENCE: 33
aggtatggca ggcatcgtca gc                                        22

<210> SEQ ID NO 34
<211> LENGTH: 23
<212> TYPE: DNA
<213> ORGANISM: Felis catus

<400> SEQUENCE: 34
caggaattgg cagaaggtca gat                                       23

<210> SEQ ID NO 35
<211> LENGTH: 24
<212> TYPE: DNA
<213> ORGANISM: Felis catus

<400> SEQUENCE: 35
ggagaaggaa attgccagaa agag                                      24

<210> SEQ ID NO 36
<211> LENGTH: 25
<212> TYPE: DNA
<213> ORGANISM: Felis catus

<400> SEQUENCE: 36
aaattgggca gagacaagag acagg                                     25

<210> SEQ ID NO 37
<211> LENGTH: 20
<212> TYPE: DNA
<213> ORGANISM: Felis catus

<400> SEQUENCE: 37
cggcaccgga accacaagag                                           20

<210> SEQ ID NO 38
<211> LENGTH: 23
<212> TYPE: DNA
<213> ORGANISM: Felis catus

<400> SEQUENCE: 38
ggggacaatt ggaaaaggaa acg                                       23

<210> SEQ ID NO 39
<211> LENGTH: 23
<212> TYPE: DNA
<213> ORGANISM: Felis catus

<400> SEQUENCE: 39
ctcaaaggcc cacgaagtca gat                                              23

<210> SEQ ID NO 40
<211> LENGTH: 24
<212> TYPE: DNA
<213> ORGANISM: Felis catus

<400> SEQUENCE: 40
aggatcatga aagggaacgg gtct                                             24

<210> SEQ ID NO 41
<211> LENGTH: 24
<212> TYPE: DNA
<213> ORGANISM: Felis catus

<400> SEQUENCE: 41
gacaaagaga aagaggcaaa atcg                                             24

<210> SEQ ID NO 42
<211> LENGTH: 24
<212> TYPE: DNA
<213> ORGANISM: Felis catus

<400> SEQUENCE: 42
ccgacaaaga gggcagaaaa agac                                             24

<210> SEQ ID NO 43
<211> LENGTH: 24
<212> TYPE: DNA
<213> ORGANISM: Felis catus

<400> SEQUENCE: 43
gacctcctcc ggctcagaag aagt                                             24

<210> SEQ ID NO 44
<211> LENGTH: 23
<212> TYPE: DNA
<213> ORGANISM: Felis catus

<400> SEQUENCE: 44
gatatacgtt gggcgctcct act                                              23

<210> SEQ ID NO 45
<211> LENGTH: 23
<212> TYPE: DNA
<213> ORGANISM: Felis catus

<400> SEQUENCE: 45
agtgaaaccc ttacagtgaa tag                                              23

<210> SEQ ID NO 46
<211> LENGTH: 24
<212> TYPE: DNA
<213> ORGANISM: Felis catus

<400> SEQUENCE: 46
caagcagtgt gacagcagca ggta                                             24

<210> SEQ ID NO 47
<211> LENGTH: 24
<212> TYPE: DNA
<213> ORGANISM: Felis catus

<400> SEQUENCE: 47
ggagaggaag gaaagaaacg caca                                              24

<210> SEQ ID NO 48
<211> LENGTH: 21
<212> TYPE: DNA
<213> ORGANISM: Felis catus

<400> SEQUENCE: 48
gaagtcctgg cttgtaatgt a                                                 21

<210> SEQ ID NO 49
<211> LENGTH: 21
<212> TYPE: DNA
<213> ORGANISM: Felis catus

<400> SEQUENCE: 49
caaaacaaac ttggggaact t                                                 21

<210> SEQ ID NO 50
<211> LENGTH: 24
<212> TYPE: DNA
<213> ORGANISM: Felis catus

<400> SEQUENCE: 50
acactggaat cgcaaagaaa cacg                                              24

<210> SEQ ID NO 51
<211> LENGTH: 24
<212> TYPE: DNA
<213> ORGANISM: Felis catus

<400> SEQUENCE: 51
gatcctcaaa gactcctcaa taag                                              24

<210> SEQ ID NO 52
<211> LENGTH: 24
<212> TYPE: DNA
<213> ORGANISM: Felis catus

<400> SEQUENCE: 52
gcacaaccag cgacatcaga catt                                              24

<210> SEQ ID NO 53
<211> LENGTH: 18
<212> TYPE: DNA
<213> ORGANISM: Felis catus

<400> SEQUENCE: 53
cccaggcgcc ccaaaaga                                                     18

<210> SEQ ID NO 54
<211> LENGTH: 24
<212> TYPE: DNA
<213> ORGANISM: Felis catus

<400> SEQUENCE: 54
gcacaaccag cgacatcaga catt                                              24

<210> SEQ ID NO 55
<211> LENGTH: 23
<212> TYPE: DNA
<213> ORGANISM: Felis catus

<400> SEQUENCE: 55
ccggtgaggg tagattattt cca                                               23

<210> SEQ ID NO 56
<211> LENGTH: 20
<212> TYPE: DNA
<213> ORGANISM: Felis catus

<400> SEQUENCE: 56
acccaggcgc cccagtatct                                                   20

<210> SEQ ID NO 57
<211> LENGTH: 20
<212> TYPE: DNA
<213> ORGANISM: Felis catus

<400> SEQUENCE: 57
gcttccggca tttttattcc                                                   20

<210> SEQ ID NO 58
<211> LENGTH: 897
<212> TYPE: DNA
<213> ORGANISM: Artificial Sequence
<220> FEATURE:
<223> OTHER INFORMATION: artificial construct R1 codon-optimized for C
      elegans

<400> SEQUENCE: 58
atgcttgatt ctatcttat tattcatttc cttcttccag ttattcaatg tcttattgga        60
gttcttgcta atggaattat tgttattgtt aatggaactg aacttattaa acaaagaaaa       120
atggttccac ttgatcttct tctttcttgt cttgctattt ctagaaattg tcttcaatct       180
ttcattttct atattaatct tgttattctt tctcttattg atttccttcc acttgttaaa      240
aatttcgctg ttttcatgtt cgttaatgaa actggacttt ggcttgctac ttggcttgga      300
gttttctatt gtgctaaaat ttctccaatt gctcatccac ttttcttctg cttaaaaga       360
agaatttcta aacttgttcc atggcttatt attggatctc ttcttttcgc ttcattcca       420
cttgttttct attctaaaca tacttgggtt ctttctcaag aagttcttct tagacttttc      480
tctccaaatg ctactactca aattaaagaa acttctgctc ttcaaattgt tttccttgct      540
agattctctc caccattcat tatttccctt acttctactc ttcttcttgt tttctctctt      600
ggaagacata cttggcaaat gagaaatact gctactggaa ctagagatgg atctactgga      660
gttcatgttt ctgctcttct ttctattctt tctttccttg ttcttatctt ttctcattat      720
atgactgctg ctcttctttc ttctcatatt ttcgaactta gatctttcat gttccttttc      780
tgtattcttg ttttcggatc ttatccatct ggacattcta ttattcttat ttctggaaat      840
agaaaactta acaaaatgc taaaaaattc cttcttcatg acaatgttg tcaataa           897

<210> SEQ ID NO 59
<211> LENGTH: 897
<212> TYPE: DNA
<213> ORGANISM: Artificial Sequence
<220> FEATURE:

<223> OTHER INFORMATION: artificial construct-R1 codon-optimized for
      Drosophila

<400> SEQUENCE: 59

```
atgctggact tctacctgat catccacttc ctgctgcccg tgatccagtg cctgatcggc    60
gtgctggcca acggcatcat cgtgatcgtg aacggcaccg agctgatcaa gcagcgcaag   120
atggtgcccc tggacctgct gctgtcctgc ctggccatct cccgcatctg cctgcagtcc   180
ttcatcttct acatcaacct ggtgatcctg tccctgatcg acttcctgcc cctggtgaag   240
aacttcgccg tgttcatgtt cgtgaacgag accggcctgt ggctggccac ctggctgggc   300
gtgttctact gcgccaagat ctcccccatc gcccacccc tgttcttctg gctgaagcgc   360
cgcatctcca gctggtgcc ctggctgatc atcggctccc tgctgttcgc ctccatcccc   420
ctggtgttct actccaagca cacctgggtg ctgtcccagg aggtgctgct cgcctgttc   480
tcccccaacg ccaccaccca gatcaaggag acctccgccc tgcagatcgt gttcctggcc   540
cgcttctccc cccccttcat catcttcctg acctccaccc tgctgctggt gttctccctg   600
ggccgccaca cctggcagat cgcaacacc gccaccggca cccgcgacgg ctccaccggc   660
gtgcacgtgt ccgccctgct gtccatcctg tccttcctgg tgctgtacct gtcccactac   720
atgaccgccg ccctgctgtc ctcccacatc ttcgagctgc gctccttcat gttcctgttc   780
tgcatcctgg tgttcggctc ctaccccctcc ggcactcca tcatcctgat ctccggcaac   840
cgcaagctga agcagaacgc caagaagttc ctgctgcacg ccagtgctg ccagtaa      897
```

<210> SEQ ID NO 60
<211> LENGTH: 897
<212> TYPE: DNA
<213> ORGANISM: Artificial Sequence
<220> FEATURE:
<223> OTHER INFORMATION: artificial construct-R1 codon-optimized for
      human cell

<400> SEQUENCE: 60

```
atgctggact tctacctgat catccacttc ctgctgcccg tgatccagtg cctgatcggc    60
gtgctggcca acggcatcat cgtgatcgtg aacggcaccg agctgatcaa gcagcgcaag   120
atggtgcccc tggacctgct gctgagctgc ctggccatca gccgcatctg cctgcagagc   180
ttcatcttct acatcaacct ggtgatcctg agcctgatcg acttcctgcc cctggtgaag   240
aacttcgccg tgttcatgtt cgtgaacgag accggcctgt ggctggccac ctggctgggc   300
gtgttctact gcgccaagat cagccccatc gcccacccc tgttcttctg gctgaagcgc   360
cgcatcagca gctggtgcc ctggctgatc atcggcagcc tgctgttcgc cagcatcccc   420
ctggtgttct acagcaagca cacctgggtg ctgagccagg aggtgctgct cgcctgttc   480
agccccaacg ccaccaccca gatcaaggag accagcgccc tgcagatcgt gttcctggcc   540
cgcttcagcc cccccttcat catcttcctg accagcaccc tgctgctggt gttcagcctg   600
ggccgccaca cctggcagat cgcaacacc gccaccggca cccgcgacgg cagcaccggc   660
gtgcacgtga gcgccctgct gagcatcctg agcttcctgg tgctgtacct gagccactac   720
atgaccgccg ccctgctgag cagccacatc ttcgagctgc gcagcttcat gttcctgttc   780
tgcatcctgg tgttcggcag ctaccccagc ggccacagca tcatcctgat cagcggcaac   840
cgcaagctga agcagaacgc caagaagttc ctgctgcacg ccagtgctg ccagtaa      897
```

<210> SEQ ID NO 61
<211> LENGTH: 897

<212> TYPE: DNA
<213> ORGANISM: Artificial Sequence
<220> FEATURE:
<223> OTHER INFORMATION: artificial construct-R1 codon-optimized for mouse

<400> SEQUENCE: 61

```
atgctggact tctacctgat catccacttc ctgctgcccg tgatccagtg cctgatcggc     60
gtgctggcca acggcatcat cgtgatcgtg aacggcaccg agctgatcaa gcagaggaag    120
atggtgcccc tggacctgct gctgagctgc ctggccatca gcaggatctg cctgcagagc    180
ttcatcttct acatcaacct ggtgatcctg agcctgatcg acttcctgcc cctggtgaag    240
aacttcgccg tgttcatgtt cgtgaacgag accggcctgt ggctggccac ctggctgggc    300
gtgttctact gcgccaagat cagccccatc gcccacccc tgttcttctg ctgaagagg     360
aggatcagca agctggtgcc ctggctgatc atcgcagcc tgctgttcgc cagcatcccc    420
ctggtgttct acagcaagca cacctgggtg ctgagccagg aggtgctgct gaggctgttc    480
agccccaacg ccaccaccca gatcaaggag accagcgccc tgcagatcgt gttcctggcc    540
aggttcagcc ccccttcat catcttcctg accagcaccc tgctgctggt gttcagcctg    600
ggcaggcaca cctggcagat gaggaacacc gccaccggca ccagggacgg cagcaccggc    660
gtgcacgtga gcgccctgct gagcatcctg agcttcctgg tgctgtacct gagccactac    720
atgaccgccg ccctgctgag cagccacatc ttcgagctga ggagcttcat gttcctgttc    780
tgcatcctgg tgttcggcag ctaccccagc ggccacagca tcatcctgat cagcggcaac    840
aggaagctga agcagaacgc caagaagttc ctgctgcacg ccagtgctg ccagtaa       897
```

<210> SEQ ID NO 62
<211> LENGTH: 897
<212> TYPE: DNA
<213> ORGANISM: Artificial Sequence
<220> FEATURE:
<223> OTHER INFORMATION: artificial construct-R1 codon-optimized for S. cervisiae

<400> SEQUENCE: 62

```
atgttggact tctacttgat catccacttc ttgttgccag ttatccaatg tttgatcggt     60
gttttggcta acggtatcat cgttatcgtt aacggtactg aattgatcaa gcaaagaaag    120
atggttccat ggacttgtt gttgtcttgt ttggctatct ctagaatctg tttgcaatct    180
ttcatcttct acatcaactt ggttatcttg tctttgatcg acttcttgcc attggttaag    240
aacttcgctg ttttcatgtt cgttaacgaa actggtttgt ggttggctac ttggttgggt    300
gttttctact gtgctaagat ctctcccaatc gctcacccat tgttcttctg gttgaagaga    360
agaatctcta agttggttcc atggttgatc atcggttctt gttgttcgc ttctatccca    420
ttggttttct actctaagca cacttgggtt ttgtctcaag aagttttgtt gagattgttc    480
tctccaaacg ctactactca aatcaaggaa acttctgctt tgcaaatcgt tttcttggct    540
agattctctc caccattcat catcttcttg acttctactt tgttgttggt tttctctttg    600
ggtagacaca cttggcaaat gagaaacact gctactggta ctagagacgg ttctactggt    660
gttcacgttt ctgctttgtt gtctatcttg tctttcttgg ttttgtactt gtctcactac    720
atgactgctg ctttgttgtc ttctcacatc ttcgaattga gatctttcat gttcttgttc    780
tgtatcttgg ttttcggttc ttacccatct ggtcactcta tcatcttgat ctctggtaac    840
agaaagttga agcaaaacgc taagaagttc ttgttgcacg tcaatgttg tcaataa       897
```

<210> SEQ ID NO 63
<211> LENGTH: 897
<212> TYPE: DNA
<213> ORGANISM: Artificial Sequence
<220> FEATURE:
<223> OTHER INFORMATION: artificial construct-R1 codon-optimized for
E. coli

<400> SEQUENCE: 63

| | | | | | |
|---|---|---|---|---|---|
| atgctggact | tctacctgat | catccacttc | ctgctgccgg | ttatccagtg | cctgatcggt | 60 |
| gttctggcta | acggtatcat | cgttatcgtt | aacggtaccg | aactgatcaa | acagcgtaaa | 120 |
| atggttccgc | tggacctgct | gctgtcttgc | ctggctatct | ctcgtatctg | cctgcagtct | 180 |
| ttcatcttct | acatcaacct | ggttatcctg | tctctgatcg | acttcctgcc | gctggttaaa | 240 |
| aacttcgctg | ttttcatgtt | cgttaacgaa | accggtctgt | ggctggctac | ctggctgggt | 300 |
| gttttctact | gcgctaaaat | ctctccgatc | gctcacccgc | tgttcttctg | ctgaaacgt | 360 |
| cgtatctcta | aactggttcc | gtggctgatc | atcggttctc | tgctgttcgc | ttctatcccg | 420 |
| ctggttttct | actctaaaca | cacctgggtt | ctgtctcagg | aagttctgct | gcgtctgttc | 480 |
| tctccgaacg | ctaccaccca | gatcaaagaa | acctctgctc | tgcagatcgt | tttcctggct | 540 |
| cgtttctctc | cgccgttcat | catcttcctg | acctctaccc | tgctgctggt | tttctctctg | 600 |
| ggtcgtcaca | cctggcagat | gcgtaacacc | gctaccggta | cccgtgacgg | ttctaccggt | 660 |
| gttcacgttt | ctgctctgct | gtctatcctg | tctttcctgg | ttctgtacct | gtctcactac | 720 |
| atgaccgctg | ctctgctgtc | ttctcacatc | ttcgaactgc | gttctttcat | gttcctgttc | 780 |
| tgcatcctgg | ttttcggttc | ttacccgtct | ggtcactcta | tcatcctgat | ctctggtaac | 840 |
| cgtaaactga | acagaacgc | taaaaaattc | ctgctgcacg | gtcagtgctg | ccagtaa | 897 |

<210> SEQ ID NO 64
<211> LENGTH: 915
<212> TYPE: DNA
<213> ORGANISM: Artificial Sequence
<220> FEATURE:
<223> OTHER INFORMATION: artificial construct-R2 codon-optimized for
C elegans

<400> SEQUENCE: 64

| | | | | | |
|---|---|---|---|---|---|
| atggcttctt | ctctttctgc | tattccacat | cttattatta | tgtctgctga | attcattact | 60 |
| ggaattactg | ttaatggatt | ccttgttatt | attaatggaa | agaacttat | taaatctaga | 120 |
| aaacttactc | caatgcaact | tctttgtatt | tgtattggaa | tttctagatt | cggacttctt | 180 |
| atggttctta | tggttcaatc | tttcttctct | gttttcttcc | cacttttcta | tagagttaaa | 240 |
| atttatggag | cttctatgct | tttcttctgg | atgttcttct | cttctgtttc | tctttggttc | 300 |
| gctacttgtc | tttctgtttt | ctattgtctt | aaaatttctg | gattcactca | atcttatttc | 360 |
| ctttggctta | aattcagaat | ttctaaactt | atgccatggc | ttcttcttgg | atctcttctt | 420 |
| gcttctatgt | ctattgctgc | tgtttctctt | gatgttggat | atccaaaaaa | tatgaataat | 480 |
| aatgatttcc | ttaaaaatgc | tactcttaaa | aaaactgaac | ttaaaattgg | accaattaat | 540 |
| ggagttcttc | ttgttaatct | tgctcttctt | ttcccacttg | ctattttcgt | tatgtgtact | 600 |
| ttcatgcttt | tcatttctct | ttatagacat | actcatagaa | tgcaaaatag | atctcatgga | 660 |
| gttagaaatg | cttctactga | agctcatatt | aatgctctta | aaactgttat | tactttcttc | 720 |
| tgtttcttca | tttcttattt | cgctgctttc | atggctaata | tgactttctc | tattccatat | 780 |
| ggatctcaat | gtttcttcgt | tgttaaagat | attatggctg | ctttcccatc | tggacattct | 840 |

| gttattatta ttcttaataa ttctaaattc caacaaccat tcagaagact tctttgtctt | 900 |
| aaaaaaaatc aataa | 915 |

<210> SEQ ID NO 65
<211> LENGTH: 915
<212> TYPE: DNA
<213> ORGANISM: Artificial Sequence
<220> FEATURE:
<223> OTHER INFORMATION: artificial construct-R2 codon-optimized for
      Drosophila

<400> SEQUENCE: 65

| atggcctcct ccctgtccgc catccccac ctgatcatca tgtccgccga gttcatcacc | 60 |
| ggcatcaccg tgaacggctt cctggtgatc atcaacggca aggagctgat caagtcccgc | 120 |
| aagctgaccc ccatgcagct gctgtgcatc tgcatcggca tctcccgctt cggcctgctg | 180 |
| atggtgctga tggtgcagtc cttcttctcc gtgttcttcc ccctgttcta ccgcgtgaag | 240 |
| atctacggcg cctccatgct gttcttctgg atgttcttct cctccgtgtc cctgtggttc | 300 |
| gccacctgcc tgtccgtgtt ctactgcctg aagatctccg gcttcaccca gtcctacttc | 360 |
| ctgtggctga agttccgcat ctccaagctg atgcccggc tgctgctggg ctccctgctg | 420 |
| gcctccatgt ccatcgccgc cgtgtccctg acgtgggct accccaagaa catgaacaac | 480 |
| aacgacttcc tgaagaacgc caccctgaag aagaccgagc tgaagatcgg ccccatcaac | 540 |
| ggcgtgctgc tggtgaacct ggccctgctg ttccccctgg ccatcttcgt gatgtgcacc | 600 |
| ttcatgctgt tcatctccct gtaccgccac acccaccgca tgcagaaccg ctcccacggc | 660 |
| gtgcgcaacg cctccaccga ggcccacatc aacgccctga gaccgtgat caccttcttc | 720 |
| tgcttcttca tctcctactt cgccgccttc atggccaaca tgaccttctc catcccctac | 780 |
| ggctcccagt gcttcttcgt ggtgaaggac atcatggccg ccttcccctc cggccactcc | 840 |
| gtgatcatca tcctgaacaa ctccaagttc agcagccct ccgccgcct gctgtgcctg | 900 |
| aagaagaacc agtaa | 915 |

<210> SEQ ID NO 66
<211> LENGTH: 915
<212> TYPE: DNA
<213> ORGANISM: Artificial Sequence
<220> FEATURE:
<223> OTHER INFORMATION: artificial construct-R2 codon-optimized for
      human

<400> SEQUENCE: 66

| atggccagca gcctgagcgc catccccac ctgatcatca tgagcgccga gttcatcacc | 60 |
| ggcatcaccg tgaacggctt cctggtgatc atcaacggca aggagctgat caagagccgc | 120 |
| aagctgaccc ccatgcagct gctgtgcatc tgcatcggca tcagccgctt cggcctgctg | 180 |
| atggtgctga tggtgcagag cttcttcagc gtgttcttcc ccctgttcta ccgcgtgaag | 240 |
| atctacggcg ccagcatgct gttcttctgg atgttcttca gcagcgtgag cctgtggttc | 300 |
| gccacctgcc tgagcgtgtt ctactgcctg aagatcagcg gcttcaccca gagctacttc | 360 |
| ctgtggctga agttccgcat cagcaagctg atgcccggc tgctgctggg cagcctgctg | 420 |
| gccagcatga gcatcgccgc cgtgagcctg acgtgggct accccaagaa catgaacaac | 480 |
| aacgacttcc tgaagaacgc caccctgaag aagaccgagc tgaagatcgg ccccatcaac | 540 |
| ggcgtgctgc tggtgaacct ggccctgctg ttccccctgg ccatcttcgt gatgtgcacc | 600 |

```
ttcatgctgt tcatcagcct gtaccgccac acccaccgca tgcagaaccg cagccacggc    660
gtgcgcaacg ccagcaccga ggcccacatc aacgccctga agaccgtgat caccttcttc    720
tgcttcttca tcagctactt cgccgccttc atggccaaca tgaccttcag catcccctac    780
ggcagccagt gcttcttcgt ggtgaaggac atcatggccg ccttccccag cggccacagc    840
gtgatcatca tcctgaacaa cagcaagttc cagcagccct ccgccgcct gctgtgcctg    900 aagaagaacc agtaa                                                      915

<210> SEQ ID NO 67
<211> LENGTH: 915
<212> TYPE: DNA
<213> ORGANISM: Artificial Sequence
<220> FEATURE:
<223> OTHER INFORMATION: artificial construct-R2 codon-optimized for
      mouse

<400> SEQUENCE: 67
atggccagca gcctgagcgc catcccccac ctgatcatca tgagcgccga gttcatcacc     60
ggcatcaccg tgaacggctt cctggtgatc atcaacggca aggagctgat caagagcagg    120
aagctgaccc ccatgcagct gctgtgcatc tgcatcggca tcagcaggtt cggcctgctg    180
atggtgctga tggtgcagag cttcttcagc gtgttcttcc ccctgttcta cagggtgaag    240
atctacggcg ccagcatgct gttcttctgg atgttcttca gcagcgtgag cctgtggttc    300
gccacctgcc tgagcgtgtt ctactgcctg aagatcagcg gcttcaccca gagctacttc    360
ctgtggctga gttcaggat cagcaagctg atgcctggc tgctgctggg cagcctgctg     420
gccagcatga gcatcgccgc cgtgagcctg gacgtgggct accccaagaa catgaacaac    480
aacgacttcc tgaagaacgc caccctgaag aagaccgagc tgaagatcgg ccccatcaac    540
ggcgtgctgc tggtgaacct ggccctgctg ttccccctgg ccatcttcgt gatgtgcacc    600
ttcatgctgt tcatcagcct gtacaggcac acccacagga tgcagaacag gagccacggc    660
gtgaggaacg ccagcaccga ggcccacatc aacgccctga agaccgtgat caccttcttc    720
tgcttcttca tcagctactt cgccgccttc atggccaaca tgaccttcag catcccctac    780
ggcagccagt gcttcttcgt ggtgaaggac atcatggccg ccttccccag cggccacagc    840
gtgatcatca tcctgaacaa cagcaagttc cagcagccct caggaggct gctgtgcctg    900 aagaagaacc agtaa                                                     915

<210> SEQ ID NO 68
<211> LENGTH: 915
<212> TYPE: DNA
<213> ORGANISM: Artificial Sequence
<220> FEATURE:
<223> OTHER INFORMATION: artificial construct-R2 codon-optimized for
      S cerevisiae

<400> SEQUENCE: 68
atggcttctt ctttgtctgc tatcccacac ttgatcatca tgtctgctga attcatcact     60
ggtatcactg ttaacggttt cttggttatc atcaacggta aggaattgat caagtctaga    120
aagttgactc caatgcaatt gttgtgtatc tgtatcggta tctctagatt cggtttgttg    180
atggttttga tggttcaatc tttcttctct gttttcttcc cattgttcta cagagttaag    240
atctacggtg cttctatgtt gttcttctgg atgttcttct cttctgtttc tttgtggttc    300
gctacttgtt tgtctgtttt ctactgtttg aagatctctg gtttcactca atcttacttc    360
ttgtggttga agttcagaat ctctaagttg atgccatggt tgttgttggg ttctttgttg    420
```

```
gcttctatgt ctatcgctgc tgtttctttg gacgttggtt acccaaagaa catgaacaac    480
aacgacttct tgaagaacgc tactttgaag aagactgaat tgaagatcgg tccaatcaac    540
ggtgttttgt tggttaactt ggctttgttg ttcccattgg ctatcttcgt tatgtgtact    600
ttcatgttgt tcatctctct ttgtacagacac actcacagaa tgcaaaacag atctcacggt    660
gttagaaacg cttctactga agctcacatc aacgctttga agactgttat cactttcttc    720
tgtttcttca tctcttactt cgctgctttc atggctaaca tgactttctc tatcccatac    780
ggttctcaat gtttcttcgt tgttaaggac atcatggctg ctttcccatc tggtcactct    840
gttatcatca tcttgaacaa ctctaagttc aacaaccat tcagaagatt gttgtgtttg    900
aagaagaacc aataa                                                     915
```

```
<210> SEQ ID NO 69
<211> LENGTH: 915
<212> TYPE: DNA
<213> ORGANISM: Artificial Sequence
<220> FEATURE:
<223> OTHER INFORMATION: artificial construct-R2 codon-optimized for
      E coli

<400> SEQUENCE: 69
atggcttctt ctctgtctgc tatcccgcac ctgatcatca tgtctgctga attcatcacc    60
ggtatcaccg ttaacggttt cctggttatc atcaacggta agaactgat caaatctcgt   120 aaactgaccc cgatgcagct gctgtgcatc tgcatcggta tctctcgttt cggtctgctg   180
atggttctga tggttcagtc tttcttctct gttttcttcc cgctgttcta ccgtgttaaa   240
atctacggtg cttctatgct gttcttctgg atgttcttct cttctgtttc tctgtggttc   300
gctacctgcc tgtctgtttt ctactgcctg aaaatctctg gtttcaccca gtcttacttc   360
ctgtggctga attccgtat ctctaaactg atgccgtggc tgctgctggg ttctctgctg   420
gcttctatgt ctatcgctgc tgtttctctg gacgttggtt acccgaaaaa catgaacaac    480
aacgacttcc tgaaaaacgc taccctgaaa aaaccgaac tgaaaatcgg tccgatcaac    540
ggtgttctgc tggttaacct ggctctgctg ttcccgctgg ctatcttcgt tatgtgcacc    600
ttcatgctgt tcatctctct gtaccgtcac acccaccgta tgcagaaccg ttctcacggt    660
gttcgtaacg cttctaccga agctcacatc aacgctctga aaaccgttat caccttcttc    720
tgcttcttca tctcttactt cgctgctttc atggctaaca tgaccttctc tatcccgtac    780
ggttctcagt gcttcttcgt tgttaaagac atcatggctg ctttcccgtc tggtcactct    840
gttatcatca tcctgaacaa ctctaaattc agcagccgt tccgtcgtct gctgtgcctg    900
aaaaaaaacc agtaa                                                    915
```

```
<210> SEQ ID NO 70
<211> LENGTH: 951
<212> TYPE: DNA
<213> ORGANISM: Artificial Sequence
<220> FEATURE:
<223> OTHER INFORMATION: artificial construct-R3 codon-optimized for
      C elegans

<400> SEQUENCE: 70
atgtctggac ttcataaatg ggttttcctt gttctttctg ctactcaatt cattcttgga    60
atgcttggaa atggattcat tgttcttgtt tctggatctt cttggttcaa aaataaaact   120
atttctcttt ctgatttcat tattgctaat cttgctcttc ctagaattgt tcttctttgg   180
```

-continued

```
attcttcttg ttgatggagt tcttattgtt ttctcttcta aagttcatga tgaaggaatt    240
attatgcaaa ttattgatat tttctggact ttcactaatc atctttctat ttggcttgct    300
acttgtcttt ctgttctttta ttgtcttaaa attgcttctt tctctcatcc aactttcctt    360
tggcttaaat ggagagtttc tagaatggtt gttcaaatga ttcttggagc tcttgttctt    420
tcttgtgctt ctgctctttc tcttattcat gaattcaaaa tgtattctat tcttggagga    480
attgatggaa ctgaaatgt tactgaacat ttcagaaaaa aaagaaatga atataaactt    540
attcatgttc ttggaactct tggaatctt ccaccactta ttgtttctct tgcttcttat    600
ttccttctta ttgtttctct tggaagacat actcaaagaa tggaacaatc tggaacttct    660
tctggagatc catctgctga agctcataaa agagctatta aaattattct ttcttttcctt    720 cttcttttcc ttctttattt ccttgctttc cttattactt cttcttctta tttcattcca    780
ggaactgaaa tggttaaaat tattggagaa cttattacta tgttctatcc agcttctcat    840
tctttcattc ttattcttgg aaattctaaa cttaaacata tgttcgttgg aatgcttaga    900
tgtgaatctg acatcttaa accaggatct aaaggaccag tttctcttta a    951
```

<210> SEQ ID NO 71
<211> LENGTH: 951
<212> TYPE: DNA
<213> ORGANISM: Artificial Sequence
<220> FEATURE:
<223> OTHER INFORMATION: artificial construct-R3 codon-optimized for Drosophila

<400> SEQUENCE: 71

```
atgtccggcc tgcacaagtg ggtgttcctg gtgctgtccg ccacccagtt catcctgggc     60
atgctgggca acggcttcat cgtgctggtg tccggctcct cctggttcaa gaacaagacc    120
atctccctgt ccgacttcat catcgccaac ctggccctgt ccgcatcgt gctgctgtgg    180 atcctgctgg tggacggcgt gctgatcgt ttctcctcca aggtgcacga cgagggcatc    240 atgcatgcaga tcatcgacat cttctggacc ttcaccaacc acctgtccat ctggctggcc    300
acctgcctgt ccgtgctgta ctgcctgaag atcgcctcct ctcccacccc caccttcctg    360
tggctgaagt ggcgcgtgtc ccgcatggtg gtgcagatga tcctgggcgc cctggtgctg    420
tcctgcgcct ccgccctgtc cctgatccac gagttcaaga tgtactccat cctgggcggc    480
atcgacggca ccggcaacgt gaccgagcac ttccgcaaga gcgcaacga gtacaagctg    540 atccacgtgc tgggcaccct gtggaacctg cccccctga tcgtgtccct ggcctcctac    600
ttcctgctga tcgtgtccct gggccgccac acccagcgca tggagcagtc cggcacctcc    660
tccggcgacc cctccgccga ggcccacaag cgcgccatca gatcatcct gtccttcctg    720 ctgctgttcc tgctgtactt cctggccttc ctgatcacct cctcctccta cttcatcccc    780
ggcaccgaga tggtgaagat catcggcgag ctgatcacca tgttctaccc cgcctcccac    840
tccttcatcc tgatcctggg caactccaag ctgaagcaca tgttcgtggg catgctgcgc    900
tgcgagtccg gccacctgaa gcccggctcc aagggccccg tgtccctgta a    951
```

<210> SEQ ID NO 72
<211> LENGTH: 951
<212> TYPE: DNA
<213> ORGANISM: Artificial Sequence
<220> FEATURE:
<223> OTHER INFORMATION: artificial construct-R3 codon-optimized for human

<400> SEQUENCE: 72

```
atgagcggcc tgcacaagtg ggtgttcctg gtgctgagcg ccacccagtt catcctgggc    60
atgctgggca acggcttcat cgtgctggtg agcggcagca gctggttcaa gaacaagacc   120
atcagcctga gcgacttcat catcgccaac ctggccctga ccgcatcgt gctgctgtgg    180 atcctgctgg tggacggcgt gctgatcgtg ttcagcagca aggtgcacga cgagggcatc   240
atcatgcaga tcatcgacat cttctggacc ttcaccaacc acctgagcat ctggctggcc   300
acctgcctga gcgtgctgta ctgcctgaag atcgccagct tcagccaccc caccttcctg   360
tggctgaagt ggcgcgtgag ccgcatggtg gtgcagatga tcctgggcgc cctggtgctg   420
agctgcgcca gcgccctgag cctgatccac gagttcaaga tgtacagcat cctgggcggc   480
atcgacggca ccggcaacgt gaccgagcac ttccgcaaga gcgcaacga gtacaagctg    540 atccacgtgc tgggcaccct gtggaacctg cccccctga tcgtgagcct ggccagctac    600
ttcctgctga tcgtgagcct gggccgccac acccagcgca tggagcagag cggcaccagc   660
agcggcgacc ccagcgccga ggcccacaag cgcgccatca gatcatcct gagcttcctg    720 ctgctgttcc tgctgtactt cctggccttc ctgatcacca gcagcagcta cttcatcccc   780
ggcaccgaga tggtgaagat catcggcgag ctgatcacca tgttctaccc cgccagccac   840
agcttcatcc tgatcctggg caacagcaag ctgaagcaca tgttcgtggg catgctgcgc   900
tgcgagagcg ccacctgaa gcccggcagc aagggccccg tgagcctgta a             951

<210> SEQ ID NO 73
<211> LENGTH: 951
<212> TYPE: DNA
<213> ORGANISM: Artificial Sequence
<220> FEATURE:
<223> OTHER INFORMATION: artificial construct-R3 codon-optimized for
      mouse

<400> SEQUENCE: 73
atgagcggcc tgcacaagtg ggtgttcctg gtgctgagcg ccacccagtt catcctgggc    60
atgctgggca acggcttcat cgtgctggtg agcggcagca gctggttcaa gaacaagacc   120
atcagcctga gcgacttcat catcgccaac ctggccctga gcaggatcgt gctgctgtgg   180
atcctgctgg tggacggcgt gctgatcgtg ttcagcagca aggtgcacga cgagggcatc   240
atcatgcaga tcatcgacat cttctggacc ttcaccaacc acctgagcat ctggctggcc   300
acctgcctga gcgtgctgta ctgcctgaag atcgccagct tcagccaccc caccttcctg   360
tggctgaagt ggagggtgag caggatggtg gtgcagatga tcctgggcgc cctggtgctg   420
agctgcgcca gcgccctgag cctgatccac gagttcaaga tgtacagcat cctgggcggc   480
atcgacggca ccggcaacgt gaccgagcac ttcaggaaga gaggaacga gtacaagctg    540 atccacgtgc tgggcaccct gtggaacctg cccccctga tcgtgagcct ggccagctac    600
ttcctgctga tcgtgagcct gggcaggcac acccagagga tggagcagag cggcaccagc   660
agcggcgacc ccagcgccga ggcccacaag agggccatca gatcatcct gagcttcctg    720 ctgctgttcc tgctgtactt cctggccttc ctgatcacca gcagcagcta cttcatcccc   780
ggcaccgaga tggtgaagat catcggcgag ctgatcacca tgttctaccc cgccagccac   840
agcttcatcc tgatcctggg caacagcaag ctgaagcaca tgttcgtggg catgctgagg   900
tgcgagagcg ccacctgaa gcccggcagc aagggccccg tgagcctgta a             951

<210> SEQ ID NO 74
<211> LENGTH: 951
```

```
<212> TYPE: DNA
<213> ORGANISM: Artificial Sequence
<220> FEATURE:
<223> OTHER INFORMATION: artificial construct-R3 codon-optimized for
      S cerevisiae

<400> SEQUENCE: 74
atgtctggtt tgcacaagtg ggttttcttg gttttgtctg ctactcaatt catcttgggt     60
atgttgggta acggtttcat cgttttggtt tctggttctt cttggttcaa gaacaagact    120
atctctttgt ctgacttcat catcgctaac ttggctttgt ctagaatcgt tttgttgtgg    180
atcttgttgg ttgacggtgt tttgatcgtt ttctcttcta aggttcacga cgaaggtatc    240
atcatgcaaa tcatcgacat cttctggact ttcactaacc acttgtctat ctggttggct    300
acttgtttgt ctgttttgta ctgtttgaag atcgcttctt tctctcaccc aactttcttg    360
tggttgaagt ggagagtttc tagaatggtt gttcaaatga tcttgggtgc tttggttttg    420
tcttgtgctt ctgctttgtc tttgatccac gaattcaaga tgtactctat cttgggtggt    480
atcgacggta ctggtaacgt tactgaacac ttcagaaaga agagaaacga atacaagttg    540
atccacgttt tgggtacttt gtggaacttg ccaccattga tcgtttcttt ggcttcttac    600
ttcttgttga tcgtttctt gggtagacac actcaaagaa tggaacaatc tggtacttct    660
tctggtgacc catctgctga agctcacaag agagctatca agatcatctt gtctttcttg    720 tgttgttct tgttgtactt cttggctttc ttgatcactt cttcttctta cttcatccca    780
ggtactgaaa tggttaagat catcggtgaa ttgatcacta tgttctaccc agcttctcac    840
tctttcatct tgatcttggg taactctaag ttgaagcaca tgttcgttgg tatgttgaga    900
tgtgaatctg gtcacttgaa gccaggttct aagggtccag tttctttgta a             951

<210> SEQ ID NO 75
<211> LENGTH: 951
<212> TYPE: DNA
<213> ORGANISM: Artificial Sequence
<220> FEATURE:
<223> OTHER INFORMATION: artificial construct-R3 codon-optimized for
      E. coli

<400> SEQUENCE: 75
atgtctggtc tgcacaaatg ggttttcctg gttctgtctg ctacccagtt catcctgggt     60
atgctgggta acggtttcat cgttctggtt tctggttctt cttggttcaa aaacaaaacc    120
atctctctgt ctgacttcat catcgctaac ctggctctgt ctcgtatcgt tctgctgtgg    180
atcctgctgg ttgacggtgt tctgatcgtt ttctcttcta aggttcacga cgaaggtatc    240
atcatgcaga tcatcgacat cttctggacc ttcaccaacc acctgtctat ctggctggct    300
acctgcctgt ctgttctgta ctgcctgaaa atcgcttctt tctctcaccc gaccttcctg    360
tggctgaaat ggcgtgtttc tcgtatggtt gttcagatga tcctgggtgc tctggttctg    420
tcttgcgctt ctgctctgtc tctgatccac gaattcaaaa tgtactctat cctgggtggt    480
atcgacggta ccggtaacgt taccgaacac ttccgtaaaa acgtaacga atacaaactg    540 atccacgttc tgggtacccct gtggaacctg ccgccgctga tcgtttctct ggcttcttac    600
ttcctgctga tcgtttctct gggtcgtcac acccagcgta tggaacagtc tggtacctct    660
tctggtgacc cgtctgctga agctcacaaa cgtgctatca aaatcatcct gtctttcctg    720
ctgctgttcc tgctgtactt cctggctttc ctgatcacct cttcttctta cttcatcccg    780
ggtaccgaaa tggttaaaat catcggtgaa ctgatcacca tgttctaccc ggcttctcac    840
```

```
tctttcatcc tgatcctggg taactctaaa ctgaaacaca tgttcgttgg tatgctgcgt    900
tgcgaatctg gtcacctgaa accgggttct aaaggtccgg tttctctgta a             951
```

<210> SEQ ID NO 76
<211> LENGTH: 921
<212> TYPE: DNA
<213> ORGANISM: Artificial Sequence
<220> FEATURE:
<223> OTHER INFORMATION: artificial construct-R4 codon-optimized for
      C elegans

<400> SEQUENCE: 76

```
atgcatcaaa ttcttttcct ttctgctctt actgtttctg ctattcttaa tttcgttgga     60
cttgttgtta atcttttcat tgttgttgtt aattatagaa cttgggttca atctcataga    120
atttcttctt ctaatagaat tcttttctct cttggagtta ctagattcat tatgcttgga    180
cttttccttc ttaatattat ttatcttttc acttctccac atgttgaaag atctgttcat    240
ctttctactt tcttccttct tgttggatg ttccttgaat ctacttctct ttggcttgtt     300
actcttctta atgctcttta ttgtgttaaa attactgatt ccaacattc tgttttcctt    360 cttcttaaaa gaaactttc tccaaaaatt ccaagacttc ttcttgcttg tgttcttatt    420
tctgctttct ctactcttct ttatgttgtt cttactcaaa cttctccatt cccagaactt    480
cttactggat ctaatggaac tgtttgtgat attaataaat ctattctttc tcttgttact    540
tctcttgttc tttcttcttt ccttcaattc attatgaatg ttacttctgc ttctcttctt    600
attcattctc ttagaagaca tattcaaaaa atgcaaaaaa atgctactga tttctggaat    660
ccacaaactg aagctcatat gggagctatg aaacttatga tttatttcct tattctttat    720
attccatatt ctcttgctac tcttcttcaa tatcttccat ctgttagaat ggatcttgga    780
gctacttcta tttgtatgat tatttctact ttctatccac caggacattc tgttcttatt    840
attcttactc atccaaaact taaaactaaa gctaaaaaaa ttctttgttt caatatttgg    900
tggaatttct cttctaaata a                                              921
```

<210> SEQ ID NO 77
<211> LENGTH: 921
<212> TYPE: DNA
<213> ORGANISM: Artificial Sequence
<220> FEATURE:
<223> OTHER INFORMATION: artificial construct-R4 codon-optimized for
      Drosophila

<400> SEQUENCE: 77

```
atgcaccaga tcctgttcct gtccgccctg accgtgtccg ccatcctgaa cttcgtgggc     60
ctggtggtga acctgttcat cgtggtggtg aactaccgca cctgggtgca gtcccaccgc    120
atctcctcct ccaaccgcat cctgttctcc ctgggcgtga cccgcttcat catgctgggc    180
ctgttcctgc tgaacatcat ctacctgttc acctcccccc acgtggagcg ctccgtgcac    240
ctgtccacct tcttcctgct gtgctggatg ttcctggagt ccacctccct gtggctggtg    300
accctgctga cgccctgta ctgcgtgaag atcaccgact ccagcactc cgtgttcctg     360 ctgctgaagc gcaagctgtc ccccaagatc cccgcctgc tgctggcctg cgtgctgatc    420
tccgccttct ccaccctgct gtacgtggtg ctgacccaga cctccccctt ccccgagctg    480
ctgaccggct ccaacggcac cgtgtgcgac atcaacaagt ccatcctgtc cctggtgacc    540
tccctggtgc tgtcctcctt cctgcagttc atcatgaacg tgacctccgc ctccctgctg    600
atccactccc tgcgccgcca catccagaag atgcagaaga acgccaccga cttctggaac    660
```

```
ccccagaccg aggcccacat gggcgccatg aagctgatga tctacttcct gatcctgtac    720
atcccctact ccctggccac cctgctgcag tacctgccct ccgtgcgcat ggacctgggc    780
gccacctcca tctgcatgat catctccacc ttctaccccc ccggccactc cgtgctgatc    840
atcctgaccc accccaagct gaagaccaag gccaagaaga tcctgtgctt caacatctgg    900
tggaacttct cctccaagta a                                              921
```

<210> SEQ ID NO 78
<211> LENGTH: 921
<212> TYPE: DNA
<213> ORGANISM: Artificial Sequence
<220> FEATURE:
<223> OTHER INFORMATION: artificial construct-R4 codon-optimized for human

<400> SEQUENCE: 78

```
atgcaccaga tcctgttcct gagcgccctg accgtgagcg ccatcctgaa cttcgtgggc     60
ctggtggtga acctgttcat cgtggtggtg aactaccgca cctgggtgca gagccaccgc    120
atcagcagca gcaaccgcat cctgttcagc ctgggcgtga cccgcttcat catgctgggc    180
ctgttcctgc tgaacatcat ctacctgttc accagccccc acgtgagcg cagcgtgcac    240 ctgagcacct cttcctgct gtgctggatg ttcctggaga gcaccagcct gtggctggtg    300
accctgctga cgccctgta ctgcgtgaag atcaccgact ccagcacag cgtgttcctg    360 ctgctgaagc gcaagctgag ccccaagatc cccgcctgc tgctggcctg cgtgctgatc    420
agcgccttca gcaccctgct gtacgtggtg ctgacccaga ccagccccct tccccgagctg    480 ctgaccggca gcaacggcac cgtgtgcgac atcaacaaga gcatcctgag cctggtgacc    540
agcctggtgc tgagcagctt cctgcagttc atcatgaacg tgaccagcgc cagcctgctg    600
atccacagcc tgcgccgcca catccagaag atgcagaaga acgccaccga cttctggaac    660
ccccagaccg aggcccacat gggcgccatg aagctgatga tctacttcct gatcctgtac    720
atcccctaca gcctggccac cctgctgcag tacctgccca gcgtgcgcat ggacctgggc    780
gccaccagca tctgcatgat catcagcacc ttctaccccc ccggccacag cgtgctgatc    840
atcctgaccc accccaagct gaagaccaag gccaagaaga tcctgtgctt caacatctgg    900
tggaacttca gcagcaagta a                                              921
```

<210> SEQ ID NO 79
<211> LENGTH: 921
<212> TYPE: DNA
<213> ORGANISM: Artificial Sequence
<220> FEATURE:
<223> OTHER INFORMATION: artificial construct-R4 codon-optimized for mouse

<400> SEQUENCE: 79

```
atgcaccaga tcctgttcct gagcgccctg accgtgagcg ccatcctgaa cttcgtgggc     60
ctggtggtga acctgttcat cgtggtggtg aactacagga cctgggtgca gagccacagg    120
atcagcagca gcaacaggat cctgttcagc ctgggcgtga ccaggttcat catgctgggc    180
ctgttcctgc tgaacatcat ctacctgttc accagccccc acgtggagag gagcgtgcac    240
ctgagcacct cttcctgct gtgctggatg ttcctggaga gcaccagcct gtggctggtg    300
accctgctga cgccctgta ctgcgtgaag atcaccgact ccagcacag cgtgttcctg    360 ctgctgaaga ggaagctgag ccccaagatc ccaggctgc tgctggcctg cgtgctgatc    420
```

```
agcgccttca gcaccctgct gtacgtggtg ctgacccaga ccagcccctt ccccgagctg    480
ctgaccggca gcaacggcac cgtgtgcgac atcaacaaga gcatcctgag cctggtgacc    540
agcctggtgc tgagcagctt cctgcagttc atcatgaacg tgaccagcgc cagcctgctg    600
atccacagcc tgaggaggca catccagaag atgcagaaga cgccaccga cttctggaac     660 ccccagaccg aggcccacat gggcgccatg aagctgatga tctacttcct gatcctgtac    720
atcccctaca gcctggccac cctgctgcag tacctgccca gcgtgaggat ggacctgggc    780
gccaccagca tctgcatgat catcagcacc ttctacccc ccggccacag cgtgctgatc     840
atcctgaccc accccaagct gaagaccaag gccaagaaga tcctgtgctt caacatctgg    900
tggaacttca gcagcaagta a                                              921

<210> SEQ ID NO 80
<211> LENGTH: 921
<212> TYPE: DNA
<213> ORGANISM: Artificial Sequence
<220> FEATURE:
<223> OTHER INFORMATION: artificial construct-R4 codon-optimized for
      S cerevisiae

<400> SEQUENCE: 80
atgcaccaaa tcttgttctt gtctgctttg actgtttctg ctatcttgaa cttcgttggt    60
ttggttgtta acttgttcat cgttgttgtt aactacagaa cttgggttca atctcacaga    120
atctcttctt ctaacagaat cttgttctct ttgggtgtta ctagattcat catgttgggt    180
ttgttcttgt tgaacatcat ctacttgttc acttctccac acgttgaaag atctgttcac    240
ttgtctactt tcttcttgtt gtgttggatg ttcttggaat ctacttcttt gtggttggtt    300
actttgttga cgctttgta ctgtgttaag atcactgact ccaacactc tgttttcttg     360 ttgttgaaga gaaagttgtc tccaaagatc ccaagattgt tgttggcttg tgttttgatc    420
tctgctttct ctactttgtt gtacgttgtt ttgactcaaa cttctccatt cccagaattg    480
ttgactggtt ctaacggtac tgtttgtgac atcaacaagt ctatcttgtc tttggttact    540
tctttggttt tgtcttcttt cttgcaattc atcatgaacg ttacttctgc ttcttttgttg    600 atccactctt tgagaagaca catccaaaag atgcaaaaga cgctactga cttctggaac    660 ccacaaactg aagctcacat gggtgctatg aagttgatga tctacttctt gatcttgtac    720
atcccatact ctttggctac tttgttgcaa tacttgccat ctgttagaat ggacttgggt    780
gctacttcta tctgtatgat catctctact ttctacccac aggtcactc tgttttgatc     840 atcttgactc acccaaagtt gaagactaag gctaagaaga tcttgtgttt caacatctgg    900
tggaacttct cttctaagta a                                              921

<210> SEQ ID NO 81
<211> LENGTH: 921
<212> TYPE: DNA
<213> ORGANISM: Artificial Sequence
<220> FEATURE:
<223> OTHER INFORMATION: artificial construct-R4 codon-optimized for
      E. coli

<400> SEQUENCE: 81
atgcaccaga tcctgttcct gtctgctctg accgtttctg ctatcctgaa cttcgttggt    60
ctggttgtta acctgttcat cgttgttgtt aactaccgta cctgggttca gtctcaccgt    120
atctcttctt ctaaccgtat cctgttctct ctggtgtta cccgtttcat catgctgggt     180
ctgttcctgc tgaacatcat ctacctgttc acctctccgc acgttgaacg ttctgttcac    240
```

```
ctgtctacct tcttcctgct gtgctggatg ttcctggaat ctacctctct gtggctggtt    300
accctgctga acgctctgta ctgcgttaaa atcaccgact ccagcactc tgttttcctg     360 ctgctgaaac gtaaactgtc tccgaaaatc ccgcgtctgc tgctggcttg cgttctgatc    420
tctgctttct ctaccctgct gtacgttgtt ctgacccaga cctctccgtt cccggaactg    480
ctgaccggtt ctaacggtac cgtttgcgac atcaacaaat ctatcctgtc tctggttacc    540
tctctggttc tgtcttcttt cctgcagttc atcatgaacg ttacctctgc ttctctgctg    600
atccactctc tgcgtcgtca catccagaaa atgcagaaaa acgctaccga cttctggaac    660
ccgcagaccg aagctcacat gggtgctatg aaactgatga tctacttcct gatcctgtac    720
atcccgtact ctctggctac cctgctgcag tacctgccgt ctgttcgtat ggacctgggt    780
gctacctcta tctgcatgat catctctacc ttctacccgc cgggtcactc tgttctgatc    840
atcctgaccc accgaaact gaaaaccaaa gctaaaaaaa tcctgtgctt caacatctgg    900
tggaacttct cttctaaata a                                              921
```

<210> SEQ ID NO 82
<211> LENGTH: 936
<212> TYPE: DNA
<213> ORGANISM: Artificial Sequence
<220> FEATURE:
<223> OTHER INFORMATION: artificial construct-R7 codon-optimized for
    C elegans

<400> SEQUENCE: 82

```
atgcttgata aagttgaatc tactcttatg cttattgctg ctggagaatt cgctatggga    60
attcttggaa atgctttcat tggacttgtt aattgtatga attggattaa aaatagaaaa   120
attgcttcta ttgatcttat tcttacttct cttgctatt ctagaatttg tcttctttgt    180
attattcttc ttgattattt cattcttgga ctttatccag atgtttatac tactggaaaa   240
aaaatgagaa ttattgattt cttctggact cttactaatc atcttaatgt ttggttcgct   300
acttgtcttt ctgttttcta tttccttaaa attgctaatt tcttccatcc acttttcctt   360
tggatgaaat ggaaaattga ttctgctatt ccaagaattc ttcttggatg tcttgctttc   420
tctgttttca tttctcttgt tgtttctgaa atcttaatg atgatttcag atcttgtgtt    480
aaagttaaaa aaaaactaa tattactgtt aaatgtagag ttaataaagc tcaatatgct   540
tctgttaaaa tttgtcttaa tcttcttact cttttcccat tctctgtttc tgttatttct   600
ttccttcttc ttcttctttc tctttggaga catactagac aaatgaaaat ttctgctact   660
ggatgtagag atccatctat tgaagctcat gttggagcta tgaaagctgt tatttctttc   720
cttcttcttt tcattgctta ttatcttgct ttccttgttg ctacttcttc ttatttcatg   780
ccagaaactg aacttgctgt tatgattgga gaacttattg ctcttatta tccatctcat   840 tctcttattc ttattcttgg aaataataaa cttagacaag cttctcttag agttctttgg   900
aaagttaaat gtattcttaa aagaagaaat cattaa                              936
```

<210> SEQ ID NO 83
<211> LENGTH: 936
<212> TYPE: DNA
<213> ORGANISM: Artificial Sequence
<220> FEATURE:
<223> OTHER INFORMATION: artificial construct-R7 codon-optimized for
    Drosophila

<400> SEQUENCE: 83

```
atgctggaca aggtggagtc caccctgatg ctgatcgccg ccggcgagtt cgccatgggc    60
atcctgggca acgccttcat cggcctggtg aactgcatga actggatcaa gaaccgcaag   120
atcgcctcca tcgacctgat cctgacctcc ctggccatct cccgcatctg cctgctgtgc   180
atcatcctgc tggactactt catcctgggc ctgtaccccg acgtgtacac caccggcaag   240
aagatgcgca tcatcgactt cttctggacc ctgaccaacc acctgaacgt gtggttcgcc   300
acctgcctgt ccgtgttcta cttcctgaag atcgccaact tcttccaccc cctgttcctg   360
tggatgaagt ggaagatcga ctccgccatc ccccgcatcc tgctgggctg cctggccttc   420
tccgtgttca tctccctggt ggtgtccgag aacctgaacg acgacttccg ctcctgcgtg   480
aaggtgaaga agaagaccaa catcaccgtg aagtgccgcg tgaacaaggc ccagtacgcc   540
tccgtgaaga tctgcctgaa cctgctgacc ctgttcccct tctccgtgtc cgtgatctcc   600
ttcctgctgc tgctgctgtc cctgtggcgc cacacccgcc agatgaagat ctccgccacc   660
ggctgccgcg acccctccat cgaggcccac gtgggcgcca tgaaggccgt gatctccttc   720
ctgctgctgt tcatcgccta ctacctggcc ttcctggtgg ccacctcctc ctacttcatg   780
cccgagaccg agctggccgt gatgatcggc gagctgatcg ccctgatcta cccctcccac   840
tccctgatcc tgatcctggg caacaacaag ctgcgccagg cctccctgcg cgtgctgtgg   900
aaggtgaagt gcatcctgaa cgccgcaac cactaa                              936
```

<210> SEQ ID NO 84
<211> LENGTH: 936
<212> TYPE: DNA
<213> ORGANISM: Artificial Sequence
<220> FEATURE:
<223> OTHER INFORMATION: artificial construct-R7 codon-optimized for human

<400> SEQUENCE: 84

```
atgctggaca aggtggagag caccctgatg ctgatcgccg ccggcgagtt cgccatgggc    60
atcctgggca acgccttcat cggcctggtg aactgcatga actggatcaa gaaccgcaag   120
atcgccagca tcgacctgat cctgaccagc ctggccatca gccgcatctg cctgctgtgc   180
atcatcctgc tggactactt catcctgggc ctgtaccccg acgtgtacac caccggcaag   240
aagatgcgca tcatcgactt cttctggacc ctgaccaacc acctgaacgt gtggttcgcc   300
acctgcctga gcgtgttcta cttcctgaag atcgccaact tcttccaccc cctgttcctg   360
tggatgaagt ggaagatcga cagcgccatc ccccgcatcc tgctgggctg cctggccttc   420
agcgtgttca tcagcctggt ggtgagcgag aacctgaacg acgacttccg cagctgcgtg   480
aaggtgaaga agaagaccaa catcaccgtg aagtgccgcg tgaacaaggc ccagtacgcc   540
agcgtgaaga tctgcctgaa cctgctgacc ctgttcccct tcagcgtgag cgtgatcagc   600
ttcctgctgc tgctgctgag cctgtggcgc cacacccgcc agatgaagat cagcgccacc   660
ggctgccgcg acccctccat cgaggcccac gtgggcgcca tgaaggccgt gatcagcttc   720
ctgctgctgt tcatcgccta ctacctggcc ttcctggtgg ccaccagcag ctacttcatg   780
cccgagaccg agctggccgt gatgatcggc gagctgatcg ccctgatcta ccccagccac   840
agcctgatcc tgatcctggg caacaacaag ctgcgccagg ccagcctgcg cgtgctgtgg   900
aaggtgaagt gcatcctgaa cgccgcaac cactaa                              936
```

<210> SEQ ID NO 85
<211> LENGTH: 936
<212> TYPE: DNA

<213> ORGANISM: Artificial Sequence
<220> FEATURE:
<223> OTHER INFORMATION: artificial construct-R7 codon-optimized for mouse

<400> SEQUENCE: 85

```
atgctggaca aggtggagag caccctgatg ctgatcgccg ccggcgagtt cgccatgggc    60
atcctgggca acgccttcat cggcctggtg aactgcatga actggatcaa gaacaggaag   120
atcgccagca tcgacctgat cctgaccagc ctggccatca gcaggatctg cctgctgtgc   180
atcatcctgc tggactactt catcctgggc ctgtaccccg acgtgtacac caccggcaag   240
aagatgagga tcatcgactt cttctggacc ctgaccaacc acctgaacgt gtggttcgcc   300
acctgcctga gcgtgttcta cttcctgaag atcgccaact tcttccaccc cctgttcctg   360
tggatgaagt ggaagatcga cagcgccatc cccaggatcc tgctgggctg cctggccttc   420
agcgtgttca tcagcctggt ggtgagcgag aacctgaacg acgacttcag gagctgcgtg   480
aaggtgaaga agaagaccaa catcaccgtg aagtgcaggg tgaacaaggc ccagtacgcc   540
agcgtgaaga tctgcctgaa cctgctgacc ctgttcccct cagcgtgag cgtgatcagc   600
ttcctgctgc tgctgctgag cctgtggagg cacaccaggc agatgaagat cagcgccacc   660
ggctgcaggg accccagcat cgaggcccac gtgggcgcca tgaaggccgt gatcagcttc   720
ctgctgctgt tcatcgccta ctacctggcc ttcctggtgg ccaccagcag ctacttcatg   780
cccgagaccg agctggccgt gatgatcggc gagctgatcg ccctgatcta ccccagccac   840
agcctgatcc tgatcctggg caacaacaag ctgaggcagg ccagcctgag ggtgctgtgg   900
aaggtgaagt gcatcctgaa gaggaggaac cactaa                              936
```

<210> SEQ ID NO 86
<211> LENGTH: 936
<212> TYPE: DNA
<213> ORGANISM: Artificial Sequence
<220> FEATURE:
<223> OTHER INFORMATION: artificial construct-R7 codon-optimized for S cerevisiae

<400> SEQUENCE: 86

```
atgttggaca aggttgaatc tactttgatg ttgatcgctg ctggtgaatt cgctatgggt    60
atcttgggta acgctttcat cggttttggtt aactgtatga actggatcaa gaacagaaag   120
atcgcttcta tcgacttgat cttgacttct ttggctatct ctagaatctg tttgttgtgt   180
atcatcttgt tggactactt catcttgggt ttgtacccag acgtttacac tactggtaag   240
aagatgagaa tcatcgactt cttctggact ttgactaacc acttgaacgt tggttcgct    300
acttgtttgt ctgttttcta cttcttgaag atcgctaact tcttccaccc attgttcttg   360
tggatgaagt ggaagatcga ctctgctatc ccaagaatct tgttgggttg tttggctttc   420
tctgttttca tctctttggt tgtttctgaa aacttgaacg acgacttcag atcttgtgtt   480
aaggttaaga agaagactaa catcactgtt aagtgtagag ttaacaaggc tcaatacgct   540
tctgttaaga tctgtttgaa cttgttgact ttgttcccat ctctgtttc tgttatctct   600
ttcttgttgt tgttgttgtc tttgtggaga cacactagac aaatgaagat ctctgctact   660
ggttgtagag acccatctat cgaagctcac gttggtgcta tgaaggctgt tatctctttc   720
ttgttgttgt tcatcgctta ctacttggct ttcttggttg ctacttcttc ttacttcatg   780
ccagaaactg aattggctgt tatgatcggt gaattgatcg ctttgatcta cccatctcac   840
tctttgatct tgatcttggg taacaacaag ttgagacaag cttctttgag agttttgtgg   900
```

```
aaggttaagt gtatcttgaa gagaagaaac cactaa                              936
```

<210> SEQ ID NO 87
<211> LENGTH: 936
<212> TYPE: DNA
<213> ORGANISM: Artificial Sequence
<220> FEATURE:
<223> OTHER INFORMATION: artificial construct-R7 codon-optimized for
      E coli

<400> SEQUENCE: 87

```
atgctggaca aagttgaatc taccctgatg ctgatcgctg ctggtgaatt cgctatgggt     60
atcctgggta acgctttcat cggtctggtt aactgcatga actggatcaa aaaccgtaaa    120
atcgcttcta tcgacctgat cctgacctct ctggctatct ctcgtatctg cctgctgtgc    180
atcatcctgc tggactactt catcctgggt ctgtacccgg acgtttacac caccggtaaa    240
aaaatgcgta tcatcgactt cttctggacc ctgaccaacc acctgaacgt ttggttcgct    300
acctgcctgt ctgttttcta cttcctgaaa tcgctaact tcttccaccc gctgttcctg    360
tggatgaaat ggaaaatcga ctctgctatc ccgcgtatcc tgctgggttg cctggctttc    420
tctgttttca tctctctggt tgtttctgaa acctgaacg acgacttccg ttcttgcgtt    480
aaagttaaaa aaaaaccaa catcaccgtt aaatgccgtg ttaacaaagc tcagtacgct    540
tctgttaaaa tctgcctgaa cctgctgacc ctgttcccgt ctctgtttc tgttatctct    600
ttcctgctgc tgctgctgtc tctgtggcgt cacacccgtc agatgaaaat ctctgctacc    660
ggttgccgtg acccgtctat cgaagctcac gttggtgcta tgaaagctgt tatctctttc    720
ctgctgctgt tcatcgctta ctacctggct ttcctggttg ctacctcttc ttacttcatg    780
ccggaaaccg aactggctgt tatgatcggt gaactgatcg ctctgatcta cccgtctcac    840
tctctgatcc tgatcctggg taacaacaaa ctgcgtcagg cttctctgcg tgttctgtgg    900
aaagttaaat gcatcctgaa acgtcgtaac cactaa                              936
```

<210> SEQ ID NO 88
<211> LENGTH: 1014
<212> TYPE: DNA
<213> ORGANISM: Artificial Sequence
<220> FEATURE:
<223> OTHER INFORMATION: artificial construct-R9 codon-optimized for
      C elegans

<400> SEQUENCE: 88

```
atgccatctg ctgttgaagt tatttatatg gttcttattg ctggagaact tactattgga     60
atttggggaa atggattcat tgttcttgtt aattgtactg gatggcttca aagaagagat    120
tcttctgtta ttgatattat tcttgttttct cttgctattt ctagaatttg tgttctttgt    180
gttgtttctg ctgaaggatt cgttcttctt cttttctccac atgcttatgc tcaaaatgaa    240
actattaata ctcttgatgc tttctggact cttttctaatc attcttctgt ttggttcact    300
gcttgtcttt ctatttcta tcttcttaaa attgctaata tttctcatcc agttttcctt    360
tggcttaaac ttaatgttac tagagttgtt cttggacttt ccttgcttc tttccttact    420
tctattatta tttctgtttt ccttaaagaa ggatcttggg acatgttga agttaatcat    480
gaagaaaata ttacttggga attcagagtt tctaaagctc catctgcttt caaacttatt    540
attcttaatc ttggagctct tgttccattc gctctttgtc ttatttcttt cgttcttctt    600
cttttctctc ttttcagaca tgctaaacaa atgcaacttt atgctactgg atctagagat    660
```

| | |
|---|---|
| tgttctactg aagctcatat gagagctatt aaagctgtta ctattttcct tcttttcttc | 720 |
| attatgtatt atgctgtttt ccttgttgtt acttcttctt tccttattcc acaaggaaga | 780 |
| cttgttctta tgttcggagg aattgttact gttattttcc catcttctca ttctttcatt | 840 |
| cttattatgg gaaattctaa acttagagaa gctttcctta aagttcttag atgtgttaaa | 900 |
| ggattccata aaagaagaaa accacttgtt ccacaaagaa ttcttaatac tggaagaaaa | 960 |
| aaatctacta aagattgtct tccatctcca agaggacttc attctttcgc ttaa | 1014 |

<210> SEQ ID NO 89
<211> LENGTH: 1014
<212> TYPE: DNA
<213> ORGANISM: Artificial Sequence
<220> FEATURE:
<223> OTHER INFORMATION: artificial construct-R9 codon-optimized for Drosophila

<400> SEQUENCE: 89

| | |
|---|---|
| atgccctccg ccgtggaggt gatctacatg gtgctgatcg ccggcgagct gaccatcggc | 60 |
| atctggggca acggcttcat cgtgctggtg aactgcaccg gctggctgca cgccgcgac | 120 |
| tcctccgtga tcgacatcat cctggtgtcc ctggccatct cccgcatctg cgtgctgtgc | 180 |
| gtggtgtccg ccgagggctt cgtgctgctg ctgtcccccc acgcctacgc ccagaacgag | 240 |
| accatcaaca ccctggacgc cttctggacc ctgtccaacc actcctccgt gtggttcacc | 300 |
| gcctgcctgt ccatcttcta cctgctgaag atcgccaaca tctcccaccc cgtgttcctg | 360 |
| tggctgaagc tgaacgtgac ccgcgtggtg ctgggcctgt cctggcctc cttcctgacc | 420 |
| tccatcatca tctccgtgtt cctgaaggag ggctcctggg ccacgtgga ggtgaaccac | 480 |
| gaggagaaca tcacctggga gttccgcgtg tccaaggccc cctccgcctt caagctgatc | 540 |
| atcctgaacc tgggcgccct ggtgcccttc gccctgtgcc tgatctcctt cgtgctgctg | 600 |
| ctgttctccc tgttccgcca cgccaagcag atgcagctgt acgccaccgg ctcccgcgac | 660 |
| tgctccaccg aggcccacat gcgcgccatc aaggccgtga ccatcttcct gctgttcttc | 720 |
| atcatgtact acgccgtgtt cctggtggtg acctcctcct tcctgatccc cagggccgc | 780 |
| ctggtgctga tgttcggcgg catcgtgacc gtgatcttcc cctcctccca ctccttcatc | 840 |
| ctgatcatgg gcaactccaa gctgcgcgag gccttcctga aggtgctgcg ctgcgtgaag | 900 |
| ggcttccaca gcgccgcaa gcccctggtg ccccagcgca tcctgaacac cggccgcaag | 960 |
| aagtccacca aggactgcct gccctccccc cgcggcctgc actccttcgc ctaa | 1014 |

<210> SEQ ID NO 90
<211> LENGTH: 1014
<212> TYPE: DNA
<213> ORGANISM: Artificial Sequence
<220> FEATURE:
<223> OTHER INFORMATION: artificial construct-R9 codon-optimized forhuman

<400> SEQUENCE: 90

| | |
|---|---|
| atgcccagcg ccgtggaggt gatctacatg gtgctgatcg ccggcgagct gaccatcggc | 60 |
| atctggggca acggcttcat cgtgctggtg aactgcaccg gctggctgca cgccgcgac | 120 |
| agcagcgtga tcgacatcat cctggtgagc ctggccatca gccgcatctg cgtgctgtgc | 180 |
| gtggtgagcg ccgagggctt cgtgctgctg ctgagccccc acgcctacgc ccagaacgag | 240 |
| accatcaaca ccctggacgc cttctggacc ctgagcaacc acagcagcgt gtggttcacc | 300 |
| gcctgcctga gcatcttcta cctgctgaag atcgccaaca tcagccaccc cgtgttcctg | 360 |

```
tggctgaagc tgaacgtgac ccgcgtggtg ctgggcctgt tcctggccag cttcctgacc    420
agcatcatca tcagcgtgtt cctgaaggag ggcagctggg gccacgtgga ggtgaaccac    480
gaggagaaca tcacctggga gttccgcgtg agcaaggccc ccagcgcctt caagctgatc    540
atcctgaacc tgggcgccct ggtgcccttc gccctgtgcc tgatcagctt cgtgctgctg    600
ctgttcagcc tgttccgcca cgccaagcag atgcagctgt acgccaccgg cagccgcgac    660
tgcagcaccg aggcccacat gcgcgccatc aaggccgtga ccatcttcct gctgttcttc    720
atcatgtact acgccgtgtt cctggtggtg accagcagct cctgatcccc cagggccgc    780 ctggtgctga tgttcggcgg catcgtgacc gtgatcttcc ccagcagcca cagcttcatc    840
ctgatcatgg gcaacagcaa gctgcgcgag gccttcctga aggtgctgcg ctgcgtgaag    900
ggcttccaca gcgccgcaa gcccctggtg ccccagcgca tcctgaacac cggccgcaag    960
aagagcacca aggactgcct gcccagcccc cgcggcctgc acagcttcgc ctaa         1014
```

<210> SEQ ID NO 91
<211> LENGTH: 1014
<212> TYPE: DNA
<213> ORGANISM: Artificial Sequence
<220> FEATURE:
<223> OTHER INFORMATION: artificial construct-R9 codon-optimized for mouse

<400> SEQUENCE: 91

```
atgcccagcg ccgtggaggt gatctacatg gtgctgatcg ccggcgagct gaccatcggc     60
atctggggca acggcttcat cgtgctggtg aactgcaccg gctggctgca gaggagggac    120
agcagcgtga tcgacatcat cctggtgagc ctggccatca gcaggatctg cgtgctgtgc    180
gtggtgagcg ccgagggctt cgtgctgctg ctgagccccc acgcctacgc ccagaacgag    240
accatcaaca ccctggacgc cttctggacc ctgagcaacc acagcagcgt gtggttcacc    300
gcctgcctga gcatcttcta cctgctgaag atcgccaaca tcagccaccc cgtgttcctg    360
tggctgaagc tgaacgtgac cagggtggtg ctgggcctgt tcctggccag cttcctgacc    420
agcatcatca tcagcgtgtt cctgaaggag ggcagctggg gccacgtgga ggtgaaccac    480
gaggagaaca tcacctggga gttcagggtg agcaaggccc ccagcgcctt caagctgatc    540
atcctgaacc tgggcgccct ggtgcccttc gccctgtgcc tgatcagctt cgtgctgctg    600
ctgttcagcc tgttcaggca cgccaagcag atgcagctgt acgccaccgg cagcagggac    660
tgcagcaccg aggcccacat gagggccatc aaggccgtga ccatcttcct gctgttcttc    720
atcatgtact acgccgtgtt cctggtggtg accagcagct cctgatcccc cagggcagg    780 ctggtgctga tgttcggcgg catcgtgacc gtgatcttcc ccagcagcca cagcttcatc    840
ctgatcatgg gcaacagcaa gctgagggag gccttcctga aggtgctgag gtgcgtgaag    900
ggcttccaca gaggaggaa gcccctggtg ccccagagga tcctgaacac cggcaggaag    960
aagagcacca aggactgcct gcccagcccc aggggcctgc acagcttcgc ctaa         1014
```

<210> SEQ ID NO 92
<211> LENGTH: 1014
<212> TYPE: DNA
<213> ORGANISM: Artificial Sequence
<220> FEATURE:
<223> OTHER INFORMATION: artificial construct-R9 codon-optimized for S cerevisiae

<400> SEQUENCE: 92

```
atgccatctg ctgttgaagt tatctacatg gttttgatcg ctggtgaatt gactatcggt      60
atctggggta acggtttcat cgttttggtt aactgtactg gttggttgca agaagagac      120
tcttctgtta tcgacatcat cttggtttct ttggctatct ctagaatctg tgttttgtgt     180
gttgtttctg ctgaaggttt cgttttgttg ttgtctccac acgcttacgc tcaaaacgaa     240
actatcaaca ctttggacgc tttctggact ttgtctaacc actcttctgt ttggttcact     300
gcttgtttgt ctatcttcta cttgttgaag atcgctaaca tctctcaccc agttttcttg     360
tggttgaagt tgaacgttac tagagttgtt ttgggtttgt tcttggcttc tttcttgact     420
tctatcatca tctctgtttt cttgaaggaa ggttcttggg gtcacgttga agttaaccac     480
gaagaaaaca tcacttggga attcagagtt tctaaggctc catctgcttt caagttgatc     540
atcttgaact ggggtgcttt ggttccattc gctttgtgtt tgatctcttt cgttttgttg     600
ttgttctctt tgttcagaca cgctaagcaa atgcaattgt acgctactgg ttctagagac     660
tgttctactg aagctcacat gagagctatc aaggctgtta ctatcttctt gttgttcttc     720
atcatgtact acgctgtttt cttggttgtt acttcttctt tcttgatccc acaaggtaga     780
ttggttttga tgttcggtgg tatcgttact gttatcttcc catcttctca ctctttcatc     840
ttgatcatgg gtaactctaa gttgagagaa gctttcttga aggttttgag atgtgttaag     900
ggtttccaca agaagaaaa gccattggtt ccacaaagaa tcttgaacac tggtagaaag     960
aagtctacta aggactgttt gccatctcca agaggtttgc actctttcgc ttaa          1014
```

<210> SEQ ID NO 93
<211> LENGTH: 1014
<212> TYPE: DNA
<213> ORGANISM: Artificial Sequence
<220> FEATURE:
<223> OTHER INFORMATION: artificial construct-R9 codon-optimized for
      E coli

<400> SEQUENCE: 93

```
atgccgtctg ctgttgaagt tatctacatg gttctgatcg ctggtgaact gaccatcggt      60
atctggggta acggtttcat cgttctggtt aactgcaccg ttggctgca gcgtcgtgac     120
tcttctgtta tcgacatcat cctggtttct ctggctatct ctcgtatctg cgttctgtgc     180
gttgtttctg ctgaaggttt cgttctgctg ctgtctccgc acgcttacgc tcagaacgaa     240
accatcaaca ccctggacgc tttctggacc ctgtctaacc actcttctgt ttggttcacc     300
gcttgcctgt ctatcttcta cctgctgaaa atcgctaaca tctctcaccc ggttttcctg     360
tggctgaaac tgaacgttac ccgtgttgtt ctgggtctgt tcctggcttc tttcctgacc     420
tctatcatca tctctgtttt cctgaagaa ggttcttggg gtcacgttga agttaaccac     480
gaagaaaaca tcacctggga attccgtgtt tctaaagctc cgtctgcttt caaactgatc     540
atcctgaacc tgggtgctct ggttccgttc gctctgtgcc tgatctcttt cgttctgctg     600
ctgttctctc tgttccgtca cgctaaacag atgcagctgt acgctaccgg ttctcgtgac     660
tgctctaccg aagctcacat gcgtgctatc aaagctgtta ccatcttcct gctgttcttc     720
atcatgtact acgctgtttt cctggttgtt acctcttctt tcctgatccc gcagggtcgt     780
ctggttctga tgttcggtgg tatcgttacc gttatcttcc cgtcttctca ctctttcatc     840
ctgatcatgg gtaactctaa actgcgtgaa gctttcctga agttctctgcg ttgcgttaaa     900
ggtttccaca acgtcgtaa accgctggtt ccgcagcgta tcctgaacac cggtcgtaaa     960
aaatctacca aagactgcct gccgtctccg cgtggtctgc actctttcgc ttaa          1014
```

<210> SEQ ID NO 94
<211> LENGTH: 903
<212> TYPE: DNA
<213> ORGANISM: Artificial Sequence
<220> FEATURE:
<223> OTHER INFORMATION: artificial construct-R10 codon-optimized for
      C elegans

<400> SEQUENCE: 94

```
atgctttcta ttgttgaagg acttcttatt ttcattgctg tttctgaatc tgttcttgga      60
gttcttggaa atggattcat tggacttgtt aattgtatgg attgtgttaa aaataaaaaa     120
ttctctatga ttggattcat tttcactgga cttgctactt ctagaatttg tcttattctt     180
attgttatgg ctgatggatt cattaaaatt ttctctccag atatgtattc ttctggacat     240
cttattgatt atatttctta tctttggatt attattaatc aatctaatat ttggttcgct     300
acttctcttt ctactttcta tttccttaaa attgctaatt tctctcatca tatgttcctt     360
tggcttaaag aagaattaa ttgggttctt ccacttctta tgggatctct tttcatttct     420
tggcttttca ctttcccaca aattgttaaa attctttctg attctaaagt tggaaatgga     480
aatgctactt ggcaacttaa tatgccaaaa tctgaattcc ttactaaaca aattcttgtt     540
aatattggag ttcttcttct tttcactctt ttccttatta cttgtttcct tcttattatt     600
tctctttgga gacattctag aagaatgcaa cttaatgtta ctggattcca agatccatct     660
actgaagctc atatgaaagc tatgaaagtt cttatttctt tcattattct tttcattctt     720
catttcattg gacttgctat tgaaattgct tgtttcacta tgccagaaaa aaaacttctt     780 ttcatttcg gaatgactac tactgttctt tatccatggg gacattcttt cattcttatt     840
cttggaaatt ctaaacttaa acaagcttct cttagagctc ttcaacaagt taaatgttgt     900
taa                                                                    903
```

<210> SEQ ID NO 95
<211> LENGTH: 903
<212> TYPE: DNA
<213> ORGANISM: Artificial Sequence
<220> FEATURE:
<223> OTHER INFORMATION: artificial construct-R10 codon-optimized for
      Drosophila

<400> SEQUENCE: 95

```
atgctgtcca tcgtggaggg cctgctgatc ttcatcgccg tgtccgagtc cgtgctgggc      60
gtgctgggca acggcttcat cggcctggtg aactgcatgg actgcgtgaa gaacaagaag     120
ttctccatga tcggcttcat cttcaccggc ctggccacct cccgcatctg cctgatcctg     180
atcgtgatgg ccgacggctt catcaagatc ttctcccccg acatgtactc ctccggccac     240
ctgatcgact acatctccta cctgtggatc atcatcaacc agtccaacat ctggttcgcc     300
acctccctgt ccaccttcta cttcctgaag atcgccaact tctcccacca catgttcctg     360
tggctgaagg ccgcatcaa ctgggtgctg cccctgctga tgggctccct gttcatctcc     420
tggctgttca ccttcccca gatcgtgaag atcctgtccg actccaaggt gggcaacggc     480
aacgccacct ggcagctgaa catgcccaag tccgagttcc tgaccaagca gatcctggtg     540
aacatcggcg tgctgctgct gttcaccctg ttcctgatca cctgcttcct gctgatcatc     600
tccctgtggc gccactcccg ccgcatgcag ctgaacgtga ccggcttcca ggacccctcc     660
accgaggccc acatgaaggc catgaaggtg ctgatctcct tcatcatcct gttcatcctg     720
cacttcatcg gcctggccat cgagatcgcc tgcttcacca tgcccgagaa gaagctgctg     780
```

```
ttcatcttcg gcatgaccac caccgtgctg tacccctggg gccactcctt catcctgatc    840
ctgggcaact ccaagctgaa gcaggcctcc ctgcgcgccc tgcagcaggt gaagtgctgc    900
taa                                                                 903
```

<210> SEQ ID NO 96
<211> LENGTH: 903
<212> TYPE: DNA
<213> ORGANISM: Artificial Sequence
<220> FEATURE:
<223> OTHER INFORMATION: artificial construct-R10 codon-optimized for
      human

<400> SEQUENCE: 96

```
atgctgagca tcgtggaggg cctgctgatc ttcatcgccg tgagcgagag cgtgctgggc     60
gtgctgggca acggcttcat cggcctggtg aactgcatgg actgcgtgaa gaacaagaag    120
ttcagcatga tcggcttcat cttcaccggc ctggccacca gccgcatctg cctgatcctg    180
atcgtgatgg ccgacggctt catcaagatc ttcagccccg acatgtacag cagcggccac    240
ctgatcgact acatcagcta cctgtggatc atcatcaacc agagcaacat ctggttcgcc    300
accagcctga gcaccttcta cttcctgaag atcgccaact tcagccacca catgttcctg    360
tggctgaagg ccgcatcaa ctgggtgctg cccctgctga tgggcagcct gttcatcagc     420
tggctgttca ccttccccca gatcgtgaag atcctgagcg cagcaaggt gggcaacggc    480 aacgccacct ggcagctgaa catgcccaag agcgagttcc tgaccaagca gatcctggtg    540
aacatcggcg tgctgctgct gttcaccctg ttcctgatca cctgcttcct gctgatcatc    600
agcctgtggc ccacagcccg ccgcatgcag ctgaacgtga ccggcttcca ggaccccagc    660
accgaggccc acatgaaggc catgaaggtg ctgatcagct tcatcatcct gttcatcctg    720
cacttcatcg gcctggccat cgagatcgcc tgcttcacca tgcccgagaa gaagctgctg    780
ttcatcttcg gcatgaccac caccgtgctg tacccctggg gccacagctt catcctgatc    840
ctgggcaaca gcaagctgaa gcaggccagc ctgcgcgccc tgcagcaggt gaagtgctgc    900
taa                                                                 903
```

<210> SEQ ID NO 97
<211> LENGTH: 903
<212> TYPE: DNA
<213> ORGANISM: Artificial Sequence
<220> FEATURE:
<223> OTHER INFORMATION: artificial construct-R10 codon-optimized for
      mouse

<400> SEQUENCE: 97

```
atgctgagca tcgtggaggg cctgctgatc ttcatcgccg tgagcgagag cgtgctgggc     60
gtgctgggca acggcttcat cggcctggtg aactgcatgg actgcgtgaa gaacaagaag    120
ttcagcatga tcggcttcat cttcaccggc ctggccacca gcaggatctg cctgatcctg    180
atcgtgatgg ccgacggctt catcaagatc ttcagccccg acatgtacag cagcggccac    240
ctgatcgact acatcagcta cctgtggatc atcatcaacc agagcaacat ctggttcgcc    300
accagcctga gcaccttcta cttcctgaag atcgccaact tcagccacca catgttcctg    360
tggctgaagg gcaggatcaa ctgggtgctg cccctgctga tgggcagcct gttcatcagc    420
tggctgttca ccttccccca gatcgtgaag atcctgagcg cagcaaggt gggcaacggc    480 aacgccacct ggcagctgaa catgcccaag agcgagttcc tgaccaagca gatcctggtg    540
```

```
aacatcggcg tgctgctgct gttcaccctg ttcctgatca cctgcttcct gctgatcatc    600
agcctgtgga ggcacagcag gaggatgcag ctgaacgtga ccggcttcca ggacccccagc   660 accgaggccc acatgaaggc catgaaggtg ctgatcagct tcatcatcct gttcatcctg    720
cacttcatcg cctggccat cgagatcgcc tgcttcacca tgcccgagaa gaagctgctg     780
ttcatcttcg gcatgaccac caccgtgctg taccctggg gccacagctt catcctgatc     840
ctgggcaaca gcaagctgaa gcaggccagc ctgagggccc tgcagcaggt gaagtgctgc    900
taa                                                                  903
```

<210> SEQ ID NO 98
<211> LENGTH: 903
<212> TYPE: DNA
<213> ORGANISM: Artificial Sequence
<220> FEATURE:
<223> OTHER INFORMATION: artificial construct-R10 codon-optimized for
    S cerevisiae

<400> SEQUENCE: 98

```
atgttgtcta tcgttgaagg tttgttgatc ttcatcgctg tttctgaatc tgttttgggt    60
gttttgggta acggtttcat cggtttggtt aactgtatgg actgtgttaa gaacaagaag    120
ttctctatga tcggtttcat cttcactggt ttggctactt ctagaatctg tttgatcttg    180
atcgttatgg ctgacggttt catcaagatc ttctctccag acatgtactc ttctggtcac    240
ttgatcgact acatctctta cttgtggatc atcatcaacc aatctaacat ctggttcgct    300
acttctttgt ctactttcta cttcttgaag atcgctaact ctctcacca catgttcttg     360 tggttgaagg gtagaatcaa ctgggttttg ccattgttga tgggttcttt gttcatctct    420
tggttgttca ctttcccaca aatcgttaag atcttgtctg actctaaggt tggtaacggt    480
aacgctactt ggcaattgaa catgccaaag tctgaattct tgactaagca atcttggtt    540 aacatcggtg ttttgttgtt gttcactttg ttcttgatca cttgtttctt gttgatcatc    600
tctttgtgga gacactctag aagaatgcaa ttgaacgtta ctggtttcca agacccatct    660
actgaagctc acatgaaggc tatgaaggtt ttgatctctt tcatcatctt gttcatcttg    720
cacttcatcg gtttggctat cgaaatcgct tgtttcacta tgccagaaaa gaagttgttg    780
ttcatcttcg gtatgactac tactgttttg tacccatggg gtcactcttt catcttgatc    840
ttgggtaact ctaagttgaa gcaagcttct ttgagagctt tgcaacaagt taagtgttgt    900
taa                                                                  903
```

<210> SEQ ID NO 99
<211> LENGTH: 903
<212> TYPE: DNA
<213> ORGANISM: Artificial Sequence
<220> FEATURE:
<223> OTHER INFORMATION: artificial construct-R10 codon-optimized for
    E coli

<400> SEQUENCE: 99

```
atgctgtcta tcgttgaagg tctgctgatc ttcatcgctg tttctgaatc tgttctgggt    60
gttctgggta acggtttcat cggtctggtt aactgcatgg actgcgttaa aaacaaaaaa    120
ttctctatga tcggtttcat cttcaccggt ctggctacct ctcgtatctg cctgatcctg    180
atcgttatgg ctgacggttt catcaaaatc ttctctccgg acatgtactc ttctggtcac    240
ctgatcgact acatctctta cctgtggatc atcatcaacc agtctaacat ctggttcgct    300
acctctctgt ctaccttcta cttcctgaaa atcgctaact ctctctcacca catgttcctg   360
```

```
tggctgaaag gtcgtatcaa ctgggttctg ccgctgctga tgggttctct gttcatctct    420
tggctgttca ccttcccgca gatcgttaaa atcctgtctg actctaaagt tggtaacggt    480
aacgctacct ggcagctgaa catgccgaaa tctgaattcc tgaccaaaca gatcctggtt    540
aacatcggtg ttctgctgct gttcaccctg ttcctgatca cctgcttcct gctgatcatc    600
tctctgtggc gtcactctcg tcgtatgcag ctgaacgtta ccggtttcca ggacccgtct    660
accgaagctc acatgaaagc tatgaaagtt ctgatctctt tcatcatcct gttcatcctg    720
cacttcatcg gtctggctat cgaaatcgct tgcttcacca tgccggaaaa aaaactgctg    780
ttcatcttcg gtatgaccac caccgttctg tacccgtggg gtcactcttt catcctgatc    840
ctgggtaact ctaaactgaa acaggcttct ctgcgtgctc tgcagcaggt taaatgctgc    900
taa                                                                 903
```

<210> SEQ ID NO 100
<211> LENGTH: 930
<212> TYPE: DNA
<213> ORGANISM: Artificial Sequence
<220> FEATURE:
<223> OTHER INFORMATION: artificial construct-R12 codon-optimized for
      C elegans

<400> SEQUENCE: 100

```
atggcttctg ttcttaaaaa tgttttcatg attcttttcg ctggagaatt cattatggga     60
attcttggaa atggattcat tattcttgtt aattgtattg attggattag aaattggaaa    120
ttcttcgtta ttgatttcat tattacttgt cttgctattt ctagaattgt tcttctttgt    180
attattattc ttggaattgg acttgatgtt ccatgtgaag aaatttggaa taaaaataat    240
caacttatta gattcgaaat tctttggact ggatctaatt atttctgtat tacttgtact    300
acttgtcttt ctgttttcta tttcttcaaa attgctaatt tctctaatcc acttttcctt    360
tggattaaat ggagaattca taaagttctt cttactattg ttcttgctgc tgttttctct    420
ttctgtcttt ctcttccatt caaagatact gttttcactt ctcttattaa aaataaagtt    480
aatgctgaaa gaaattggac tgtttctttc actactagaa cttatgaact ttcccttttct    540 catatgcttc ttaatattat gttcattatt ccattcgctg tttctcttgc ttctttcgtt    600
cttcttattt gttctctttg gtctcatact agacaaatga aaggaagagg aggagatcca    660
actactaaag ttcatgttag agctatgaaa gctatgattt ctttccttct tttcttcttc    720
atgtattatc tttctactat tatgatgaat cttgcttatg ttattcttga ttctcttgtt    780
gctaaaattt tcgctaatac tcttgttttc ctttatccat ctggacatac tttccttctt    840
attctttgga cttctaaact taaacaagct tctctttgtg ttcttaaaaa acttaaatgt    900
cttcatctta gaaaaccaac tagaccataa                                    930
```

<210> SEQ ID NO 101
<211> LENGTH: 930
<212> TYPE: DNA
<213> ORGANISM: Artificial Sequence
<220> FEATURE:
<223> OTHER INFORMATION: artificial construct-R12 codon-optimized for
      Drosophila

<400> SEQUENCE: 101

```
atggcctccg tgctgaagaa cgtgttcatg atcctgttcg ccggcgagtt catcatgggc     60
atcctgggca acggcttcat catcctggtg aactgcatcg actggatccg caactggaag    120
```

| | |
|---|---|
| ttcttcgtga tcgacttcat catcacctgc ctggccatct cccgcatcgt gctgctgtgc | 180 |
| atcatcatcc tgggcatcgg cctggacgtg ccctgcgagg agatctggaa caagaacaac | 240 |
| cagctgatcc gcttcgagat cctgtggacc ggctccaact acttctgcat cacctgcacc | 300 |
| acctgcctgt ccgtgttcta cttcttcaag atcgccaact tctccaaccc cctgttcctg | 360 |
| tggatcaagt ggcgcatcca aaggtgctg ctgaccatcg tgctggccgc cgtgttctcc | 420 |
| ttctgcctgt ccctgccctt caaggacacc gtgttcacct ccctgatcaa gaacaaggtg | 480 |
| aacgccgagc gcaactggac cgtgtccttc accacccgca cctacgagct gttcctgtcc | 540 |
| cacatgctgc tgaacatcat gttcatcatc cccttcgccg tgtccctggc ctccttcgtg | 600 |
| ctgctgatct gctccctgtg gtcccacacc cgccagatga agggccgcgg cggcgacccc | 660 |
| accaccaagg tgcacgtgcg cgccatgaag gccatgatct ccttcctgct gttcttcttc | 720 |
| atgtactacc tgtccaccat catgatgaac ctggcctacg tgatcctgga ctccctggtg | 780 |
| gccaagatct tcgccaacac cctggtgttc ctgtacccct ccggccacac cttcctgctg | 840 |
| atcctgtgga cctccaagct gaagcaggcc tccctgtgcg tgctgaagaa gctgaagtgc | 900 |
| ctgcacctgc gcaagcccac ccgcccctaa | 930 |

<210> SEQ ID NO 102
<211> LENGTH: 930
<212> TYPE: DNA
<213> ORGANISM: Artificial Sequence
<220> FEATURE:
<223> OTHER INFORMATION: artificial construct-R12 codon-optimized for human

<400> SEQUENCE: 102

| | |
|---|---|
| atggccagcg tgctgaagaa cgtgttcatg atcctgttcg ccggcgagtt catcatgggc | 60 |
| atcctgggca acggcttcat catcctggtg aactgcatcg actggatccg caactggaag | 120 |
| ttcttcgtga tcgacttcat catcacctgc ctggccatca gccgcatcgt gctgctgtgc | 180 |
| atcatcatcc tgggcatcgg cctggacgtg ccctgcgagg agatctggaa caagaacaac | 240 |
| cagctgatcc gcttcgagat cctgtggacc ggcagcaact acttctgcat cacctgcacc | 300 |
| acctgcctga gcgtgttcta cttcttcaag atcgccaact tcagcaaccc cctgttcctg | 360 |
| tggatcaagt ggcgcatcca aaggtgctg ctgaccatcg tgctggccgc cgtgttcagc | 420 |
| ttctgcctga gcctgccctt caaggacacc gtgttcacca gcctgatcaa gaacaaggtg | 480 |
| aacgccgagc gcaactggac cgtgagcttc accacccgca cctacgagct gttcctgagc | 540 |
| cacatgctgc tgaacatcat gttcatcatc cccttcgccg tgagcctggc cagcttcgtg | 600 |
| ctgctgatct gcagcctgtg gagccacacc cgccagatga agggccgcgg cggcgacccc | 660 |
| accaccaagg tgcacgtgcg cgccatgaag gccatgatca gcttcctgct gttcttcttc | 720 |
| atgtactacc tgagcaccat catgatgaac ctggcctacg tgatcctgga cagcctggtg | 780 |
| gccaagatct tcgccaacac cctggtgttc ctgtacccca gcggccacac cttcctgctg | 840 |
| atcctgtgga cccagcaagct gaagcaggcc agcctgtgcg tgctgaagaa gctgaagtgc | 900 |
| ctgcacctgc gcaagcccac ccgcccctaa | 930 |

<210> SEQ ID NO 103
<211> LENGTH: 930
<212> TYPE: DNA
<213> ORGANISM: Artificial Sequence
<220> FEATURE:
<223> OTHER INFORMATION: artificial construct-R12 codon-optimized for mouse

<400> SEQUENCE: 103

```
atggccagcg tgctgaagaa cgtgttcatg atcctgttcg ccggcgagtt catcatgggc    60
atcctgggca acggcttcat catcctggtg aactgcatcg actggatcag gaactggaag   120
ttcttcgtga tcgacttcat catcacctgc ctggccatca gcaggatcgt gctgctgtgc   180
atcatcatcc tgggcatcgg cctggacgtg ccctgcgagg agatctggaa caagaacaac   240
cagctgatca ggttcgagat cctgtggacc ggcagcaact acttctgcat cacctgcacc   300
acctgcctga gcgtgttcta cttcttcaag atcgccaact cagcaacccc cctgttcctg   360
tggatcaagt ggaggatcca aaggtgctgc tgaccatcg tgctggccgc cgtgttcagc   420
ttctgcctga gcctgcccct caaggacacc gtgttcacca gcctgatcaa gaacaaggtg   480
aacgccgaga ggaactggac cgtgagcttc accaccagga cctacgagct gttcctgagc   540
cacatgctgc tgaacatcat gttcatcatc cccttcgccg tgagcctggc cagcttcgtg   600
ctgctgatct gcagcctgtg gagccacacc aggcagatga agggcagggg cggcgacccc   660
accaccaagg tgcacgtgag ggccatgaag gccatgatca gcttcctgct gttcttcttc   720
atgtactacc tgagcaccat catgatgaac ctggcctacg tgatcctgga cagcctggtg   780
gccaagatct tcgccaacac cctggtgttc ctgtacccca gcggccacac cttcctgctg   840
atcctgtgga ccagcaagct gaagcaggcc agcctgtgcg tgctgaagaa gctgaagtgc   900
ctgcacctga ggaagcccac caggccctaa                                    930
```

<210> SEQ ID NO 104
<211> LENGTH: 930
<212> TYPE: DNA
<213> ORGANISM: Artificial Sequence
<220> FEATURE:
<223> OTHER INFORMATION: artificial construct-R12 codon-optimized for
      S cerevisiae

<400> SEQUENCE: 104

```
atggcttctg ttttgaagaa cgttttcatg atcttgttcg ctggtgaatt catcatgggt    60
atcttgggta acggtttcat catcttggtt aactgtatcg actggatcag aaactggaag   120
ttcttcgtta tcgacttcat catcacttgt ttggctatct ctagaatcgt tttgttgtgt   180
atcatcatct tgggtatcgg tttggacgtt ccatgtgaag aaatctggaa caagaacaac   240
caattgatca gattcgaaat cttgtggact ggttctaact acttctgtat cacttgtact   300
acttgtttgt ctgttttcta cttcttcaag atcgctaact ctctaaccc attgttcttg   360
tggatcaagt ggagaatcca aaggttttg ttgactatcg ttttggctgc tgtttttctct  420
ttctgttttgt ctttgccatt caaggacact gttttcactt ctttgatcaa gaacaaggtt  480
aacgctgaaa gaaactggac tgtttcttc actactagaa cttacgaatt gttcttgtct   540
cacatgttgt tgaacatcat gttcatcatc ccattcgctg tttcttggc ttctttcgtt   600
ttgttgatct gttctttgtg gtctcacact agacaaatga agggtagagg tggtgaccca   660
actactaagg ttcacgttag agctatgaag gctatgatct cttttcttgtt gttcttcttc   720
atgtactact tgtctactat catgatgaac ttggcttacg ttatcttgga ctcttggtt    780
gctaagatct tcgctaacac tttggttttc ttgtacccat ctggtcacac tttcttgttg   840
atcttgtgga cttctaagtt gaagcaagct tctttgtgtg ttttgaagaa gttgaagtgt   900
ttgcacttga gaaagccaac tagaccataa                                    930
```

<210> SEQ ID NO 105
<211> LENGTH: 930
<212> TYPE: DNA
<213> ORGANISM: Artificial Sequence
<220> FEATURE:
<223> OTHER INFORMATION: artificial construct-R12 codon-optimized for
      E coli

<400> SEQUENCE: 105

| | | | | | |
|---|---|---|---|---|---|
| atggcttctg | ttctgaaaaa | cgttttcatg | atcctgttcg | ctggtgaatt | catcatgggt | 60 |
| atcctgggta | acggtttcat | catcctggtt | aactgcatcg | actggatccg | taactggaaa | 120 |
| ttcttcgtta | tcgacttcat | catcacctgc | ctggctatct | ctcgtatcgt | tctgctgtgc | 180 |
| atcatcatcc | tgggtatcgg | tctggacgtt | ccgtgcgaag | aaatctggaa | caaaaacaac | 240 |
| cagctgatcc | gtttcgaaat | cctgtggacc | ggttctaact | acttctgcat | cacctgcacc | 300 |
| acctgcctgt | ctgttttcta | cttcttcaaa | atcgctaact | tctctaaccc | gctgttcctg | 360 |
| tggatcaaat | ggcgtatcca | aaagttctg | ctgaccatcg | ttctggctgc | tgtttttctct | 420 |
| ttctgcctgt | ctctgccgtt | caagacacc | gttttcacct | ctctgatcaa | aaacaaagtt | 480 |
| aacgctgaac | gtaactggac | cgtttctttc | accaccgta | cctacgaact | gttcctgtct | 540 |
| cacatgctgc | tgaacatcat | gttcatcatc | ccgttcgctg | tttctctggc | ttctttcgtt | 600 |
| ctgctgatct | gctctctgtg | gtctcacacc | cgtcagatga | aggtcgtgg | tggtgacccg | 660 |
| accaccaaag | ttcacgttcg | tgctatgaaa | gctatgatct | cttttcctgct | gttcttcttc | 720 |
| atgtactacc | tgtctaccat | catgatgaac | ctggcttacg | ttatcctgga | ctctctggtt | 780 |
| gctaaaatct | tcgctaacac | cctggttttc | ctgtacccgt | ctggtcacac | cttcctgctg | 840 |
| atcctgtgga | cctctaaact | gaaacaggct | tctctgtgcg | ttctgaaaaa | actgaaatgc | 900 |
| ctgcacctgc | gtaaaccgac | ccgtccgtaa | | | | 930 |

<210> SEQ ID NO 106
<211> LENGTH: 1005
<212> TYPE: DNA
<213> ORGANISM: Artificial Sequence
<220> FEATURE:
<223> OTHER INFORMATION: artificial construct-R38 codon-optimized for
      C elegans

<400> SEQUENCE: 106

| | | | | | |
|---|---|---|---|---|---|
| atgcttgctc | ttactccagt | tattactgtt | tcttatgaag | ttaaatctgc | tttccttttc | 60 |
| ctttctattc | ttgaattcac | tgttggagtt | cttgctaatg | ctttcatttt | ccttgttaat | 120 |
| ttctgggatg | ttgttagaaa | acaaccactt | tctaattgtg | atcttattct | tctttctctt | 180 |
| tctcttacta | gacttttcct | tcatggactt | cttttccttg | atgctcttca | acttacttat | 240 |
| ttccaaagaa | tgaaagatcc | actttctctt | tcttatcaaa | ctattattat | gctttggatg | 300 |
| attactaatc | aagttggact | ttggcttact | acttgtcttt | ctcttcttta | ttgttctaaa | 360 |
| attgctagat | tctctcatac | tcttcttcat | tgtgttgctt | cttgggtttc | tagaaaagtt | 420 |
| ccacaaatgc | ttcttggagc | tatgcttttc | tcttgtattt | gtactgctat | ttgtcttgga | 480 |
| gatttcttct | ctagatctgg | attcactttc | actactatgc | ttttcgttaa | taatactgaa | 540 |
| ttcaatcttc | aaattgctaa | actttctttc | tatcattctt | tcattttctg | tactcttgct | 600 |
| tctattccat | ctcttctttt | ttccttatt | tcttctggag | ttcttattgt | ttctcttgga | 660 |
| agacatatga | gaactatgag | agctaaaact | aaagattctc | atgatccatc | tcttgaagct | 720 |
| catattaaag | ctcttagatc | tcttgtttct | ttcctttgtc | tttatgttgt | ttcttctcgt | 780 |

```
gctgctcttg tttctgttcc acttcttatg ctttggcata ataaaattgg agttatgatt       840
tgtgttggaa ttcttgctgc ttgtccatct attcatgctg ctattcttat ttctggaaat       900
gctaaactta gaagagctgt tgaaactatt cttctttggg ttcaaaattc tcttaaaatt       960
ggagctgatc ataaagctga tgctagaact ccaggacttt gttaa                      1005
```

<210> SEQ ID NO 107
<211> LENGTH: 1005
<212> TYPE: DNA
<213> ORGANISM: Artificial Sequence
<220> FEATURE:
<223> OTHER INFORMATION: artificial construct-R38 codon-optimized for
      Drosophila

<400> SEQUENCE: 107

```
atgctggccc tgaccccgt gatcaccgtg tcctacgagg tgaagtccgc cttcctgttc        60
ctgtccatcc tggagttcac cgtgggcgtg ctggccaacg ccttcatctt cctggtgaac       120
ttctgggacg tggtgcgcaa gcagcccctg tccaactgcg acctgatcct gctgtccctg       180
tccctgaccc gcctgttcct gcacggcctg ctgttcctgg acgccctgca gctgacctac       240
ttccagcgca tgaaggaccc cctgtccctg tcctaccaga ccatcatcat gctgtggatg       300
atcaccaacc aggtgggcct gtggctgacc acctgcctgt ccctgctgta ctgctccaag       360
atcgcccgct ctcccacac cctgctgcac tgcgtggcct cctgggtgtc cgcaaggtg        420 ccccagatgc tgctgggcgc catgctgttc tcctgcatct gcaccgccat ctgcctgggc       480
gacttcttct cccgctccgg cttcaccttc accaccatgc tgttcgtgaa caacaccgag       540
ttcaacctgc agatcgccaa gctgtccttc taccactcct tcatcttctg caccctggcc       600
tccatcccct ccctgctgtt cttcctgatc tcctccggcg tgctgatcgt gtccctgggc       660
cgccacatgc gcaccatgcg cgccaagacc aaggactccc acgacccctc cctggaggcc       720
cacatcaagg ccctgcgctc cctggtgtcc ttcctgtgcc tgtacgtggt gtccttctgc       780
gccgccctgg tgtccgtgcc cctgctgatg ctgtggcaca acaagatcgg cgtgatgatc       840
tgcgtgggca tcctggccgc ctgccccctcc atccacgccg ccatcctgat ctccggcaac       900
gccaagctgc gccgcgccgt ggagaccatc ctgctgtggg tgcagaactc cctgaagatc       960
ggcgccgacc acaaggccga cgcccgcacc cccggcctgt gctaa                      1005
```

<210> SEQ ID NO 108
<211> LENGTH: 1005
<212> TYPE: DNA
<213> ORGANISM: Artificial Sequence
<220> FEATURE:
<223> OTHER INFORMATION: artificial construct-R38 codon-optimized for
      human

<400> SEQUENCE: 108

```
atgctggccc tgaccccgt gatcaccgtg agctacgagg tgaagagcgc cttcctgttc        60
ctgagcatcc tggagttcac cgtgggcgtg ctggccaacg ccttcatctt cctggtgaac       120
ttctgggacg tggtgcgcaa gcagcccctg agcaactgcg acctgatcct gctgagcctg       180
agcctgaccc gcctgttcct gcacggcctg ctgttcctgg acgccctgca gctgacctac       240
ttccagcgca tgaaggaccc cctgagcctg agctaccaga ccatcatcat gctgtggatg       300
atcaccaacc aggtgggcct gtggctgacc acctgcctga gcctgctgta ctgcagcaag       360
atcgcccgct cagccacac cctgctgcac tgcgtggcca gctgggtgag ccgcaaggtg       420
ccccagatgc tgctgggcgc catgctgttc agctgcatct gcaccgccat ctgcctgggc       480
```

```
gacttcttca gccgcagcgg cttcaccttc accaccatgc tgttcgtgaa caacaccgag    540
ttcaacctgc agatcgccaa gctgagcttc taccacagct tcatcttctg caccctggcc    600
agcatcccca gcctgctgtt cttcctgatc agcagcggcg tgctgatcgt gagcctgggc    660
cgccacatgc gcaccatgcg cgccaagacc aaggacagca cgacccccag cctggaggcc    720
cacatcaagg ccctgcgcag cctggtgagc ttcctgtgcc tgtacgtggt gagcttctgc    780
gccgccctgg tgagcgtgcc cctgctgatg ctgtggcaca acaagatcgg cgtgatgatc    840
tgcgtgggca tcctggccgc ctgccccagc atccacgccg ccatcctgat cagcggcaac    900
gccaagctgc gccgcgccgt ggagaccatc ctgctgtggg tgcagaacag cctgaagatc    960
ggcgccgacc acaaggccga cgcccgcacc cccggcctgt gctaa                  1005

<210> SEQ ID NO 109
<211> LENGTH: 1005
<212> TYPE: DNA
<213> ORGANISM: Artificial Sequence
<220> FEATURE:
<223> OTHER INFORMATION: artificial construct-R38 codon-optimized for
      mouse

<400> SEQUENCE: 109
atgctggccc tgacccccgt gatcaccgtg agctacgagg tgaagagcgc cttcctgttc     60
ctgagcatcc tggagttcac cgtgggcgtg ctggccaacg ccttcatctt cctggtgaac    120
ttctgggacg tggtgaggaa gcagcccctg agcaactgcg acctgatcct gctgagcctg    180
agcctgacca ggctgttcct gcacggcctg ctgttcctgg acgccctgca gctgacctac    240
ttccagagga tgaaggaccc cctgagcctg agctaccaga ccatcatcat gctgtggatg    300
atcaccaacc aggtgggcct gtggctgacc acctgcctga gctgctgta ctgcagcaag    360 atcgccaggt tcagccacac cctgctgcac tgcgtggcca gctgggtgag caggaaggtg    420
ccccagatgc tgctgggcgc catgctgttc agctgcatct gcaccgccat ctgcctgggc    480
gacttcttca gcaggagcgg cttcaccttc accaccatgc tgttcgtgaa caacaccgag    540
ttcaacctgc agatcgccaa gctgagcttc taccacagct tcatcttctg caccctggcc    600
agcatcccca gcctgctgtt cttcctgatc agcagcggcg tgctgatcgt gagcctgggc    660
aggcacatga ggaccatgag ggccaagacc aaggacagcc acgacccag cctggaggcc    720 cacatcaagg ccctgaggag cctggtgagc ttcctgtgcc tgtacgtggt gagcttctgc    780
gccgccctgg tgagcgtgcc cctgctgatg ctgtggcaca acaagatcgg cgtgatgatc    840
tgcgtgggca tcctggccgc ctgccccagc atccacgccg ccatcctgat cagcggcaac    900
gccaagctga gggggccgt ggagaccatc ctgctgtggg tgcagaacag cctgaagatc    960
ggcgccgacc acaaggccga cgccaggacc cccggcctgt gctaa                  1005

<210> SEQ ID NO 110
<211> LENGTH: 1005
<212> TYPE: DNA
<213> ORGANISM: Artificial Sequence
<220> FEATURE:
<223> OTHER INFORMATION: artificial construct-R38 codon-optimized for
      S cerevisiae

<400> SEQUENCE: 110
atgttggctt tgactccagt tatcactgtt tcttacgaag ttaagtctgc tttcttgttc     60
ttgtctatct tggaattcac tgttggtgtt ttggctaacg cttttcatctt cttggttaac   120
```

```
ttctgggacg ttgttagaaa gcaaccattg tctaactgtg acttgatctt gttgtctttg      180
tctttgacta gattgttctt gcacggtttg ttgttcttgg acgctttgca attgacttac      240
ttccaaagaa tgaaggaccc attgtctttg tcttaccaaa ctatcatcat gttgtggatg      300
atcactaacc aagttggttt gtggttgact acttgtttgt ctttgttgta ctgttctaag      360
atcgctagat tctctcacac tttgttgcac tgtgttgctt ctttgggtttc tagaaaggtt     420 ccacaaatgt tgttgggtgc tatgttgttc tcttgtatct gtactgctat ctgtttgggt      480
gacttcttct ctagatctgg tttcactttc actactatgt tgttcgttaa caacactgaa      540
ttcaacttgc aaatcgctaa gttgtctttc taccactctt tcatcttctg tactttggct      600
tctatcccat ctttgttgtt cttcttgatc tcttctggtg ttttgatcgt ttctttgggt      660
agacacatga aactatgag agctaagact aaggactctc acgacccatc tttggaagct      720
cacatcaagg ctttgagatc tttggtttct tcttgtgttt tgtacgttgt ttctttctgt      780
gctgctttgg tttctgttcc attgttgatg ttgtggcaca acaagatcgg tgttatgatc      840
tgtgttggta tcttggctgc ttgtccatct atccacgctg ctatcttgat ctctggtaac      900
gctaagttga agagctgt tgaaactatc ttgttgtggg ttcaaaactc tttgaagatc       960
ggtgctgacc acaaggctga cgctagaact ccaggtttgt gttaa                    1005

<210> SEQ ID NO 111
<211> LENGTH: 1005
<212> TYPE: DNA
<213> ORGANISM: Artificial Sequence
<220> FEATURE:
<223> OTHER INFORMATION: artificial construct-R38 codon-optimized for
      E coli

<400> SEQUENCE: 111
atgctggctc tgaccccggt tatcaccgtt tcttacgaag ttaaatctgc tttcctgttc       60
ctgtctatcc tggaattcac cgttggtgtt ctggctaacg cttttcatctt cctggttaac     120 ttctgggacg ttgttcgtaa acagccgctg tctaactgcg acctgatcct gctgtctctg      180
tctctgaccc gtctgttcct gcacggtctg ctgttcctgg acgctctgca gctgacctac      240
ttccagcgta tgaaagaccc gctgtctctg cttaccaga ccatcatcat gctgtggatg       300
atcaccaacc aggttggtct gtggctgacc acctgcctgt ctctgctgta ctgctctaaa      360
atcgctcgtt tctctcacac cctgctgcac tgcgttgctt ctttgggttc tcgtaaagtt      420
ccgcagatgc tgctgggtgc tatgctgttc tcttgcatct gcaccgctat ctgcctgggt      480
gacttcttct ctcgttctgg tttccacttc accaccatgc tgttcgttaa caacaccgaa      540
ttcaacctgc agatcgctaa actgtctttc taccactctt tcatcttctg caccctggct      600
tctatcccgt ctctgctgtt cctgctgatc tcttctggtg ttctgatcgt ttctctgggt      660
cgtcacatgc gtaccatgcg tgctaaaacc aaagactctc acgacccgtc tctggaagct      720
cacatcaaag ctctgcgttc tctggttct tcctgtgtcc tgtacgttgt ttctttctgc       780
gctgctctgg tttctgttcc gctgctgatg ctgtggcaca acaaaatcgg tgttatgatc      840
tgcgttggta tcctggctgc ttgcccgtct atccacgctg ctatcctgat ctctggtaac      900
gctaaactgc gtcgtgctgt tgaaaccatc ctgctgtggg ttcagaactc tctgaaaatc      960
ggtgctgacc acaaagctga cgctcgtacc ccgggtctgt gctaa                    1005

<210> SEQ ID NO 112
<211> LENGTH: 969
<212> TYPE: DNA
```

<213> ORGANISM: Artificial Sequence
<220> FEATURE:
<223> OTHER INFORMATION: artificial construct-R42 codon-optimized for
      C elegans

<400> SEQUENCE: 112

```
atgcttgctg gacttgataa aatttttcctt actctttcta ctgctgaatt cgttattgga    60
atgtctggaa atgttttcgt tggacttgtt aattgttctg aatggattaa aaatcaaaaa   120
atttctttcg ttgatttcat tcttacttgt cttgctcttt ctagaattac tcaacttctt   180
gtttctcttt ggcaatcttt cgttatgact ctttctccac cattctattc tacttggaaa   240
tctgctaaac ttattactct tctttggaga attactaatc attggactac ttggttcact   300
acttgtcttt ctattttcta tcttcttaaa attgctcatt tctctcattc tttcttcctt   360
tggcttaaat ggagaactaa tagagttgtt cttgctattc ttgttctttc tcttccattc   420
cttcttttcg atttccttgt tcttgaatct cttaatgatt tcttccttaa tgtttatgtt   480
atggatgaat ctaatcttac tcttcatact aatgattgta atctctttta tattaaaact   540
cttattcttc tttctttctc ttatactatt ccaattgttc tttctcttac ttctcttgtt   600
cttcttttcc tttctcttgt tagacatatt agaaatcttc aacttaatgt tatgggatct   660
ggagatgctt ctactcaagc tcataaagga gctattaaaa tggttatgtc tttccttctt   720
cttttcactg ttcatttctt ctctattcaa cttactaatt ggatgcttct tattttctgg   780
aataataaat tcactaaatt cattatgctt gctatttatg tttttcccatc tggacattct   840
cttattctta ttcttggaaa ttctaaactt agacaaactg ctcttaaagt tcttagacat   900
cttaaatcta ctcttaaaag agaaaaaact gtttcttctc ttcaaattga tgttccagga   960
tctttctaa                                                          969
```

<210> SEQ ID NO 113
<211> LENGTH: 969
<212> TYPE: DNA
<213> ORGANISM: Artificial Sequence
<220> FEATURE:
<223> OTHER INFORMATION: artificial construct-R42 codon-optimized for
      Drosophila

<400> SEQUENCE: 113

```
atgctggccg gcctggacaa gatcttcctg accctgtcca ccgccgagtt cgtgatcggc    60
atgtccggca acgtgttcgt gggcctggtg aactgctccg agtggatcaa gaaccagaag   120
atctccttcg tggacttcat cctgacctgc ctggccctgt cccgcatcac ccagctgctg   180
gtgtccctgt ggcagtcctt cgtgatgacc ctgtcccccc ccttctactc cacctggaag   240
tccgccaagc tgatcaccct gctgtggcgc atcaccaacc actggaccac ctggttcacc   300
acctgcctgt ccatcttcta cctgctgaag atcgcccact tctcccactc cttcttcctg   360
tggctgaagt ggcgcaccaa ccgcgtggtg ctggccatcc tggtgctgtc cctgcccttc   420
ctgctgttcg acttcctggt gctggagtcc ctgaacgact tcttcctgaa cgtgtacgtg   480
atggacgagt ccaacctgac cctgcacacc aacgactgca gtccctgta catcaagacc   540
ctgatcctgc tgtccttctc ctacaccatc cccatcgtgc tgtccctgac ctccctggtg   600
ctgctgttcc tgtccctggt gcgccacatc cgcaacctgc agctgaacgt gatgggctcc   660
ggcgacgcct ccacccaggc ccacaagggc gccatcaaga tggtgatgtc cttcctgctg   720
ctgttcaccg tgcacttctt ctccatccag ctgaccaact ggatgctgct gatcttctgg   780
aacaacaagt tcaccaagtt catcatgctg gccatctacg tgttcccctc cggccactcc   840
```

```
ctgatcctga tcctgggcaa ctccaagctg cgccagaccg ccctgaaggt gctgcgccac    900
ctgaagtcca ccctgaagcg cgagaagacc gtgtcctccc tgcagatcga cgtgcccggc    960
tccttctaa                                                            969
```

<210> SEQ ID NO 114
<211> LENGTH: 969
<212> TYPE: DNA
<213> ORGANISM: Artificial Sequence
<220> FEATURE:
<223> OTHER INFORMATION: artificial construct-R42 codon-optimized for human

<400> SEQUENCE: 114

```
atgctggccg gcctggacaa gatcttcctg accctgagca ccgccgagtt cgtgatcggc     60
atgagcggca acgtgttcgt gggcctggtg aactgcagcg agtggatcaa gaaccagaag    120
atcagcttcg tggacttcat cctgacctgc ctggccctga ccgcatcac ccagctgctg     180 gtgagcctgt ggcagagctt cgtgatgacc ctgagccccc ccttctacag cacctggaag    240
agcgccaagc tgatcaccct gctgtggcgc atcaccaacc actggaccac ctggttcacc    300
acctgcctga gcatcttcta cctgctgaag atcgcccact tcagccacag cttcttcctg    360
tggctgaagt ggcgcaccaa ccgcgtggtg ctggccatcc tggtgctgag cctgcccttc    420
ctgctgttcg acttcctggt gctggagagc ctgaacgact tcttcctgaa cgtgtacgtg    480
atggacgaga gcaacctgac cctgcacacc aacgactgca agagcctgta catcaagacc    540
ctgatcctgc tgagcttcag ctacaccatc cccatcgtgc tgagcctgac cagcctggtg    600
ctgctgttcc tgagcctggt gcgccacatc cgcaacctgc agctgaacgt gatgggcagc    660
ggcgacgcca gcacccaggc ccacaagggc gccatcaaga tggtgatgag cttcctgctg    720
ctgttcaccg tgcacttctt cagcatccag ctgaccaact ggatgctgct gatcttctgg    780
aacaacaagt tcaccaagtt catcatgctg gccatctacg tgttccccag cggccacagc    840
ctgatcctga tcctgggcaa cagcaagctg cgccagaccg ccctgaaggt gctgcgccac    900
ctgaagagca ccctgaagcg cgagaagacc gtgagcagcc tgcagatcga cgtgcccggc    960
agcttctaa                                                            969
```

<210> SEQ ID NO 115
<211> LENGTH: 969
<212> TYPE: DNA
<213> ORGANISM: Artificial Sequence
<220> FEATURE:
<223> OTHER INFORMATION: artificial construct-R42 codon-optimized for mouse

<400> SEQUENCE: 115

```
atgctggccg gcctggacaa gatcttcctg accctgagca ccgccgagtt cgtgatcggc     60
atgagcggca acgtgttcgt gggcctggtg aactgcagcg agtggatcaa gaaccagaag    120
atcagcttcg tggacttcat cctgacctgc ctggccctga gcaggatcac ccagctgctg    180
gtgagcctgt ggcagagctt cgtgatgacc ctgagccccc ccttctacag cacctggaag    240
agcgccaagc tgatcaccct gctgtggagg atcaccaacc actggaccac ctggttcacc    300
acctgcctga gcatcttcta cctgctgaag atcgcccact tcagccacag cttcttcctg    360
tggctgaagt ggaggaccaa cagggtggtg ctggccatcc tggtgctgag cctgcccttc    420
ctgctgttcg acttcctggt gctggagagc ctgaacgact tcttcctgaa cgtgtacgtg    480
```

| | | |
|---|---|---|
| atggacgaga gcaacctgac cctgcacacc aacgactgca agagcctgta catcaagacc | 540 | |
| ctgatcctgc tgagcttcag ctacaccatc cccatcgtgc tgagcctgac cagcctggtg | 600 | |
| ctgctgttcc tgagcctggt gaggcacatc aggaacctgc agctgaacgt gatgggcagc | 660 | |
| ggcgacgcca gcacccaggc ccacaagggc gccatcaaga tggtgatgag cttcctgctg | 720 | |
| ctgttcaccg tgcacttctt cagcatccag ctgaccaact ggatgctgct gatcttctgg | 780 | |
| aacaacaagt tcaccaagtt catcatgctg gccatctacg tgttccccag cggccacagc | 840 | |
| ctgatcctga tcctgggcaa cagcaagctg aggcagaccg ccctgaaggt gctgaggcac | 900 | |
| ctgaagagca ccctgaagag ggagaagacc gtgagcagcc tgcagatcga cgtgcccggc | 960 | |
| agcttctaa | 969 | |

<210> SEQ ID NO 116
<211> LENGTH: 969
<212> TYPE: DNA
<213> ORGANISM: Artificial Sequence
<220> FEATURE:
<223> OTHER INFORMATION: artificial construct-R42 codon-optimized for
      S cerevisiae

<400> SEQUENCE: 116

| | | |
|---|---|---|
| atgttggctg gtttggacaa gatcttcttg actttgtcta ctgctgaatt cgttatcggt | 60 | |
| atgtctggta acgttttcgt tggtttggtt aactgttctg aatggatcaa gaaccaaaag | 120 | |
| atctctttcg ttgacttcat cttgacttgt ttggctttgt ctagaatcac tcaattgttg | 180 | |
| gtttctttgt ggcaatcttt cgttatgact ttgtctccac cattctactc tacttggaag | 240 | |
| tctgctaagt tgatcacttt tgttgtggaga atcactaacc actggactac ttggttcact | 300 | |
| acttgtttgt ctatcttcta cttgttgaag atcgctcact ctctcactc tttcttcttg | 360 | |
| tggttgaagt ggagaactaa cagagttgtt ttggctatct tggttttgtc tttgccattc | 420 | |
| ttgttgttcg acttcttggt tttggaatct ttgaacgact tcttcttgaa cgtttacgtt | 480 | |
| atggacgaat ctaacttgac tttgcacact aacgactgta agtctttgta catcaagact | 540 | |
| ttgatcttgt tgtctcttctc ttacactatc ccaatcgttt tgtctttgac ttctttggtt | 600 | |
| ttgttgttct tgtctcttggt tagacacatc agaaacttgc aattgaacgt tatgggttct | 660 | |
| ggtgacgctt ctactcaagc tcacaagggt gctatcaaga tggttatgtc tttcttgttg | 720 | |
| ttgttcactg ttcacttctt ctctatccaa ttgactaact ggatgttgtt gatcttctgg | 780 | |
| aacaacaagt tcactaagtt catcatgttg gctatctacg tttttcccatc tggtcactct | 840 | |
| ttgatcttga tcttgggtaa ctctaagttg agacaaactg ctttgaaggt tttgagacac | 900 | |
| ttgaagtcta ctttgaagag agaaaagact gtttcttctt tgcaaatcga cgttccaggt | 960 | |
| tctttctaa | 969 | |

<210> SEQ ID NO 117
<211> LENGTH: 969
<212> TYPE: DNA
<213> ORGANISM: Artificial Sequence
<220> FEATURE:
<223> OTHER INFORMATION: artificial construct-R42 codon-optimized for
      E coli

<400> SEQUENCE: 117

| | | |
|---|---|---|
| atgctggctg gtctggacaa aatcttcctg accctgtcta ccgctgaatt cgttatcggt | 60 | |
| atgtctggta acgttttcgt tggtctggtt aactgctctg aatggatcaa aaaccagaaa | 120 | |
| atctctttcg ttgacttcat cctgacctgc ctggctctgt ctcgtatcac ccagctgctg | 180 | |

```
gtttctctgt ggcagtcttt cgttatgacc ctgtctccgc cgttctactc tacctggaaa      240
tctgctaaac tgatcaccct gctgtggcgt atcaccaacc actggaccac ctggttcacc      300
acctgcctgt ctatcttcta cctgctgaaa atcgctcact ctctcactc tttcttcctg       360 tggctgaaat ggcgtaccaa ccgtgttgtt ctggctatcc tggttctgtc tctgccgttc      420
ctgctgttcg acttcctggt tctggaatct ctgaacgact tcttcctgaa cgtttacgtt      480
atggacgaat ctaacctgac cctgcacacc aacgactgca atctctgta catcaaaacc       540 ctgatcctgc tgtctttctc ttacaccatc ccgatcgttc tgtctctgac ctctctggtt      600
ctgctgttcc tgtctctggt tcgtcacatc cgtaacctgc agctgaacgt tatgggttct      660
ggtgacgctt ctacccaggc tcacaaaggt gctatcaaaa tggttatgtc tttcctgctg      720
ctgttcaccg ttcacttctt ctctatccag ctgaccaact ggatgctgct gatcttctgg      780
aacaacaaat tcaccaaatt catcatgctg gctatctacg ttttcccgtc tggtcactct      840
ctgatcctga tcctgggtaa ctctaaactg cgtcagaccg ctctgaaagt tctgcgtcac      900
ctgaaatcta ccctgaaacg tgaaaaaacc gtttcttctc tgcagatcga cgttccgggt      960
tctttctaa                                                              969

<210> SEQ ID NO 118
<211> LENGTH: 900
<212> TYPE: DNA
<213> ORGANISM: Artificial Sequence
<220> FEATURE:
<223> OTHER INFORMATION: artificial construct-R43 codon-optimized for
      C elegans

<400> SEQUENCE: 118
atggttactg ctcttccatc tattttctct attgttgtta ttattgaatt ccttcttgga       60
aatttcgcta atggattcat tgctcttgtt aatttcattg attggactaa aagacaaaaa      120
atttcttctg ttgatcatat tcttactgct cttgctgttt ctagaattgg acttcttttgg    180 gttattctta ttaattggta tgctactctt ttctctccag atttctattc tcttgaagtt      240
agaattattt tccaaactgc ttggactgtt tctaatcatt tctctatttg gcttgctact      300 tctcttttcta ttttctatct tttcaaaatt gctaatttct cttctcttat tttccttaga    360
cttaaatgga gagttaaatc tattgttctt gttattcttc ttggatctct tttcttcctt     420
gtttgtcatg ttgttgctgt ttctgttgt gaaaaagttc aaactgatgt ttatgaagga      480
aatggaacta gaaaaactaa acttagagat attcttcaac tttctaatat gactattttc      540
actcttgcta atttcattcc attcggaatg tctcttactt ctttcgttct tcttattttc     600
tctctttgga aacatcttaa aagaatgcaa ctttgtgata aaggatctca agatccatct     660
actaaagttc atattagagc tatgcaaact gttgtttctt tccttctttt cttcgctgga    720
tatttcttca ctcttactat tactatttgg tcttctaatt ggccacaaaa tgaattcgga     780
ttccttcttt gtcaagttat tggaattctt tatccatcta ttcattctct tatgcttatt     840
agaggaaata aaaaacttag acaagctttc ctttctttcc tttggcaact taaatgttaa     900

<210> SEQ ID NO 119
<211> LENGTH: 900
<212> TYPE: DNA
<213> ORGANISM: Artificial Sequence
<220> FEATURE:
<223> OTHER INFORMATION: artificial construct-R43 codon-optimized for
      Drosophila
```

<400> SEQUENCE: 119

```
atggtgaccg ccctgccctc catcttctcc atcgtggtga tcatcgagtt cctgctgggc    60
aacttcgcca acggcttcat cgccctggtg aacttcatcg actggaccaa gcgccagaag   120
atctcctccg tggaccacat cctgaccgcc ctggccgtgt cccgcatcgg cctgctgtgg   180
gtgatcctga tcaactggta cgccaccctg ttctccccg acttctactc cctggaggtg   240
cgcatcatct tccagaccgc ctggaccgtg tccaaccact ctccatctg gctggccacc   300
tccctgtcca tcttctacct gttcaagatc gccaacttct cctccctgat cttcctgcgc   360
ctgaagtggc gcgtgaagtc catcgtgctg gtgatcctgc tgggctccct gttcttcctg   420
gtgtgccacg tggtggccgt gtccgtgtgc gagaaggtgc agaccgacgt gtacgagggc   480
aacggcaccc gcaagaccaa gctgcgcgac atcctgcagc tgtccaacat gaccatcttc   540
accctggcca acttcatccc cttcggcatg tccctgacct ccttcgtgct gctgatcttc   600
tccctgtgga gcacctgaa gcgcatgcag ctgtgcgaca agggctccca ggacccctcc   660
accaaggtgc acatccgcgc catgcagacc gtggtgtcct cctgctgtt cttcgccggc   720
tacttcttca ccctgaccat caccatctgg tcctccaact ggccccagaa cgagttcggc   780
ttcctgctgt gccaggtgat cggcatcctg taccccctca tccactccct gatgctgatc   840
cgcggcaaca agaagctgcg ccaggccttc ctgtccttcc tgtggcagct gaagtgctaa   900
```

<210> SEQ ID NO 120
<211> LENGTH: 900
<212> TYPE: DNA
<213> ORGANISM: Artificial Sequence
<220> FEATURE:
<223> OTHER INFORMATION: artificial construct-R43 codon-optimized for human

<400> SEQUENCE: 120

```
atggtgaccg ccctgcccag catcttcagc atcgtggtga tcatcgagtt cctgctgggc    60
aacttcgcca acggcttcat cgccctggtg aacttcatcg actggaccaa gcgccagaag   120
atcagcagcg tggaccacat cctgaccgcc ctggccgtga gccgcatcgg cctgctgtgg   180
gtgatcctga tcaactggta cgccaccctg ttcagccccg acttctacag cctggaggtg   240
cgcatcatct tccagaccgc ctggaccgtg agcaaccact cagcatctg gctggccacc   300
agcctgagca tcttctacct gttcaagatc gccaacttca gcagcctgat cttcctgcgc   360
ctgaagtggc gcgtgaagag catcgtgctg gtgatcctgc tgggcagcct gttcttcctg   420
gtgtgccacg tggtggccgt gagcgtgtgc gagaaggtgc agaccgacgt gtacgagggc   480
aacggcaccc gcaagaccaa gctgcgcgac atcctgcagc tgagcaacat gaccatcttc   540
accctggcca acttcatccc cttcggcatg agcctgacca gcttcgtgct gctgatcttc   600
agcctgtgga gcacctgaa gcgcatgcag ctgtgcgaca agggcagcca ggaccccagc   660
accaaggtgc acatccgcgc catgcagacc gtggtgagct cctgctgtt cttcgccggc   720
tacttcttca ccctgaccat caccatctgg agcagcaact ggccccagaa cgagttcggc   780
ttcctgctgt gccaggtgat cggcatcctg taccccagca tccacagcct gatgctgatc   840
cgcggcaaca agaagctgcg ccaggccttc ctgagcttcc tgtggcagct gaagtgctaa   900
```

<210> SEQ ID NO 121
<211> LENGTH: 900
<212> TYPE: DNA
<213> ORGANISM: Artificial Sequence
<220> FEATURE:

<223> OTHER INFORMATION: artificial construct-R43 codon-optimized for mouse

<400> SEQUENCE: 121

```
atggtgaccg ccctgcccag catcttcagc atcgtggtga tcatcgagtt cctgctgggc    60
aacttcgcca acggcttcat cgccctggtg aacttcatcg actggaccaa gaggcagaag   120
atcagcagcg tggaccacat cctgaccgcc ctggccgtga gcaggatcgg cctgctgtgg   180
gtgatcctga tcaactggta cgccaccctg ttcagcccg acttctacag cctggaggtg    240
aggatcatct ccagaccgc ctggaccgtg agcaaccact cagcatctg gctggccacc     300
agcctgagca tcttctacct gttcaagatc gccaacttca gcctgat cttcctgagg      360
ctgaagtgga gggtgaagag catcgtgctg gtgatcctgc tgggcagcct gttcttcctg   420
gtgtgccacg tggtggccgt gagcgtgtgc gagaaggtgc agaccgacgt gtacgagggc   480
aacggcacca ggaagaccaa gctgagggac atcctgcagc tgagcaacat gaccatcttc   540
accctggcca acttcatccc cttcggcatg agcctgacca gcttcgtgct gctgatcttc   600
agcctgtgga agcacctgaa gaggatgcag ctgtgcgaca agggcagcca ggaccccagc   660
accaaggtgc acatcagggc catgcagacc gtggtgagct cctgctgtt cttcgccggc   720
tacttcttca ccctgaccat caccatctgg agcagcaact ggccccagaa cgagttcggc   780
ttcctgctgt gccaggtgat cggcatcctg taccccagca tccacagcct gatgctgatc   840
aggggcaaca agaagctgag gcaggccttc ctgagcttcc tgtggcagct gaagtgctaa   900
```

<210> SEQ ID NO 122
<211> LENGTH: 900
<212> TYPE: DNA
<213> ORGANISM: Artificial Sequence
<220> FEATURE:
<223> OTHER INFORMATION: artificial construct-R43 codon-optimized for S cerevisiae

<400> SEQUENCE: 122

```
atggttactg ctttgccatc tatcttctct atcgttgtta tcatcgaatt cttgttgggt    60
aacttcgcta acggtttcat cgcttttggtt aacttcatcg actggactaa gagacaaaag  120
atctcttctg ttgaccacat cttgactgct ttggctgttt ctagaatcgg tttgttgtgg   180
gttatcttga tcaactggta cgctactttg ttctctccag acttctactc tttggaagtt   240
agaatcatct ccaaaactgc ttggactgtt tctaaccact ctctatctg gttggctact    300
tctttgtcta tcttctactt gttcaagatc gctaacttct cttcttttgat cttcttgaga   360
ttgaagtgga gagttaagtc tatcgttttg gttatcttgt tgggttcttt gttcttcttg   420
gtttgtcacg ttgttgctgt ttctgttttgt gaaaaggttc aaactgacgt ttacgaaggt   480
aacggtacta gaaagactaa gttgagagac atcttgcaat tgtctaacat gactatcttc   540
actttggcta acttcatccc attcggtatg tctttgactt cttttcgtttt gttgatcttc   600
tctttgtgga agcacttgaa gagaatgcaa ttgtgtgaca agggttctca agacccatct   660
actaaggttc acatcagagc tatgcaaact gttgtttctt tcttgttgtt cttcgctggt   720
tacttcttca ctttgactat cactatctgg tcttctaact ggccacaaaa cgaattcggt   780
ttcttgttgt gtcaagttat cggtatcttg taccatcta tccactcttt gatgttgatc    840
agaggtaaca agaagttgag acaagctttc ttgtctttct gtggcaatt gaagtgttaa    900
```

<210> SEQ ID NO 123
<211> LENGTH: 900

```
<212> TYPE: DNA
<213> ORGANISM: Artificial Sequence
<220> FEATURE:
<223> OTHER INFORMATION: artificial construct-R43 codon-optimized for
      E coli

<400> SEQUENCE: 123
atggttaccg ctctgccgtc tatcttctct atcgttgtta tcatcgaatt cctgctgggt      60
aacttcgcta acggtttcat cgctctggtt aacttcatcg actggaccaa acgtcagaaa     120
atctcttctg ttgaccacat cctgaccgct ctggctgttt ctcgtatcgg tctgctgtgg     180
gttatcctga tcaactggta cgctacccct gttctctccgg acttctactc tctggaagtt   240
cgtatcatct ccagaccgc ttggaccgtt tctaaccact tctctatctg gctggctacc     300
tctctgtcta cttctacct gttcaaaatc gctaacttct cttctctgat cttcctgcgt    360
ctgaaatggc gtgttaaatc tatcgttctg gttatcctgc tgggttctct gttcttcctg    420
gtttgccacg ttgttgctgt ttctgtttgc gaaaaagttc agaccgacgt ttacgaaggt    480
aacggtaccc gtaaaaccaa actgcgtgac atcctgcagc tgtctaacat gaccatcttc    540
accctggcta acttcatccc gttcggtatg tctctgacct cttttcgttct gctgatcttc   600 tctctgtgga acaccctgaa acgtatgcag ctgtgcgaca aggttctca ggacccgtct    660 accaaagttc acatccgtgc tatgcagacc gttgtttctt cctgctgtt cttcgctggt    720 tacttcttca ccctgaccat caccatctgg tcttctaact ggccgcagaa cgaattcggt    780
ttcctgctgt gccaggttat cggtatcctg tacccgtcta ccactctct gatgctgatc    840 cgtggtaaca aaaaactgcg tcaggctttc ctgtctttcc tgtggcagct gaaatgctaa    900

<210> SEQ ID NO 124
<211> LENGTH: 927
<212> TYPE: DNA
<213> ORGANISM: Artificial Sequence
<220> FEATURE:
<223> OTHER INFORMATION: artificial construct-R44 codon-optimized for
      C elegans

<400> SEQUENCE: 124
atggtttctg ctcttccatc tatttttctct attgctgtta ttattgaatt ccttcttgga    60
aatttcgcta atggattcat tgctcttgtt aatttcattg attggactaa aagacaaaaa    120
atttcttctg ttgatcatat tcttgctgct cttgctgttt ctagaattgg acttcttttgg   180 gttatgatta ttaattggta tgctacttgg ttctctccag atttcaaatc tcttgaagtt    240
agaattattt ccaaactgc ttggactgtt tctaatcatt tctctatttg cttgctact     300 tctcttttcta ttttctatct tttcaaaatt gctaatttct cttctcttat tttccttaga    360
cttaaatgga gagttaaatc tgttgttctt gttatgcttc ttggatctct ttttccttctt   420 ttctctcatg ttgctgctgt ttctatttat gaaaaagttc aaactaaagc ttatgaagga   480
aatgttactt ggagaactaa atggactgga atggctcatc tttctaatat gactgttttc   540
actcttgcta atttcattcc attcgctact tctcttactt cttcgttct tcttattttc     600 tctctttgga gacatcttaa aagaatgcaa ctttgtggaa aaggatctca agatccatct   660
actaaagttc atattagagc tatgcaaact gttgtttctt ccttcttttt cttcgctgga   720
tatgttctta tcttattgt tactgtttgg tctttcaatg gacttcaaaa agaacttttc    780
atgttctgtc aagttcttgc tttcgtttat ccatcattc attctcttat gcttatttgg    840
ggaaataaaa aacttaaaca agctttcctt tctgttcttt atcaagaaaa atattggctt   900
```
aaagaacaaa aacattctac tccataa                                    927

<210> SEQ ID NO 125
<211> LENGTH: 927
<212> TYPE: DNA
<213> ORGANISM: Artificial Sequence
<220> FEATURE:
<223> OTHER INFORMATION: artificial construct-R44 codon-optimized for
      Drosophila

<400> SEQUENCE: 125
atggtgtccg ccctgccctc catcttctcc atcgccgtga tcatcgagtt cctgctgggc    60
aacttcgcca acggcttcat cgccctggtg aacttcatcg actggaccaa gcgccagaag   120
atctcctccg tggaccacat cctggccgcc ctggccgtgt cccgcatcgg cctgctgtgg   180
gtgatgatca tcaactggta cgccacctgg ttctcccccg acttcaagtc cctggaggtg   240
cgcatcatct tccagaccgc ctggaccgtg tccaaccact ctccatctg gctggccacc    300
tccctgtcca tcttctacct gttcaagatc gccaacttct cctccctgat cttcctgcgc   360
ctgaagtggc gcgtgaagtc cgtggtgctg gtgatgctgc tgggctccct gttcctgctg   420
ttctcccacg tggccgccgt gtccatctac gagaaggtgc agaccaaggc ctacgagggc   480
aacgtgacct ggcgcaccaa gtggaccggc atggccacc tgtccaacat gaccgtgttc    540
accctggcca acttcatccc cttcgccacc tccctgacct ccttcgtgct gctgatcttc   600
tccctgtggc gccacctgaa gcgcatgcag ctgtgcggca agggctccca ggacccctcc   660
accaaggtgc acatccgcgc catgcagacc gtggtgtcct tcctgctgtt cttcgccggc   720
tacgtgctga acctgatcgt gaccgtgtgg tccttcaacg gcctgcagaa ggagctgttc   780
atgttctgcc aggtgctggc cttcgtgtac ccctccatcc actccctgat gctgatctgg   840
ggcaacaaga gctgaagca ggccttcctg tccgtgctgt accaggagaa gtactggctg    900
aaggagcaga agcactccac cccctaa                                      927

<210> SEQ ID NO 126
<211> LENGTH: 927
<212> TYPE: DNA
<213> ORGANISM: Artificial Sequence
<220> FEATURE:
<223> OTHER INFORMATION: artificial construct-R44 codon-optimized for
      human

<400> SEQUENCE: 126
atggtgagcg ccctgcccag catcttcagc atcgccgtga tcatcgagtt cctgctgggc    60
aacttcgcca acggcttcat cgccctggtg aacttcatcg actggaccaa gcgccagaag   120
atcagcagcg tggaccacat cctggccgcc ctggccgtga gccgcatcgg cctgctgtgg   180
gtgatgatca tcaactggta cgccacctgg ttcagccccg acttcaagag cctggaggtg   240
cgcatcatct tccagaccgc ctggaccgtg agcaaccact tcagcatctg gctggccacc   300
agcctgagca tcttctacct gttcaagatc gccaacttca gcagcctgat cttcctgcgc   360
ctgaagtggc gcgtgaagag cgtggtgctg gtgatgctgc tgggcagcct gttcctgctg   420
ttcagccacg tggccgccgt gagcatctac gagaaggtgc agaccaaggc ctacgagggc   480
aacgtgacct ggcgcaccaa gtggaccggc atggccacc tgagcaacat gaccgtgttc    540
accctggcca acttcatccc cttcgccacc agcctgacca gcttcgtgct gctgatcttc   600
agcctgtggc gccacctgaa gcgcatgcag ctgtgcggca agggcagcca ggaccccagc   660
accaaggtgc acatccgcgc catgcagacc gtggtgagct tcctgctgtt cttcgccggc   720

```
tacgtgctga acctgatcgt gaccgtgtgg agcttcaacg gcctgcagaa ggagctgttc    780
atgttctgcc aggtgctggc cttcgtgtac cccagcatcc acagcctgat gctgatctgg    840
ggcaacaaga agctgaagca ggccttcctg agcgtgctgt accaggagaa gtactggctg    900
aaggagcaga agcacagcac cccctaa                                        927
```

<210> SEQ ID NO 127
<211> LENGTH: 927
<212> TYPE: DNA
<213> ORGANISM: Artificial Sequence
<220> FEATURE:
<223> OTHER INFORMATION: artificial construct-R44 codon-optimized for
      mouse

<400> SEQUENCE: 127

```
atggtgagcg ccctgcccag catcttcagc atcgccgtga tcatcgagtt cctgctgggc     60
aacttcgcca acggcttcat cgccctggtg aacttcatcg actggaccaa gaggcagaag    120
atcagcagcg tggaccacat cctggccgcc ctggccgtga gcaggatcgg cctgctgtgg    180
gtgatgatca tcaactggta cgccacctgt tcagccccg acttcaagag cctggaggtg    240
aggatcatct tccagaccgc ctggaccgtg agcaaccact tcagcatctg gctggccacc    300
agcctgagca tcttctacct gttcaagatc gccaacttca gcagcctgat cttcctgagg    360
ctgaagtgga gggtgaagag cgtggtgctg gtgatgctgc tgggcagcct gttcctgctg    420
ttcagccacg tggccgccgt gagcatctac gagaaggtgc agaccaaggc ctacgagggc    480
aacgtgacct ggaggaccaa gtggaccggc atggcccacc tgagcaacat gaccgtgttc    540
accctggcca acttcatccc cttcgccacc agcctgacca gcttcgtgct gctgatcttc    600
agcctgtgga ggcacctgaa gaggatgcag ctgtgcggca agggcagcca ggaccccagc    660
accaaggtgc acatcagggc catgcagacc gtggtgagct tcctgctgtt cttcgccggc    720
tacgtgctga acctgatcgt gaccgtgtgg agcttcaacg gcctgcagaa ggagctgttc    780
atgttctgcc aggtgctggc cttcgtgtac cccagcatcc acagcctgat gctgatctgg    840
ggcaacaaga agctgaagca ggccttcctg agcgtgctgt accaggagaa gtactggctg    900
aaggagcaga agcacagcac cccctaa                                        927
```

<210> SEQ ID NO 128
<211> LENGTH: 927
<212> TYPE: DNA
<213> ORGANISM: Artificial Sequence
<220> FEATURE:
<223> OTHER INFORMATION: artificial construct-R44 codon-optimized for
      S cerevisiae

<400> SEQUENCE: 128

```
atggtttctg ctttgccatc tatcttctct atcgctgtta tcatcgaatt cttgttgggt     60
aacttcgcta acggtttcat cgctttggtt aacttcatcg actggactaa gagacaaaag    120
atctcttctg ttgaccacat cttggctgct ttggctgttt ctagaatcgg tttgttgtgg    180
gttatgatca tcaactggta cgctacttgg ttctctccag acttcaagtc tttggaagtt    240
agaatcatct tccaaactgc ttggactgtt tctaaccact tctctatctg gttggctact    300
tctttgtcta tcttctactt gttcaagatc gctaacttct cttctttgat cttcttgaga    360
ttgaagtgga gagttaagtc tgttgttttg gttatgttgt tgggttcttt gttcttgttg    420
ttctctcacg ttgctgctgt ttctatctac gaaaaggttc aaactaaggc ttacgaaggt    480
```

```
aacgttactt ggagaactaa gtggactggt atggctcact tgtctaacat gactgttttc      540
actttggcta acttcatccc attcgctact tctttgactt ctttcgtttt gttgatcttc      600
tctttgtgga gacacttgaa gagaatgcaa ttgtgtggta agggttctca agacccatct      660
actaaggttc acatcagagc tatgcaaact gttgtttctt tcttgttgtt cttcgctggt      720
tacgttttga acttgatcgt tactgtttgg tctttcaacg gtttgcaaaa ggaattgttc      780
atgttctgtc aagttttggc tttcgtttac ccatctatcc actctttgat gttgatctgg      840
ggtaacaaga agttgaagca agctttcttg tctgttttgt accaagaaaa gtactggttg      900
aaggaacaaa agcactctac tccataa                                         927
```

```
<210> SEQ ID NO 129
<211> LENGTH: 927
<212> TYPE: DNA
<213> ORGANISM: Artificial Sequence
<220> FEATURE:
<223> OTHER INFORMATION: artificial construct-R44 codon-optimized for
      E coli

<400> SEQUENCE: 129
atggtttctg ctctgccgtc tatcttctct atcgctgtta tcatcgaatt cctgctgggt       60
aacttcgcta acggtttcat cgctctggtt aacttcatcg actggaccaa cgtcagaaa      120 atctcttctg ttgaccacat cctggctgct ctggctgttt ctcgtatcgg tctgctgtgg      180
gttatgatca tcaactggta cgctacctgg ttctctccgg acttcaaatc tctggaagtt      240
cgtatcatct tccagaccgc ttggaccgtt tctaaccact tctctatctg ctggctacc       300 tctctgtcta tcttctacct gttcaaaatc gctaacttct cttctctgat cttcctgcgt      360
ctgaaatggc gtgttaaatc tgttgttctg gttatgctgc tgggttctct gttcctgctg      420
ttctctcacg ttgctgctgt ttctatctac gaaaaagttc agaccaaagc ttacgaaggt      480
aacgttacct ggcgtaccaa atggaccggt atggctcacc tgtctaacat gaccgttttc      540
accctggcta acttcatccc gttcgctacc tctctgacct ctttcgttct gctgatcttc      600
tctctgtggc gtcacctgaa acgtatgcag ctgtgcggta aaggttctca ggacccgtct      660
accaaagttc acatccgtgc tatgcagacc gttgtttctt tcctgctgtt cttcgctggt      720
tacgttctga acctgatcgt taccgtttgg tctttcaacg gtctgcagaa agaactgttc      780
atgttctgcc aggttctggc tttcgtttac ccgtctatcc actctctgat gctgatctgg      840
ggtaacaaaa aactgaaaca ggctttcctg tctgttctgt accaggaaaa atactggctg      900
aaagaacaga aacactctac cccgtaa                                         927
```

```
<210> SEQ ID NO 130
<211> LENGTH: 939
<212> TYPE: DNA
<213> ORGANISM: Artificial Sequence
<220> FEATURE:
<223> OTHER INFORMATION: artificial construct-R67 codon-optimized for
      C elegans

<400> SEQUENCE: 130
atgccatctg gaattgaaaa tactttcctt actgctgctg ttggaacttt catgattgga       60
atgcttggaa atggattcat tgctcttgtt aattgtattg attgggttaa acatagaaaa      120
ctttctccag ctgattgtat tcttacttct cttgctgttt ctagaattat tcttctttgg      180
atgattcttt tcgatcttct tgttatggtt ttctggccac atcttataa tattgaaaaa       240 cttgctactg ctgttaatat tgttggact  cttactaatc atcttgctac ttggttcgct      300
```

```
acttgtcttt ctgttttcta tttcttcaga attgctaatt tctctcatag atatttcact      360
tggcttagaa aagaatttc tagagttctt ccagttcttc cacttggatc tcttttcctt       420
cttgttttca attataaact tcttgttgga ttctctgatc tttgggctac tatttatcat      480
aattatgaaa gaaattctac tagaccactt gatgtttcta aaactggata tcttaattct      540
cttgttattc tttctttcat ttatcttatt ccattcttc tttctcttac ttctcttctt      600
cttcttttcc tttctcttat gagacatact agaaatgttc aacttaattc ttcttctaga      660
gatttctcta ctgaagctca taaaagagct atgaaaatgg ttatttctt ccttcttctt      720 tctactgttc atttcttctc tattcaactt actggatgga ttttccttct tcttaaaaaa     780
catcatgcta atcttactgt tactcttact tctgctcttt tcccatctgg acattctttc      840
attcttattt tcggaaattc taacttaga caaactgctc ttggacttct ttggcatctt      900
aattgtcatc ttaaaatggt taaaccactt gcttcttaa                            939

<210> SEQ ID NO 131
<211> LENGTH: 939
<212> TYPE: DNA
<213> ORGANISM: Artificial Sequence
<220> FEATURE:
<223> OTHER INFORMATION: artificial construct-R67 codon-optimized for
      Drosophila

<400> SEQUENCE: 131
atgccctccg gcatcgagaa caccttcctg accgccgccg tgggcacctt catgatcggc      60
atgctgggca acggcttcat cgccctggtg aactgcatcg actgggtgaa gcaccgcaag     120
ctgtcccccg ccgactgcat cctgacctcc ctggccgtgt cccgcatcat cctgctgtgg     180
atgatcctgt cgacctgct ggtgatggtg ttctggcccc acctgtacaa catcgagaag      240
ctggccaccg ccgtgaacat ctgctggacc ctgaccaacc acctggccac ctggttcgcc     300
acctgcctgt ccgtgttcta cttcttccgc atcgccaact tctcccaccg ctacttcacc     360
tggctgcgcc gccgcatctc ccgcgtgctg cccgtgctgc ccctgggctc cctgttcctg     420
ctggtgttca actacaagct gctggtgggc ttctccgacc tgtgggccac catctaccac     480
aactacgagc gcaactccac ccgccccctg gacgtgtcca gaccggcta cctgaactcc      540 ctggtgatcc tgtccttcat ctacctgatc cccttcctgc tgtccctgac ctccctgctg     600
ctgctgttcc tgtccctgat gcgccacacc cgcaacgtgc agctgaactc ctcctcccgc     660
gacttctcca ccgaggccca caagcgcgcc atgaagatgg tgatctcctt cctgctgctg     720
tccaccgtgc acttcttctc catccagctg accggctgga tcttcctgct gctgaagaag    780
caccacgcca acctgaccgt gaccctgacc tccgccctgt tcccctccgg ccactccttc     840
atcctgatct tcggcaactc caagctgcgc cagaccgccc tgggcctgct gtggcacctg     900
aactgccacc tgaagatggt gaagcccctg gcctcctaa                            939

<210> SEQ ID NO 132
<211> LENGTH: 939
<212> TYPE: DNA
<213> ORGANISM: Artificial Sequence
<220> FEATURE:
<223> OTHER INFORMATION: artificial construct-R67 codon-optimized for
      human

<400> SEQUENCE: 132
atgcccagcg gcatcgagaa caccttcctg accgccgccg tgggcacctt catgatcggc      60
```

| | |
|---|---|
| atgctgggca acggcttcat cgccctggtg aactgcatcg actgggtgaa gcaccgcaag | 120 |
| ctgagccccg ccgactgcat cctgaccagc ctggccgtga gccgcatcat cctgctgtgg | 180 |
| atgatcctgt tcgacctgct ggtgatggtg ttctggcccc acctgtacaa catcgagaag | 240 |
| ctggccaccg ccgtgaacat ctgctggacc ctgaccaacc acctggccac ctggttcgcc | 300 |
| acctgcctga gcgtgttcta cttcttccgc atcgccaact tcagccaccg ctacttcacc | 360 |
| tggctgcgcc gccgcatcag ccgcgtgctg cccgtgctgc ccctgggcag cctgttcctg | 420 |
| ctggtgttca actacaagct gctggtgggc ttcagcgacc tgtgggccac catctaccac | 480 |
| aactacgagc gcaacagcac ccgccccctg gacgtgagca agaccggcta cctgaacagc | 540 |
| ctggtgatcc tgagcttcat ctacctgatc cccttcctgc tgagcctgac cagcctgctg | 600 |
| ctgctgttcc tgagcctgat cgccacacc cgcaacgtgc agctgaacag cagcagccgc | 660 |
| gacttcagca ccgaggccca caagcgcgcc atgaagatgg tgatcagctt cctgctgctg | 720 |
| agcaccgtgc acttcttcag catccagctg accggctgga tcttcctgct gctgaagaag | 780 |
| caccacgcca acctgaccgt gaccctgacc agcgccctgt tccccagcgg ccacagcttc | 840 |
| atcctgatct tcggcaacag caagctgcgc cagaccgccc tgggcctgct gtggcacctg | 900 |
| aactgccacc tgaagatggt gaagcccctg gccagctaa | 939 |

<210> SEQ ID NO 133
<211> LENGTH: 939
<212> TYPE: DNA
<213> ORGANISM: Artificial Sequence
<220> FEATURE:
<223> OTHER INFORMATION: artificial construct-R67 codon-optimized for mouse

<400> SEQUENCE: 133

| | |
|---|---|
| atgcccagcg gcatcgagaa caccttcctg accgccgccg tgggcacctt catgatcggc | 60 |
| atgctgggca acggcttcat cgccctggtg aactgcatcg actgggtgaa gcacaggaag | 120 |
| ctgagccccg ccgactgcat cctgaccagc ctggccgtga gcaggatcat cctgctgtgg | 180 |
| atgatcctgt tcgacctgct ggtgatggtg ttctggcccc acctgtacaa catcgagaag | 240 |
| ctggccaccg ccgtgaacat ctgctggacc ctgaccaacc acctggccac ctggttcgcc | 300 |
| acctgcctga gcgtgttcta cttcttcagg atcgccaact tcagccacag gtacttcacc | 360 |
| tggctgagga ggaggatcag cagggtgctg cccgtgctgc ccctgggcag cctgttcctg | 420 |
| ctggtgttca actacaagct gctggtgggc ttcagcgacc tgtgggccac catctaccac | 480 |
| aactacgaga ggaacagcac cagggcccctg gacgtgagca agaccggcta cctgaacagc | 540 |
| ctggtgatcc tgagcttcat ctacctgatc cccttcctgc tgagcctgac cagcctgctg | 600 |
| ctgctgttcc tgagcctgat gaggcacacc aggaacgtgc agctgaacag cagcagcagg | 660 |
| gacttcagca ccgaggccca caagagggcc atgaagatgg tgatcagctt cctgctgctg | 720 |
| agcaccgtgc acttcttcag catccagctg accggctgga tcttcctgct gctgaagaag | 780 |
| caccacgcca acctgaccgt gaccctgacc agcgccctgt tccccagcgg ccacagcttc | 840 |
| atcctgatct tcggcaacag caagctgagg cagaccgccc tgggcctgct gtggcacctg | 900 |
| aactgccacc tgaagatggt gaagcccctg gccagctaa | 939 |

<210> SEQ ID NO 134
<211> LENGTH: 939
<212> TYPE: DNA
<213> ORGANISM: Artificial Sequence
<220> FEATURE:

<223> OTHER INFORMATION: artificial construct-R67 codon-optimized for
    S cerevisiae

<400> SEQUENCE: 134

```
atgccatctg gtatcgaaaa cactttcttg actgctgctg ttggtacttt catgatcggt      60
atgttgggta acggtttcat cgctttggtt aactgtatcg actgggttaa gcacagaaag     120
ttgtctccag ctgactgtat cttgacttct ttggctgttt ctagaatcat cttgttgtgg     180
atgatcttgt tcgacttgtt ggttatggtt ttctggccac acttgtacaa catcgaaaag     240
ttggctactg ctgttaacat ctgttggact ttgactaacc acttggctac ttggttcgct     300
acttgtttgt ctgttttcta cttcttcaga atcgctaact tctctcacag atacttcact     360
tggttgagaa gaagaatctc tagagttttg ccagttttgc cattgggttc tttgttcttg     420
ttggttttca actacaagtt gttggttggt ttctctgact gtgggctac tatctaccac     480
aactacgaaa gaaactctac tagaccattg gacgtttcta agactggtta cttgaactct     540
ttggttatct gtctttcat ctacttgatc ccattcttgt tgtctttgac ttctttgttg     600
ttgttgttct tgtctttgat gagacacact agaaacgttc aattgaactc ttcttctaga     660
gacttctcta ctgaagctca aagagagct atgaagatgg ttatctcttt cttgttgttg     720
tctactgttc acttcttctc tatccaattg actggtggga tcttcttgtt gttgaagaag     780
caccacgcta acttgactgt actttgact tctgctttgt tcccatctgg tcactctttc     840
atcttgatct tcggtaactc taagttgaga caaactgctt tgggtttgtt gtggcacttg     900
aactgtcact tgaagatggt taagccattg gcttcttaa                            939
```

<210> SEQ ID NO 135
<211> LENGTH: 939
<212> TYPE: DNA
<213> ORGANISM: Artificial Sequence
<220> FEATURE:
<223> OTHER INFORMATION: artificial construct-R67 codon-optimized for
    E coli

<400> SEQUENCE: 135

```
atgccgtctg gtatcgaaaa caccttcctg accgctgctg ttggtaccttt catgatcggt     60
atgctgggta acggtttcat cgctctggtt aactgcatcg actgggttaa acaccgtaaa    120
ctgtctccgg ctgactgcat cctgaccttct ctggctgttt ctcgtatcat cctgctgtgg    180
atgatcctgt tcgacctgct ggttatggtt ttctggccgc acctgtacaa catcgaaaaa    240
ctggctaccg ctgttaacat ctgctggacc ctgaccaacc acctggctac ctggttcgct    300
acctgcctgt ctgttttcta cttcttccgt atcgctaact ctctcaccg ttacttcacc    360
tggctgcgtc gtcgtatctc tcgtgttctg ccggttctgc cgctgggttc tctgttcctg    420
ctggttttca actacaaact gctggttggt ttctctgacc tgtgggctac catctaccac    480
aactacgaac gtaactctac ccgtccgctg acgtttcta aaaccggtta cctgaactct    540
ctggttatcc tgtctttcat ctacctgatc ccgttcctgc tgtctctgac ctctctgctg    600
ctgctgttcc tgtctctgat gcgtcacacc cgtaacgttc agctgaactc ttcttctcgt    660
gacttctcta ccgaagctca aaacgtgct atgaaaatgg ttatctcttt cctgctgctg    720
tctaccgttc acttcttctc tatccagctg accggttgga tcttcctgct gctgaaaaaa    780
```

```
caccacgcta acctgaccgt taccctgacc tctgctctgt tcccgtctgg tcactctttc    840
atcctgatct tcggtaactc taaactgcgt cagaccgctc tgggtctgct gtggcacctg    900
aactgccacc tgaaaatggt taaaccgctg gcttcttaa                           939
```